(12) United States Patent
Vendeville et al.

(10) Patent No.: US 11,464,783 B2
(45) Date of Patent: Oct. 11, 2022

(54) HETEROCYCLIC COMPOUNDS

(71) Applicant: Aligos Therapeutics, Inc., South San Francisco, CA (US)

(72) Inventors: Sandrine Vendeville, Brussels (BE); Pierre Jean-Marie Bernard Raboisson, Wavre (BE)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/891,703

(22) Filed: Jun. 3, 2020

(65) Prior Publication Data
US 2020/0397797 A1 Dec. 24, 2020

Related U.S. Application Data

(60) Provisional application No. 62/858,236, filed on Jun. 6, 2019.

(51) Int. Cl.
| | |
|---|---|
| *A61K 31/541* | (2006.01) |
| *A61P 31/20* | (2006.01) |
| *A61K 31/54* | (2006.01) |
| *C07D 279/12* | (2006.01) |
| *C07D 417/04* | (2006.01) |
| *C07D 417/14* | (2006.01) |

(52) U.S. Cl.
CPC ............ *A61K 31/541* (2013.01); *A61K 31/54* (2013.01); *A61P 31/20* (2018.01); *C07D 279/12* (2013.01); *C07D 417/04* (2013.01); *C07D 417/14* (2013.01)

(58) Field of Classification Search
None
See application file for complete search history.

(56) References Cited

U.S. PATENT DOCUMENTS

| | | |
|---|---|---|
| 3,530,124 A | 9/1970 | Ilvespaa et al. |
| 2020/0147124 A1 | 5/2020 | Beigelman et al. |

FOREIGN PATENT DOCUMENTS

| | | |
|---|---|---|
| CN | 107652217 A | 2/2018 |
| WO | WO 2006/113704 | 10/2006 |
| WO | WO 2014/037480 | 3/2014 |
| WO | WO 2016/073847 | 5/2016 |
| WO | WO 2017/079519 | 5/2017 |
| WO | WO 2017/156255 | 9/2017 |
| WO | WO 2018/165673 | 9/2018 |
| WO | WO 2018/167269 | 9/2018 |

OTHER PUBLICATIONS

Database Registry Chemical Abstracts Service, Columbus, Ohio, Accession No. RN 1786370-99-7, Entered STN: Jun. 22, 2015.*
"IUPAC-IUB Commission on Biochemical Nomenclature Abbreviated Nomenclature of Synthetic Polypeptides (Polymerized Amino Acids) Revised Recommendations (1971)" *Biochemistry*. (1972) 11(5):942-944.
Liang, "Hepatitis B: The Virus and Disease" Hepatology (2009) 49(S5):S13-S21.
Second Written Opinion dated May 6, 2021 for PCT Application No. PCT/US2020/035929, filed Jun. 3, 2020.
CAS RN 1436314-17-8, STN Entry Date Jun. 9, 2013.
CAS RN 1595224-36-4, STN Entry Date May 1, 2014.
CAS RN 1922099-02-2, STN Entry Date May 31, 2016.
CAS RN 1946968-37-1, STN Entry Date Jul. 7, 2016.
CAS RN 1955278-24-6, STN Entry Date Jul. 19, 2016.
CAS RN 2106097-05-4, STN Entry Date Aug. 1, 2017.
CAS RN 2106105-41-1, STN Entry Date Aug. 1, 2017.
CAS RN 2107192-86-7, STN Entry Date Aug. 2, 2017.
CAS RN 2128920-81-8, STN Entry Date Sep. 21, 2017.
CAS RN 2129484-49-5, STN Entry Date Sep. 22, 2017.
CAS RN 2159988-41-5, STN Entry Date Dec. 18, 2017.
CAS RN 2175894-02-5, STN Entry Date Feb. 19, 2018.
CAS RN 2196326-79-9, STN Entry Date Mar. 22, 2018.
Idson et al., "1,4-thiazans. I. C-Alkyl Thiomorpholines" J. Am. Chem. Soc. (1954) 76(11):2902-2906.
International Search Report and Written Opinion dated Aug. 26, 2020 for PCT Application No. PCT/US2020/035929, filed Jun. 3, 2020.
CAS Reg. No. 1786188-33-7, Entered Jun. 22, 2015.
CAS Reg. No. 1786272-37-4, Entered Jun. 22, 2015.
CAS Reg. No. 1786370-99-7, Entered Jun. 22, 2015.
CAS Reg. No. 1788725-61-0, Entered Jun. 25, 2015.
CAS Reg. No. 1789087-56-4, Entered Jun. 26, 2015.
CAS Reg. No. 1795602-79-7, Entered Jul. 6, 2015.
CAS Reg. No. 1790469-20-3, Entered Jun. 28, 2015.
CAS Reg. No. 1791316-34-1, Entered Jun. 29, 2015.
CAS Reg. No. 1790468-48-2, Entered Jun. 28, 2015.
CAS Reg. No. 1786371-04-7, Entered Jun. 22, 2015.
CAS Reg. No. 1790469-02-1, Entered Jun. 28, 2015.
CAS Reg. No. 2224393-87-5, Entered May 20, 2018.
CAS Reg. No. 1791180-76-1, Entry Date Jun. 29, 2015.
Third Written Opinion dated Jul. 15, 2021 for PCT Application No. PCT/US2020/035929, filed Jun. 3, 2020.
International Preliminary Report on Patentability dated Sep. 12, 2021 for PCT Application No. PCT/US2020/035929, filed Jun. 3, 2020.

* cited by examiner

*Primary Examiner* — Samantha L Shterengarts
(74) *Attorney, Agent, or Firm* — Knobbe Martens Olson & Bear LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

21 Claims, 1 Drawing Sheet
Specification includes a Sequence Listing.

The plate map of compound treatment

| | 1 | 2 | 3 | 4 | 5 | 6 | 7 | 8 | 9 | 10 | 11 | 12 |
|---|---|---|---|---|---|---|---|---|---|---|---|---|
| A | | High dose | | 4-fold dilution, 8 dilution points, duplicate | | | | | Low dose | | | |
| B | compound 1 | | | | | | | | | ETV(1µM) | 0.5%DMSO control | Blank |
| C | | | | | | | | | | | | |
| D | compound 2 | | | | | | | | | ETV(1µM) | 0.5%DMSO control | Blank |
| E | | | | | | | | | | | | |
| F | compound 3 | | | | | | | | | ETV(1µM) | 0.5%DMSO control | Blank |
| G | | | | | | | | | | | | |
| H | | High dose | | 4-fold dilution, 8 dilution points, duplicate | | | | | Low dose | | | |

HETEROCYCLIC COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/858,236, filed Jun. 6, 2019.

BACKGROUND

Field

The present application relates to the fields of chemistry, biochemistry and medicine. Disclosed herein are compounds of Formula (I), or pharmaceutically acceptable salt thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

The hepatitis B virus (HBV) is a DNA virus and a member of the Hepadnaviridae family. HBV infects more than 300 million worldwide, and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

REFERENCE TO SEQUENCE LISTING

The present application is filed with a Sequence Listing in Electronic format. The Sequence Listing is provided as a file entitled ALIG021.txt, created Jun. 3, 2020, which is approximately 2 kb in size. The information in the electronic format of the sequence listing is incorporated herein by reference in its entirety.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

BRIEF DESCRIPTION OF THF DRAWINGS

FIG. 1 shows the plate map of compound treatment for the HBV-DNA Antiviral Assay described herein.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Hepatology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Definitions

Unless defined otherwise, all technical and scientific terms used herein have the same meaning as is commonly understood by one of ordinary skill in the art. All patents applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from deuterium, alkyl, alkenyl, alkynyl, cycloalkyl, cycloalkenyl, aryl, heteroaryl, heterocyclyl, aryl (alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$, $(CH_3)_2CHCH_2-$ and $(CH_3)_3C-$. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s), 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom (s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "optionally substituted" and/or by substituting both hydrogens on the same carbon with a cycloalkyl group

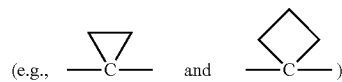

or a monocyclic heterocyclyl (such as

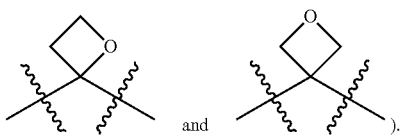 [SMILES: *C1(*)CCO1 ; *C1(*)COC1]

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, isobutoxy, sec-butoxy, tert-butoxy, phenoxy and benzoxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "alkoxyalkyl" refers to an alkyl group in which one or more of the hydrogen atoms are replaced by a alkoxy group. Exemplary alkoxyalkyl groups include but are not limited to, methoxymethyl, ethoxymethyl, methoxyethyl and ethoxy ethyl. An alkoxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomeric ally enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

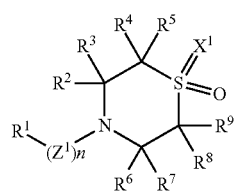

(I)

wherein: n can be 0 or 1; $Z^1$ can be —C(=O)—, —NH—C(=O)— or —O—C(=O)—; $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^2$ and $R^3$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^4$ and $R^5$ can be independently selected from hydrogen, an unsubstituted CM alkyl, an unsubstituted CM haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^6$ and $R^7$ can be independently selected from hydrogen, an unsubstituted CM alkyl and an unsubstituted CM haloalkyl; $R^8$ can be hydrogen, halogen or an unsubstituted CM alkyl; $R^9$ can be selected from an optionally substituted CM alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl), an optionally substituted heterocyclyl ($C_{1-4}$ alkyl), —$NR^{10}R^{11}$ and —C(=O)$NR^{12}R^{13}$, wherein when the CM alkyl is substituted, the substituted CM alkyl can be substituted with one or more substituents selected from the group consisting of halogen, cyano, hydroxy, an unsubstituted $C_{1-4}$ alkoxy, amino, C-amido and N-amido; $R^{10}$ and $R^{12}$ can be independently hydrogen or an unsubstituted $C_{1-4}$ alkyl; $R^{11}$ and $R^{13}$ can be independently selected from hydrogen, an optionally substituted $C_{1-4}$ alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl), wherein when the $C_{1-4}$ alkyl is substituted, the substituted $C_{1-4}$ alkyl can be substituted with one or more substituents selected from the group consisting of halogen, cyano, hydroxy, an unsubstituted $C_{1-4}$ alkoxy, amino, C-amido and N-amido; or $R^{10}$ and $R^{11}$ can be taken together along with the nitrogen to which $R^{10}$ and $R^{11}$ are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl; $R^{12}$ and $R^{13}$ can be taken together along with the nitrogen to which $R^{12}$ and $R^{13}$ are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl; $R^2$ and $R^3$ can be taken together along with the carbon to which $R^2$ and $R^3$ are attached to form an optionally substituted monocyclic $C_{3-6}$ cycloalkyl or an optionally substituted 3 to 6 member monocyclic heterocyclyl; or $R^4$ and $R^5$ can be taken together along with the carbon to which $R^4$ and $R^5$ are attached to form an optionally substituted monocyclic $C_{3-6}$ cycloalkyl or an optionally substituted 3 to 6 member monocyclic heterocyclyl; or $R^2$ and $R^4$ can be taken together along with the carbons to which $R^2$ and $R^4$ are each attached to form an optionally monocyclic $C_{5-7}$ cycloalkyl or an optionally substituted 5 to 7 member monocyclic heterocyclyl; or $R^3$ and $R^5$ can be taken together along with the carbons to which $R^3$ and $R^5$ are each attached to form an optionally monocyclic $C_{5-7}$ cycloalkyl or an optionally substituted 5 to 7 member monocyclic heterocyclyl; or $R^6$ and $R^7$ can be taken together along with the carbon to which $R^6$ and $R^7$ are attached to form an optionally substituted monocyclic $C_{3-4}$ cycloalkyl, an optionally substituted oxetane or an optionally substituted thietane; and $X^1$ can be O (oxygen) or $NR^{14}$, wherein $R^{14}$ can be hydrogen, an unsubstituted $C_{1-4}$ alkyl, an unsubstituted $C_{1-4}$ haloalkyl, an optionally substituted aryl or an optionally substituted aryl($C_{1-4}$ alkyl).

Some embodiments disclosed herein relate to a compound of Formula (I), or a pharmaceutically acceptable salt thereof, wherein: n can be 0 or 1; $Z^1$ can be —C(=O)—, —NH—C(=O)— or —O—C(=O)—; $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^2$ and $R^3$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^4$ and $R^5$ can be independently selected from hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl); $R^6$ and $R^7$ can be independently selected from hydrogen, an unsubstituted $C_{1-4}$ alkyl and an unsubstituted $C_{1-4}$ haloalkyl; $R^8$ can be hydrogen or an unsubstituted $C_{1-4}$ alkyl; $R^9$ can be selected from an optionally substituted $C_{1-4}$ alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl), an optionally substituted heterocyclyl ($C_{1-4}$ alkyl), —$NR^{10}R^{11}$ and —C(=O)$NR^{12}R^{13}$, wherein when the $C_{1-4}$ alkyl is substituted, the substituted $C_{1-4}$ alkyl can be substituted with one or more substituents selected from the group consisting of halogen, cyano, hydroxy, an unsubstituted $C_{1-4}$ alkoxy, amino, C-amido and N-amido; $R^{10}$ and $R^{12}$ can be independently hydrogen or an unsubstituted $C_{1-4}$ alkyl; $R^{11}$ and $R^{13}$ can be independently selected from hydrogen, an optionally substituted $C_{1-4}$ alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl), wherein when the $C_{1-4}$ alkyl is substituted, the substituted $C_{1-4}$ alkyl can be substituted with one or more substituents selected from the group consisting of halogen, cyano, hydroxy, an unsubstituted $C_{1-4}$ alkoxy, amino, C-amido and N-amido; or $R^{10}$ and $R^{11}$ can be taken together along with the nitrogen to which $R^{10}$ and $R^{11}$ are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl; $R^{12}$ and $R^{13}$ can be taken together along with the nitrogen to which $R^{12}$ and $R^{13}$ are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl; $R^2$ and $R^3$ can be taken together along with the carbon to which $R^2$ and $R^3$ are attached to form an optionally substituted monocyclic $C_{3-6}$ cycloalkyl or an optionally substituted 3 to 6 member monocyclic heterocyclyl; or $R^4$ and $R^5$ can be taken together along with the carbon to which $R^4$ and $R^5$ are attached to form an optionally substituted monocyclic $C_{3-6}$ cycloalkyl or an optionally substituted 3 to 6 member monocyclic heterocyclyl; or $R^2$ and $R^4$ can be taken together along with the carbons to which $R^2$ and $R^4$ are each attached to form an optionally monocyclic $C_{5-7}$ cycloalkyl or an optionally substituted 5 to 7 member monocyclic heterocyclyl; or $R^3$ and $R^5$ can be taken together along with the carbons to which $R^3$ and $R^5$ are each attached to form an optionally monocyclic $C_{5-7}$ cycloalkyl or an optionally substituted 5 to 7 member monocyclic heterocyclyl; or $R^6$ and $R^7$ can be taken together along with the carbon to which $R^6$ and $R^7$ are attached to form an optionally substituted monocyclic $C_{3-4}$ cycloalkyl, an optionally substituted oxetane or an optionally substituted thietane; and $X^1$ can be O (oxygen) or $NR^{14}$, wherein $R^{14}$ can be hydrogen, an unsubstituted $C_{1-4}$ alkyl, an unsubstituted $C_{1-4}$ haloalkyl, an optionally substituted aryl or an optionally substituted aryl($C_{1-4}$ alkyl).

As described herein, various moieties can be present for $Z^1$ and $R^1$. In some embodiments, n can be 0; and $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl) such that Formula (I), and pharmaceutically acceptable salts thereof can be Formula (Ia), or a pharmaceutically acceptable salt thereof. In other embodiments, n can be 1; $Z^1$ can be —C(=O)—, —NH—C(=O)— or —O—C(=O)—; and $R^1$ can be selected from an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl). As shown herein, when $Z^1$ is —C(=O)—, —NH—C(=O)— or —O—C(=O)—, Formula (I) can be Formula (Ib), (Ic) or (Id), or a pharmaceutically acceptable salt thereof, respectively. As described herein, n can be 0 and $R^1$ can be an optionally substituted heteroaryl or an optionally substituted heterocyclyl. An example of n being 0; and $R^1$ being an optionally substituted heteroaryl or an optionally substituted heterocyclyl is

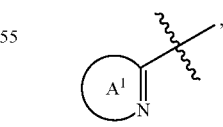

wherein Ring $A^1$ can be an optionally substituted bicyclic heteroaryl or an optionally substituted bicyclic heterocyclyl such that Formula (I), and pharmaceutically acceptable salts thereof can be Formula (Ie), or a pharmaceutically acceptable salt thereof.

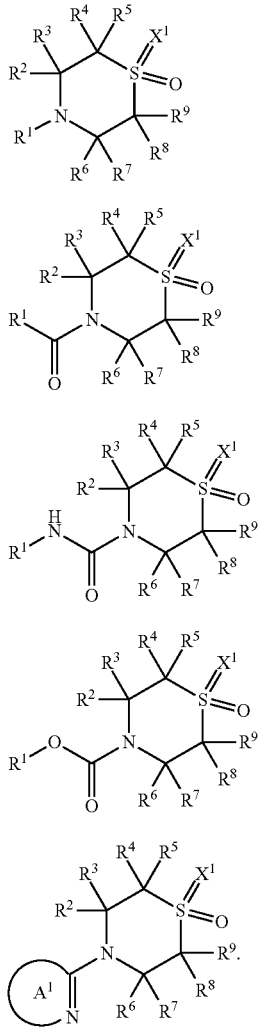

(Ia)

(Ib)

(Ic)

(Id)

(Ie)

eroaryl. In other embodiments, R$^1$ can be an unsubstituted or a substituted bicyclic heteroaryl. Exemplary bicyclic heteroaryls include, but are not limited to, an unsubstituted or a substituted 9-membered or an unsubstituted or a substituted 10-membered heteroaryl. The heteroaryl can include one or more heteroatoms, such as N (nitrogen), O (oxygen) and/or S (sulfur).

In some embodiments, R$^1$ can be an optionally substituted heterocyclyl. The heterocyclyl can be a monocyclic heterocyclyl or a bicyclic heterocyclyl. In some embodiments, R$^1$ can be an unsubstituted or a substituted monocyclic heterocyclyl, such as an unsubstituted or a substituted 5-membered or an unsubstituted or a substituted 6-membered monocyclic heterocyclyl. In other embodiments, R$^1$ can be an unsubstituted or a substituted bicyclic heterocyclyl, such as an unsubstituted or a substituted 9-membered or an unsubstituted or a substituted 10-membered heterocyclyl. The number and types of heteroatoms that can be present in a heterocyclyl for R$^1$ can vary. For example, 1, 2, 3 or more than 3 heteroatoms, such as N (nitrogen), O (oxygen) and/or S (sulfur), can be present in a heterocyclyl of R$^1$.

In some embodiments, n can be 0; and R$^1$ can be

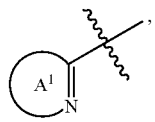

wherein Ring A$^1$ can be an optionally substituted bicyclic heteroaryl. In other embodiments, R$^1$ can be

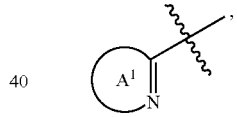

Several cyclic moieties can be present for R$^1$. In some embodiments, R$^1$ can be an optionally substituted aromatic carbocyclic moiety, for example an optionally substituted aryl. For example, R$^1$ can be an optionally substituted phenyl. In some embodiments, R$^1$ can be an unsubstituted phenyl. In other embodiments, R$^1$ can be a substituted phenyl. When R$^1$ is a substituted phenyl, the phenyl can be mono-substituted. The mono-substituted phenyl can be a para-substituted phenyl, a meta-substituted phenyl or an ortho-substituted phenyl. The substituted phenyl can be substituted by multiple moieties, such as 2, 3 or 4 or more times. In some embodiments, R$^1$ can be a di-substituted phenyl. When more than one moiety is present, the moieties can be the same or different moieties can be different. In some embodiments, R$^1$ can be an unsubstituted or substituted naphthyl.

As described herein, R$^1$ can be a monocyclic or multicyclic (for example, a bicyclic) moiety that includes one or more heteroatoms in the ring(s). In some embodiments, R$^1$ can be an optionally substituted heteroaryl. In some embodiments, R$^1$ can be an unsubstituted or a substituted monocyclic heteroaryl. For example, R$^1$ can be an unsubstituted or a substituted monocyclic 5-membered or an unsubstituted or a substituted monocyclic 6-membered monocyclic hetwherein Ring A$^1$ can be an optionally substituted bicyclic heterocyclyl. In some embodiments, Ring A$^1$ can be an optionally substituted nitrogen-containing, 9-membered bicyclic heteroaryl. In other embodiments, Ring A$^1$ can be an optionally substituted nitrogen-containing, 10-membered bicyclic heteroaryl. In still other embodiments, Ring A$^1$ can be an optionally substituted nitrogen-containing, 9-membered bicyclic heterocyclyl. In yet still other embodiments, Ring A$^1$ can be an optionally substituted nitrogen-containing, 10-membered bicyclic heterocyclyl.

In some embodiments, R$^1$ can be a nitrogen-containing, bicyclic heteroaryl or a nitrogen-containing, bicyclic heterocyclyl. In some embodiments, R$^1$ can be selected from an unsubstituted or a substituted [5,5] bicyclic heteroaryl, an unsubstituted or a substituted [5,6] bicyclic heteroaryl, an unsubstituted or a substituted [6,5] bicyclic heteroaryl, an unsubstituted or a substituted [6,6] bicyclic heteroaryl, an unsubstituted or a substituted [5,5] bicyclic heterocyclyl, an unsubstituted or a substituted [5,6] bicyclic heterocyclyl, an unsubstituted or a substituted [6,5] bicyclic heterocyclyl and an unsubstituted or a substituted [6,6] bicyclic heterocyclyl. In some embodiments, R$^1$ can have the general structure

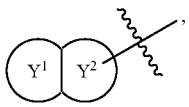

wherein Ring $Y^2$ indicates the point of attachment to the remaining portion of Formula (I); and wherein Ring $Y^1$ and Ring $Y^2$ can be independently selected from phenyl, furan, furazan, thiophene, phthalazine, pyrrole, oxazole, 1,2,3-oxadiazole, 1,2,4-oxadiazole, thiazole, 1,2,3-thiadiazole, 1,2,4-thiadiazole, imidazole, pyrazole, isoxazole, isothiazole, triazole, thiadiazole, tetrazole, pyridine, pyridazine, pyrimidine, pyrazine, 1,2,3-triazine, 1,2,4-triazine, 1,2,3,4-tetrazine, 2H-1,2-oxazine, hexahydro-1,3,5-triazine, imidazoline, imidazolidine, isoxazoline, isoxazolidine, oxazoline, oxazolidine, thiazoline, thiazolidine, morpholine, piperidine, piperazine, pyrrolidine, pyrazoline, pyrazolidine and thiamorpholine, wherein Ring $Y^1$ and Ring $Y^2$ can be each optionally substituted. In some embodiments, Ring $Y^1$ can be selected from an optionally substituted phenyl, an optionally substituted pyridine, an optionally substituted pyridazine, an optionally substituted pyrimidine, an optionally substituted pyrazine, an optionally substituted 1,2,3-triazine, an optionally substituted 1,2,4-triazine and an optionally substituted 1,2,3,4-tetrazine. In some embodiments, Ring $Y^2$ can be selected from an optionally substituted phenyl, an optionally substituted pyridine, an optionally substituted pyridazine, an optionally substituted pyrimidine, an optionally substituted pyrazine, an optionally substituted 1,2,3-triazine, an optionally substituted 1,2,4-triazine and an optionally substituted 1,2,3,4-tetrazine. In other embodiments, Ring $Y^2$ can be selected from an optionally substituted furan, an optionally substituted thiophene, an optionally substituted pyrrole, an optionally substituted oxazole, an optionally substituted thiazole, an optionally substituted imidazole, an optionally substituted pyrazole, an optionally substituted isoxazole and an optionally substituted isothiazole.

Various cyclic groups described herein for $R^1$ can be attached via a $C_{1-4}$ alkyl linker. In some embodiments, $R^1$ can be an optionally substituted aryl($C_{1-4}$ alkyl), for example, an unsubstituted or a substituted benzyl. In other embodiments, $R^1$ can be an optionally substituted heteroaryl ($C_{1-4}$ alkyl). In still other embodiments, $R^1$ can be an optionally substituted heterocyclyl($C_{1-4}$ alkyl). Examples of heteroaryls and heterocyclyls are described herein, and include those of the previous paragraph. As described herein, the linker can include 1 to 4 carbons. The aryl, heteroaryl, heterocyclyl and $C_{1-4}$ alkyl of aryl($C_{1-4}$ alkyl), heteroaryl($C_{1-4}$ alkyl) and heterocyclyl($C_{1-4}$ alkyl) can be each unsubstituted or unsubstituted. When the $C_{1-4}$ alkyl linker is substituted, one or more hydrogens can be replaced with a moiety, such as those provided in the definition of "optionally substituted," and/or two or more hydrogens can be taken together along with the carbon to which the hydrogens are attached to form an optionally substituted CM cycloalkyl or an optionally substituted 3-, 4- or 5-membered heterocyclyl. In some embodiments, the $C_{1-4}$ alkyl linker of aryl($C_{1-4}$ alkyl), heteroaryl($C_{1-4}$ alkyl) and heterocyclyl($C_{1-4}$ alkyl) can be substituted with one or more moieties selected from halogen (such as F), cyano, $C_{1-2}$ haloalkyl (for example, $CF_3$), OH, an unsubstituted $C_{1-4}$ alkoxy and an unsubstituted C-amido (such as —C(=O)$NH_2$, —C(=O)NH($C_{1-4}$ alkyl) and —C(=O)N($C_{1-4}$ alkyl)$_2$). In some embodiments, the CM alkyl linker for $R^1$ can be —$CH_2$—, —$CH_2CH_2$—, —CH($CH_3$)$CH_2$—, —$CH_2CH_2CH_2$—, —$CH_2CH_2CH_2CH_2$—,

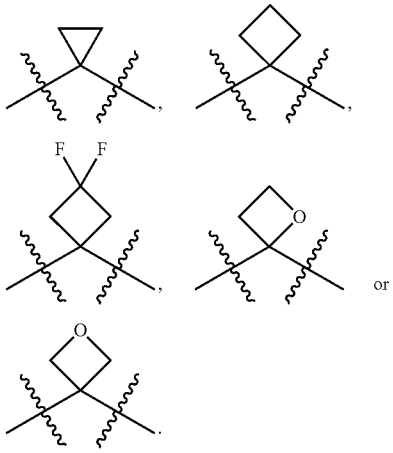

As described herein, the $R^1$ groups can be unsubstituted or substituted. When $R^1$ is substituted, a variety of substituents can be present on a $R^1$ group described herein. In some embodiments, $R^1$ can be substituted with one or more substituents selected from deuterium, halogen (such as F, Cl and/or Br), cyano, an unsubstituted $C_{1-6}$ alkyl (for example, methyl, ethyl, n-propyl, isopropyl, n-butyl, iso-butyl, sec-butyl, tert-butyl, pentyl (straight-changed or branched) and hexyl (straight-chained or branched)), an unsubstituted $C_{1-6}$ haloalkyl (such as —$CHF_2$, —$CH_2F$, —$CF_3$, —CHClF, —$CH_2Cl$, —$CHCl_2$ and —$CCl_3$), an unsubstituted $C_{1-6}$ alkoxy (for example, methoxy, ethoxy, isopropoxy, n-butoxy, sec-butoxy, isobutoxy and tert-butoxy), an unsubstituted acyl (for example, —C(=O)—$C_{1-4}$ alkyl), an unsubstituted C-amido (such as such as —C(=O)$NH_2$, —C(=O)NH($C_{1-4}$ alkyl) and —C(=O)N($C_{1-4}$ alkyl)$_2$), an unsubstituted sulfonyl (such as —S(=O)$_2NH_2$, —S(=O)$_2$NH($C_{1-4}$ alkyl) and —S(=O)$_2$N($C_{1-4}$ alkyl)$_2$), an unsubstituted amino, a mono-substituted amine (for example, an mono-alkyl substituted amine) and a di-substituted amine (such as a di-alkyl substituted amine).

Exemplary $R^1$ groups include, but are not limited to, the following:

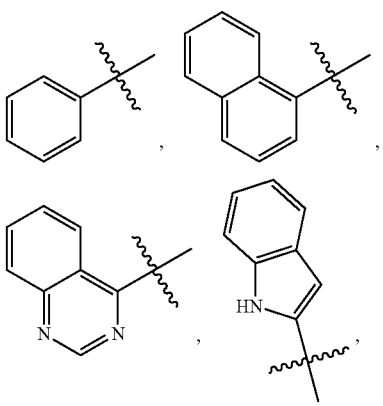

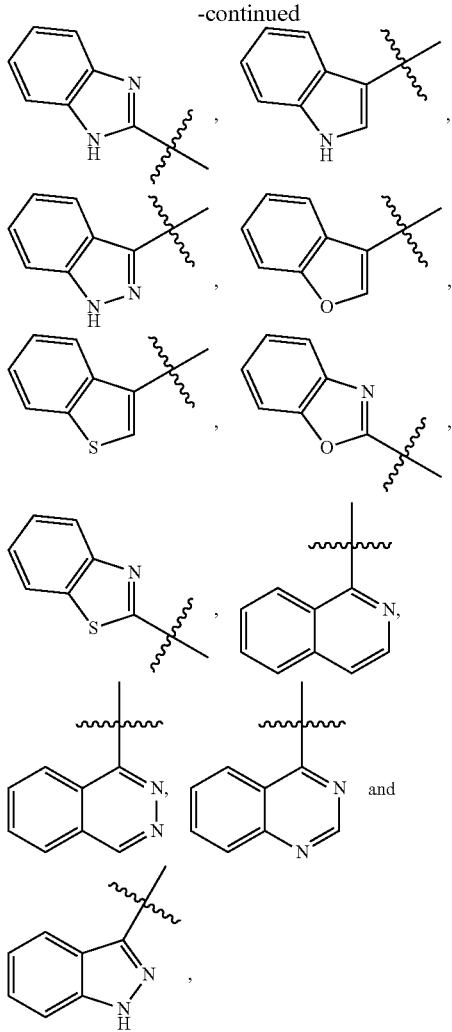
wherein each of these moieties can be unsubstituted or substituted. Examples of substituted R¹ groups include
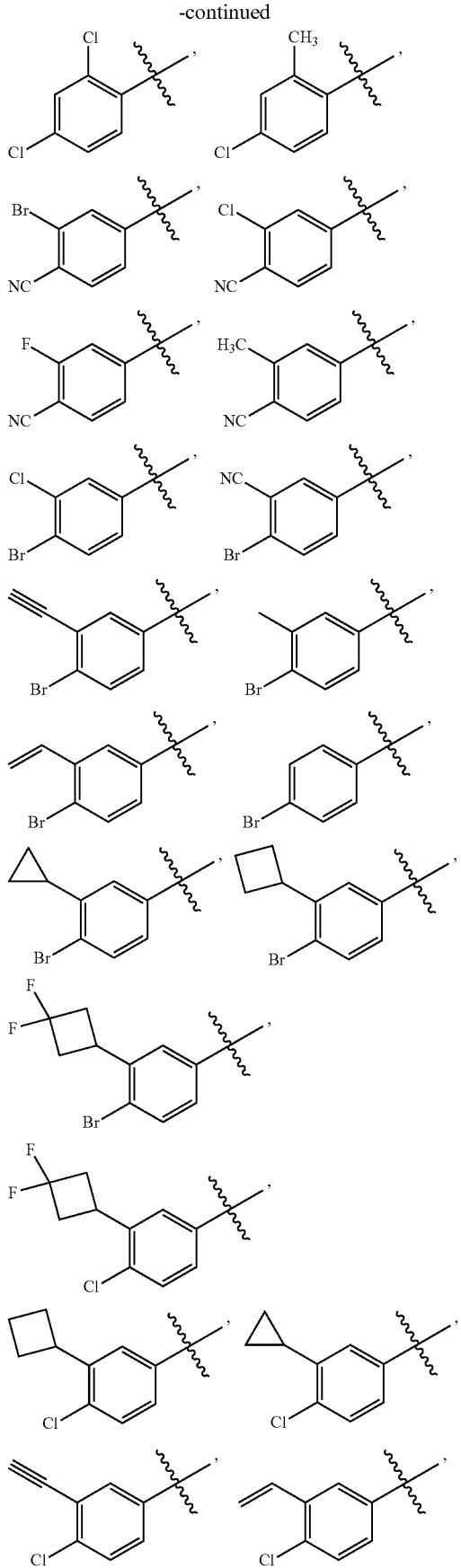

an optionally substituted heteroaryl or an optionally substituted heterocyclyl. In some embodiments, $R^2$ can be an optionally substituted aryl($C_{1-4}$ alkyl), an optionally substituted heteroaryl($C_{1-4}$ alkyl) or an optionally substituted heterocyclyl($C_{1-4}$ alkyl). Exemplary $R^2$ groups include, but are not limited to, an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl).

Hydrogen and non-hydrogen moieties as described herein can be also present for $R^3$. In some embodiments, $R^3$ can be hydrogen. In other embodiments, $R^3$ can be an unsubstituted $C_{1-4}$ alkyl, such as those described herein. In still other embodiments, $R^3$ can be an unsubstituted $C_{1-4}$ haloalkyl, for example, $-CHF_2$, $-CH_2F$, $-CF_3$, $-CH_2Cl$, $-CHCl_2$ and $-CCl_3$. In yet still other embodiments, $R^3$ can be an optionally substituted aryl, an optionally substituted heteroaryl or an optionally substituted heterocyclyl. In some embodiments, $R^3$ can be an optionally substituted aryl($C_{1-4}$ alkyl), an optionally substituted heteroaryl($C_{1-4}$ alkyl) or an optionally substituted heterocyclyl($C_{1-4}$ alkyl). In other embodiments, $R^3$ can be an optionally substituted phenyl, an optionally substituted monocyclic heteroaryl or an optionally substituted monocyclic heterocyclyl. In other embodiments, $R^2$ and $R^3$ can be taken together along with the carbon to which $R^2$ and $R^3$ are attached to form an optionally substituted monocyclic $C_{3-6}$ cycloalkyl or an optionally substituted 3 to 6 member monocyclic heterocyclyl. For example, $R^2$ and $R^3$ can be taken together along with the carbon to which $R^2$ and $R^3$ are attached to form an optionally substituted cyclopropyl, an optionally substituted cyclobutyl, an optionally substituted cyclopentyl, an optionally substituted cyclohexyl, an optionally substituted oxetane, an optionally substituted thietane, an optionally substituted thietane oxide or an optionally substituted thietane dioxide.

Each of $R^4$ and $R^5$ can be independently hydrogen or selected from the non-hydrogen moieties described herein. In some embodiments, $R^4$ can be hydrogen. In other embodiments, $R^4$ can be an unsubstituted $C_{1-4}$ alkyl, such as methyl, ethyl, n-propyl, iso-propyl, n-butyl, iso-butyl, sec-butyl and tert-butyl. In still other embodiments, $R^4$ can be an unsubstituted $C_{1-4}$ haloalkyl. Exemplary unsubstituted $C_{1-4}$ haloalkyls are described herein, and include $-CHF_2$, $-CH_2F$, $-CF_3$, $-CH_2Cl$, $-CHCl_2$ and $-CCl_3$. In yet still other embodiments, $R^4$ can be an optionally substituted aryl, an optionally substituted heteroaryl or an optionally substituted heterocyclyl. In some embodiments, $R^4$ can be an optionally substituted aryl($C_{1-4}$ alkyl), an optionally substituted heteroaryl($C_{1-4}$ alkyl) or an optionally substituted heterocyclyl ($C_{1-4}$ alkyl). For example, $R^4$ can be an optionally substituted phenyl, an optionally substituted benzyl, an optionally substituted monocyclic heteroaryl (an optionally substituted 5- or 6-membered monocyclic heteroaryl) or an optionally substituted monocyclic heterocyclyl (an optionally substituted 5- or 6-membered monocyclic heterocyclyl).

In some embodiments, $R^5$ can be hydrogen. In other embodiments, $R^5$ can be an unsubstituted $C_{1-4}$ alkyl. In still other embodiments, $R^5$ can be an unsubstituted $C_{1-4}$ haloalkyl. Exemplary unsubstituted $C_{1-4}$ alkyls and unsubstituted $C_{1-4}$ haloalkyls are described herein and include those described with respect to $R^4$. In yet still other embodiments, $R^5$ can be an optionally substituted aryl (such as an optionally phenyl), an optionally substituted heteroaryl (such as an optionally substituted monocyclic heteroaryl) or an option- In some embodiments, $X^1$ can be O (oxygen). In other embodiments, $X^1$ can be NH. In still other embodiments, $X^1$ can be $NR^{14}$, wherein $R^{14}$ can be an unsubstituted $C_{1-4}$ alkyl or an unsubstituted $C_{1-4}$ haloalkyl. Suitable unsubstituted $C_{1-4}$ alkyls and an unsubstituted $C_{1-4}$ haloalkyls are provided herein, and include, but are not limited to, methyl, ethyl, n-propyl, iso-propyl, n-butyl, iso-butyl, sec-butyl, tert-butyl, $-CHF_2$, $-CH_2F$, $-CF_3$, $-CH_2Cl$, $-CHCl_2$ and $-CCl_3$. In still other embodiments, $X^1$ can be $NR^{14}$, wherein $R^{14}$ can be an optionally substituted aryl (such as an unsubstituted or a substituted phenyl) or an optionally substituted aryl($C_{1-4}$ alkyl) (such as an unsubstituted or a substituted benzyl).

As provided herein, both hydrogen and non-hydrogen moieties can be present on the shown 6-membered ring of a compound of Formula (I), or a pharmaceutically acceptable salt thereof. In some embodiments, $R^2$ can be hydrogen. In other embodiments, $R^2$ can be an unsubstituted $C_{1-4}$ alkyl. In still other embodiments, $R^2$ can be an unsubstituted $C_{1-4}$ haloalkyl. For example, $R^2$ can be methyl, ethyl, n-propyl, iso-propyl, n-butyl, iso-butyl, sec-butyl, tert-butyl, $-CHF_2$, $-CH_2F$, $-CF_3$, $-CH_2Cl$, $-CHCl_2$ and $-CCl_3$. In yet still other embodiments, $R^2$ can be an optionally substituted aryl, ally substituted heterocyclyl (for example, an optionally substituted monocyclic heterocyclyl). The heteroaryl and heterocyclyl can include 3, 4, 5 or 6 ring(s) atoms and include 1, 2 or 3 heteroatoms such as N (nitrogen), O (oxygen) and S (sulfur). In some embodiments, $R^5$ can be an optionally substituted aryl($C_{1-4}$ alkyl), an optionally substituted heteroaryl($C_{1-4}$ alkyl) or an optionally substituted heterocyclyl($C_{1-4}$ alkyl). For example, $R^5$ can be can be an unsubstituted or a substituted benzyl, an unsubstituted or a substituted 5-membered monocyclic heteroaryl, an unsubstituted or a substituted 6-membered monocyclic heteroaryl, an unsubstituted or a substituted 5-membered monocyclic heterocyclyl or an unsubstituted or a substituted 6-membered monocyclic heterocyclyl. In some embodiments, $R^4$ and $R^5$ can be taken together along with the carbon to which $R^4$ and $R^5$ are attached to form an optionally substituted monocyclic $C_{3-6}$ cycloalkyl or an optionally substituted 3 to 6 member monocyclic heterocyclyl. Exemplary monocyclic $C_{3-6}$ cycloalkyls and 3 to 6 member monocyclic heterocyclyls include, but are limited to, the following: cyclopropyl, cyclobutyl, cyclopentyl, cyclohexyl, oxetane, thietane, thietane oxide and thietane dioxide, each of the aforementioned can be optionally substituted.

In some embodiments, $R^3$ and $R^5$ can be taken together along with the carbons to which $R^3$ and $R^5$ are each attached to form an optionally substituted monocyclic $C_{5-7}$ cycloalkyl. In other embodiments, $R^3$ and $R^5$ can be taken together along with the carbons to which $R^3$ and $R^5$ are each attached to form an optionally substituted 5 to 7 member monocyclic heterocyclyl. In some embodiments, $R^2$ and $R^4$ can be taken together along with the carbons to which $R^2$ and $R^4$ are each attached to form an optionally monocyclic $C_{5-7}$ cycloalkyl. In other embodiments, $R^2$ and $R^4$ can be taken together along with the carbons to which $R^2$ and $R^4$ are each attached to form an optionally substituted 5 to 7 member monocyclic heterocyclyl. Exemplary 5 to 7 member monocyclic heterocyclyls include, but are not limited to, tetrahydrofuran, pyrrolidine, piperidine and tetrahydro-2H-pyran.

In some embodiments, $R^6$ can be hydrogen. In other embodiments, $R^6$ can be an unsubstituted $C_{1-4}$ alkyl. In still other embodiments, $R^6$ can be an unsubstituted $C_{1-4}$ haloalkyl. Suitable unsubstituted $C_{1-4}$ alkyls and unsubstituted $C_{1-4}$ haloalkyls include methyl, ethyl, n-propyl, iso-propyl, n-butyl, iso-butyl, sec-butyl, tert-butyl, —CHF$_2$, —CH$_2$F, —CF$_3$, —CH$_2$Cl, —CHCl$_2$ and —CCl$_3$.

In some embodiments, $R^7$ can be hydrogen. In other embodiments, $R^7$ can be an unsubstituted $C_{1-4}$ alkyl, such as methyl, ethyl, n-propyl, iso-propyl, n-butyl, iso-butyl, sec-butyl or tert-butyl. In still other embodiments, $R^7$ can be an unsubstituted $C_{1-4}$ haloalkyl, for example, —CHF$_2$, —CH$_2$F, —CF$_3$, —CH$_2$Cl, —CHCl$_2$ and —CCl$_3$. In some embodiments, $R^6$ and $R^7$ are taken together along with the carbon to which $R^6$ and $R^7$ are attached to form an unsubstituted monocyclic $C_{3-4}$ cycloalkyl. In other embodiments, $R^6$ and $R^7$ are taken together along with the carbon to which $R^6$ and $R^7$ are attached to form a substituted monocyclic $C_{3-4}$ cycloalkyl. In still other embodiments, $R^6$ and $R^7$ are taken together along with the carbon to which $R^6$ and $R^7$ are attached to form an unsubstituted oxetane or an unsubstituted thietane. In yet still other embodiments, $R^6$ and $R^7$ are taken together along with the carbon to which $R^6$ and $R^7$ are attached to form a substituted oxetane or a substituted thietane.

As provided herein, $R^9$ can be selected from an optionally substituted $C_{1-4}$ alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl), an optionally substituted heterocyclyl($C_{1-4}$ alkyl), —NR$^{10}$R$^{11}$ and —C(=O)NR$^{12}$R$^{13}$, wherein when the $C_{1-4}$ alkyl is substituted, the substituted $C_{1-4}$ alkyl can be substituted with one or more substituents selected from the group consisting of halogen, cyano, hydroxy, an unsubstituted $C_{1-4}$ alkoxy, amino, C-amido and N-amido. In some embodiments, $R^9$ can be an unsubstituted $C_{1-4}$ alkyl, such as methyl, ethyl, n-propyl, isopropyl, n-butyl, isobutyl, sec-butyl and tert-butyl. In other embodiments, $R^9$ can be a substituted $C_{1-4}$ alkyl, wherein the substituted $C_{1-4}$ alkyl can be substituted with one or more substituents selected from the group consisting of halogen (such as F and $C_1$), cyano, hydroxy, an unsubstituted $C_{1-4}$ alkoxy, amino, C-amido (for example, —C(=O)NH$_2$, —C(=O)NH($C_{1-4}$ alkyl) and —C(=O)N($C_{1-4}$ alkyl)$_2$) and N-amido (for example, —NH—C(=O)($C_{1-4}$ alkyl and —N($C_{1-4}$ alkyl)-C(=O)($C_{1-4}$ alkyl).

Several cyclic moieties can be present at $R^9$. For example, in some embodiments, $R^9$ can be an optionally substituted cycloalkyl or an optionally substituted cycloalkenyl. The optionally substituted cycloalkyl and the optionally substituted cycloalkenyl can be monocyclic, such as an optionally substituted $C_{3-6}$ cycloalkyl or an optionally substituted $C_{3-6}$ cycloalkenyl. Alternatively, the optionally substituted cycloalkyl and/or the optionally substituted cycloalkenyl can be multicyclic, for example, an optionally substituted fused-bicyclic cycloalkyl, an optionally substituted fused-bicyclic cycloalkenyl, an optionally substituted spiro-bicyclic cycloalkyl and an optionally substituted spiro-bicyclic cycloalkenyl. In other embodiments, $R^9$ can be an optionally substituted aryl, an optionally substituted heteroaryl or an optionally substituted heterocyclyl. Exemplary $R^9$ aryls, heteroaryls and heterocyclyls include, but are not limited to, phenyl, 5-membered monocyclic heteroaryls, 6-membered monocyclic heteroaryls, 5-membered monocyclic heterocyclyls and 6-membered monocyclic heterocyclyls, wherein each of the aforementioned moieties can be unsubstituted or substituted. The heteroatom(s) that can be present in an optionally substituted heteroaryl and an optionally substituted heterocyclyl for $R^9$ include N (nitrogen), O (oxygen) and/or S (sulfur). In some embodiments, $R^9$ can be selected from an unsubstituted or a substituted phenyl, an unsubstituted or a substituted furan, an unsubstituted or a substituted thiophene, an unsubstituted or a substituted oxazole, an unsubstituted or a substituted thiazole, an unsubstituted or a substituted 1,3,4-oxadiazole, an unsubstituted or a substituted imidazole, an unsubstituted or a substituted isoxazole, an unsubstituted or a substituted pyrazole, an unsubstituted or a substituted triazole, an unsubstituted or a substituted pyridine, an unsubstituted or a substituted pyrazine, an unsubstituted or a substituted pyrimidine and an unsubstituted or a substituted pyridazine.

The cyclic moieties described herein for $R^9$ can be attached via a $C_{1-4}$ alkyl linker, such as those described herein. In some embodiments, $R^8$ can be an optionally substituted cycloalkyl($C_{1-4}$ alkyl). In other embodiments, $R^9$ can be an optionally substituted cycloalkenyl($C_{1-4}$ alkyl). In still other embodiments, $R^9$ can be an optionally substituted aryl($C_{1-4}$ alkyl). In yet still other embodiments, $R^9$ can be an optionally substituted heteroaryl($C_{1-4}$ alkyl). In some embodiments, $R^9$ can be an optionally substituted heterocyclyl($C_{1-4}$ alkyl). The cycloalkyls, cycloalkenyls, aryls, heteroaryls and heterocyclyls can be monocyclic or bicyclic (for example, fused bicyclic). For example, $R^9$ can be an optionally substituted monocyclic $C_{3-6}$ cycloalkyl($C_{1-4}$ alkyl), an optionally substituted monocyclic $C_{3-6}$ cycloalkenyl($C_{1-4}$ alkyl), an optionally substituted benzyl, an optionally substituted monocyclic heteroaryl($C_{1-4}$ alkyl) (such as a 5-membered monocyclic heteroaryl($C_{1-4}$ alkyl) or 6-membered monocyclic heteroaryl($C_{1-4}$ alkyl)) or an optionally substituted monocyclic heterocyclyl($C_{1-4}$ alkyl) (such as a 5-membered monocyclic heterocyclyl($C_{1-4}$ alkyl) or 6-membered monocyclic heterocyclyl($C_{1-4}$ alkyl)).

The $C_{1-4}$ alkyls of cycloalkyl($C_{1-4}$ alkyl), cycloalkenyl($C_{1-4}$ alkyl), aryl($C_{1-4}$ alkyl), heteroaryl($C_{1-4}$ alkyl) and heterocyclyl($C_{1-4}$ alkyl) can be unsubstituted or substituted. When the $C_{1-4}$ alkyl is substituted, one or more hydrogens can be replaced with a moiety, such as those provided in the definition of "optionally substituted," and/or two or more hydrogens can be taken together along with the carbon to which the hydrogens are attached to form an optionally substituted $C_{3-4}$ cycloalkyl or an optionally substituted 3-, 4- or 5-membered heterocyclyl. In some embodiments, the $C_{1-4}$ alkyl linker of cycloalkyl($C_{1-4}$ alkyl), cycloalkenyl($C_{1-4}$ alkyl), aryl($C_{1-4}$ alkyl), heteroaryl($C_{1-4}$ alkyl) and heterocyclyl($C_{1-4}$ alkyl) can be substituted with one or more moieties selected from halogen (such as F), cyano, $C_{1-2}$ haloalkyl (for example, $CF_3$), OH, an unsubstituted $C_{1-4}$ alkoxy and an unsubstituted C-amido (such as —C(=O)NH$_2$, —C(=O)NH($C_{1-4}$ alkyl) and —C(=O)N($C_{1-4}$ alkyl)$_2$). Exemplary linkers that can attached the cyclic moieties for $R^8$ include, but are not limited to, —CH$_2$—, —CH$_2$CH$_2$—, —CH(CH$_3$)CH$_2$—, —CH$_2$CH$_2$CH$_2$—, —CH$_2$CH$_2$CH$_2$CH$_2$—,

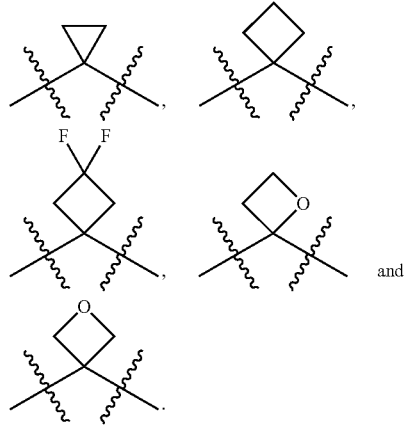

In some embodiments, $R^9$ can be —NR$^{10}$R$^{11}$. In other embodiments, $R^9$ can be —C(=O)NR$^{12}$R$^{13}$. In some embodiments, $R^{10}$ can be hydrogen. In other embodiments, $R^{10}$ can be unsubstituted $C_{1-4}$ alkyl. For example, $R^{10}$ can be methyl, ethyl, n-propyl, iso-propyl, n-butyl, iso-butyl, sec-butyl or tert-butyl.

In some embodiments, $R^{11}$ can be hydrogen. In other embodiments, $R^{11}$ can be an unsubstituted $C_{1-4}$ alkyl. In still other embodiments, $R^{11}$ can be a substituted $C_{1-4}$ alkyl, wherein the substituted $C_{1-4}$ alkyl can be substituted with one or more substituents selected from the group consisting of halogen (such as F and $C_1$), cyano, hydroxy, an unsubstituted $C_{1-4}$ alkoxy, amino, C-amido (for example, —C(=O)NH$_2$, —C(=O)NH($C_{1-4}$ alkyl) and —C(=O)N($C_{1-4}$ alkyl)$_2$) and N-amido (for example, —NH—C(=O)($C_{1-4}$ alkyl and —N($C_{1-4}$ alkyl)-C(=O)($C_{1-4}$ alkyl).

As described herein, $R^{11}$ can be various carbocyclic, heteroaryl or heterocyclic groups. In some embodiments, $R^{11}$ can be an optionally substituted cycloalkyl, for example, an optionally substituted $C_{3-8}$ cycloalkyl. In other embodiments, $R^{11}$ can be an optionally substituted cycloalkenyl, such as an optionally substituted $C_{3-8}$ cycloalkenyl. In some embodiments, $R^{11}$ can be an optionally substituted aryl. For example, $R^{11}$ can be an unsubstituted or substituted phenyl. In still other embodiments, $R^{11}$ can be an optionally substituted heteroaryl. The heteroaryl for $R^{11}$ can be an optionally substituted monocyclic heteroaryl (such as an optionally substituted 5- or 6-membered monocyclic heteroaryl) or an optionally substituted bicyclic heteroaryl (for example, an optionally substituted 9- or 10-membered bicyclic heteroaryl). In some embodiments, $R^{11}$ can be an optionally substituted heterocyclyl.

A variety cyclic groups can be attached via a $C_{1-4}$ alkyl linker for $R^{11}$. Examples of $C_{1-4}$ alkyl linkers are described herein and include —CH$_2$—, —CH$_2$CH$_2$—, —CH(CH$_3$)CH$_2$—, —CH$_2$CH$_2$CH$_2$—, —CH$_2$CH$_2$CH$_2$CH$_2$—,

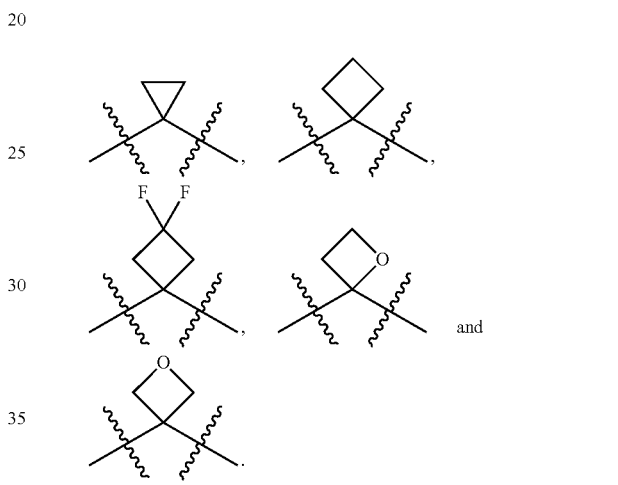

As shown and described herein, the $C_{1-4}$ alkyl linkers for R can be unsubstituted or substituted. When the $C_{1-4}$ alkyls for $R^{11}$ are substituted, one or more hydrogens can be replaced with a moiety, such as those provided in the definition of "optionally substituted," and/or two or more hydrogens can be taken together along with the carbon to which the hydrogens are attached to form an optionally substituted $C_{3-4}$ cycloalkyl or an optionally substituted 3-, 4- or 5-membered heterocyclyl. In some embodiments, the $C_{1-4}$ alkyl linker for the $R^{11}$ groups can be substituted with one or more moieties selected from halogen (such as F), cyano, $C_{1-2}$ haloalkyl (for example, $CF_3$), OH, an unsubstituted $C_{1-4}$ alkoxy and an unsubstituted C-amido (such as —C(=O)NH$_2$, —C(=O)NH($C_{1-4}$ alkyl) and —C(=O)N($C_{1-4}$ alkyl)$_2$). In some embodiments, $R^{11}$ can be an optionally substituted cycloalkyl($C_{1-4}$ alkyl), such as an optionally substituted monocyclic $C_{3-8}$ cycloalkyl($C_{1-4}$ alkyl). In other embodiments, $R^{11}$ can be an optionally substituted cycloalkenyl($C_{1-4}$ alkyl), such as an optionally substituted monocyclic $C_{3-8}$ cycloalkenyl($C_{1-4}$ alkyl). In still other embodiments, $R^{11}$ can be an optionally substituted aryl($C_{1-4}$ alkyl). As an example, $R^{11}$ can be an optionally substituted benzyl. In yet still other embodiments, $R^{11}$ can be an optionally substituted heteroaryl($C_{1-4}$ alkyl). In some embodiments, $R^{11}$ can be an optionally substituted heterocyclyl($C_{1-4}$ alkyl). The heteroaryl of the optionally substituted heteroaryl($C_{1-4}$ alkyl) can be an optionally substituted monocyclic heteroaryl (such as a 5- or 6-membered monocyclic heteroaryl)

or an optionally substituted bicyclic heteroaryl (such as a 9- or 10-membered bicyclic heteroaryl).

In some embodiments, $R^{10}$ and $R^{11}$ can be taken together along with the nitrogen to which $R^{10}$ and $R^{11}$ are attached to form an optionally substituted 4 to 8 member monocyclic heterocyclyl. In other embodiments, $R^{10}$ and $R^{11}$ can be taken together along with the nitrogen to which $R^{10}$ and $R^{11}$ are attached to form an optionally substituted 8 to 13 membered fused-bicyclic heterocyclyl. In still other embodiments, $R^{10}$ and $R^{11}$ can be taken together along with the nitrogen to which $R^{10}$ and $R^{11}$ are attached to form an optionally substituted 7 to 13 membered spiro-bicyclic heterocyclyl. The 4 to 8 member monocyclic heterocyclyl, 8 to 13 membered fused-bicyclic heterocyclyl and/or 7 to 13 membered spiro-bicyclic heterocyclyl can include one or more ring nitrogens.

In some embodiments, $R^{10}$ can be hydrogen; and $R^{11}$ can be a non-hydrogen moiety described herein. For example, $R^8$ can be —NH(an unsubstituted $C_{1-4}$ alkyl) or —NH(an optionally substituted phenyl).

In some embodiments, $R^{12}$ can be hydrogen. In other embodiments, $R^{12}$ can be unsubstituted $C_{1-4}$ alkyl. Examples of unsubstituted $C_{1-4}$ alkyls are described herein and include methyl, ethyl, n-propyl, iso-propyl, n-butyl, iso-butyl, sec-butyl and tert-butyl.

As described herein, $R^{13}$ can be cyclic and non-cyclic moieties. In some embodiments, $R^{13}$ can be hydrogen. In other embodiments, $R^{13}$ can be an unsubstituted $C_{1-4}$ alkyl. In still other embodiments, $R^{13}$ can be a substituted CM alkyl, wherein the substituted CM alkyl can be substituted with one or more substituents selected from the group consisting of halogen (such as F and $C_1$), cyano, hydroxy, an unsubstituted CM alkoxy, amino, C-amido (for example, —C(=O)NH$_2$, —C(=O)NH($C_{1-4}$ alkyl) and —C(=O)N($C_{1-4}$ alkyl)$_2$) and N-amido (for example, —NH—C(=O) ($C_{1-4}$ alkyl and —N($C_{1-4}$ alkyl)-C(=O)($C_{1-4}$ alkyl).

Various carbocyclic, heteroaryl or heterocyclic groups are suitable for $R^{13}$. In some embodiments, $R^{13}$ can be an optionally substituted cycloalkyl, for example, an optionally substituted $C_{3-8}$ cycloalkyl. In other embodiments, $R^{13}$ can be an optionally substituted cycloalkenyl, such as an optionally substituted $C_{3-8}$ cycloalkenyl. In some embodiments, $R^{13}$ can be an optionally substituted aryl. For example, $R^{13}$ can be an unsubstituted or a substituted phenyl. In still other embodiments, $R^{13}$ can be an optionally substituted heteroaryl. The heteroaryl for $R^{13}$ can be an optionally substituted monocyclic heteroaryl (such as an optionally substituted 5- or 6-membered monocyclic heteroaryl) or an optionally substituted bicyclic heteroaryl (for example, an optionally substituted 9- or 10-membered bicyclic heteroaryl). In some embodiments, $R^{13}$ can be an optionally substituted heterocyclyl.

As described herein, $R^{13}$ can be an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) or an optionally substituted heterocyclyl($C_{1-4}$ alkyl). In some embodiments, $R^{13}$ can be an optionally substituted cycloalkyl($C_{1-4}$ alkyl), such as an optionally substituted monocyclic $C_{3-8}$ cycloalkyl($C_{1-4}$ alkyl). In other embodiments, $R^{13}$ can be an optionally substituted cycloalkenyl($C_{1-4}$ alkyl), such as an optionally substituted monocyclic $C_{3-8}$ cycloalkenyl($C_{1-4}$ alkyl). In still other embodiments, $R^{13}$ can be an optionally substituted aryl($C_{1-4}$ alkyl). As an example, $R^{13}$ can be an optionally substituted benzyl. In yet still other embodiments, $R^{13}$ can be an optionally substituted heteroaryl($C_{1-4}$ alkyl). In some embodiments, $R^{13}$ can be an optionally substituted heterocyclyl($C_{1-4}$ alkyl). The heteroaryl of the optionally substituted heteroaryl($C_{1-4}$ alkyl) can be an optionally substituted monocyclic heteroaryl (such as a 5- or 6-membered monocyclic heteroaryl) or an optionally substituted bicyclic heteroaryl (such as a 9- or 10-membered bicyclic heteroaryl).

Various $C_{1-4}$ alkyls are described herein for an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and/or an optionally substituted heterocyclyl($C_{1-4}$ alkyl) of $R^{13}$ are described herein. For example, the $C_{1-4}$ alkyl of an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl ($C_{1-4}$ alkyl) and/or an optionally substituted heterocyclyl ($C_{1-4}$ alkyl) can be selected from —CH$_2$—, —CH$_2$CH$_2$—, —CH(CH$_3$)CH$_2$—, —CH$_2$CH$_2$CH$_2$—, —CH$_2$CH$_2$CH$_2$CH$_2$—,

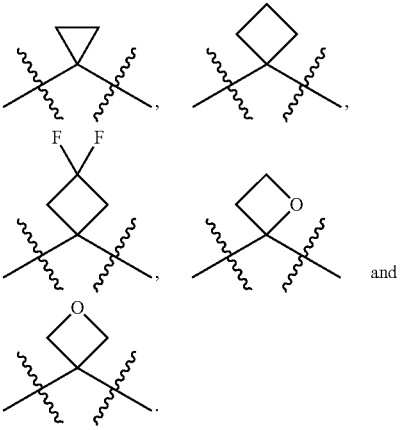

As shown and described herein, the $C_{1-4}$ alkyl linkers for $R^{13}$ can be unsubstituted or substituted. When the $C_{1-4}$ alkyls for $R^{13}$ are substituted, one or more hydrogens can be replaced with a moiety, such as those provided in the definition of "optionally substituted," and/or two or more hydrogens can be taken together along with the carbon to which the hydrogens are attached to form an optionally substituted $C_{3-4}$ cycloalkyl or an optionally substituted 3-, 4- or 5-membered heterocyclyl. In some embodiments, the $C_{1-4}$ alkyl linker for the $R^{13}$ groups can be substituted with one or more moieties selected from halogen (such as F), cyano, $C_{1-2}$ haloalkyl (for example, CF$_3$), OH, an unsubstituted $C_{1-4}$ alkoxy and an unsubstituted C-amido (such as —C(=O) NH$_2$, —C(=O)NH($C_{1-4}$ alkyl) and —C(=O) N($C_{1-4}$ alkyl)$_2$).

In some embodiments, $R^{12}$ and $R^{13}$ can be taken together along with the nitrogen to which $R^{12}$ and $R^{13}$ are attached to form an optionally substituted 4 to 8 member monocyclic heterocyclyl. In other embodiments, $R^{12}$ and $R^{13}$ can be taken together along with the nitrogen to which $R^{10}$ and $R^{11}$ are attached to form an optionally substituted 8 to 13 membered fused-bicyclic heterocyclyl. In still other embodiments, $R^{12}$ and $R^{13}$ can be taken together along with the nitrogen to which $R^{10}$ and $R^{11}$ are attached to form an optionally substituted 7 to 13 membered spiro-bicyclic heterocyclyl. The 4 to 8 member monocyclic heterocyclyl, 8 to 13 membered fused-bicyclic heterocyclyl and/or 7 to 13 membered spiro-bicyclic heterocyclyl can include one or more ring nitrogens.

In some embodiments, $R^{12}$ can be hydrogen; and $R^{13}$ can be a non-hydrogen moiety described herein. Examples of when $R^{12}$ is hydrogen and $R^{13}$ is a non-hydrogen moiety include, but are not limited to, the following: —NH(C=O) (an unsubstituted $C_{1-4}$ alkyl), —NH(C=O)(a substituted $C_{1-4}$ alkyl as describe herein), —NH(C=O)(an optionally substituted phenyl), —NH(C=O)(an optionally substituted benzyl) and —NH(C=O)—(CH$_2$)$_2$-(an optionally substituted phenyl).

Exemplary $R^9$ groups include, but are not limited to, the following:

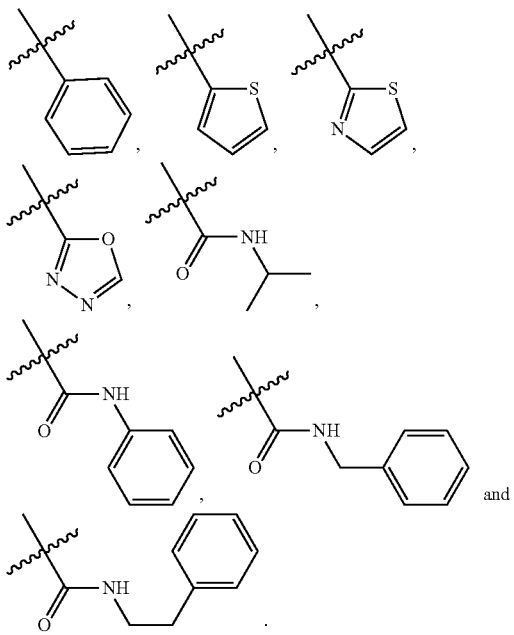

The $R^9$ substituent including those of the previous paragraph can be substituted one or more times with a moiety selected from with halogen (such as F, Cl and Br), an unsubstituted $C_{1-4}$ alkyl (for example, methyl, ethyl, n-propyl, isopropyl, n-butyl, isobutyl, sec-butyl and tert-butyl), an unsubstituted or a substituted aryl (for example, an unsubstituted or a substituted phenyl or an unsubstituted or a substituted naphthyl), an unsubstituted or a substituted heteroaryl, an unsubstituted or a substituted aryl($C_{1-4}$ alkyl) (such as an unsubstituted or a substituted benzyl), an unsubstituted or a substituted heteroaryl($C_{1-4}$ alkyl), an amino, a mono-substituted amine and a di-substituted amine. As described herein, a $R^9$ substituent can be substituted with a mono-substituted amine and/or a di-substituted amine. In some embodiments, the mono-substituted amine that can be present on a $R^9$ substituent can have the formula —NHR$^{A1}$, wherein $R^{A1}$ can be an unsubstituted or a substituted aryl or an unsubstituted or a substituted heteroaryl. In some embodiments, the di-substituted amine that can be present on a $R^9$ substituent can have the formula —NR$^{A1}$R$^{B1}$, wherein $R^{A1}$ and $R^{B1}$ can be independently an unsubstituted $C_{1-4}$ alkyl, an unsubstituted or a substituted aryl or an unsubstituted or a substituted heteroaryl. In some embodiments, $R^9$ can be a substituted heteroaryl, such as those of the previous paragraph, wherein the heteroaryl is substituted by $R^{C1}$, wherein $R^{C1}$ can be selected from an unsubstituted $C_{1-4}$ alkyl, an unsubstituted or a substituted aryl, an unsubstituted or a substituted heteroaryl, an unsubstituted or a substituted aryl($C_{1-4}$ alkyl), an unsubstituted or a substituted heteroaryl ($C_{1-4}$ alkyl), an amino, a mono-substituted amine and a di-substituted amine.

The group(s) that are present on a $R^9$ substituent, such as $R^{C1}$, can be further substituted. When a group present on a $R^9$ substituent is further substituted, one or more of the following groups can be present: halogen (for example, F, Cl and Br), an unsubstituted $C_{1-4}$ alkyl (such as methyl, ethyl, n-propyl, isopropyl, n-butyl, isobutyl, sec-butyl and tert-butyl), an unsubstituted $C_{1-4}$ alkoxy (such as methoxy, ethoxy, n-propoxy, isopropoxy, n-butoxy, isobutoxy, sec-butoxy and tert-butoxy) and an substituted or a substituted heteroaryl. The heteroaryl that are present on a $R^9$ substituent, such as $R^{C1}$, can be 5- to 6-membered monocyclic heteroaryl or 9- to 10-membered bicyclic heteroaryl, wherein the mono- and/or bicyclic heteroaryl can include 1, 2, or 3 heteroatoms selected from O, S and N. A non-limiting list of suitable heteroaryls that are present on a $R^9$ substituent, such as $R^{C1}$, include furan, thiophene, pyrazole, imidazole, oxazole, thiazole, pyridazine, pyrimidine, pyrazine, quinolone, quinazoline and quinoxaline. The substituted heteroaryl of this paragraph can be substituted one or more times, for example, substituted one or more times with a halogen, an unsubstituted $C_{1-4}$ alkyl and/or an unsubstituted $C_{1-4}$ alkoxy.

In some embodiments, $R^9$ that is further substituted can be selected from

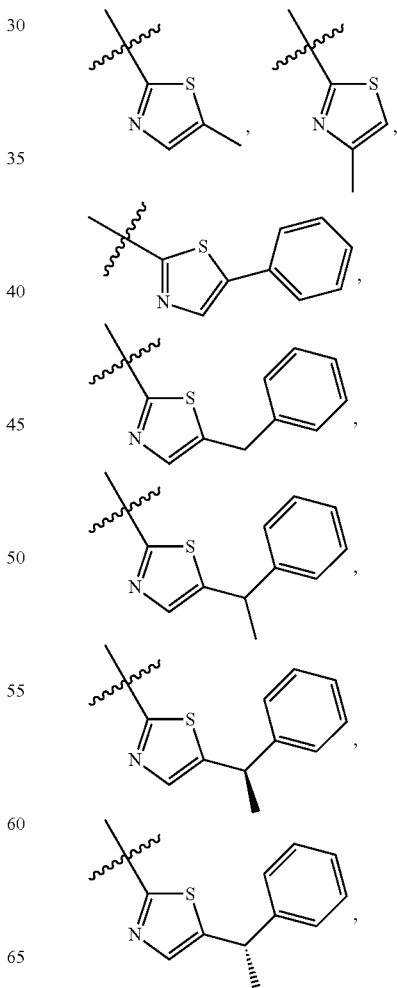

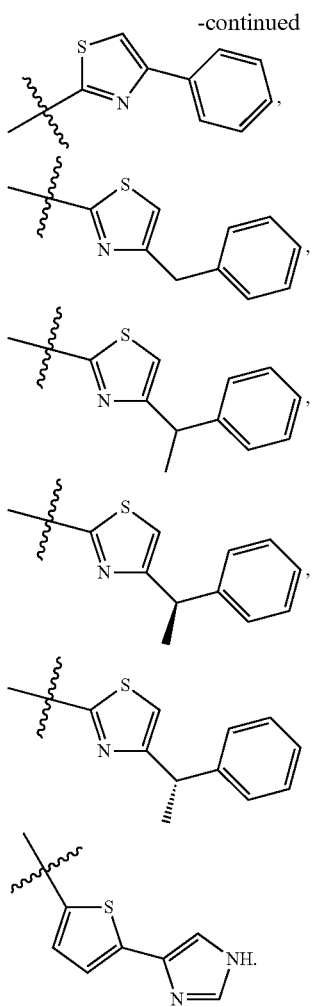

As provided herein, each of the substituents of this paragraph can be further substituted, including the hydrogen of NH group, with one or more of the following groups selected from halogen (for example, F, Cl and Br), an unsubstituted $C_{1-4}$ alkyl (such as methyl, ethyl, n-propyl, isopropyl, n-butyl, isobutyl, sec-butyl and tert-butyl), an unsubstituted $C_{1-4}$ alkoxy (such as methoxy, ethoxy, n-propoxy, isopropoxy, n-butoxy, isobutoxy, sec-butoxy and tert-butoxy) and an substituted or a substituted heteroaryl.

In some embodiments, $R^8$ can be hydrogen. In other embodiments, $R^8$ can be an unsubstituted $C_{1-4}$ alkyl, such as those described herein. For example, $R^8$ can be methyl, ethyl, n-propyl, iso-propyl, n-butyl, iso-butyl, sec-butyl and tert-butyl. In still other embodiments, $R^8$ can be halogen. For example, $R^8$ can be fluoro, chloro or bromo.

In some embodiments, $R^2$, $R^3$, $R^4$, $R^5$, $R^6$, $R^7$ and $R^8$ can be each hydrogen. In other embodiments, at least one of $R^2$, $R^3$, $R^4$, $R^5$, $R^6$, $R^7$ and $R^8$ can be a non-hydrogen group, such as those described herein in the previous paragraphs. In still other embodiments, $R^2$, $R^4$, $R^5$, $R^6$, $R^7$ and $R^8$ can be each hydrogen, and $R^3$ can be an unsubstituted $C_{1-4}$ alkyl, for example, methyl. In yet still other embodiments, $R^2$, $R^3$, $R^4$, $R^5$ and $R^8$ can be each hydrogen, and $R^6$ and $R^7$ are taken together along with the carbon to which $R^6$ and $R^7$ are attached to form an optionally substituted monocyclic $C_{3-4}$ cycloalkyl. In some embodiments, $R^2$, $R^3$, $R^4$, $R^5$ and $R^8$ can be each hydrogen, and $R^6$ and $R^7$ are taken together along with the carbon to which $R^6$ and $R^7$ are attached to form an unsubstituted or a substituted oxetane or an unsubstituted or a substituted thietane. In some embodiments, $R^2$, $R^3$, $R^4$, $R^5$, $R^6$ and $R^7$ can each be hydrogen; and $R^8$ can be a non-hydrogen group, such as halogen (for example, F) or an unsubstituted $C_{1-4}$ alkyl (for example, methyl) In other embodiments, $R^2$, $R^4$, $R^5$, $R^6$ and $R^7$ can be each hydrogen; $R^3$ can be an unsubstituted $C_{1-4}$ alkyl, for example, methyl; and $R^8$ can be halogen or an unsubstituted $C_{1-4}$ alkyl (for example, $R^8$ can be fluoro or methyl). In any of the embodiments described herein, $R^9$ can be an unsubstituted or a substituted heteroaryl, including those described herein.

Examples of compounds of Formula (I), including pharmaceutically acceptable salts thereof, include the following:

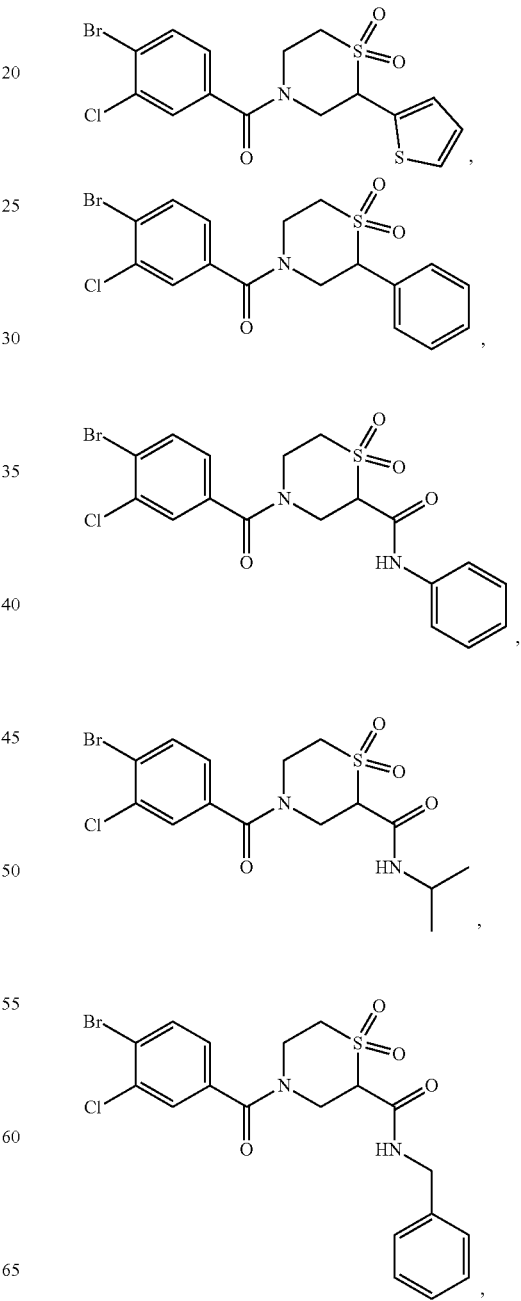

31
-continued
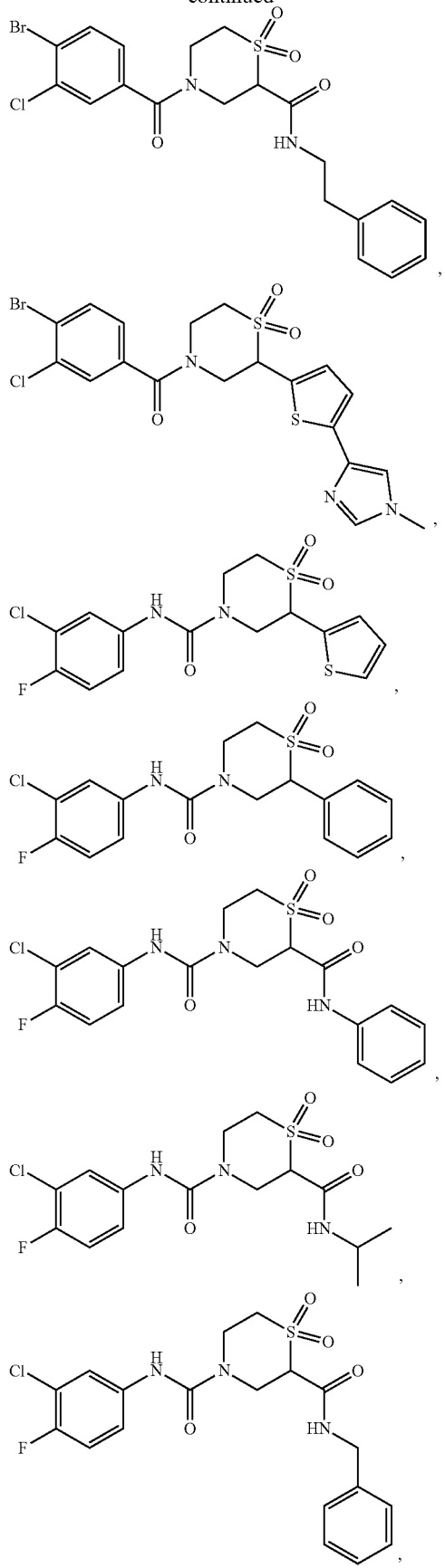
32
-continued
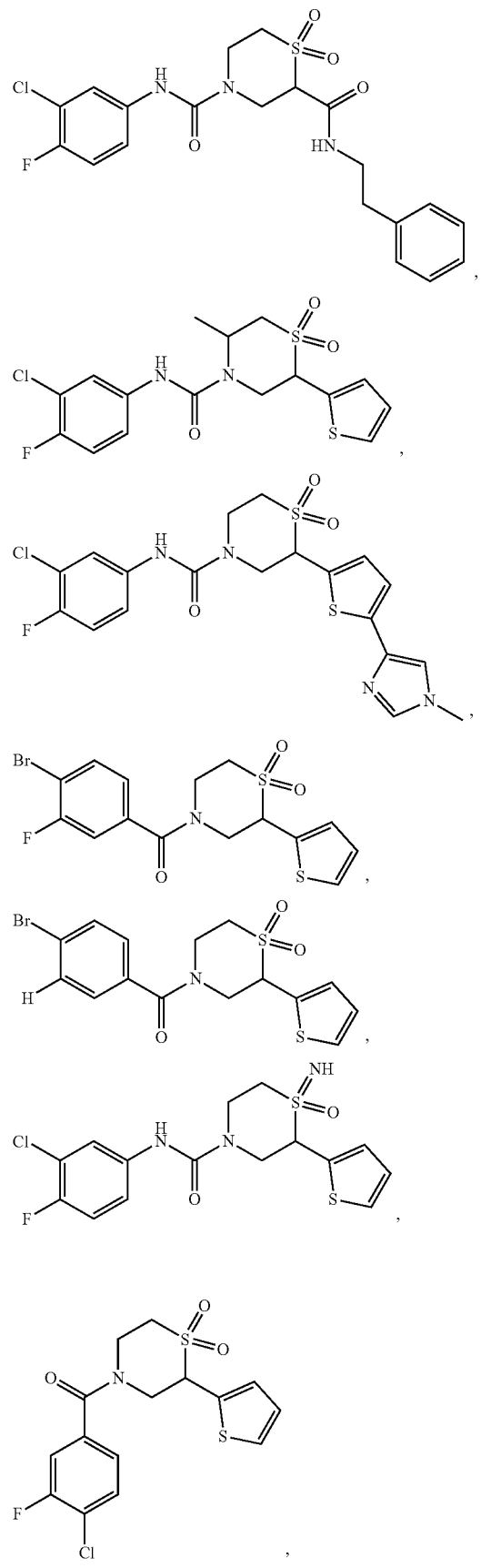

33
-continued
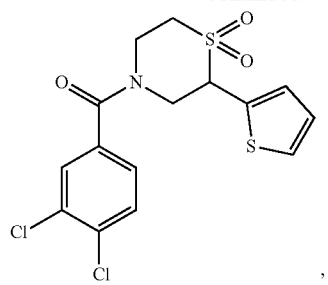
,
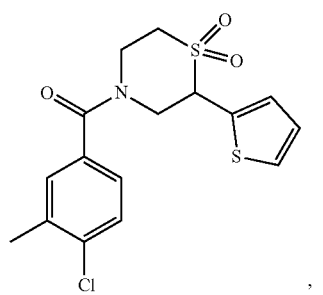
,
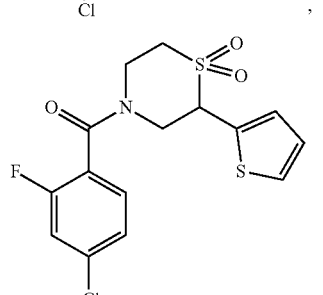
,
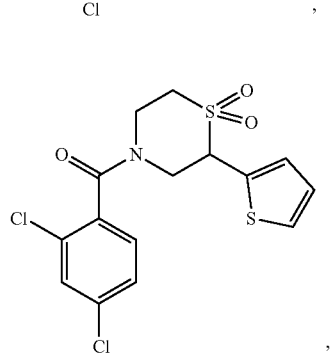
,
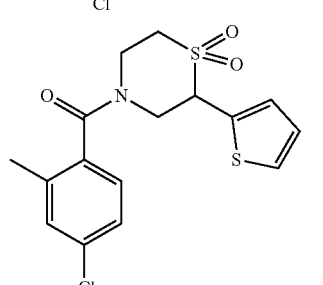
,
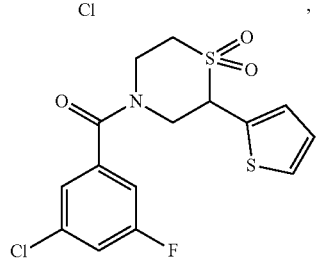
,
34
-continued
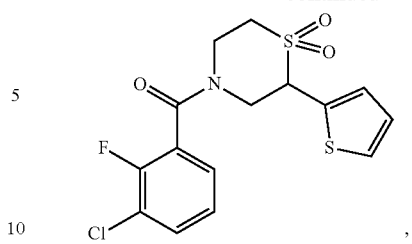
,
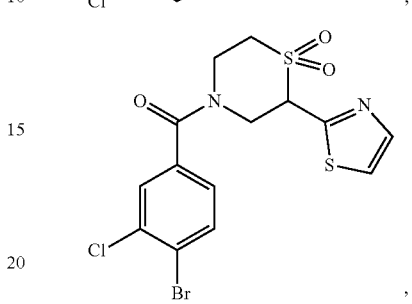
,
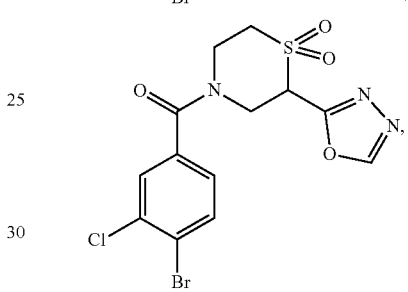
,
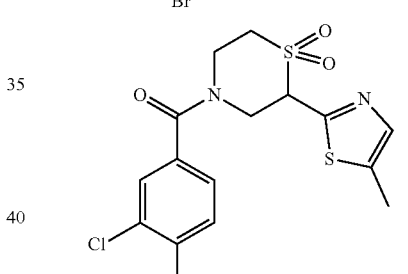
,
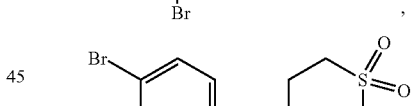
,
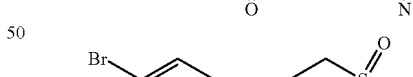
,
,

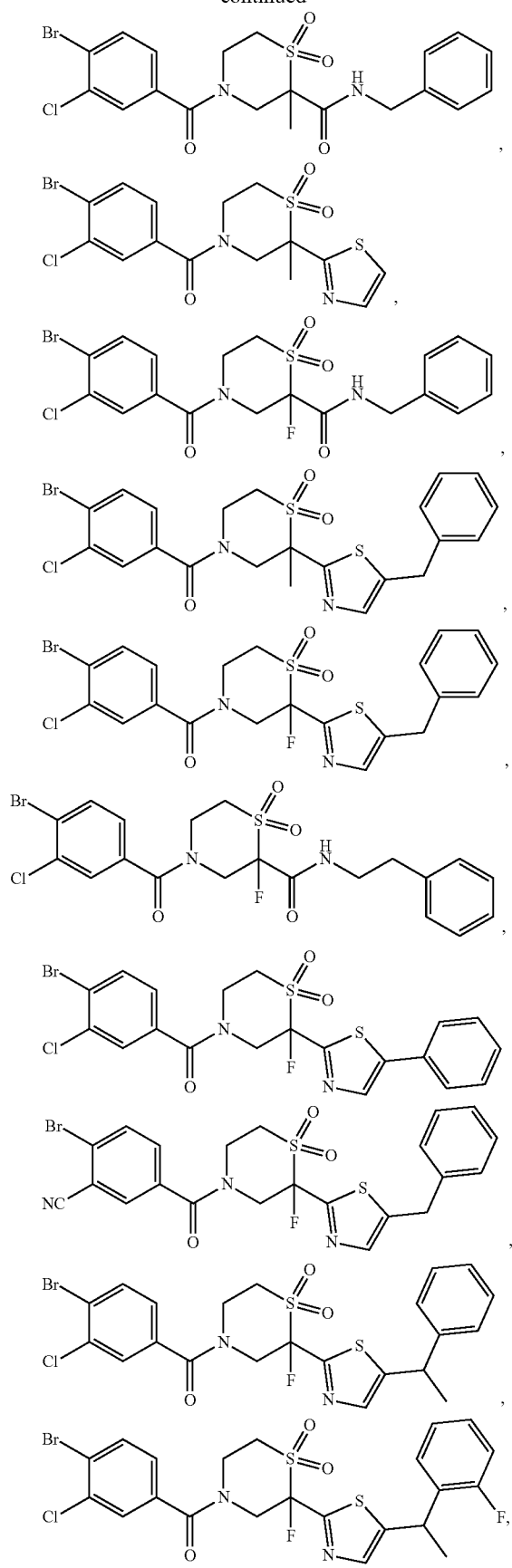
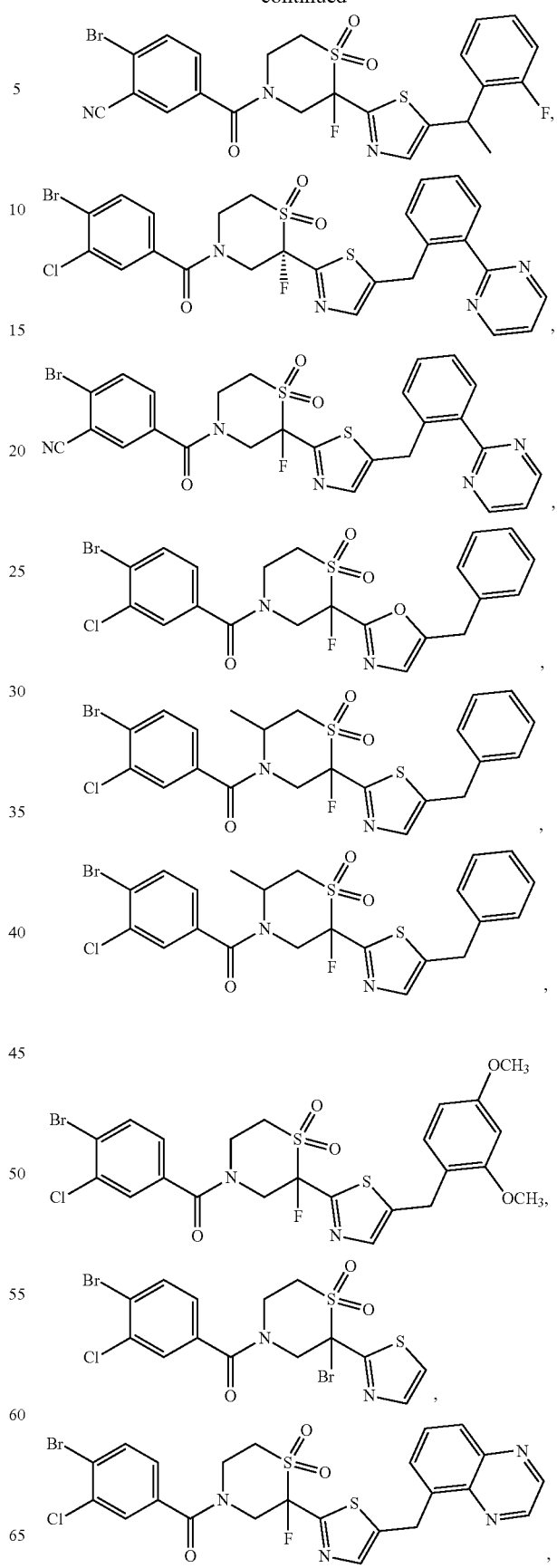

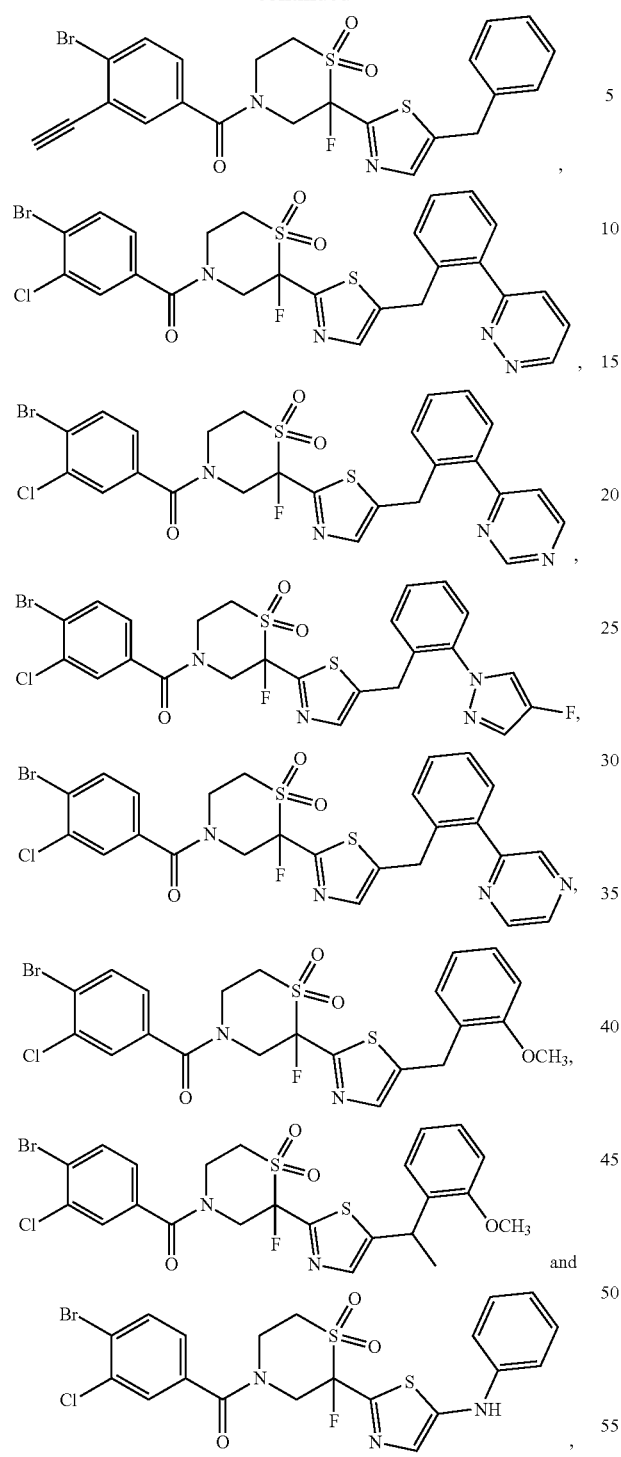
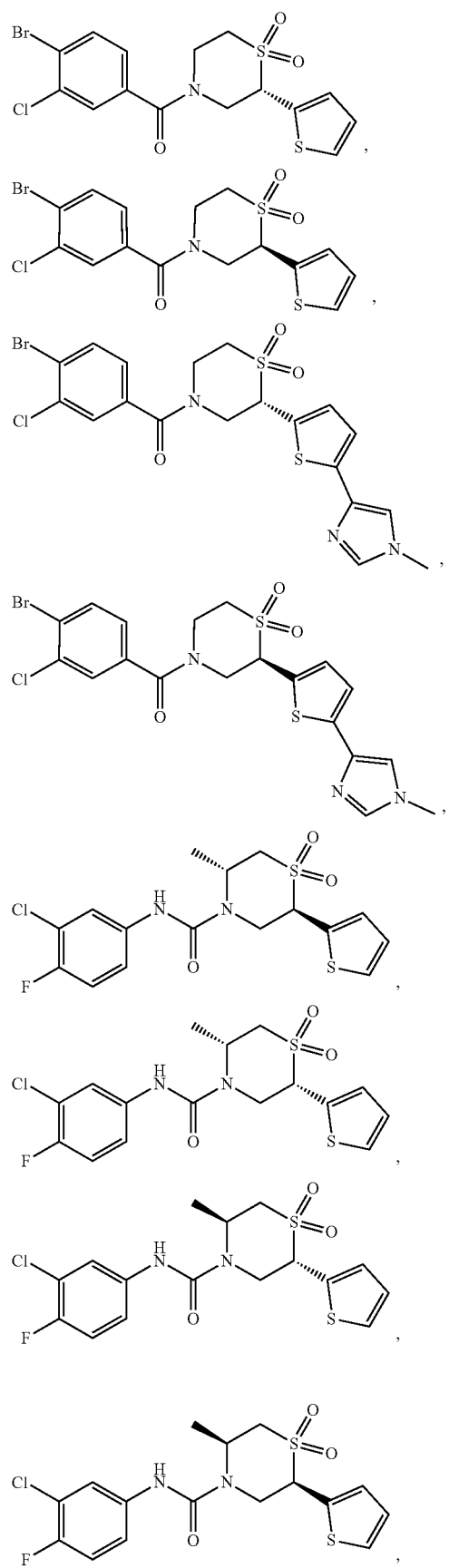
or a pharmaceutically acceptable salt of any of the foregoing.
Additional examples of compounds of Formula (I), including pharmaceutically acceptable salts thereof, include the following:

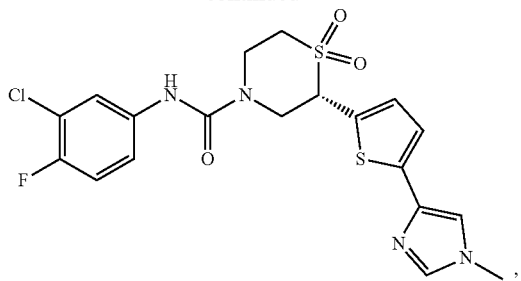
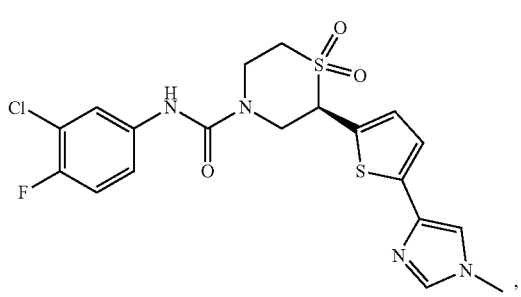
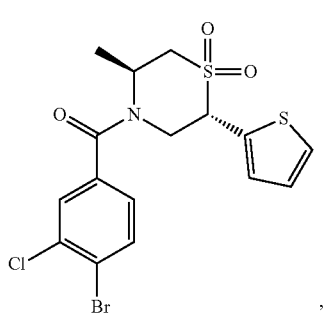
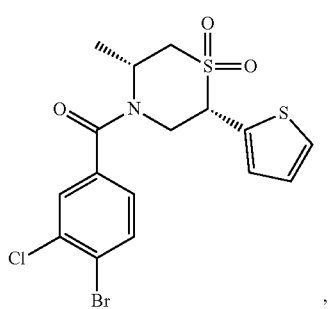
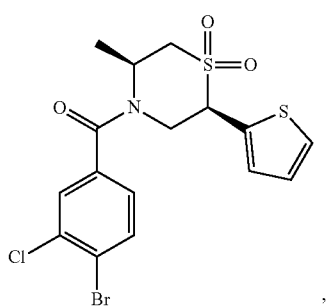
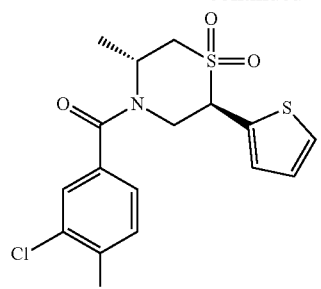
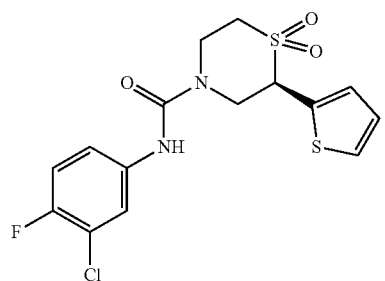
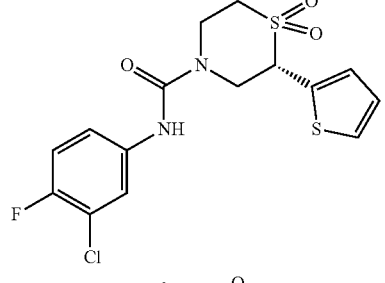
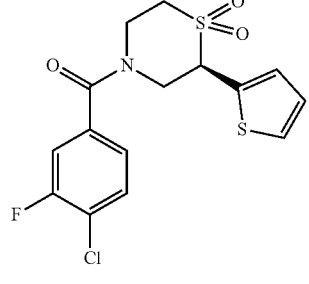
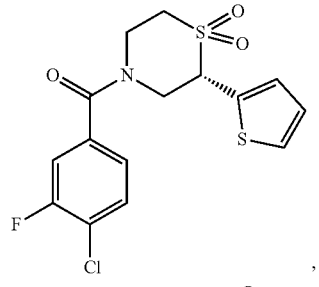
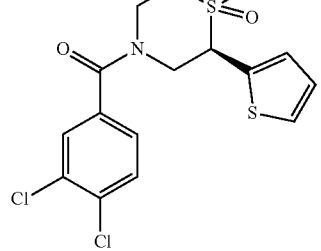

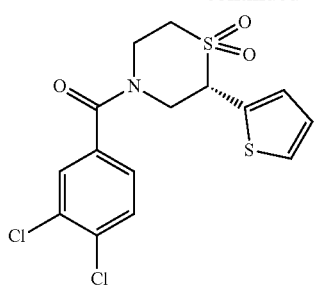,
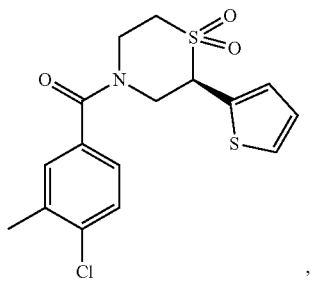,
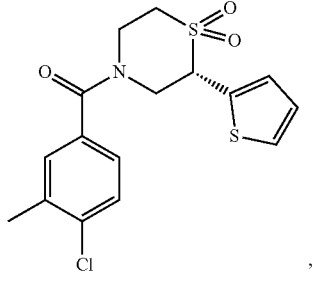,
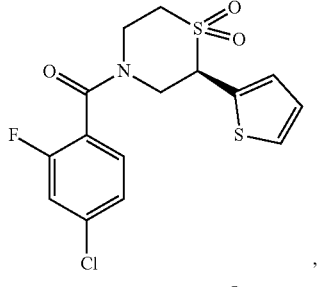,
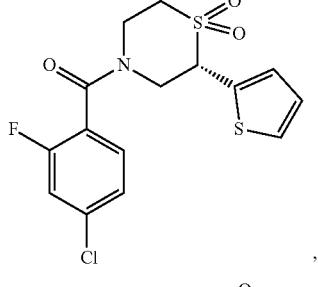,
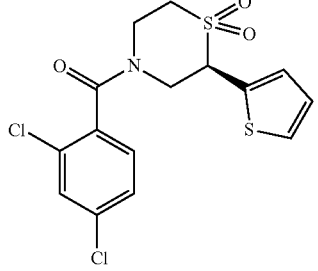,
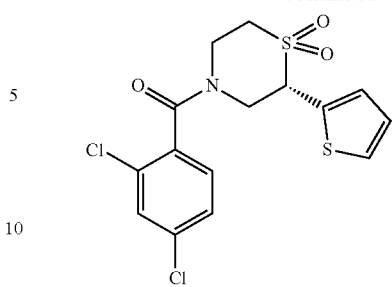,
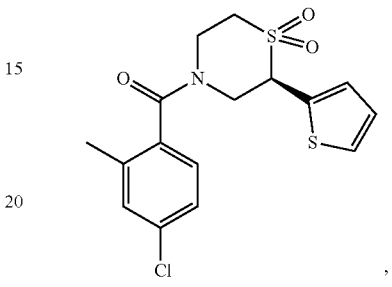,
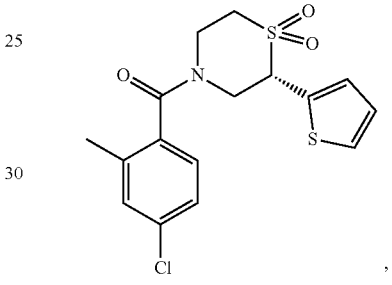,
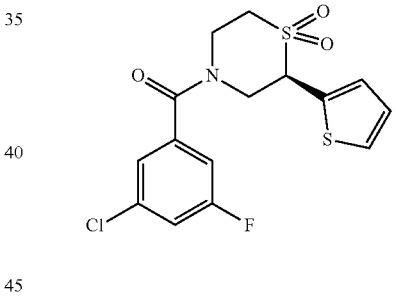,
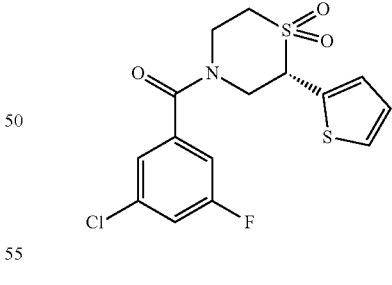,
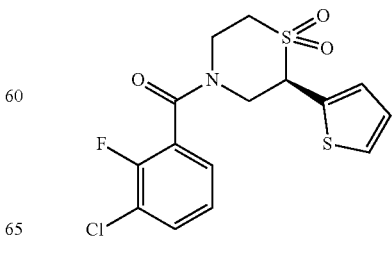, -continued
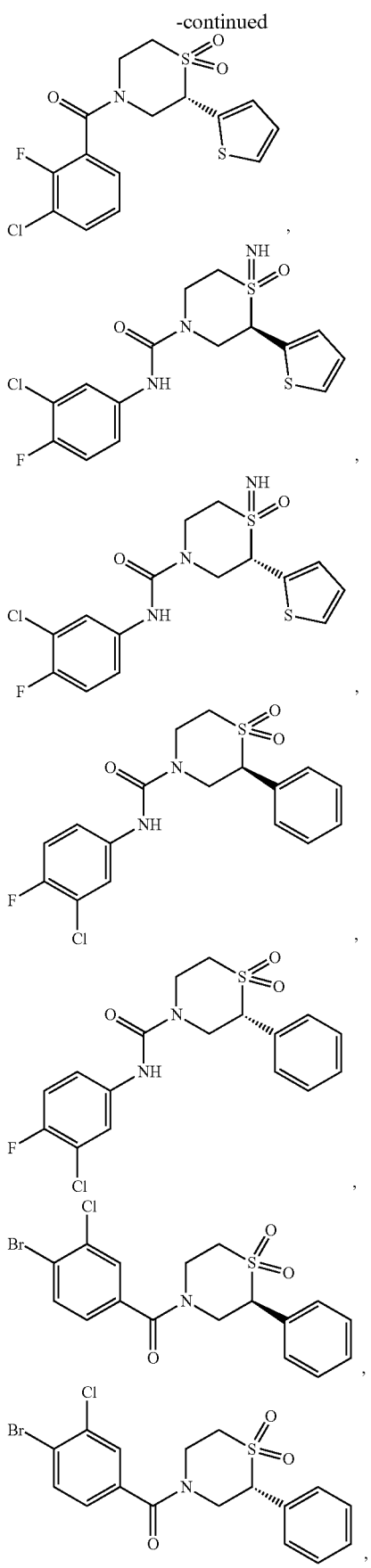
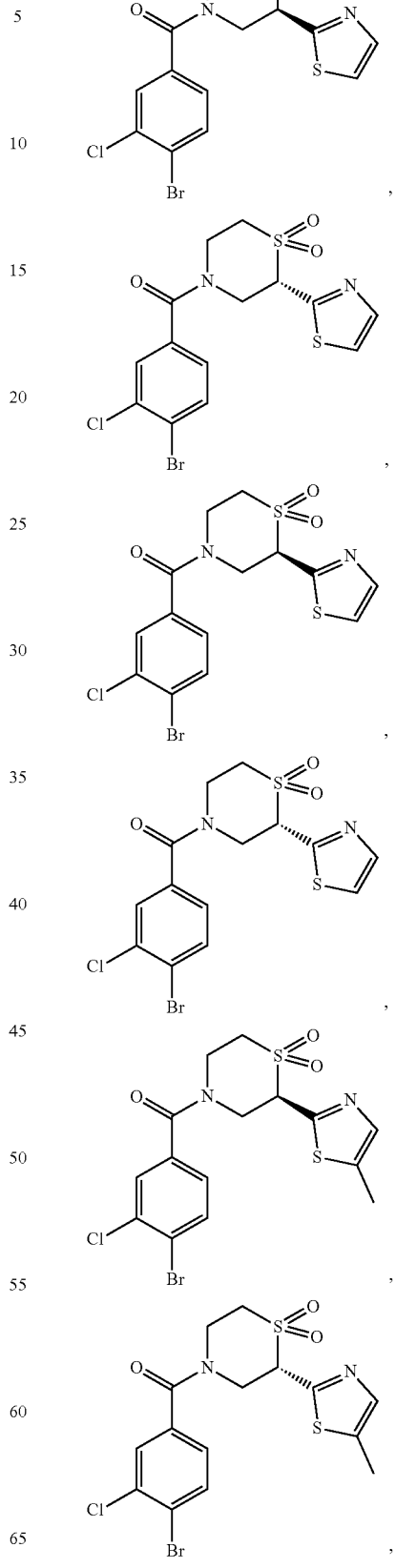

45
-continued
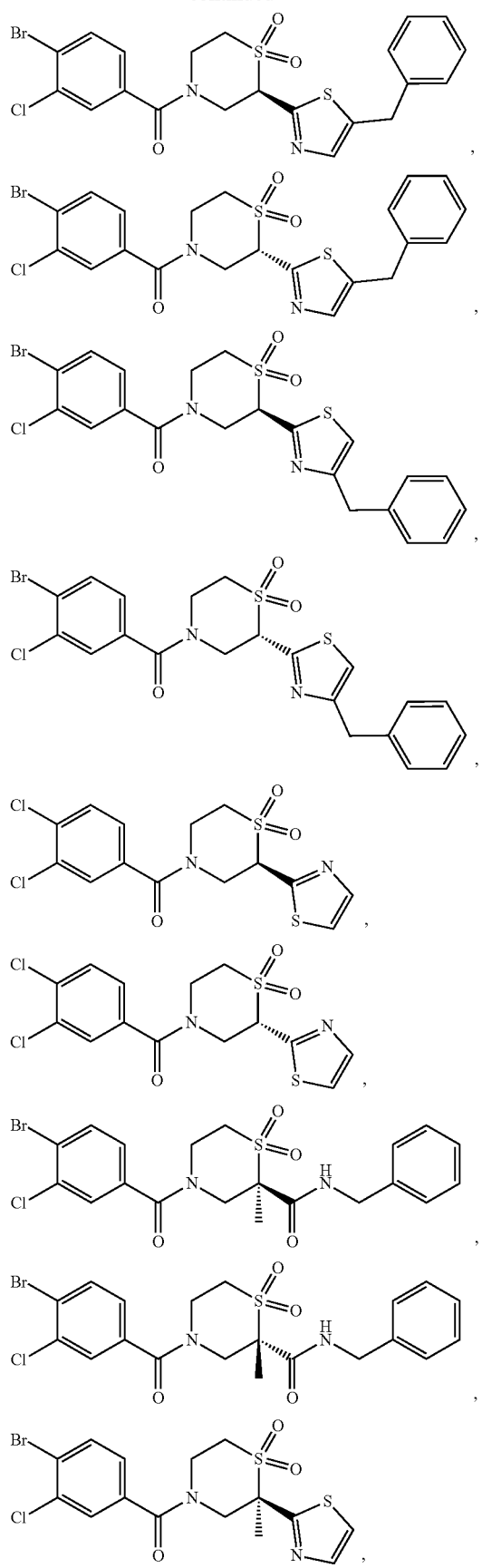
46
-continued
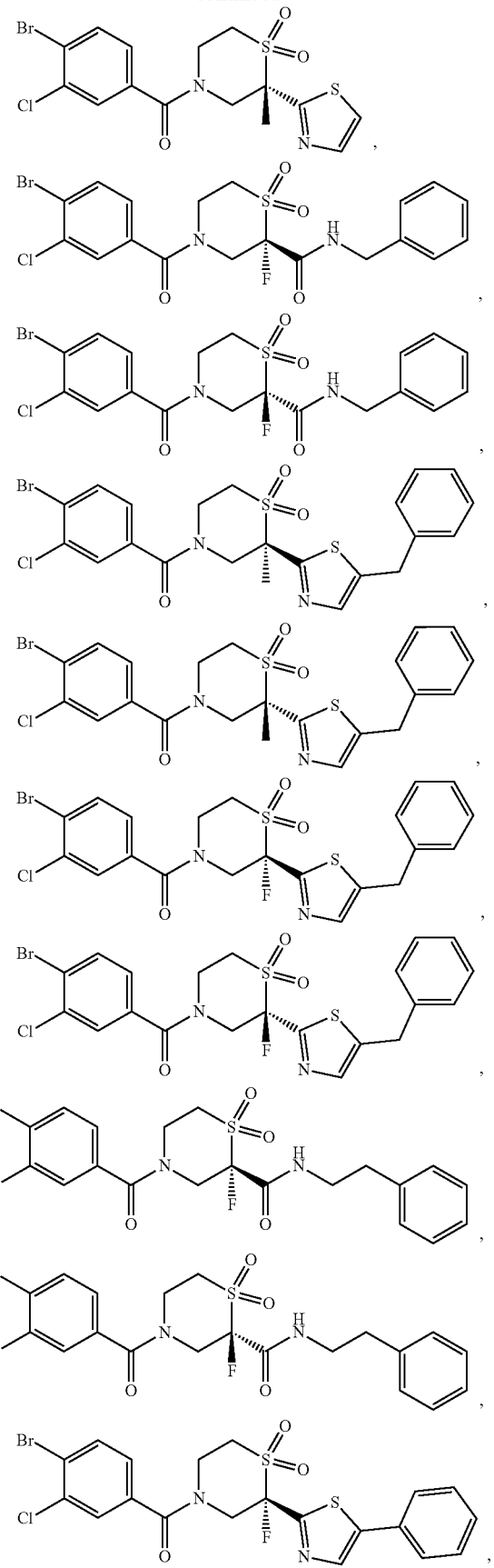

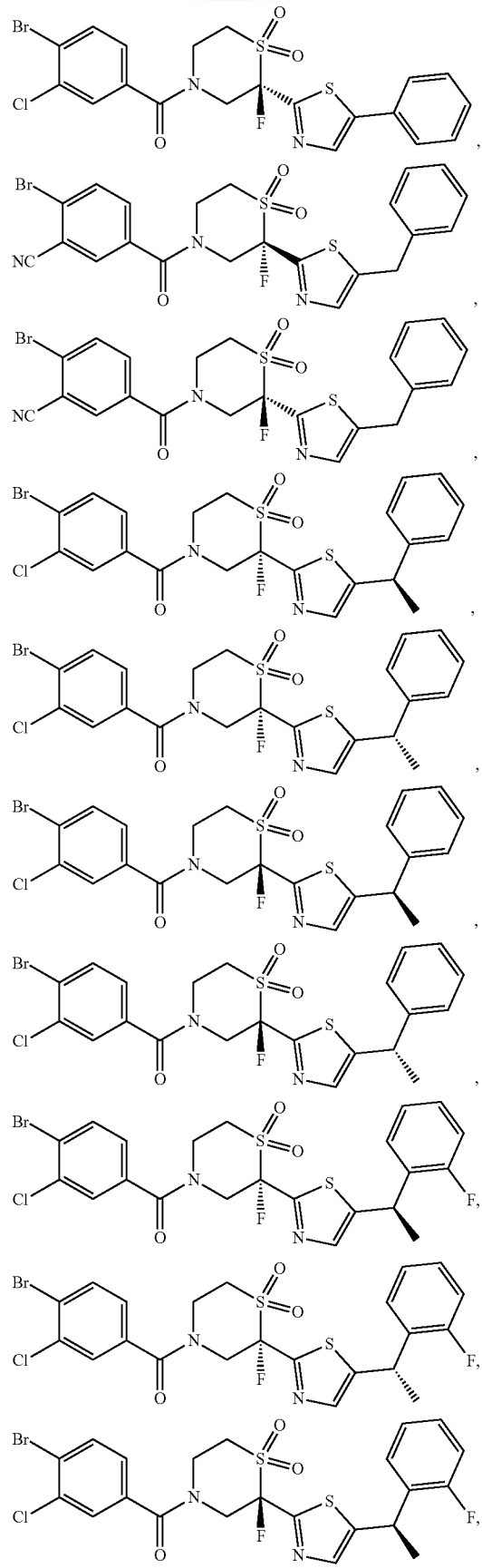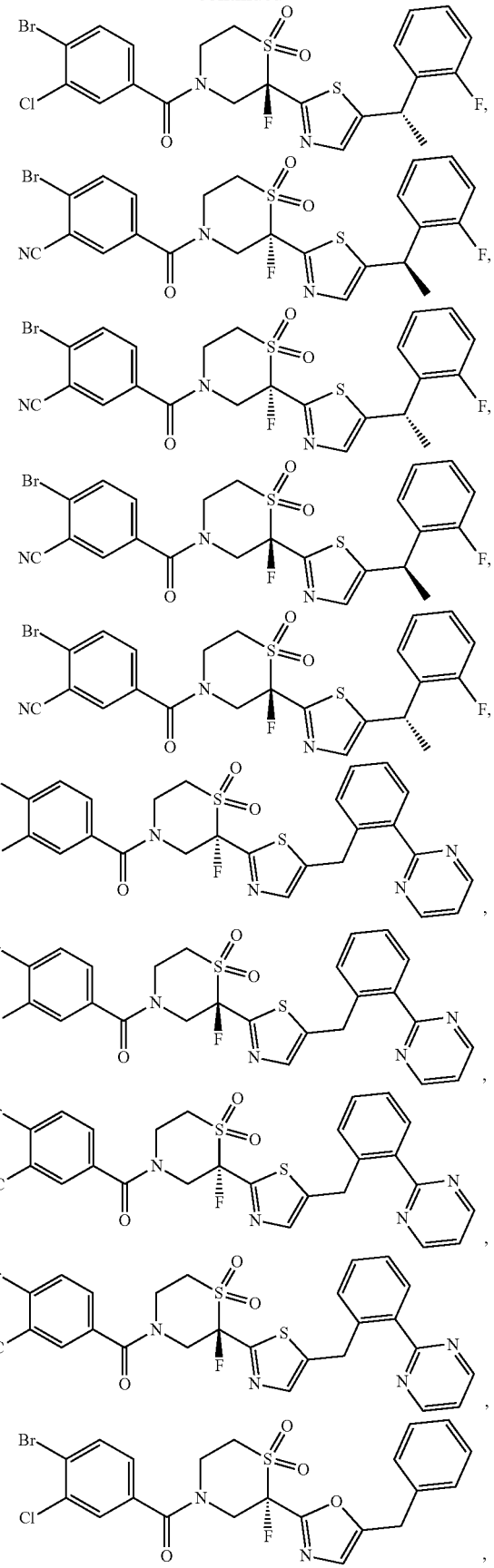

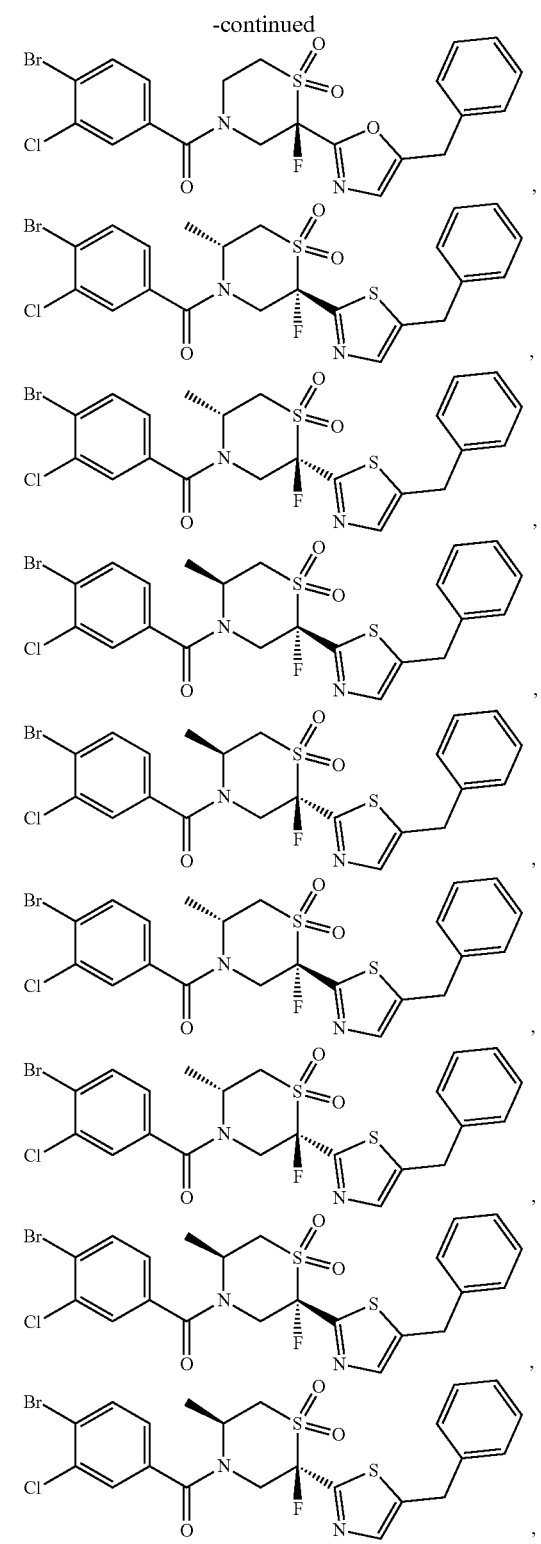
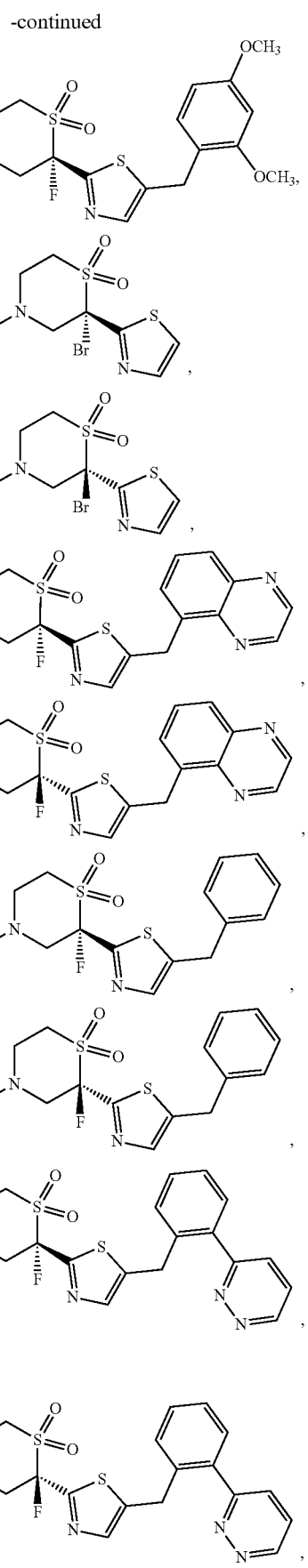

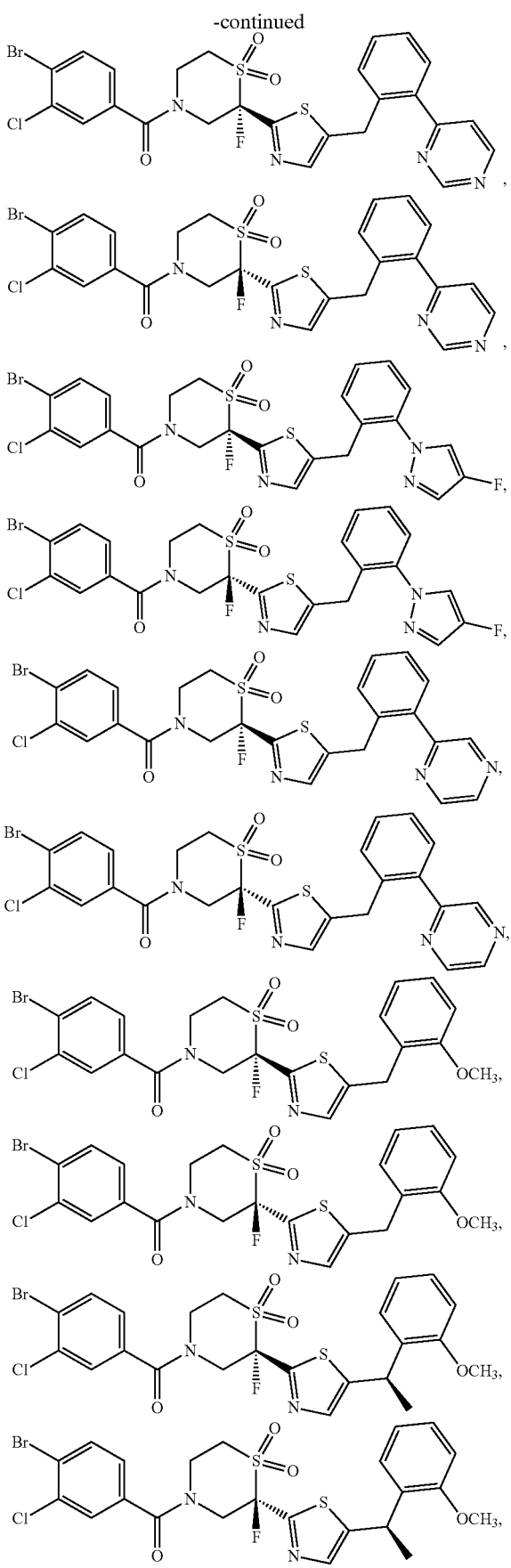

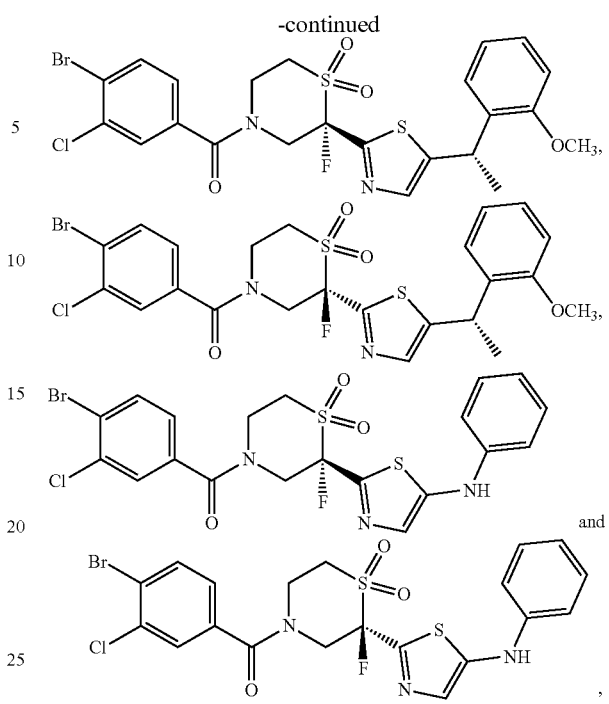

or a pharmaceutically acceptable salt of any of the foregoing.

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

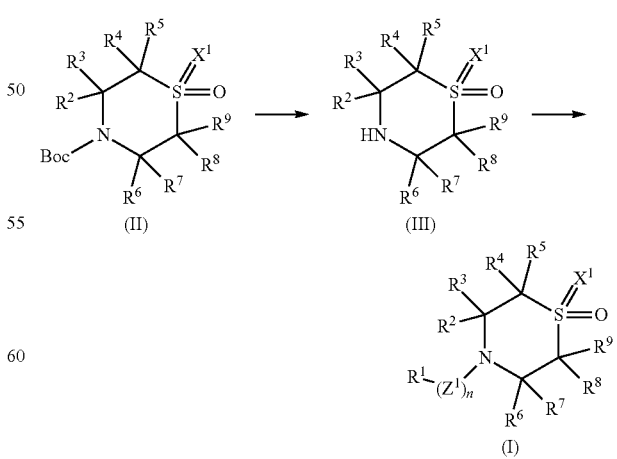

Compounds of Formula (I), along with pharmaceutically acceptable salts thereof, can be prepared from an intermediate of Formula (II) by cleaving the Boc protecting group in acidic condition (for example, by using trifluoroactetic acid) in a suitable solvent, such as dichloromethane, to provide a compound of Formula (III). As another example, the Boc protecting group can be removed by using cupper triflate to give a compound of Formula (III). Utilizing a compound of Formula (III), compounds of Formula (I), and pharmaceutically acceptable salts thereof, can be obtained using methods known to those skilled in the art. For example, a urea of Formula (I), wherein $Z^1$ being —NH—C(=O)— and n=1, can be obtained by coupling a compound of Formula (III) with a carbamate (for example, $R^1NHC(=O)$—OPh) or by using an isocyanate of general formula $R^1$—N=C=O in presence of a base(such as trimethylamine) in a suitable solvent (such as THF). An acyl of Formula (I), wherein $Z^1$ being —C(=O)— and n=1, can be obtained by coupling a compound of Formula (III) with an acyl chloride of the general formula $R^1$—C(=O)—$C_1$ in presence of a suitable base (for example, trimethylamine), or by using an acid (such as $R^1$—C(=O)—OH) in presence of a suitable coupling agent (such as HATU) in presence of a base (such as trimethylamine). Other $R^1$—$(Z^1)_n$— groups can be introduced to a compound of Formula (III) by methods known to those skilled in the art to give a compound of Formula (I), along with pharmaceutically acceptable salts thereof.

amine). As another example acyls of Formula (VI), wherein $Z^1$ being —C(=O)— and n=1, can be obtained using an acid (such as $R^1$—C(=O)—OH) in presence of a suitable coupling agent (such as HATU) in presence of a base (such as trimethylamine). Other $R^1$—$(Z^1)_n$— group can be introduced to a compound of Formula (V) by methods known to those skilled in the art to obtain a compound of Formula (VI).

Compounds of Formula (I) along with pharmaceutically acceptable salts thereof, wherein $X^1$ represents N—$R^{14}$, can be obtained from a compound of Formula (VI) by various methods known in those skilled in the art. For example, a compound of Formula (VI) can be treated with trifluoroacetamide, in presence of MgO, $Rh_2(OAc)$ and iodobenzenediacetate in a suitable solvent to afford a compound of Formula (I) in which $X^1$ represents N—$COCF_3$. Suitable solvents are known to those skilled in the art and include dichloromethane. Treatment of a compound of Formula (I), wherein $X^1$ represents N—$COCF_3$, with a suitable base (such as potassium carbonate) in a suitable solvent (such as dichloromethane) can provide a compound of Formula (I) in which $X^1$ represents NH. Pharmaceutically acceptable salts of a compound of Formula (I) in which $X^1$ represents NH can be obtained following procedures known to those skilled in the art.

Scheme 2

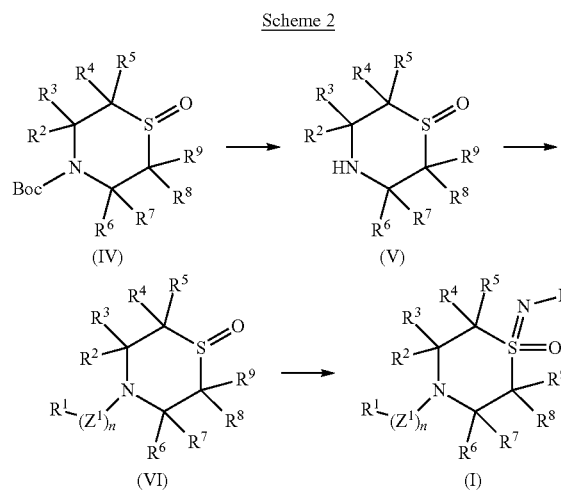

Scheme 3

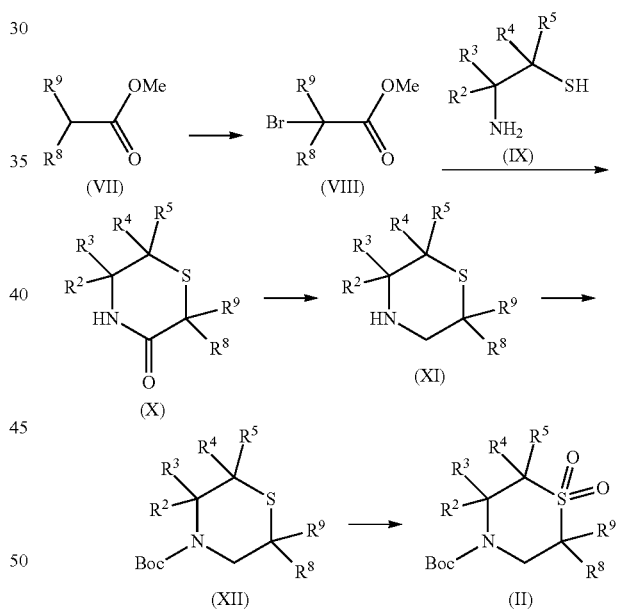

Compounds of Formula (I), in which $X^1$ represents $NR^{14}$, along with pharmaceutically acceptable salts thereof, can be prepared from a compound of Formula (IV) by cleaving the Boc protecting group under acidic condition or by using cupper triflate to give a compound of Formula (V), which can be isolated either as a free base or as a salt. Exemplary acidic conditions include using trifluoroactetic acid in a suitable solvent such as dichloromethane. Compounds of Formula (VI) can be obtained using methods known in the art. For example, ureas of Formula (VI), wherein $Z^1$ being —NH—C(=O)— and n=1, can be obtained by coupling a compound of Formula (V) with a carbamate (for example, $R^1NHC(=O)$—OPh) or by using an isocyanate of general formula $R^1$—N=C=O in presence of a base (such as trimethylamine) in a suitable solvent (such as THF). Acyls of Formula (VI), wherein $Z^1$ being —C(=O)— and n=1, can be obtained by coupling a compound of Formula (V) with an acyl chloride of the general formula $R^1$—C(=O)—$C_1$ in presence of a suitable base (for example, trimethyl- Compounds of Formula (II) can be prepared by different methods known in the art. For instance, compounds of formula (II) in which both $R^6$ and $R^7$ represent hydrogen and $X^1$ is oxygen can be prepared following the procedures reported in Scheme 3. An ester of formula (VII) can be brominated using standard procedures, for instance by a treatment with dibenzoylperoxide and N-bromosuccinimide in a suitable solvent such as $CCl_4$ to afford an alpha-bromo ester of formula (VIII). Cyclization of intermediate (VIII) in presence of an optionally substituted cysteamine derivative of formula (IX) affords compounds of formula (X). Alternatively, the optionally substituted cysteamine derivative of formula (IX) can be replaced in Scheme 3 by a N-Boc protected S-Acetyl cysteamine derivative, which is reacted with the bromo intermediate of formula (VIII) in presence of a base such as potassium carbonate in a suitable solvent such as methanol, then the deprotection of the Boc protecting group in standard acidic procedure, for instance using TFA, followed by a treatment with a base gives an intermediate of formula (X). The reduction of the carbonyl in a compound of formula (X) can be achieved by know procedures, for instance using DIBAL-H or BH$_3$ in a suitable solvent such as THF to afford a compound of formula (XI). The Boc protecting group can be introduced onto compound (XI) using BOC$_2$O in presence of DMAP and a base such as triethylamine in a suitable solvent such as THF to afford a compound of formula (XII). Oxidation of a compound of formula (XII) to corresponding compound of formula (II) in which both R$^6$ and R$^7$ represent hydrogen and X$^1$ is oxygen can be achieved by the treatment of (XII) with an oxidizing agent such as m-CPBA in a suitable solvent such as dichloromethane.

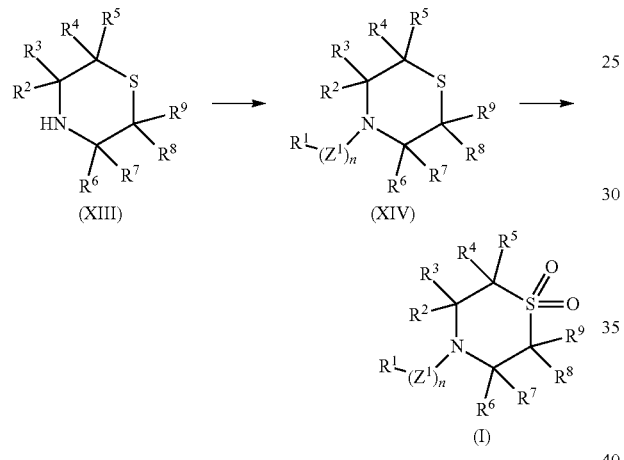

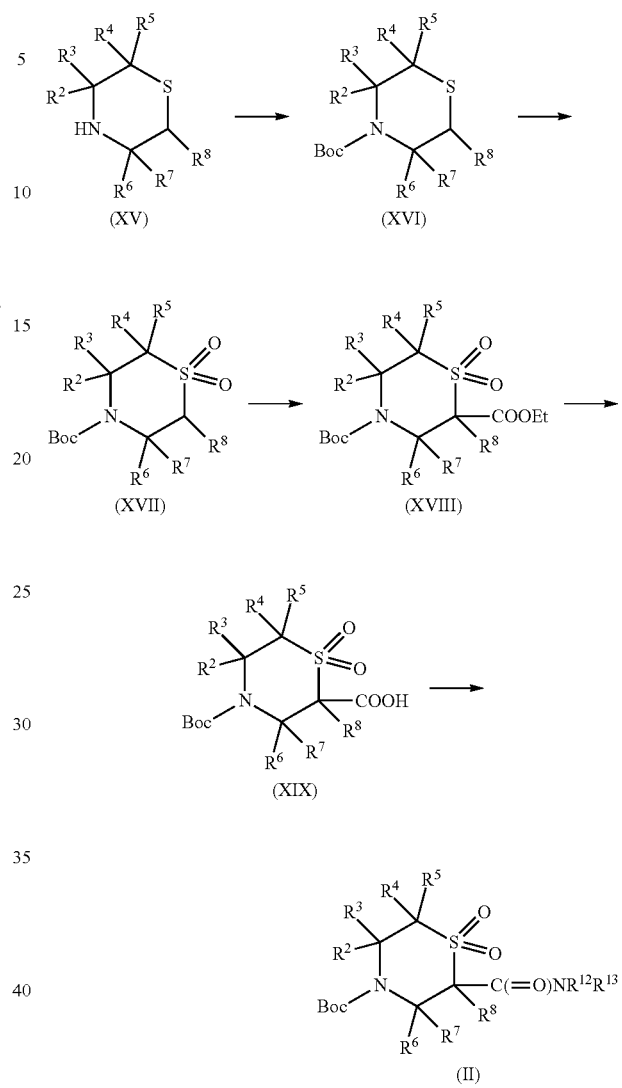

Compounds of Formula (I) in which X$^1$ represents oxygen, along with pharmaceutically acceptable salts thereof, can be prepared from an intermediate of Formula (XIII) as depicted in Scheme 4. Compounds of Formula (XIV) can be prepared from a compound of formula (XIII) by methods know in the art. For instance, ureas of Formula (XIV) having Z$^1$ being —NH—C(=O)— and n=1, can be obtained by coupling Formula (XIII) with a carbamate (for example, R$^1$NHC(=O)—OPh) or by using an isocyanate of general formula R$^1$—N=C=O in presence of a base such as triethylamine in a suitable solvent such as THF. Alternatively, acyls of Formula (XIV) having Z$^1$ being —C(=O)— and n=1, can be obtained by coupling Formula (XIII) with an acyl chloride of the general formula R$^1$—C(=O)—Cl in presence of a suitable base such as triethylamine, or by using a carboxylic acid of general formula R$^1$—C(=O)—OH in presence of a suitable coupling agent such as HATU in presence of a base such as triethylamine. Other R$^1$—(Z$^1$)$_n$— group can be introduced onto intermediate (XIII) by methods known in those skilled in the art to give a compound of formula (XIV). The oxidation of intermediate of formula (XIV) can be achieved by an oxidating agent such as m-CPBA in a suitable solvent such as dichloromethane to afford a compounds of Formula (I) in which X$^1$ represents oxygen, along with pharmaceutically acceptable salts thereof.

Compounds of Formula (II) in which X$^1$ represents oxygen, and R$^9$ represents —C(=O)NR$^{12}$R$^{13}$, can be prepared from a compound of formula (XV) following the procedures depicted in Scheme 5. The Boc protection of intermediate (XV) is achieved using BOC$_2$O in presence of a base such as triethylamine in a suitable solvent such as dichloromethane. The oxidation of the Sulphur atom of intermediate (XVI) can be achieved using an oxidative agent such as mCPBA in a suitable solvent such as dichloromethane. Treatment of a compound of formula (XVII) with a base, such as LiHMDS followed by a reaction with ethylchloroformate in a suitable solvent affords an ester of formula (XVIII), which can be subsequently saponified by using an hydroxide such as LiOH in a mixture of solvents such as water and THF to afford, after acidification of the reaction mixture an acid of formula (XIX). The coupling of the acid of formula (XIX) with an amine of general formula H$_2$NR$^{12}$R$^{13}$ in presence of a coupling agent such as TCFH, NMI in a suitable solvent such as acetonitrile affords the compound of Formula (II) in which X$^1$ represents oxygen, and R$^9$ represents —C(=O)NR$^{12}$R$^{13}$.

Scheme 6

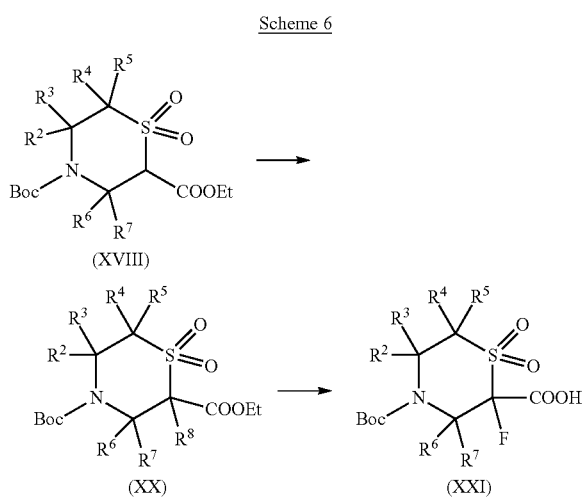

Compounds of Formula (XXI) in which $X^1$ represents oxygen, $R^8$ represents —F and $R^9$ represents —C(=O)OH, can be prepared from a compound of Formula (XVIII) in which $R^8$ is hydrogen following the procedures depicted in Scheme 6. Fluorination of a compound of Formula (XVIII) can be performed in presence of a base (such as NaH) with NFSI in a suitable solvent (such as THF). The resulting ester of Formula (XX) can be subsequently saponified by using a hydroxide (such as LiOH) in a mixture of solvents (for example, water and THF) to afford, after acidification of the mixture, an acid of Formula (XXI).

Scheme 7

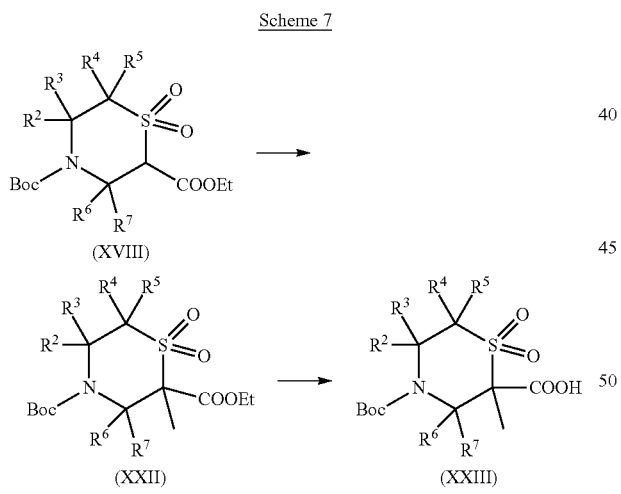

Compounds of Formula (XXIII) in which $X^1$ represents oxygen, $R^8$ represents -Me and $R^9$ represents —C(=O)OH, can be prepared from a compound of Formula (XVIII) in which $R^8$ is hydrogen following the procedures depicted in Scheme 7. Methylation of a compound of Formula (XVIII) can be performed in presence of a base (such as NaH) with MeI in a suitable solvent (such as THF). The resulting ester of Formula (XXII) can be saponified by using an hydroxide (such as LiOH) in a mixture of solvents (such as water and THF) to afford, after acidification of the mixture, an acid of Formula (XXIII).

Scheme 8

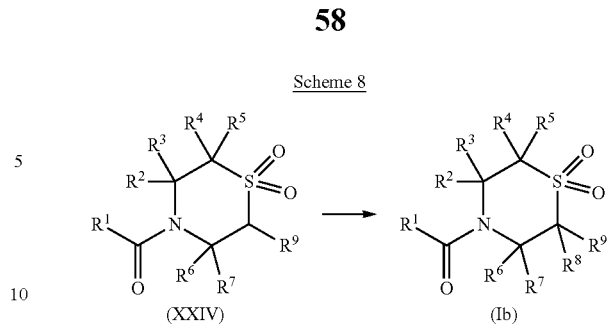

Compounds of Formula (Ib) in which $X^1$ represents oxygen, $R^8$ represents -Me or halogen and $R^9$ is selected from an optionally substituted $C_{1-4}$ alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl), can be prepared from a compound of Formula (XXIV) in which $R^8$ is hydrogen, following the procedures depicted in Scheme 8. Treatment of a compound of Formula (XXIV) with a base (such as NaH) in a suitable solvent (such as dry THF) with an alkylating agent (such as MeI) or a fluorinating agent (such as NFSI) can give a compound of Formula (Ib) in which $R^8$ represents -Me or —F, respectively.

The same procedures can be applied to a compound of Formula (II) in which $X^1$ represents oxygen, $R^8$ represents hydrogen and $R^9$ is selected from an optionally substituted $C_{1-4}$ alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl) to give the corresponding methylated or fluorinated derivatives. Alternatively, treatment of a compound of Formula (XXIV) with a brominating agent, such as NBS, in acetic acid can give a compound of Formula (Ib) in which $R^8$ represents —Br.

Scheme 9

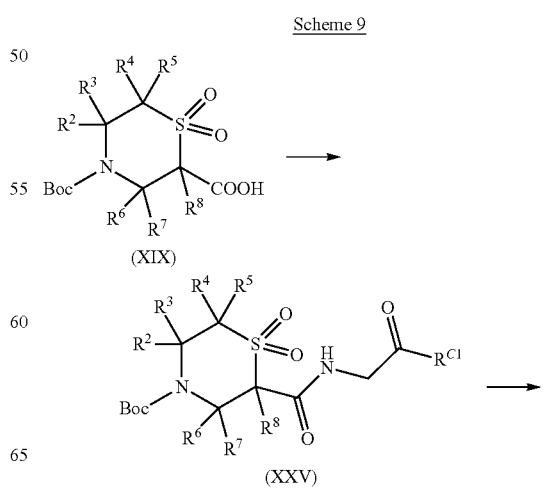

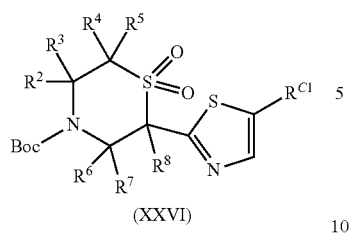

(XXVI)

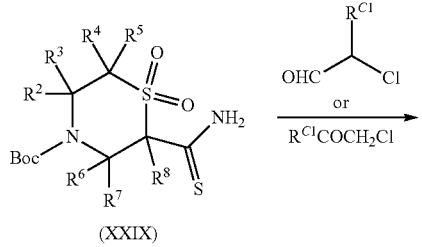

(XXIX)

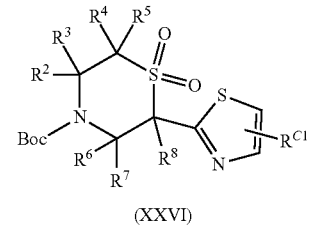

(XXVI)

The coupling of the acid of Formula (XIX) in which $R^8$ can be a hydrogen, methyl or halogen, with an amine of general formula $NH_2CH_2(CO)R^{C1}$ in which $R^{C1}$ represents an unsubstituted $C_{1-4}$ alkyl, an unsubstituted or a substituted aryl, an unsubstituted or a substituted heteroaryl, an unsubstituted or a substituted aryl($C_{1-4}$ alkyl), an unsubstituted or a substituted heteroaryl($C_{1-4}$ alkyl) or a mono-substituted amine, can be performed using conditions known in the art for the formation of amide bonds. For example, treatment of a compound of Formula (XIX) with a coupling agent (such as TCFH-NMI) in a suitable solvent (such as acetonitrile) can give a compound of Formula (XXV) after addition of the amine of general formula $NH_2CH_2(CO)R^{C1}$. Alternatively, the carboxylic acid of Formula (XIX) can be transformed to the corresponding acyl chloride using oxalyl chloride in presence of DMF, in a suitable solvent (such as DCM) before reacting with the amine of general formula $NH_2CH_2(CO)R^{C1}$ in the presence of a base (such as $Et_3N$) in a suitable solvent (such as THF). Cyclization of a compound of Formula (XXV) can be performed in the presence of $P_2S_5$ or Lawesson's reagent in a suitable solvent (such as toluene) under heating conditions to give a thiazole derivative of Formula (XXVI), substituted at the $C_5$ position with a $R^{C1}$ group, in which $R^8$ can be a hydrogen, methyl or halogen and $R^{C1}$ can be as defined above. Compound of Formula (XXVI) can then be treated in a similar manner as a compound of Formula (II) in Scheme 1 to provide compounds of Formula (I). Treatment of a compound of Formula (XXV) with $POCl_3$, instead of $P_2S_5$ or Lawesson's reagent, can give the corresponding oxazole derivative instead of the thiazole derivative.

Scheme 10

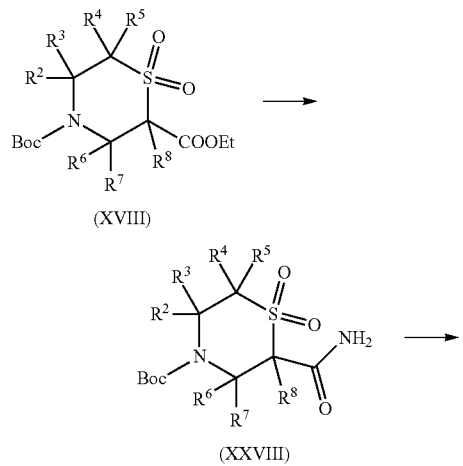

A compound of Formula (XXVI) in which $R^8$ can be a hydrogen, methyl or halogen, and $R^{C1}$ represents hydrogen or an optionally substituted $C_{1-4}$ alkyl, can be prepared as depicted in Scheme 10. Treatment of an ester of Formula (XVIII) with ammonia in a suitable solvent (such as methanol) can give an amide of Formula (XXVIII) which can be further reacted with Lawesson's reagent in a suitable solvent (for example, toluene) under heating conditions to give a thioamide of Formula (XXIX). Reaction of the thioamide of Formula (XXIX) with a chloro aldehyde of general formula $R^{C1}CHClCHO$ or an alpha chloro or bromoketone of general formula $R^{C1}COCH_2X$ can give the corresponding C5-substituted thiazole derivative of Formula (XXVI) and C4-substituted thiazole derivative of Formula (XXVI), respectively. Compound of Formula (XXVI) can then be treated in a similar manner as a compound of Formula (II) in Scheme 1 to provide compounds of Formula (I).

Scheme 11

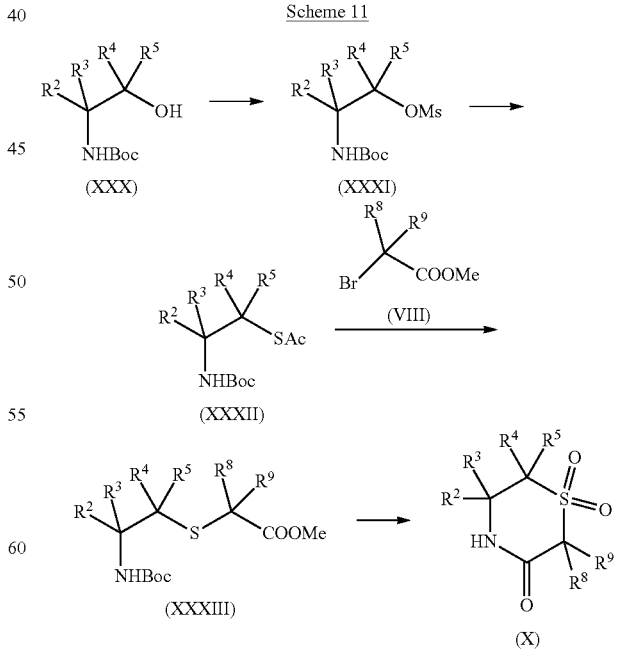

A compound of Formula (X) can be alternatively synthetized as depicted in Scheme 11. A Boc protected aminoalcohol of Formula (XXX) can be transformed to the corresponding mesylate derivative of Formula (XXXI) using conditions known in the art, for example, mesylchloride in presence of a base (such as Et$_3$N) in a suitable solvent (such as DCM). Treatment of a compound of Formula (XXXI) with potassium thioacetate in a suitable solvent (such as DMF) can give a compound of Formula (XXXII) which can further be reacted with a bromoester derivative of Formula (VIII) in the presence of a base (such as potassium carbonate) in a suitable solvent (such as methanol) to give a compound of Formula (XXXIII). A compound of Formula (X) can be obtained by treating successively a compound of Formula (XXXIII) with TFA in DCM, followed by cyclization of the Boc deprotected derivative in presence of a base (such as sodium bicarbonate) in a suitable solvent (such as DCM). Compound of Formula (X) can then be treated in a similar manner as shown in Scheme 3 to obtain compounds of Formula (II).

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction $<10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

Subjects who are clinically diagnosed with a HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT>twice the upper normal limit and detectable serum HBV DNA by hybridization assays). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-α-2a); and examples of nucleosides/nucleotides include lamivudine, telbivudine, adefovir dipivoxil, clevudine, entecavir, tenofovir alafenamide and tenofovir disoproxil. However, some of the drawbacks associated with interferon treatment are the adverse side effects, the need for subcutaneous administration and high cost. Potential advantages of a compound of Formula (I), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

Previously known compounds, such as those provided in WO 2017/156255, were shown to form adducts with glutathione in in vitro assays. Formation of glutathione adducts can be a signal that a compound has the potential to induce liver injury. Thus, the formation of glutathione adducts can be used as a signal to predict safety. Unexpectedly, compounds described herein, such as many compounds of Formula (I), and pharmaceutically acceptable salts thereof, have been shown not to form adducts with glutathione in in vitro assays. Further, known compounds (for example, those described in WO 2017/156255), have demonstrated potency in a HepG2.2.15 cell based assay with an $EC_{50}$ of >1000 pM. Many compounds described herein, such as compounds of Formula (I), and pharmaceutically acceptable salts thereof, unexpectedly show improved potency in a HepG2.2.15 cell based assay with an $EC_{50}$<1000 pM range. Thus, compounds described herein, including compounds of Formula (I), and pharmaceutically acceptable salts thereof, can be at least 16 times more potent than previously known compounds. In some embodiments, improved potency can lead to a significantly lower dose requirement and therefore improve daily dose burden as well as lead to improved safety margins.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a sequence specific oligonucleotide (such as anti-sense oligonucleotide and siRNA), nucleic acid polymers (NAPs, such as nucleic acid polymers that reduce HBsAg levels) an entry inhibitor and/or a small molecule immunomodulator. Examples of additional agents include recombinant interferon alpha 2b, IFN-α, PEG-IFN-α-2a, lamivudine, telbivudine, adefovir dipivoxil, clevudine, entecavir, tenofovir alafenamide and tenofovir disoproxil. Examples of NAPs include, but are not limited to, REP 2139, REP 2165 and those described in U.S. Application No. 62/757,632, filed Nov. 8, 2018, which is hereby incorporated by reference for the purpose of the NAPs described therein.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Example 1

4-(tert-butoxycarbonyl)thiomorpholine-2-carboxylic acid 1,1-dioxide

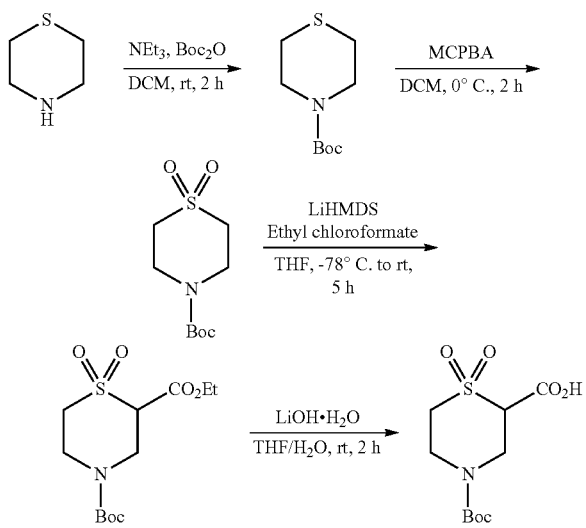

Et₃N (1.2 eq., 12.93 mL, 93.04 mmol) was added to a solution of thiomorpholine (1.0 eq., 7.35 mL, 77.53 mmol) in CH₂Cl₂ (320 mL). A solution of Boc₂O (1.0 eq., 16.92 g, 77.53 mmol) in CH₂Cl₂ (80 mL) was added dropwise, and the mixture was stirred for 2 h at room temperature (rt). The mixture was evaporated to dryness. Water (100 mL) and HCl 1 M (100 mL) were added, and the aqueous layer was extracted with AcOEt (3×100 mL). The combined organic layers were washed with HCl 1 M (50 mL), water (50 mL) and brine (50 mL), dried over MgSO₄, filtered and evaporated to dryness to give tert-butyl thiomorpholine-4-carboxylate (15.17 g, 74.62 mmol, 96%) as a white solid. ¹H-NMR (CDCl₃, 400 MHz, 25° C.): 1.43 (s, 9H); 2.52-2.57 (m, 4H); 3.63-3.68 (m, 4H) ppm.

MCPBA (2.1 eq., 28.7 g, 83.15 mmol, purity 50%) was added to a solution of tert-butyl thiomorpholine-4-carboxylate (1.0 eq., 8.05 g, 39.60 mmol) in CH₂Cl₂ (350 mL) under N₂ at 0° C., and the mixture was stirred for 2 h at this temperature. Sat. Na₂CO₃ (75 mL) and water (75 mL) were added, and the aqueous layer was extracted with DCM (3×100 mL). The combined organic layers were washed with water (100 mL) and brine (100 mL) dried over MgSO₄, filtered and evaporated to dryness. The resulting solid was dissolved in AcOEt, and the solution was washed with sat. Na₂CO₃, sat. NaHCO₃, water and brine, dried over MgSO₄, filtered and evaporated to dryness to give tert-butyl thiomorpholine-4-carboxylate 1,1-dioxide (8.70 g, 36.97 mmol, 93%) as a white solid. ¹H-NMR (CDCl₃, 400 MHz, 25° C.): 1.46 (s, 9H); 2.97 (m, 4H); 3.90 (m, 4H) ppm.

LiHMDS (1.0 eq., 1.65 mL, 17.21 mmol, 1 M in THF) was added to a solution tert-butyl thiomorpholine-4-carboxylate 1,1-dioxide (1.0 eq., 4.05 g, 17.21 mmol) in THF (127 mL) under N₂ at −78° C., and the mixture was stirred for 1 h at this temperature. Ethyl chloroformate (1.0 eq., 1.65 mL, 17.21 mmol) was added, and the mixture was stirred for 1.5 h at −78° C. Additional LiHMDS (1.0 eq., 1.65 mL, 17.21 mmol, 1 M in THF) was added, and the mixture was stirred for 1.5 h at −78° C., before being allowed to warm to rt. A sat. solution of NH₄Cl (100 mL) and AcOEt (100 mL) were added, and the aqueous layer was extracted with AcOEt (3×100 mL). The combined organic layers were washed with sat. NH₄Cl (100 mL) and brine (50 mL), dried over MgSO₄, filtered and evaporated to dryness to give 4-(tert-butyl) 2-ethyl thiomorpholine-2,4-dicarboxylate 1,1-dioxide (4.70 g, 15.29 mmol, 89%) as a white solid. ¹H-NMR (DMSO, 400 MHz, 25° C.): 1.22 (t, J=7.2 Hz, 3H); 1.38 (s, 9H); 3.21-3.29 (m, 1H); 3.33-3.42 (m, 1H); 3.47-3.93 (m, 1H); 3.76-4.24 (m, 5H); 4.31 (s, 1H) ppm.

LiOH•H₂O (3.0 eq., 0.41 g, 9.76 mmol) was added to a solution of 4-(tert-butyl) 2-ethyl thiomorpholine-2,4-dicarboxylate 1,1-dioxide (1.0 eq., 1.0 g, 3.25 mmol) in THF (27 mL) and water (11 mL). The mixture was stirred for 2 h at rt. Water (10 mL) and NaOH (1 M, 20 mL) were added, and the aqueous layer was extracted with Et₂O (3×30 mL). The aqueous layer was acidified with HCl 1 M to reach a pH of 2 and extracted with AcOEt (3×30 mL). The combined organic layers were dried over MgSO₄, filtered and evaporated to dryness to give 4-(tert-butoxycarbonyl)thiomorpholine-2-carboxylic acid 1,1-dioxide (821 mg, 2.94 mmol, 90%) as a white solid. ¹H-NMR (DMSO, 400 MHz, 25° C.): 3.10-3.26 (m, 1H); 3.27-3.42 (m, 2H); 3.43-3.61 (m, 1H); 3.71-3.85 (m, 1H); 3.88-4.03 (m, 1H); 4.08 (s, 1H); 13.09-14.18 (br. s. 1H) ppm.

Example 2

General Procedure for the Peptide Coupling with the Amine

TCFH (1.3 eq.), N-methylimidazole (5.0 eq.) and the corresponding amine (1.2 eq.) were added to a suspension of 4-(tert-butoxycarbonyl)thiomorpholine-2-carboxylic acid 1,1-dioxide (1.0 eq.) in MeCN (0.1 M) under N₂ at rt. The mixture was stirred at rt until complete conversion of the starting material. Sat. Na₂CO₃ was added, and the aqueous layer was extracted with AcOEt (3×). The combined organic layers were washed with sat. Na₂CO₃ and brine, dried over MgSO₄, filtered and evaporated to dryness to give a crude product which was purified by flash chromatography on silica gel (30% to 60% AcOEt in cyclohexane) to give the corresponding amide.

Example 3 tert-butyl 2-(isopropylcarbamoyl)thiomorpholine-4-carboxylate 1,1-dioxide

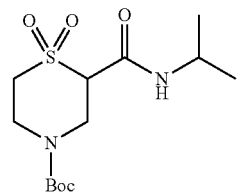 [SMILES: CC(C)NC(=O)C1CN(C(=O)OC(C)(C)C)CCS1(=O)=O]

Using the general procedure as described in Example 2 and isopropylamine, tert-butyl 2-(isopropylcarbamoyl)thiomorpholine-4-carboxylate 1,1-dioxide was obtained and used in the next step without purification (460 mg, 1.44 mmol, 100%). LCMS: $C_{13}H_{24}N_2O_5S$ [M+Na]⁺: 344.1.

Example 4 tert-butyl 2-(phenylcarbamoyl)thiomorpholine-4-carboxylate 1,1-dioxide

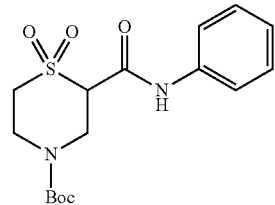 [SMILES: CC(C)(C)OC(=O)N1CCS(=O)(=O)C(C(=O)Nc2ccccc2)C1]

Using the general procedure as described in Example 2 and aniline, tert-butyl 2-(phenylcarbamoyl)thiomorpholine-4-carboxylate 1,1-dioxide was obtained as a white solid (445 mg, 1.26 mmol, 81%). LCMS: $C_{16}H_{22}N_2O_5S$ [M+Na]⁺: 377.0.

Example 5 tert-butyl 2-(benzylcarbamoyl)thiomorpholine-4-carboxylate 1,1-dioxide

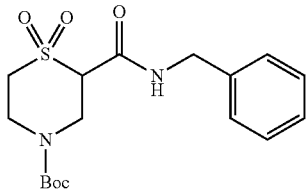 [SMILES: CC(C)(C)OC(=O)N1CCS(=O)(=O)C(C(=O)NCc2ccccc2)C1]

Using the general procedure as described in Example 2 and phenylmethanamine, tert-butyl 2-(benzylcarbamoyl) thiomorpholine-4-carboxylate 1,1-dioxide was obtained as a white solid (270 mg, 0.73 mmol, 56%). LCMS: $C_{17}H_{24}N_2O_5S$ [M+Na]$^+$: 391.0.

Example 6 tert-butyl 2-(phenethylcarbamoyl)thiomorpholine-4-carboxylate 1,1-dioxide

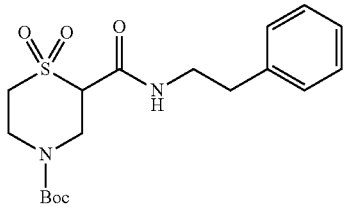 [SMILES: CC(C)(C)OC(=O)N1CCS(=O)(=O)C(C(=O)NCCc2ccccc2)C1]

Using the general procedure as described in Example 2 and 2-phenylethan-1-amine, tert-butyl 2-(phenethylcarbamoyl)thiomorpholine-4-carboxylate 1,1-dioxide was obtained as a white solid (254 mg, 0.66 mmol, 49%). LCMS: $C_{18}H_{26}N_2O_5S$ [M+Na]$^+$: 405.1.

Example 7

General Procedure for the Deprotection and the Peptide Coupling with 4-Bromo-3-Chlorobenzoic Acid A solution of HCl in dioxane (4N, 20 eq.) was added to the carbamate (1.0 eq.) at 0° C., and the mixture was stirred for 2 h. Then, the volatiles were removed under reduced pressure. The resulting hydrochloride salt was used without further purification in the next step.

TCFH (1.3 eq.), N-methylimidazole (5.0 eq.) and the corresponding hydrochloride salt (1.0 eq.) were added to a suspension of 4-bromo-3-chlorobenzoic acid (1.2 eq.) in MeCN (0.2 M) under $N_2$ at rt, and the mixture was stirred until complete conversion. Sat. $Na_2CO_3$ was added, and the aqueous layer was extracted with AcOEt (3×). The combined organic layers were washed with sat. $Na_2CO_3$ and brine, dried over $MgSO_4$, filtered and evaporated to dryness to give a crude product which was purified by flash chromatography on silica gel (20% to 40% AcOEt in cyclohexane) to give the corresponding amide. Recrystallization or trituration were performed as needed.

Example 8

4-(4-bromo-3-chlorobenzoyl)-N-isopropylthiomorpholine-2-carboxamide 1,1-dioxide (1)

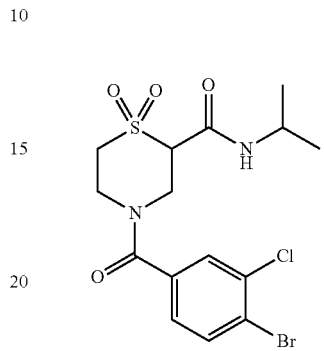

Using tert-butyl 2-(isopropylcarbamoyl)thiomorpholine-4-carboxylate 1,1-dioxide and following Example 7, compound 1 was obtained as a white solid (334 mg, 0.76 mmol, 52%) after trituration in n-heptane. $^1$H-NMR (DMSO, 400 MHz, 80° C.): 1.05 (br. s. 3H); 1.07 (d, J=6.2 Hz, 1H); 3.09 (s, 1H); 3.14-3.28 (m, 1H); 3.58 (d, J=10.0 Hz, 1H); 3.77-3.93 (m, 3H); 3.99-4.80 (br. s. 2H); 7.31 (d, J=8.3 Hz, 1H); 7.62 (s, 1H); 7.83 (d, J=8.3 Hz, 1H); 7.88 (br. s. 1H) ppm. LCMS: $C_{15}H_{18}BrClN_2O_4S$ [M+H]$^+$: 436.9/438.9/440.9.

Example 9

4-(4-bromo-3-chlorobenzoyl)-N-phenylthiomorpholine-2-carboxamide 1,1-dioxide (2)

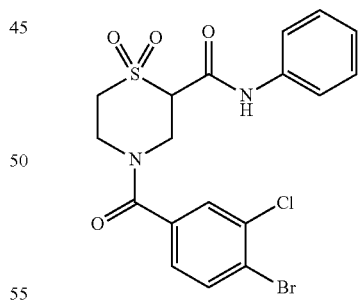

Using tert-butyl 2-(phenylcarbamoyl)thiomorpholine-4-carboxylate 1,1-dioxide and following Example 7, compound 2 was obtained as a white solid (215 mg, 0.46 mmol, 64%) after trituration in n-heptane. $^1$H-NMR (DMSO, 400 MHz, 80° C.): 3.30 (d, J=12.2 Hz, 1H); 3.56-3.63 (m, 1H); 3.63-3.77 (m, 1H); 3.98 (dd, J=14.8 Hz, 3.2 Hz, 1H); 4.14 (s, 1H); 4.41 (br. s. 1.5H); 7.06-7.20 (m, 1H); 7.29-7.34 (m, 1H); 7.34-7.39 (m, 2H); 7.44-7.58 (m, 2H); 7.63 (s, 1H); 7.76 (br. s. 1H), 10.11 (s, 1H) ppm. LCMS: $C_{18}H_{16}BrClN_2O_4S$ [M+H]$^+$: 470.9/472.9/474.9.

Example 10

N-benzyl-4-(4-bromo-3-chlorobenzoyl)thiomorpholine-2-carboxamide 1,1-dioxide (3)

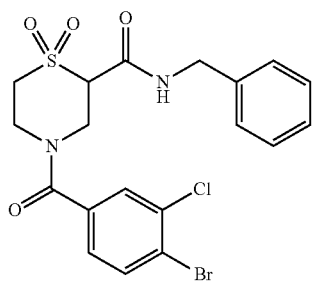 [SMILES: O=C(NCc1ccccc1)C1CN(C(=O)c2ccc(Br)c(Cl)c2)CCS1(=O)=O]

Using tert-butyl 2-(benzylcarbamoyl)thiomorpholine-4-carboxylate 1,1-dioxide and following Example 7, compound 3 was obtained as a white solid (220 mg, 0.45 mmol, 62%) after recrystallization in EtOH. $^1$H-NMR (DMSO, 400 MHz, 25° C.): 3.25 (d, J=12.4 Hz, 1H); 3.53-3.59 (m, 1H); 3.64-3.70 (m, 1H); 3.95 (d, J=15.4 Hz, 1H); 4.03 (br. s. 1H); 4.10-4.37 (m, 4H); 7.24 (m, 3H); 7.31 (m, 3H); 7.64 (s, 1H); 7.81 (d, J=8.0 Hz, 1H); 8.47 (br. s. 1H) ppm. LCMS: $C_{19}H_{18}BrClN_2O_4S$ [M+H]$^+$: 485.0/487.0/489.0.

Example 11

4-(4-bromo-3-chlorobenzoyl)-N-phenethylthiomorpholine-2-carboxamide 1,1-dioxide (4)

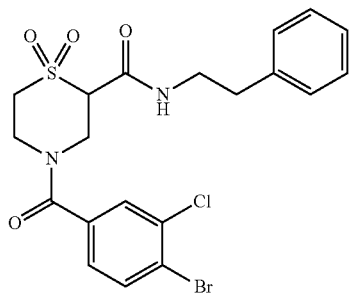 [SMILES: O=C(NCCc1ccccc1)C1CN(C(=O)c2ccc(Br)c(Cl)c2)CCS1(=O)=O]

Using tert-butyl 2-(phenethylcarbamoyl)thiomorpholine-4-carboxylate 1,1-dioxide and following Example 7, compound 4 was obtained as a white solid (41 mg, 0.082 mmol, 13%) after recrystallization in EtOH. $^1$H-NMR (DMSO, 400 MHz, 25° C.): 2.70 (t, J=6.9 Hz, 2H); 3.19-3.27 (m, 1H); 3.27-3.37 (m, 2H); 3.55 (ddd, J=13.8 Hz, 9.8 Hz, 3.6 Hz, 1H); 3.65-3.72 (m, 1H); 3.86-4.00 (m, 2H); 4.15 (br. s. 2H); 7.15-7.22 (m, 3H); 7.24-7.30 (m, 2H); 7.33 (d, J=8.3 Hz, 1H); 7.65 (d, J=1.5 Hz, 1H); 7.85 (d, J=8.3 Hz, 1H); 8.05 (br. s. 0.95 H) ppm. LCMS: $C_{20}H_{20}BrClN_2O_4S$ [M+H]$^+$: 498.9/500.9/502.9.

Example 12

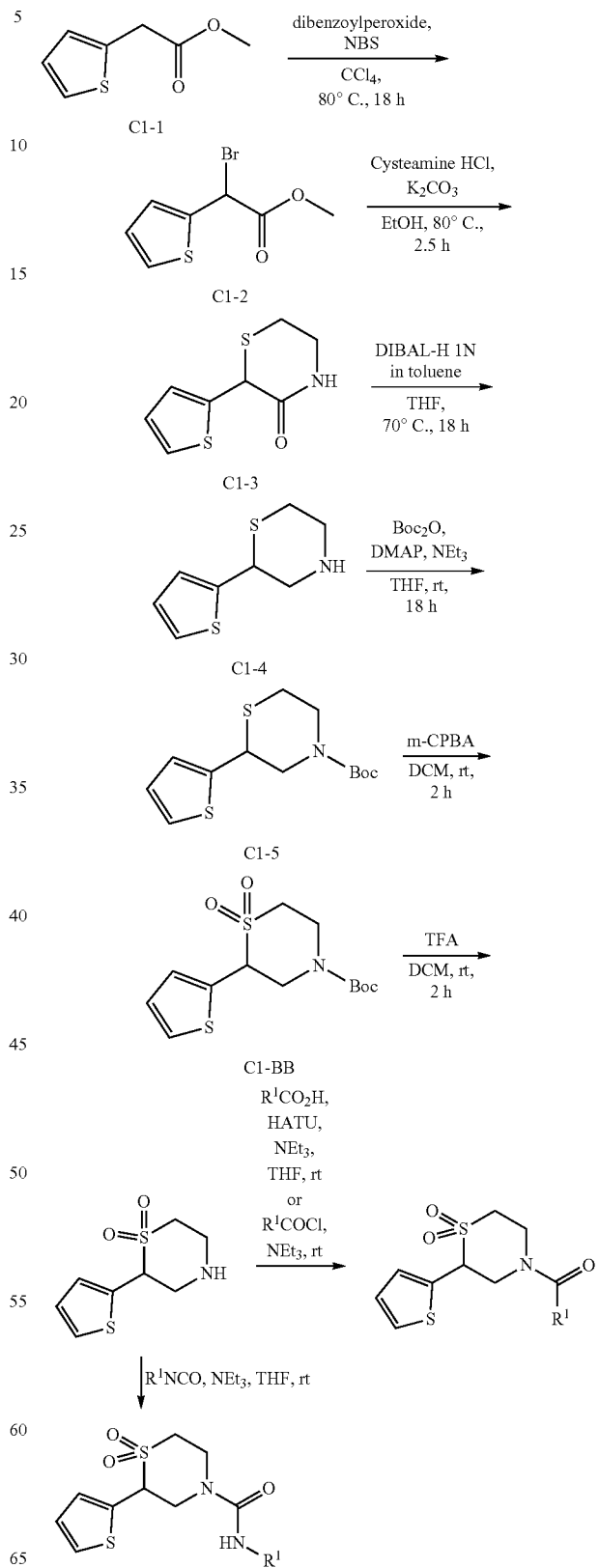

To a solution of methyl 2-(thiophen-2-yl)acetate C1-1 (21.00 g, 17.65 mL, 134.44 mmol, 1 eq.) in CCl$_4$ (450 mL) was added dibenzoylperoxide (870 mg, 2.69 mmol, 1.01 eq.) at rt. The mixture was stirred at reflux for 18 h. After cooling the mixture to rt, water (200 mL) was added, and the aqueous layer was extracted with dichloromethane (3×100 mL). The combined organic layers were dried over sodium sulfate, filtered and concentrated to dryness to afford C1-2 (33.75 g, quantitative) as an orange oil. C1-2 was used in the next step without further purification. $^1$H NMR (400 MHz, CDCl$_3$, 25° C.): 3.82 (s, 3H), 5.70 (s, 1H), 6.95 (dd, J=4.8 Hz, 3.6 Hz, 1H), 7.25 (dd, J=3.6 Hz, 0.8 Hz, 1H), 7.41 (dd, J=5.2 Hz, 0.8 Hz, 1H).

To a solution of C1-2 (31.60 g, 134.41 mmol, 1 eq.) in ethanol (1 L) were added cysteamine hydrochloride (15.27 g, 20.36 mL, 134.41 mmol, 1 eq.) and potassium carbonate (55.73 g, 403.23 mmol, 3 eq.). The mixture was stirred at 80° C. for 2.5 h. After cooling the mixture to rt and evaporation of solvents, the resulting residue was diluted with water (400 mL) and aq. solution of brine (300 mL). The aqueous layer was extracted with ethyl acetate (EA) (5×300 mL). The combined organic layers were dried over sodium sulfate, filtered and concentrated to dryness to afford C1-3 as a crude. The crude was purified by flash chromatography on silica gel using dichloromethane:EA (95:5 to 6:/40) as the eluent to afford C$_{1-3}$ (11.00 g, 55.20 mmol, 41%) as an orange gum. LCMS: m/z calcd C$_8$H$_9$NOS$_2$ 199.01, found 200.0 [M+H]$^+$.

To a solution of C1-3 (11.00 g, 55.20 mmol, 1 eq.) in THF (185 mL) was added DIBAL-H 1N in toluene (220 mL, 220 mmol, 4 eq.) at 0° C. The mixture was stirred at 70° C. for 18 h. After cooling the mixture to rt, water (300 mL) and an aq. solution of potassium tartrate 1N (300 mL) were added at 0° C. The aqueous layer was extracted with dichloromethane (3×300 mL). The combined organic layers were dried over sodium sulfate, filtered and concentrated to dryness. After co-evaporation with ethanol, C$_{1-4}$ was obtained (9.37 g, 50.57 mmol, 92%) as an orange oil. C$_{1-4}$ was used in the next step without further purification. LCMS: m/z calcd C$_8$H$_{11}$NS$_2$ 185.03, found 186.0 [M+H]$^+$.

To a solution of Boc$_2$O (12.14 g, 11.9 mL, 55.62 mmol, 1.1 eq.) in THF (400 mL) were added C$_{1-4}$ (9.37 g, 50.57 mmol, 1 eq.), triethylamine (8.43 mL, 60.68 mmol, 1.2 eq.) and DMAP (620 mg, 5.057 mmol, 0.1 eq.). The mixture was stirred at rt for 18 h. Water (100 mL) and an aq. solution of HCl 1N (100 mL) were added. The aqueous layer was extracted with EA (3×200 mL). The combined organic layers were dried over sodium sulfate, filtered and concentrated to dryness to afford C1-5 as a crude. The residue was purified by flash chromatography on silica gel using cyclohexane:EA (98:2 to 90:10) as the eluent to afford C1-5 (9.67 g, 33.88 mmol, 67%) as an yellow solid. LCMS: m/z calcd C$_{13}$H$_{19}$NO$_2$S$_2$ 285.09, m/z found 186.0 [M-Boc+H]$^+$.

To a solution of C1-5 (8.17 g, 28.62 mmol, 1 eq.) in dichloromethane (230 mL) was added m-CPBA (77%, 24.05 mL, 13.47 g, 60.11 mmol, 2.1 eq.) at 0° C. The mixture was stirred at rt for 2 h. Water (100 mL) and an aq. solution of sodium carbonate (50 mL) were added, and the aqueous layer was extracted with dichloromethane (3×100 mL). The combined organic layers were dried over sodium sulfate, filtered and concentrated to dryness to afford the crude mixture as a yellow oil. The resulting residue was purified by flash chromatography on silica gel using cyclohexane:EA (90:10 to 70:30) as the eluent to afford C1-BB (7.63 g, 24.04 mmol, 84%) as a white solid. LCMS: m/z calcd C$_{13}$H$_{19}$NO$_4$S 317.08, found 218.0 [M-Boc+H]$^+$.

Conditions for the chiral separation of both enantiomers: C1-BB was dissolved in a mixture of isopropanol/DCM (2/1) and then purified by SFC using Lux iC5 (21.2 mm×250 mm, 5 um) with isopropanol/CO$_2$ 40/60 as eluent (isocratic).

General procedure for urea coupling: To a solution of C1-BB (0.60 mmol, 1 eq.) in dichloromethane (5 mL) was added TFA (20 eq.) at rt. The mixture was stirred for 2 h, and then concentrated to dryness. The resulting residue was diluted in THF (5 mL). The appropriate isocyanate (1.1 eq.) and triethylamine (4 eq.) were added. The mixture was stirred at rt for 16 h. Water (15 mL) was added, and the aqueous layer was extracted with EA (3×10 mL). The combined organic layers were dried over sodium sulfate, filtered and concentrated to dryness to afford the crude product, which was purified by column chromatography on silica gel.

General procedure for amide coupling: To a solution of C1-BB (0.40 mmol, 1 eq.) in dichloromethane (3.5 mL) was added TFA (20 eq.) at rt. The mixture was stirred for 2 h and then concentrated to dryness. The resulting residue was diluted in THF (4 mL). The appropriate acid (1.2 eq.), HATU (1.5 eq.) and triethylamine (4 eq.) were added. The mixture was stirred at rt for 16 h. Water (15 mL) was added, and the aqueous layer was extracted with EA (3×10 mL). The combined organic layers were dried over sodium sulfate, filtered and concentrated to dryness to afford the crude product, which was purified by column chromatography on silica gel. Alternatively, the coupling can be accomplished using an acid chloride (1.2 eq.) and triethylamine (2 eq.).

Example 12

N-(3-chloro-4-fluoro-phenyl)-2-[5-(1-methylimidazol-4-yl)-2-thienyl]-1,1-dioxo-1,4-thiazinane-4-carboxamide (5)

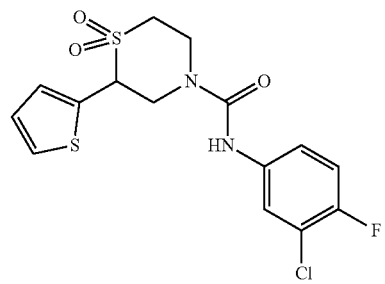 [SMILES: O=C(Nc1ccc(F)c(Cl)c1)N1CCS(=O)(=O)C(c2cccs2)C1]

Compound 5 was obtained as a white powder (90%) by using the general procedure for urea coupling using 3-chloro-4-fluorophenyl isocyanate. $^1$H NMR (400 MHz, DMSO-d$_6$, 80° C.): 3.32-3.42 (m, 2H); 3.51 (ddd, J=14.4 Hz, 9.1 Hz, 5.1 Hz, 1H); 3.66 (dd, J=14.4 Hz, 11.1 Hz, 1H); 4.50-4.59 (m, 2H); 4.90 (dd, J=10.99 Hz, 3.5 Hz, 1H); 7.14 (dd, J=5.1 Hz, 3.5 Hz, 1H); 7.22 (m, 1H), 7.27 (t, J=9.1 Hz, 1H); 7.41 (ddd, J=9.1 Hz, 4.4 Hz, 2.7 Hz, 1H); 7.63 (dd, J=5.1 Hz, 1.2 Hz, 1H); 7.73 (dd, J=6.9 Hz, 2.6 Hz, 1H); 8.89 (s, 1H). LCMS: m/z calcd C$_{15}$H$_{14}$ClFN$_2$O$_3$S$_2$ 388.01, found 388.94 [M+H]$^+$.

Separation of both enantiomers of compound 5 has been performed by Prep-HPLC using Chiralpak IG (20 mm×250 mm, 5 um) as column with ethanol 100% as eluent(isocratic) to give compounds 5a and 5b, the enantiomers of compound 5.

Example 13

(4-bromo-3-chloro-phenyl)-[1,1-dioxo-2-(2-thienyl)-1,4-thiazinan-4-yl]methanone (6)

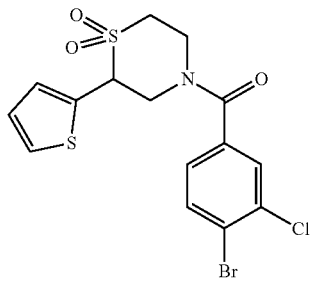 [SMILES: O=C(c1ccc(Br)c(Cl)c1)N1CCS(=O)(=O)C(c2cccs2)C1]

Compound 6 was obtained as a white powder (96%) by using the general procedure for amide coupling using 4-bromo-3-chlorobenzoic acid. $^1$H NMR (400 MHz, DMSO-$d_6$, 80° C.): 3.30-3.39 (m, 1H); 3.48 (td, J=12 Hz, 4.0 Hz, 1H); 3.59 (t, J=12.8 Hz, 1H); 3.72 (t, J=12.8 Hz, 1H); 4.36 (br s, 2H); 5.08 (dd, J=11.2 Hz, 3.2 Hz, 1H); 7.12 (dd, J=5.2 Hz, 3.6 Hz, 1H); 7.17-7.22 (m, 1H); 7.42 (dd, J=8.4 Hz, 2.0 Hz, 1H); 7.62 (dd, J=5.2 Hz, 0.8 Hz, 1H); 7.79 (d, J=2.0 Hz, 1H); 7.85 (d, J=8.0 Hz, 1H). LCMS: m/z calcd $C_{15}H_{13}BrClNO_3S_2$ 432.92, found 433.87-435.87 [M+H]$^+$.

Separation of both enantiomers of compound 6 has been performed by Prep-HPLC using Chiralpak IG (20 mm×250 mm, 5 um) as column with acetonitrile 100% as eluent (isocratic) to give compounds 6a and 6b, the enantiomers of compound 6.

Example 14

(4-chloro-3-fluoro-phenyl)-[1,1-dioxo-2-(2-thienyl)-1,4-thiazinan-4-yl]methanone (7)

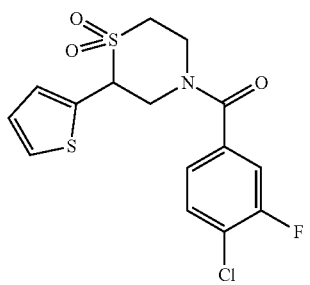 [SMILES: O=C(c1ccc(Cl)c(F)c1)N1CCS(=O)(=O)C(c2cccs2)C1]

Both enantiomers of compound 7 (7a and 7b) were obtained as white solids (30-91%) by using the general procedure for amide coupling using 4-chloro-3-fluorobenzoic acid and each enantiomers of C1-BB. $^1$H NMR (400 MHz, DMSO-$d_6$, 80° C.): 3.34 (d, J=13.2 Hz, 1H), 3.48 (td, J=13.4 Hz, 3.6 Hz, 1H), 3.60 (t, J=12.4 Hz, 1H), 3.73 (dd, J=13.8 Hz, 12 Hz, 1H), 4.38 (br s, 2H), 5.07 (dd, J=11.2 Hz, 3.6 Hz, 1H), 7.12 (dd, J=5.1 Hz, 3.7 Hz, 1H), 7.19 (d, J7=3.2 Hz, 1H), 7.39 (dd, J=8.0 Hz, 1.3 Hz, 1H), 7.58 (dd, J=9.6 Hz, 2.0 Hz, 1H), 7.62 (dd, J=5.2 Hz, 1.2 Hz, 1H), 7.67 (t, J=7.6 Hz, 1H). LCMS: m/z calcd $C_{15}H_{13}ClFNO_3S_2$ 373.00, found 373.93 [M+H]$^+$.

Example 15

(3,4-dichlorophenyl)-[1,1-dioxo-2-(2-thienyl)-1,4-thiazinan-4-yl]methanone (8)

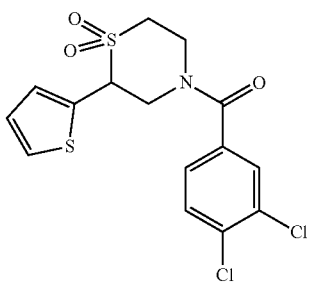 [SMILES: O=C(c1ccc(Cl)c(Cl)c1)N1CCS(=O)(=O)C(c2cccs2)C1]

Both enantiomers of compound 8 (8a and 8b) were obtained as white solids (50-58%) by using the general procedure for amide coupling using 3,4-dichlorobenzoyl chloride and each enantiomers of C1-BB. $^1$H NMR (400 MHz, DMSO-$d_6$, 80° C.): 3.35 (d, J=13.6 Hz, 1H); 3.50 (td, J=13.6 Hz, 3.6 Hz, 1H); 3.60 (t, J=12.8 Hz, 1H); 3.73 (t, J=12.4 Hz, 1H); 4.38 (br s, 2H), 5.08 (dd, J=10.8 Hz, 3.2 Hz, 1H) 7.12 (dd, J=3.2 Hz, 4.8 Hz, 1H); 7.19 (d, J=3.2 Hz, 1H); 7.51 (dd, J=8.0 Hz, 1.6 Hz, 1H); 7.62 (dd, J=5.2 Hz, 1.2 Hz, 1H); 7.71 (dd, J=8.0 Hz, 1H); 7.81 (d, J7=2.0 Hz, 1H). LCMS: m/z calcd $C_{15}H_{13}Cl_2NO_3S_2$ 388.97, found 389.92 [M+H]$^+$.

Example 16

(4-chloro-3-methyl-phenyl)-[1,1-dioxo-2-(2-thienyl)-1,4-thiazinan-4-yl]methanone (9)

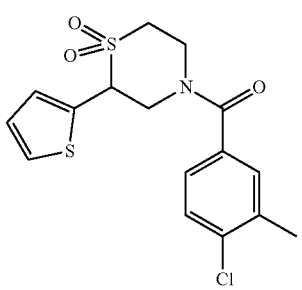 [SMILES: Cc1cc(C(=O)N2CCS(=O)(=O)C(c3cccs3)C2)ccc1Cl]

Both enantiomers of compound 9 (9a and 9b) were obtained as white solids (50-85%) by using the general procedure for amide coupling using 4-chloro-3-methylbenzoyl chloride and each enantiomers of C1-BB. $^1$H NMR (400 MHz, DMSO-$d_6$, 80° C.): 2.37 (s, 3H), 3.33-3.37 (m, 1H); 3.47 (td, J=12.6 Hz, 3.6 Hz, 1H); 3.58 (t, J=12 Hz, 1H); 3.72 (dd, J=11.2 Hz, 14.4 Hz, 1H); 4.39 (br s, 2H), 5.07 (dd, J=11.2 Hz, 3.6 Hz, 1H); 7.11 (dd, J=3.6 Hz, 5.2 Hz, 1H); 7.20 (d, J7=3.6 Hz, 1H); 7.37 (dd, J=8.0 Hz, 2.0 Hz, 1H); 7.48 (d, J7=8.0 Hz, 1H); 7.51 (d, J7=1.6 Hz, 1H); 7.62 (dd, J=5.2 Hz, 1.2 Hz, 1H). LCMS: m/z calcd $C_{16}H_{16}ClNO_3S_2$ 369.03, found 369.96 [M+H]$^+$.

Example 17

(4-chloro-2-fluoro-phenyl)-[1,1-dioxo-2-(2-thienyl)-1,4-thiazinan-4-yl]methanone (10)

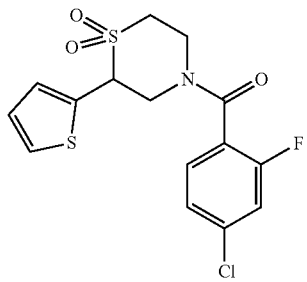 [SMILES: O=C(c1ccc(Cl)cc1F)N1CCS(=O)(=O)C(c2cccs2)C1]

Both enantiomers of compound 10 (10a and 10b) were obtained as white solids (41-46%) by using the general procedure for amide coupling using 4-chloro-2-fluorobenzoic acid and each enantiomers of C1-BB. $^1$H NMR (400 MHz, DMSO-$d_6$, 80° C.): 3.40 (br s, 2H), 3.71 (m, 3H), 4.83 (br s, 1H), 5.01 (d, J=12.0 Hz, 1H), 7.12 (br s, 1H), 7.21 (br s, 1H), 7.40 (d, J=7.6 Hz, 1H), 7.51 (d, J=8.8 Hz, 1H), 7.64 (m, 2H). LCMS: m/z calcd $C_{15}H_{13}ClFNO_3S_2$ 373.00, found 373.94 [M+H]$^+$.

Example 18

(2,4-dichlorophenyl)-[1,1-dioxo-2-(2-thienyl)-1,4-thiazinan-4-yl]methanone (11)

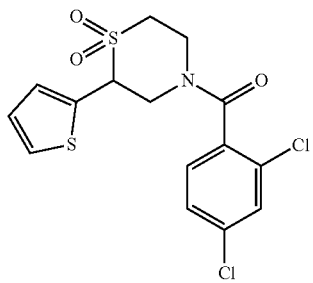 [SMILES: O=C(c1ccc(Cl)cc1Cl)N1CCS(=O)(=O)C(c2cccs2)C1]

Both enantiomers of compound 11 (11a and 11b) were obtained as white solids (60-80%) by using the general procedure for amide coupling using 2,4-dichlorobenzoyl chloride and each enantiomers of C1-BB. $^1$H NMR (400 MHz, DMSO-$d_6$, 25° C.): 3.24-3.91 (m, 5H), 4.83-5.18 (m, 2H), 7.06-7.83 (m, 6H). LCMS: m/z calcd $C_{15}H_{13}Cl_2NO_3S_2$ 389.91, found 389.91 [M+H]$^+$.

Example 19

(4-chloro-2-methyl-phenyl)-[1,1-dioxo-2-(2-thienyl)-1,4-thiazinan-4-yl]methanone (12)

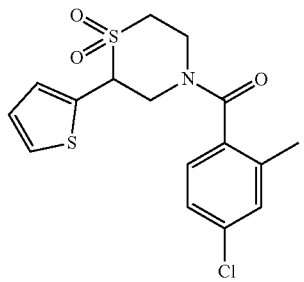 [SMILES: Cc1cc(Cl)ccc1C(=O)N1CCS(=O)(=O)C(c2cccs2)C1]

Both enantiomers of compound 12 (12a and 12b) were obtained as white solids (39-78%) by using the general procedure for amide coupling using 4-chloro-2-methylbenzoic acid and each enantiomers of C1-BB. $^1$H NMR (400 MHz, DMSO-$d_6$, 80° C.): 2.28 (s, 3H), 3.36 (m, 2H), 3.59 (t, J=12.7 Hz, 1H), 3.74 (t, J=12.7 Hz, 1H), 4.41 (br s, 2H), 4.97 (d, J=10.9 Hz, 1H), 7.09-7.11 (m, 1H), 7.20 (br s, 1H), 7.30 (d, J=8.2 Hz, 1H), 7.35 (s, 1H), 7.44 (d, J=8.3 Hz, 1H), 7.59 (d, J=4.8 Hz, 1H). LCMS: m/z calcd $C_{16}H_{16}ClNO_3S_2$ 369.03, found 369.96 [M+H]$^+$.

Example 20

(3-chloro-5-fluoro-phenyl)-[1,1-dioxo-2-(2-thienyl)-1,4-thiazinan-4-yl]methanone (13)

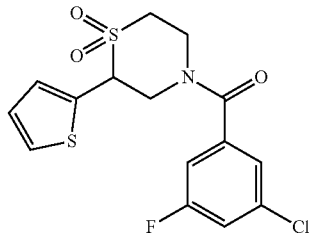 [SMILES: O=C(c1cc(F)cc(Cl)c1)N1CCS(=O)(=O)C(c2cccs2)C1]

Both enantiomers of compound 13 (13a and 13b) were obtained as white solids (67-68%) by using the general procedure for amide coupling using 3-chloro-5-fluorobenzoic acid and each enantiomers of C1-BB. $^1$H NMR (400 MHz, DMSO-$d_6$, 80° C.): 3.29-3.35 (m, 1H), 3.48 (td, J=12.3 Hz, 4.8 Hz, 1H), 3.61 (t, J=13.3 Hz, 1H), 3.74 (dd, J=11.0 Hz, 14.2 Hz, 1H), 4.35 (br s, 2H), 5.05 (ddd, J=10.7 Hz, 3.7 Hz, 0.8 Hz, 1H), 7.12 (dd, J=5.2 Hz, 3.6 Hz, 1H), 7.17-7.21 (m, 1H), 7.36 (dq, J=8.8 Hz, 1.2 Hz, 1H), 7.42-7.48 (m, 2H), 7.60 (dd, J=5.2 Hz, 1.2 Hz, 1H). LCMS: m/z calcd $C_{15}H_{13}ClFNO_3S_2$ 373.00, found 373.94 [M+H]$^+$.

Example 21
(3-chloro-2-fluoro-phenyl)-[1,1-dioxo-2-(2-thienyl)-1,4-thiazinan-4-yl]methanone (14)
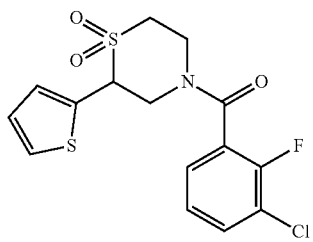 [SMILES: O=C(c1cccc(Cl)c1F)N1CCS(=O)(=O)C(c2cccs2)C1]
Both enantiomers of compound 14 (14a and 14b) were obtained as white solids (49-81%) by using the general procedure for amide coupling using 3-chloro-2-fluorobenzoyl chloride and each enantiomers of C1-BB. $^1$H NMR (400 MHz, DMSO-d$_6$, 25° C.): 3.41-3.95 (m, 5H); 4.83-5.16 (m, 2H); 7.06-7.76 (m, 6H). LCMS: m/z calcd C$_{15}$H$_{13}$ClFNO$_3$S$_2$ 373.00, found 373.93 [M+H]$^+$.
Example 22
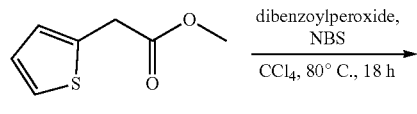
C1-1
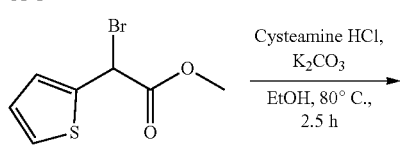
C1-2
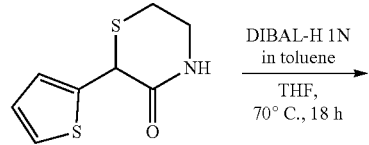
C1-3
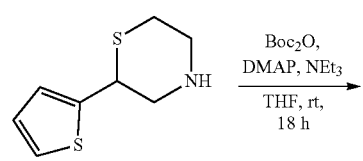
C1-4
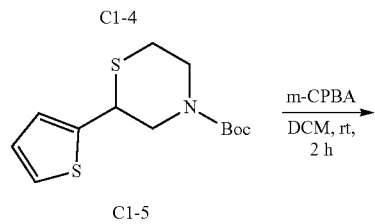
C1-5
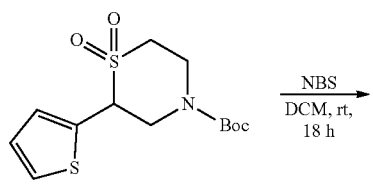
C1-BB
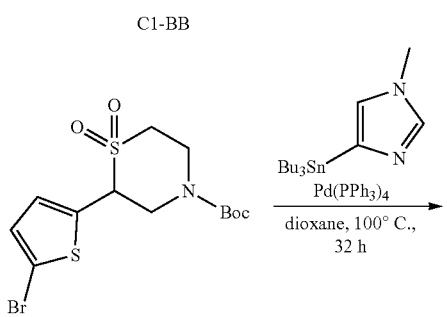
C2-2
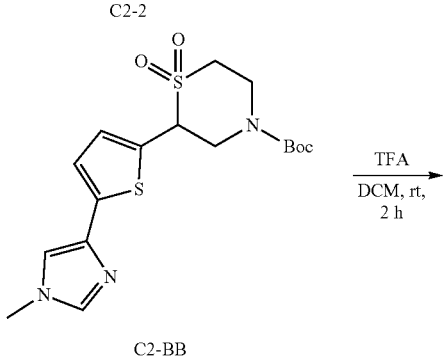
C2-BB
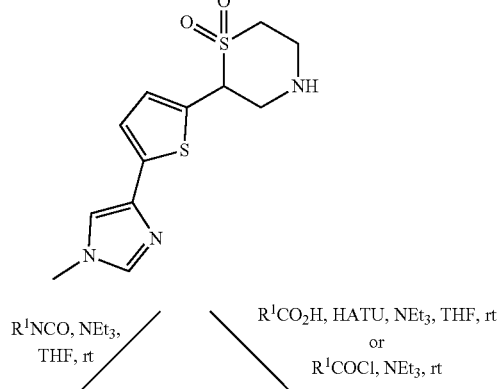
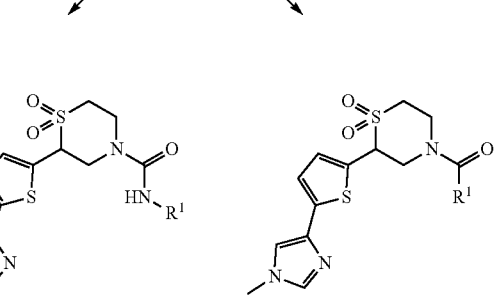

To a solution of C1-BB (2.0 g, 6.3 mmol, 1 eq.) in dimethylformamide (45 mL) was added portion wise at 0° C., NBS (2.47 g, 13.86 mmol, 2.2 eq.). The mixture was stirred at rt for 18 h. Water (100 mL) was added, and the aqueous layer was extracted with LA (3×100 mL). The combined organic layers were washed with a sat. solution of brine (5×60 mL), dried over sodium sulfate, filtered and concentrated to dryness to afford the crude mixture. The resulting residue was purified by flash chromatography on silica gel using cyclohexane:EA (80:20 to 50:50) as the eluent to afford compound C2-2 (2.01 g, 5.07 mmol, 80%) as a white solid. LCMS: m/z calcd $C_{13}H_{18}BrNO_4S_2$ 394.99, found 295.9-297.9 [M-Boc+H]$^+$.

To a solution of C2-2 (2.01 g, 5.072 mmol, 1 eq.) and 1-methyl-4-(tributylstannyl)-1H-imidazole (1.88 g, 5.06 mmol, 1 eq.) in dioxane (25 mL) purged with Ar was added Pd(PPh$_3$)$_4$ (586 mg, 0.507 mmol, 0.1 eq.). The mixture was purged again with Ar. The mixture was heated to 100° C. and stirred for 18 h. 1-methyl-4-(tributylstannyl)-1H-imidazole (620 mg, 1.67 mmol, 0.33 eq.) and Pd(PPh$_3$)$_4$ (293 mg, 0.25 mmol, 0.05 eq.) were added. After 24 h of stirring, water (50 mL) was added, and the aqueous layer was extracted with EA (3×50 mL). The combined organic layers were dried over sodium sulfate, filtered and concentrated to afford the crude mixture. The resulting orange oil was purified by flash chromatography on silica gel using dichloromethane:methanol (99:1 to 90:10) as then eluent to afford C2-BB (1.42 g, 3.57 mmol, 71%) as a pink solid. C2-BB was used in the next step without further purification. LCMS: m/z calcd $C_{17}H_{23}N_3O_4S_2$ 397.11, found 398.0 [M+H]$^+$.

Conditions for the chiral separation of both enantiomers: Compound C2-BB was dissolved in methanol and then purified by SEC using Lux C1 (21.2 mm×250 mm, 5 um) and methanol:CO$_2$ 35:65 (isocratic) as the eluent.

General procedure for urea coupling: To a solution of C2-BB (0.60 mmol, 1 eq.) in dichloromethane (5 mL) was added TFA (20 eq.) at rt. The mixture was stirred for 2 h, and then the mixture was concentrated to dryness. The resulting residue was diluted in THF (5 mL). The appropriate isocyanate (1.1 eq.) and triethylamine (4 eq.) were added. The mixture was stirred at rt for 16 h. Water (15 mL) was added, and the aqueous layer was extracted with EA (3×10 mL). The combined organic layers were dried over sodium sulfate, filtered and concentrated to dryness to afford the crude product, which was purified by flash chromatography on silica gel.

General procedure for amide coupling: To a solution of C2-BB (0.40 mmol, 1 eq.) in dichloromethane (3.5 mL) was added TFA (20 eq.) at rt. The mixture was stirred for 2 h, and then concentrated to dryness. The resulting residue was diluted in THF (4 mL). The appropriate acid (1.2 eq.), HATU (1.5 eq.) and triethylamine (4 eq.) were added. The mixture was stirred at rt for 16 h. Water (15 mL) was added, and the aqueous layer was extracted with EA (3×10 mL). The combined organic layers were dried over sodium sulfate, filtered and concentrated to dryness to afford the crude product, which was purified by flash chromatography on silica gel. Alternatively, the coupling can be accomplished using an acid chloride (1.2 eq.) and triethylamine (2 eq.).

Example 23

N-(3-chloro-4-fluoro-phenyl)-2-[5-(1-methylimidazol-4-yl)-2-thienyl]-1,1-dioxo-1,4-thiazinane-4-carboxamide (15)

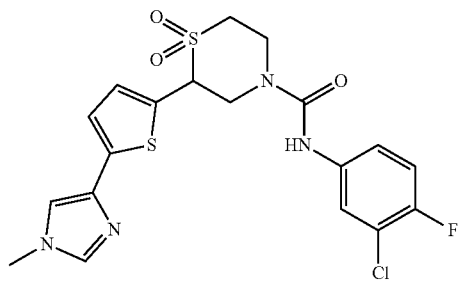 [SMILES: Cn1cnc(-c2ccc(C3CN(C(=O)Nc4ccc(F)c(Cl)c4)CCS3(=O)=O)s2)c1]

Compound 15 was obtained a pink solid (21%) by using the general procedure for urea coupling using 3-chloro-4-fluorophenyl isocyanate starting from C2-BB. $^1$H NMR (400 MHz, DMSO-d$_6$, 25° C.): 3.37-3.50 (m, 3H), 3.59-3.70 (m, 1H), 3.68 (s, 3H), 4.48-4.59 (m, 2H), 4.88 (dd, J=11.2 Hz, 2.8 Hz, 1H), 7.07 (d, J7=3.6 Hz, 1H), 7.20 (d, J7=3.6 Hz, 1H), 7.31 (t, J=9.2 Hz, 1H), 7.36-7.41 (m, 1H), 7.52 (d, J7=0.8 Hz, 1H), 7.61 (s, 1H), 7.73 (dd, J=6.8 Hz, 2.4 Hz, 1H), 9.04 (s, 1H). LCMS: m/z calcd $C_{19}H_{18}ClFN_4O_3S_2$ 468.05, found 469.00 [M+H]$^+$.

Separation of both enantiomers were done by Prep-HPLC using Lux iC5 (21.2 mm×250 mm, 5 um) as column and methanol (0.2% v/v NH$_3$, isocratic) as the eluent to give compounds 15a and 15b, the enantiomers of compound 15.

Example 24

(4-bromo-3-chloro-phenyl)-[2-[5-(1-methylimidazol-4-yl)-2-thienyl]-1,1-dioxo-1,4-thiazinan-4-yl]methanone (16)

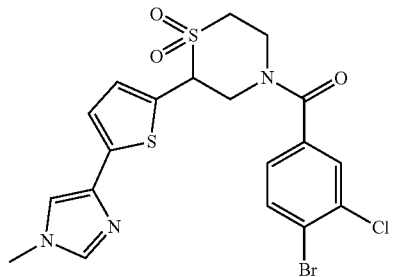 [SMILES: Cn1cnc(-c2ccc(C3CN(C(=O)c4ccc(Br)c(Cl)c4)CCS3(=O)=O)s2)c1]

Compound 16 was obtained a white solid (45%) by using the general procedure for amide coupling using 4-bromo-3-chlorobenzoic acid starting from C2-BB. $^1$H NMR (400 MHz, DMSO-d$_6$, 80° C.): 3.29-3.37 (m, 1H), 3.49 (td, J=13.7 Hz, 3.5 Hz, 1H), 3.6 (t, J=13.7 Hz, 1H), 3.69 (s, 3H), 3.72 (t, J=3.7 Hz, 1H), 4.15-4.66 (br s, 2H), 5.01 (dd, J=11.2 Hz, 3.2 Hz, 1H), 7.07 (d, J7=3.2 Hz, 1H), 7.17 (d, J7=3.6 Hz, 1H), 7.43 (dd, J=4.4 Hz, 2.0 Hz, 1H), 7.44-7.45 (m, 1H), 7.56-7.58 (m, 1H), 7.82 (d, J=2.0 Hz, 1H), 7.87 (d, J=8.4 Hz, 1H). LCMS: m/z calcd $C_{19}H_{17}BrClN_3O_3S_2$ 512.96, found 515.92 [M+H]$^+$.

Separation of both enantiomers were done by SFC using Lux C3 (20 mm×250 mm, 5 um) as column and methanol:CO$_2$ (0.2% v/v NH$_3$, 50:50) as the eluent to give compounds 16a and 16b, the enantiomers of compound 16.

Example 25

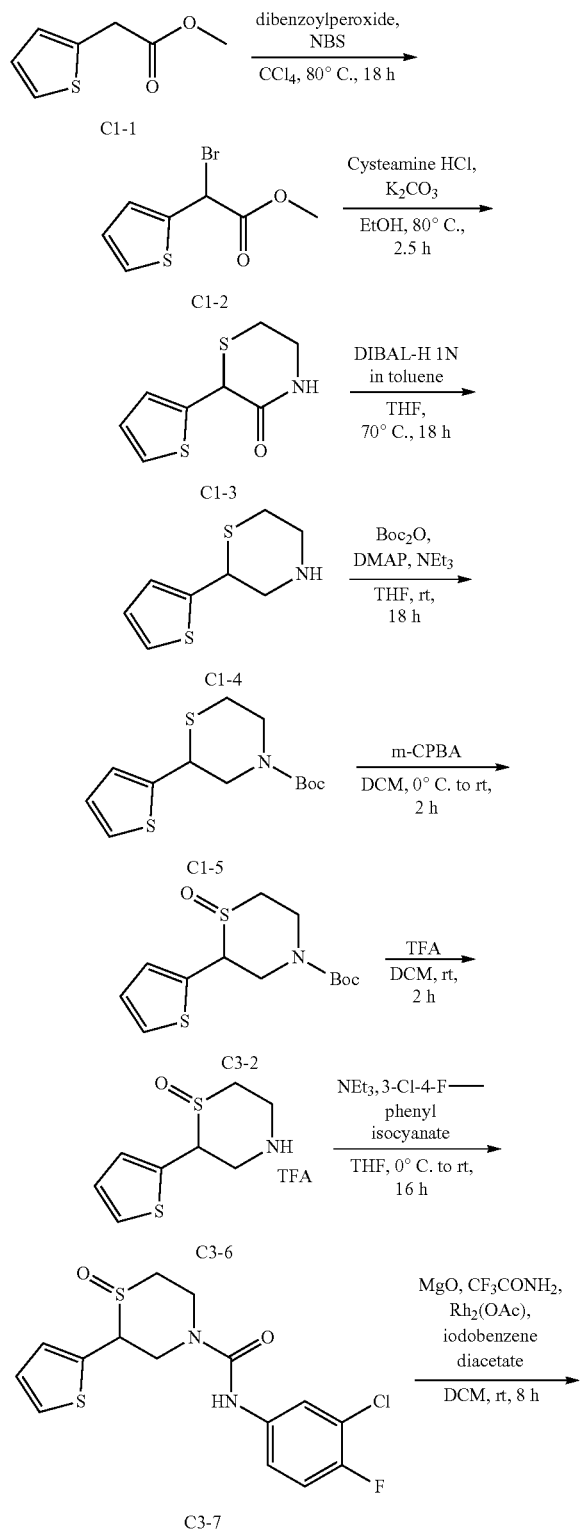

C1-5 was prepared as described herein. To a solution of C1-5 (1.75 g, 6.13 mmol, 1 eq.) in dichloromethane (50 mL) was added portion wise at 0° C. m-CPBA (77%, 1.37 g, 6.13 mmol, 1 eq.). The mixture was stirred at rt for 2 h. Water (10 mL) and a sat. aq. solution of sodium carbonate (60 mL) were added. The aqueous layer was extracted with dichloromethane (3×60 mL). The combined organic layers were dried over sodium sulfate, filtered and concentrated to dryness to afford C3-2 (1.84 g, 6.10 mmol, 99%) as a yellow solid (mixture of diastereomers). LCMS: m/z calcd C$_{13}$H$_{19}$NO$_3$S$_2$ 301.08, found 201.9 [M-Boc+H]$^+$.

To a solution of C3-5 (1.93 g, 6.40 mmol, 1 eq.) in dichloromethane (107 mL) was added TFA (9.50 mL, 128.060 mmol, 20 eq.) at rt. The mixture was stirred et rt for 2 h, and then concentrated to dryness to afford C3-6 as a TFA salt (2.1 g, 6.40 mmol, quantitative) as a blue oil. C3-6 was used without further purification (mixture of diastereomers). LCMS: m/z calcd C$_8$H$_{11}$NOS$_2$ 201.03, found 201.9 [M+H]$^+$.

To a solution of C3-6 (2.02 g, 6.4 mmol, 1 eq.) in THF (56 mL) were added triethylamine (4.45 mL, 32.01 mmol, 5 eq.) and 3-chloro-4-fluorophenyl isocyanate (0.88 mL, 7.043 mmol, 1.1 eq.) at 0° C. The mixture was allowed to reach rt, and then stirred at rt for 16 h. Water (15 mL) was added, and the aqueous layer was extracted with EA (3×10 mL). The combined organic layers were dried over sodium sulfate, filtered and concentrated to dryness to afford the crude mixture as an orange oil. The resulting residue was purified by flash chromatography on silica gel using dichloromethane:methanol (99:1 to 95:5) as the eluent to afford C3-7 (1.82 g, 4.88 mmol, 76%) as a brown solid (mixture of diastereomers). LCMS: m/z calcd C$_{15}$H$_{14}$ClFN$_2$O$_2$S$_2$ 372.02, found 372.9-374.8 [M+H]$^+$.

To a solution of C3-7 (400 mg, 1.08 mmol, 1 eq.) in dichloromethane (10 mL) were added magnesium oxide (173 mg, 4.30 mmol, 4 eq.), trifluoroacetamide (250 mg, 0.19 mmol, 2 eq.), rhodium acetate (13 mg, 3.2 μmol, 0.03 eq.) and iodobenzene diacetate (525 mg, 0.17 mmol, 1.5 eq.). The suspension was stirred at rt for 8 h. The mixture was filtered on Celite®, and the residue was purified by flash chromatography on silica gel using cyclohexane:EA (80:20 to 60:40) as the eluent to afford C3-8 (125 mg, 0.26 mmol, 24%) as an orange solid (mixture of diastereomers). LCMS: m/z calcd C$_{17}$H$_{14}$ClF$_4$N$_3$O$_3$S$_2$ 483.01, found 483.9-485.9 [M+H]$^+$.

Example 26

N-(3-chloro-4-fluoro-phenyl)-1-imino-1-oxo-2-(2-thienyl)-1,4-thiazinane-4-carboxamide (17)

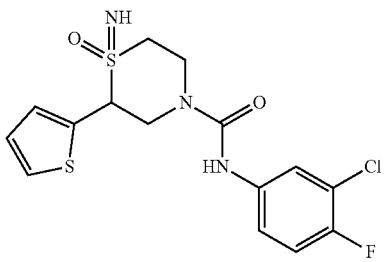 [SMILES: N=S1(=O)CCN(C(=O)Nc2ccc(F)c(Cl)c2)CC1c1cccs1]

To a solution of C3-8 (120 mg, 0.25 mmol, 1 eq.) in methanol (8.6 mL) was added potassium carbonate (171.4 mg, 1.24 mmol, 5 eq.). The mixture was stirred at rt for 1 h, and then filtered on cotton. The solvent was removed under reduced pressure. The resulting residue was purified by flash chromatography on silica gel using dichloromethane:methanol (99:1 to 95:5) as the eluent to afford compound 17 (62 mg, 0.016 mmol, 64%) as a white solid (mixture of diastereomers). $^1$H NMR (400 MHz, DMSO, 25° C.): 3.11-3.25 (m, 2H), 3.35-3.62 (m, 2.8H), 3.78 (s, 0.6H), 4.34-4.49 (m, 2H), 4.54 (dd, J=10.8 Hz, 2.7 Hz, 0.6H), 4.77 (dd, J=11.0 Hz, 2.2 Hz, 0.4H), 7.06-7.11 (m, 1H), 7.12-7.16 (m, 1H), 7.26 (t, J=9.1 Hz, 1H), 7.31-7.37 (m, 1H), 7.59 (t, J=4.8 Hz, 1H), 7.70 (dd, J=7.0 Hz, 2.5 Hz, 1H), 8.94 (s, 0.4H), 8.95 (s, 0.6H). LCMS: m/z calcd $C_{15}H_{15}Cl_1FN_3O_2S_2$ 387.03, found 387.9-389.9 [M+H]$^+$.

To a solution of 2-phenylthiomorpholin-3-one (1 eq., 2.5 g, 12.94 mmol, 1 eq.) in THF (45 mL) was added at 0° C., DIBAL-H 1N in toluene (4 eq., 51.8 mL, 51.74 mmol, 4 eq.). The mixture was stirred at 80° C. for 5 h. EA (5 mL), water (20 mL) and an aqueous solution of tartrate de sodium and potassium 1N (50 mL) were added. The aqueous layer was extracted with EA (3×50 mL). The organic layer was dried over sodium sulfate, filtered and concentrated to afford the crude mixture as a colorless oil. The resulting residue was purified by flash chromatography on silica gel using dichloromethane:methanol (100:0 to 95:5) as the eluent to afford C23-2 (1.37 g, 7.63 mmol, 59%) as a yellow solid. LCMS: m/z calcd $C_{10}H_{13}NS$ 179.28, found 180.0 [M+H]$^+$.

To a solution of C23-2 (1.00 g, 5.58 mmol, 1 eq.) in THF (44. mL) were added Boc$_2$O (1.34 g, 6.14 mmol, 1.1 eq.), DMAP (68 mg, 0.56 mmol, 0.1 eq.) and then triethylamine (0.68 g, 930 μL, 6.69 mmol, 1.2 eq.). The mixture was stirred at rt for 18 h. Water (100 mL) and an aq. solution of HCl 1 M (50 mL) were added. The aqueous layer was extracted with EA (3×200 mL). The combined organic layers were dried over sodium sulfate, filtered and concentrated to dryness to afford the crude mixture as an orange oil. The resulting residue was purified by flash chromatography on silica gel using cyclohexane:EA (98:2 to 90:10) as the eluent to afford C23-3 (620 mg, 2.23 mmol, 40%) as a white solid. LCMS: m/z calcd $C_{15}H_{21}NO_2S$ 279.13, found 180.0 [M-Boc+H]$^+$.

To a solution of C23-3 (980 mg, 3.51 mmol, 1 eq.) in dichloromethane (28. mL) was added m-CPBA (77%, 1.65 g, 7.37 mmol, 2.1 eq.) at rt. The mixture was stirred for 2 h at rt. Water (100 mL) and an aq. Sat. solution of sodium carbonate (50 mL) were added. The aqueous layer was extracted with dichloromethane (3×100 mL). The combined organic layers were dried over sodium sulfate, filtered and

Example 27

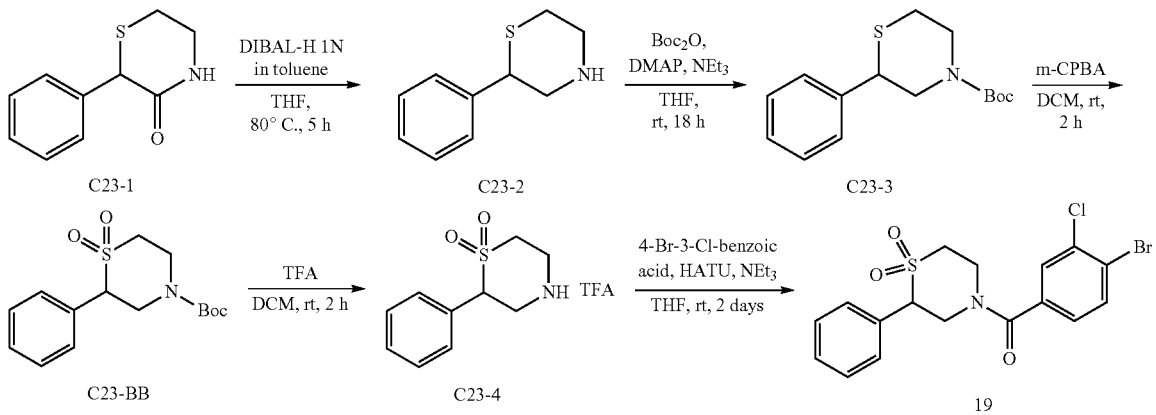

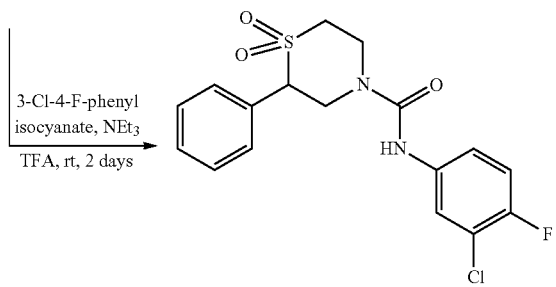

Example 28

N-(3-chloro-4-fluoro-phenyl)-1,1-dioxo-2-phenyl-1,4-thiazinane-4-carboxamide (18)

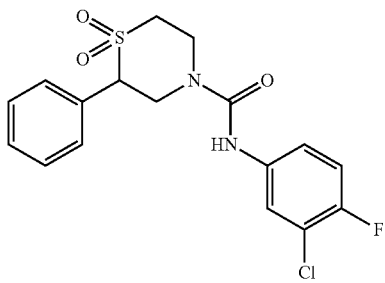 [SMILES: O=C(Nc1ccc(F)c(Cl)c1)N1CCS(=O)(=O)C(c2ccccc2)C1]

To a solution of C23-BB (100 mg, 0.32 mmol, 1 eq.) in dichloromethane (2 mL) was added TFA (500 μL, 6.73 mmol, 21 eq.). The mixture was stirred at rt for 2 h. The mixture was concentrated to dryness and co-evaporated with diethyl ether. The resulting residue was suspended in THF (2 mL) and then 3-chloro-4-fluorophenyl isocyanate (66.11 mg, 0.048 mL, 0.39 mmol, 1.2 eq.) and triethylamine (130 μL, 0.96 mmol, 3 eq.) were added. The mixture was stirred at rt for 2 days. Water (15 mL) was added, and the aqueous layer was extracted with EA (3×20 mL). The combined organic layers were dried over sodium sulfate, filtered and concentrated to dryness to afford the crude product as a white foam. The crude was purified by flash chromatography on silica gel using dichloromethane:EA (100:0 to 80:20) as the eluent to afford compound 18 as a white solid. $^1$H NMR (400 MHz, DMSO-d$_6$, 25° C.): 3.36-3.48 (m, 3H), 3.78 (dd, J=13.9 Hz, 11.6 Hz, 1H), 4.49-4.54 (m, 1H), 4.59 (dd, J=12.0 Hz, 2.8 Hz, 2H), 7.30 (t, J=8.8 Hz, 1H), 7.37-7.46 (m, 6H), 7.75 (dd, J=6.8 Hz, 2.4 Hz, 1H), 9.00 (s, 1H). LCMC: m/z calcd $C_{17}H_{16}C_1FN_2O_3S$ 382.06, found 382.98 [M+H]$^+$.

Separation of both enantiomers of compound 18 was done by Prep-HPLC using Chiralpak IG (20 mm×250 mm, 5 um) as column and heptane:ethanol (80:20) as the eluent to give compounds 18a and 18b, the enantiomers of compound 18.

Example 29

(4-bromo-3-chloro-phenyl)-(1,1-dioxo-2-phenyl-1,4-thiazinan-4-yl)methanone (19)

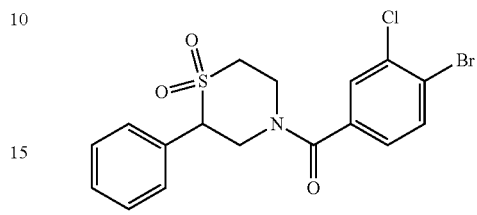

To a solution of C23-BB (100 mg, 0.32 mmol, 1 eq.) in dichloromethane (2 mL) was added TFA (500 μL, 6.73 mmol, 21 eq.). The mixture was stirred at rt for 2 h. The mixture was concentrated to dryness and co-evaporated with diethyl ether. The residue was suspended in THF (3 mL) and then 4-bromo-3-chlorobenzoic acid (90.74 mg, 0.39 mmol, 1.2 eq.), HATU (146.53 mg, 0.39 mmol, 1.2 eq.) and triethylamine (130 μL, 0.96 mmol, 3 eq.) were added. The mixture was stirred at rt for 2 days. Water (15 mL) was added, and the aqueous layer was extracted with EA (3×20 mL). The combined organic layers were dried over sodium sulfate, filtered and concentrated to dryness to afford the crude product as a white foam. The crude product was purified by flash chromatography on silica gel using dichloromethane:EA (100:0 to 80:20) as the eluent to afford compound 19 (83.00 mg, 0.19 mmol, 60%) as a white solid. NMR (400 MHz, DMSO-d$_6$, 80° C.): 3.25-3.32 (m, 1H), 3.45-3.54 (m, 1H), 3.58-3.63 (m, 1H), 3.78-3.88 (m, 1H), 4.37 (br s, 2H), 4.72 (dd, J=. 11.6 Hz, 0.4 Hz, 1H), 7.38-7.46 (m, 6H), 7.81 (d, J=2.0 Hz, 1H), 7.84 (d, J=8.0 Hz, 1H). LCMS: m/z calcd $C_{17}H_{15}BrClFNO_3S$ 426.96, found 429.92 [M+H]$^+$.

Separation of both enantiomers of compound 19 was done by Prep-HPLC using Lux C4 (20 mm×250 mm, 5 um) as column and methanol (100%, isocratic) as the eluent to give compounds 19a and 19b, the enantiomers of compound 19.

Example 30

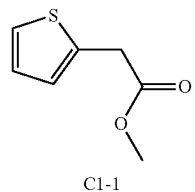

C1-1 dibenzoylperoxide, NBS, CCl$_4$, 80° C., 18 h
100%

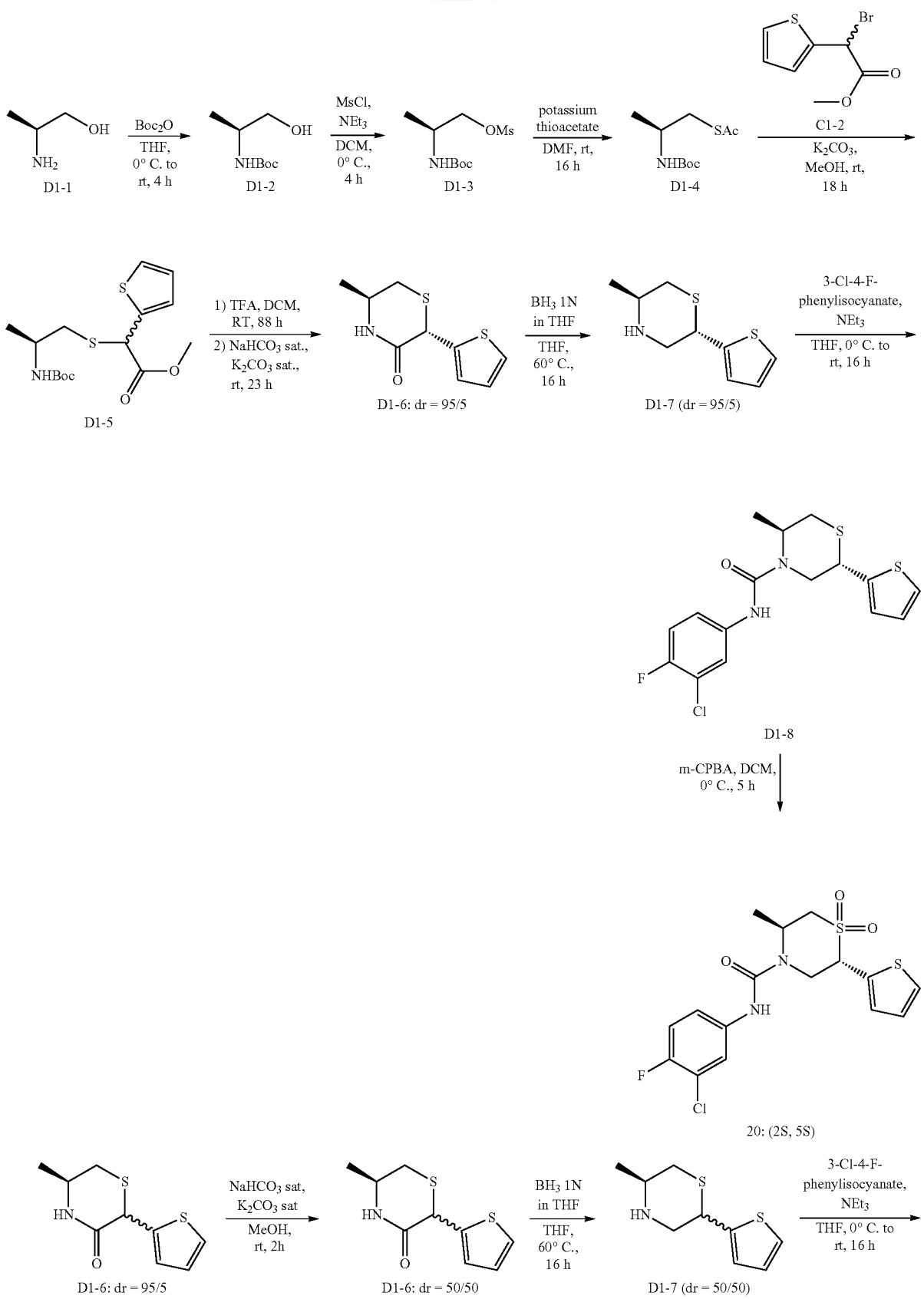

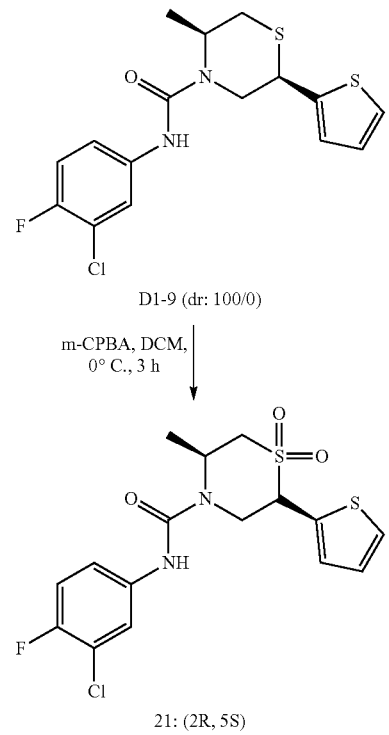

D1-9 (dr: 100/0)

m-CPBA, DCM,
0° C., 3 h

21: (2R, 5S)

To a solution of methyl 2-(thiophen-2-yl)acetate C1-1 (21.00 g, 17.65 mL, 134.44 mmol, 1 eq.) in carbon tetrachloride (450 mL) was added dibenzoylperoxide (870 mg, 2.69 mmol, 1.01 eq.) at rt. The mixture was stirred at reflux overnight. After cooling the mixture to rt, water (200 mL) was added, and the aqueous layer was extracted with dichloromethane (3×100 mL). The combined organic layers were dried over sodium sulfate, filtered and concentrated to dryness to afford C1-2 (33.75 g, quantitative) as an orange oil. C1-2 was used in the next step without further purification.

To a solution of L-alaninol (5.00 g, 66.57 mmol, 1 eq.) in THF (337 mL) was added dropwise a solution of $Boc_2O$ (14.53 g, 14.24 mL, 66.57 mmol, 1 eq.) in THF (843 mL) at 0° C. in 10 mins. The white slurry was stirred at rt for 4 h. The THF was evaporated, and the residue was diluted in EA (200 mL). Water (200 mL) was added, and the aqueous layer was extracted with EA (2×200 mL). The combined organic layers were dried over sodium sulfate, filtered and concentrated to dryness to afford the crude D1-2 (11.17 g, 63.75 mmol, 96%) as a white solid.

To a solution of D1-2 (11.17 g, 63.75 mmol, 1 eq.) in dichloromethane (200 mL) were added at 0° C., triethylamine (14.80 mL, 106.51 mmol, 1.6 eq.) and mesyl chloride (6.7 mL, 86.54 mmol, 1.3 eq.). The beige solution was stirred at 0° C. for 4 h. The mixture was diluted with water (200 mL), and the aqueous layer was extracted with dichloromethane (200 mL). The combined organic layers were dried over sodium sulfate, filtered and concentrated to dryness to afford D1-3 (16.15 g, 63.75 mmol, 100%) as a pale beige solid. LCMS: m/z calcd $C_9H_{19}NO_5S$ 253.10, m/z found 276.1 [M+Na]$^+$.

To a solution of D1-3 (16.15 g, 63.76 mmol, 1 eq.) in dimethylformamide (200 mL) was added at rt, potassium thioacetate (10.92 g, 95.63 mmol, 1.5 eq.). The yellow solution was stirred at rt for 16 h, and then water (200 mL) and diethyl ether (200 mL) were added. The aqueous layer was extracted with diethyl ether (200 mL). The combined organic layers were washed with water (2×400 mL), dried over sodium sulfate, filtered and concentrated to dryness to afford D1-4 (13.6 g, 58.29 mmol, 91%) as a pale yellow solid. LCMS: m/z calcd $C_{10}H_{19}NO_3S$ 233.11, m/z found 256.1 [M+Na]$^+$.

To a solution of C1-2 (2.0 g, 8.507 mmol, 1.5 eq.) in methanol (56 mL) were added D1-4 (1.32 g, 5.67 mmol, 1 eq.) and potassium carbonate (1.18 g, 8.507 mmol, 1.5 eq.). The brown solution was stirred at rt for 18 h. Water (100 mL) was added, and the aqueous layer was extracted with EA (2×50 mL). The combined organic layers were dried over sodium sulfate, filtered and concentrated to dryness to give the crude mixture. The residue was purified by flash chromatography on silica gel using cyclohexane:EA (100:0 to 80:20) as the eluent to afford D1-5 (1.13 g, 3.26 mmol, 57%) as a pale yellow solid. LCMS: m/z calcd $C_{15}H_{23}NO_4S_2$ 345.11, m/z found 368.0 [M+Na]$^+$.

To a solution of D1-5 (7.38 g, 21.36 mmol, 1 eq.) in dichloromethane (60 mL) was added TEA (8.28 g, 5.4 mL, 72.65 mmol, 3.4 eq.). The yellow solution was stirred at rt for 88 h. A sat. aq. solution of sodium hydrogen carbonate (450 mL) and a sat. solution of potassium carbonate (70 mL) were added. The mixture was stirred for 23 h, and the aqueous layer was extracted with dichloromethane (3×300 mL). The organic layer was dried over sodium sulfate, filtered and concentrated to dryness to afford D1-6 (3.67 g, 17.20 mmol, 81%) as a red solid. D1-6 was isolated as a quasi-pure diastereomer (2S,5S, dr=95/5).

D1-6 (1.0 g) was solubilized in methanol (400 mL), and a sat. aq. solution of sodium hydrogen carbonate (80 mL) was added. The solution was stirred at rt for 2 h. Racemization was monitored by $^1$H NMR. Water (300 mL) and dichloromethane (200 mL) were added. The aqueous layer was extracted with dichloromethane (3×200 mL). The organic phase was dried over sodium sulfate, filtered and concentrated to dryness to afford D1-6 as a racemic mixture (0.94 g). LCMS: m/z calcd $C_9H_{11}NOS_2$ 213.03, m/z found 214.0 $[M+H]^+$.

To a solution of D1-6 (dr=95/5, 500 mg, 2.34 mmol, 1 eq.) in THF (14 mL) was added a solution of 1N $BH_3$ in THF (11.72 mL, 11.72 mmol, 5 eq.). The mixture was stirred in a sealed tube at 60° C. for 16 h. After cooling the solution to rt, methanol (10 mL) was added dropwise, and the reaction mixture was stirred at reflux for 2 h. After cooling the solution to rt, the mixture was concentrated to dryness. The resting residue was purified by flash chromatography on silica gel using dichloromethane:methanol (100:0 to 95:5) as the eluent to afford D1-7 (dr=95/5, 314 mg, 1.58 mmol, 67%) as a yellow oil. LCMS: m/z calcd $C_9H_{13}NOS_2$ 199.05, m/z found 200.0 $[M+H]^+$.

To a solution of D1-7 (dr=95/5, 284 mg, 1.42 mmol, 1 eq.) in THF (1.2 mL) at 0° C., were added triethylamine (18 µL, 5.7 mmol, 4 eq.) and 3-chloro-4-fluorophenyl isocyanate (268.88 mg, 1.57 mmol, 1.1 eq.). The mixture was stirred at rt for 16 h. Water (10 mL) was added, and the aqueous layer was extracted with dichloromethane (3×50 mL). The organic layer was dried over sodium sulfate, filtered and concentrated to dryness to afford the crude product. The resulting residue was purified by flash chromatography on silica gel using cyclohexane:EA (10:0 to 70:30) as the eluent, followed by a flash chromatography on reverse phase using ACN:water (0:100 to 45:55) as the eluent to afford D1-8 (dr=100/0, 165 mg, 0.44 mmol, 31%) as a white solid. LCMS: m/z calcd $C_{16}H_{16}ClFN_2OS_2$ 370.04, m/z found 370.9-372.9 $[M+H]^+$.

Example 30

(2S,5S)—N-(3-chloro-4-fluoro-phenyl)-5-methyl-1,1-dioxo-2-(2-thienyl)-1,4-thiazinane-4-carboxamide (20)

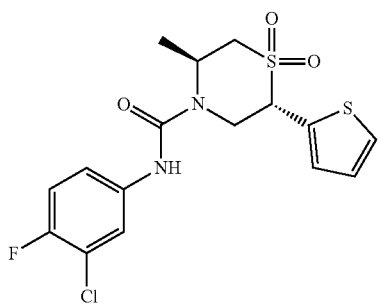 [SMILES: C[C@H]1CS(=O)(=O)[C@H](c2cccs2)CN1C(=O)Nc1ccc(F)c(Cl)c1]

To a solution of D1-8 (dr=100/0, 163 mg, 0.44 mmol, 1 eq.) in dichloromethane (5 mL) was added at 0° C., m-CPBA (77%, 196.98 mg, 0.88 mmol, 2 eq.). The mixture was stirred at 0° C. for 3 h. In order to complete the conversion, an additional equivalent of m-CPBA (77%, 19.7 mg, 0.088 mmol, 0.2 eq.) was added, and the mixture was stirred at rt for 2 h. Water (4 mL) was added, and a sat. aq. solution of sodium carbonate (18 mL) were added. The aqueous layer was extracted with dichloromethane (3×15 mL). The organic layer was dried over sodium sulfate, filtered and concentrated to dryness to afford the crude mixture as an orange solid. The resulting residue was triturated in diethyl ether and diisopropylether, precipitated in a mixture of dichloromethane:pentane to afford compound 20 (dr=100/0, 60.3 mg, 0.15 mmol, 67%) as a white solid. NMR (400 MHz, DMSO-$d_6$, 25° C.): 1.46 (d, J=7.2 Hz, 3H), 3.37-3.39 (m, 1H), 3.47 (dd, J=14.8 Hz, 5.2 Hz, 1H), 4.09 (dd, J=15.1 Hz, 3.1 Hz, 1H), 4.53 (dd, J=15.1 Hz, 5.2 Hz, 1H), 4.73-4.81 (m, 1H), 4.91-4.96 (m, 1H), 7.07 (dd, J=5.1 Hz, 3.6 Hz, 1H), 7.23-7.25 (m, 1H), 7.31 (t, J=9.0 Hz, 1H), 7.34-7.38 (m, 1H), 7.59 (dd, J=5.1 Hz, 1.1 Hz, 1H), 7.72 (dd, J=6.8 Hz, 2.6 Hz, 1H), 9.04 (s, 1H). LCMS: m/z calcd $C_{16}H_{16}ClF_2N_2O_3S_2$ 402.03, found 402.96-404.96 $[M+H]^+$.

Example 31

(2R,5S)—N-(3-chloro-4-fluoro-phenyl)-5-methyl-1,1-dioxo-2-(2-thienyl)-1,4-thiazinane-4-carboxamide (21)

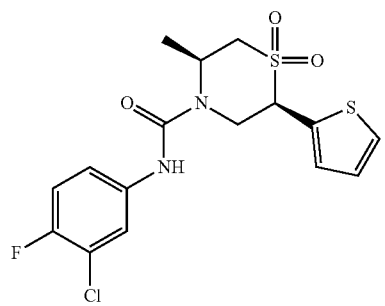 [SMILES: C[C@H]1CS(=O)(=O)[C@@H](c2cccs2)CN1C(=O)Nc1ccc(F)c(Cl)c1]

To a solution of D1-6 (dr=50/50, 974 mg, 4.57 mmol, 1 eq.) in THF (27 mL) was added a solution of 1N $BH_3$ in THF (22.83 mL, 22.83 mmol, 5 eq.). The mixture was stirred in a sealed tube at 60° C. for 16 h. After cooling the solution to rt, methanol (20 mL) was added dropwise, and the mixture was stirred at reflux for 2 h. After cooling to rt, the mixture was concentrated to dryness. The resting residue was purified by flash chromatography on silica gel using dichloromethane:methanol (100:0 to 95:5) as the eluent to afford D1-7 (dr=50/50, 570 mg, 2.86 mmol, 63%) as a yellow oil. LCMS: m/z calcd $C_9H_{13}NOS_2$ 199.05, found 200.0 $[M+H]^+$.

To a solution of D1-7 (dr=50/50, 570 mg, 2.86 mmol, 1 eq.) in THF (24 mL) at 0° C., were added triethylamine (1.59 mL, 11.44 mmol, 4 eq.) and 3-chloro-4-fluorophenyl isocyanate (539.65 mg, 3.15 mmol, 1.1 eq.). The reaction was stirred at rt for 16 h. Water (100 mL) wad added, and the aqueous layer was extracted with dichloromethane (3×100 mL). The organic layer was dried over sodium sulfate, filtered and concentrated to dryness to afford the crude product. The resulting residue was purified by flash chromatography on reverse phase using ACN:water (43:57 to 45:55) as the eluent to afford D1-9 (dr=0/100, 137 mg, 0.37 mmol, 13%) as a white solid. LCMS: m/z calcd $C_{16}H_{16}ClFN_2OS_2$ 370.04, found 371.0-373.0 $[M+H]^+$.

To a solution of D1-9 (dr=0/100, 172.00 mg, 0.46 mmol, 1 eq.) in dichloromethane (5.3 mL) was added at 0° C., m-CPBA (77%, 207.86 mg, 0.93 mmol, 2 eq.). The mixture was stirred at 0° C. for 3 h. Water (5 mL) and a sat. aq. solution of sodium carbonate (18 mL) were added. The aqueous layer was extracted with dichloromethane (3×15 mL). The organic layer was dried over sodium sulfate, filtered and concentrated to dryness to afford the crude mixture as an orange solid. The resulting residue was purified by flash chromatography on silica gel using cyclohexane:EA (100:0 to 50:50) as the eluent to afford compound 21 (dr=0/100, 78.47 mg, 0.19 mmol, 42%) as a white solid. $^1$H NMR (400 MHz, DMSO-$d_6$, 25° C.): 1.47 (d, J7=7.2 Hz, 3H), 3.40 (dd, J=14.2 Hz, 2.1 Hz, 1H), 3.53 (dd, J=14.5 Hz, 5.4 Hz, 1H), 3.79 (dd, J=15.0 Hz, 11.5 Hz, 1H), 4.52 (dt, J=14.8 Hz, 3.2 Hz, 1H), 4.92 (dd, J=11.6 Hz, 3.4 Hz, 1H), 5.02 (m, 1H), 7.16 (dd, J=5.1 Hz, 3.7 Hz, 1H), 7.26 (d, J7=3.5 Hz, 1H), 7.31 (t, J=9.1 Hz, 1H), 7.36-7.40 (m, 1H), 7.67 (d, J7=5.0 Hz, 1H), 7.72 (dd, J=2.4 Hz, 6.8 Hz, 1H), 9.01 (s, 1H). LCMS: m/z calcd $C_{16}H_{16}ClFN_2O_3S_2$ 402.03, found 402.96-404.96 [M+H]$^+$.
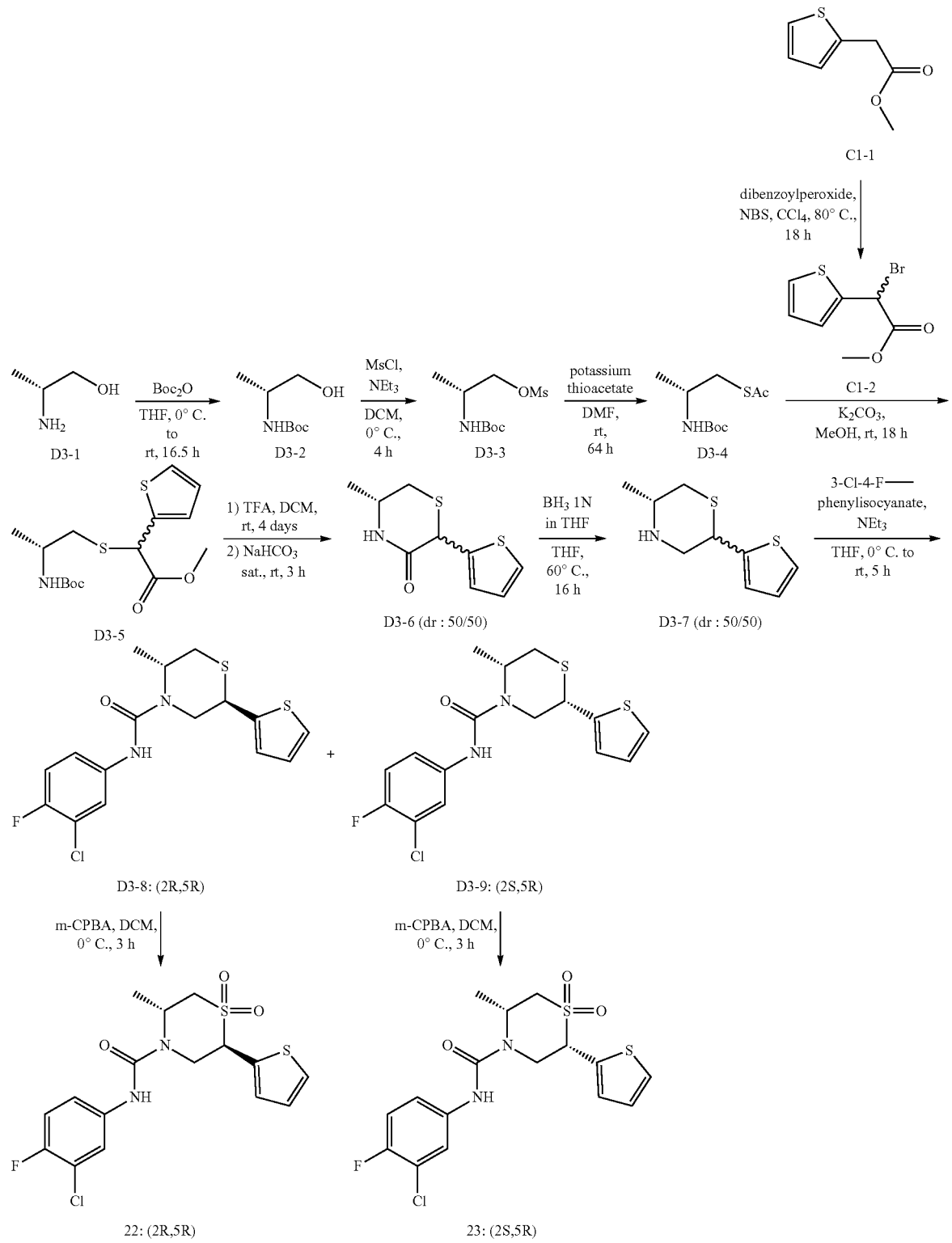

To a solution of methyl 2-(thiophen-2-yl)acetate C1-1 (21.00 g, 17.65 mL, 134.44 mmol, 1 eq.) in CCl$_4$ (450 mL) was added dibenzoylperoxide (870 mg, 2.69 mmol, 1.01 eq.) at rt. The mixture was stirred at reflux overnight. After cooling the mixture to rt, water (200 mL) was added. The aqueous layer was extracted with dichloromethane (3×100 mL). The combined organic layers were dried over sodium sulfate, filtered and concentrated to dryness to afford C1-2 (33.75 g, quantitative) as an orange oil. C1-2 was used in the next step without further purification.

To a solution of R-alaninol (3.40 g, 3.52 mL; 45.30 mmol, 1 eq.) in THF (35 mL) was added dropwise a solution of Boc$_2$O (9.88 g, 9.69 mL, 45.30 mmol, 1 eq.) in THF (100 mL) at 0° C. in 10 mins. The white slurry was stirred at rt for 16 h. THF was evaporated, and the residue was diluted in EA (200 mL). An aq. solution of hydrochloric acid 0.1N (35 mL) was added, and the aqueous layer was extracted with EA (3×35 mL). The combined organic layers were dried over sodium sulfate, filtered and concentrated to dryness to afford the crude D3-2 (6.87 g, 39.23 mmol, 87%) as a white solid.

To a solution of D3-2 (6.80 g, 38.81 mmol, 1 eq.) in dichloromethane (110 mL) were added at 0° C., triethylamine (8.63 mL, 62.09 mmol, 1.6 eq.) and mesyl chloride (3.9 mL, 50.45 mmol, 1.3 eq.). The beige solution was stirred at 0° C. for 4 h. The mixture was diluted with water (110 mL). The aqueous layer was extracted with dichloromethane (110 mL). The combined organic layers were dried over sodium sulfate, filtered and concentrated to dryness to afford D3-3 (9.83 g, 38.81 mmol, 100%) as an orange solid. LCMS: m/z calcd C$_9$H$_{19}$NO$_5$S 253.10, found 276.0 [M+Na]$^+$.

To a solution of D3-3 (9.83 g, 38.81 mmol, 1 eq.) in dimethylformamide (128 mL) was added at rt, potassium thioacetate (6.65 g, 58.21 mmol, 1.5 eq.). The yellow solution was stirred at rt for 64 h. Water (130 mL) and diethyl ether (130 mL) were added. The aqueous layer was extracted with diethyl ether (130 mL). The combined organic layers were washed with water (2×200 mL), dried over sodium sulfate, filtered and concentrated to dryness to afford D3-4 (6.46 g, 27.69 mmol, 71%) as a pale yellow oil. LCMS: m/z calcd C$_{10}$H$_{19}$NO$_3$S 233.11, found 256.2 [M+Na]$^+$.

To a solution of C1-2 (9.6 g, 40.82 mmol, 1.5 eq.) in methanol (260 mL) were added D3-4 (6.35 g, 27.21 mmol, 1 eq.) and potassium carbonate (5.64 g, 40.82 mmol, 1.5 eq.). The brown solution was stirred at rt for 18 h. Water (250 mL) was added, and the aqueous layer was extracted with EA (3×250 mL). The combined organic layers were dried over sodium sulfate, filtered and concentrated to dryness to give the crude mixture. The resulting residue was purified by flash chromatography on silica gel using cyclohexane:EA (100:0 to 70:30) as the eluent to afford D3-5 (5.47 g, 15.83 mmol, 40%) as a pale yellow oil. LCMS: m/z calcd C$_{15}$H$_{23}$NO$_4$S$_2$ 345.11, found 368.0 [M+Na]$^+$.

To a solution of D3-5 (5.47 g, 15.83 mmol, 1 eq.) in dichloromethane (46 mL) was added TFA (6.14 g, 4.0 mL, 53.85 mmol, 3.4 eq.). The yellow solution was stirred at rt for 4 days. A sat. aq. solution of sodium hydrogen carbonate (300 mL) was added, and the mixture was stirred for 3 h. The aqueous layer was extracted with dichloromethane (3×150 mL). The organic layer was dried over sodium sulfate, filtered and concentrated to dryness to afford the crude mixture. The resulting residue was purified by flash chromatography on silica gel using cyclohexane:EA (80:20 to 50:50) as the eluent to afford D3-6 (990 mg, 4.64 mmol, 29%) as a red solid. D3-6 was isolated as a racemic mixture (dr=50/50). LCMS: m/z calcd C9H$_{11}$NOS$_2$ 213.03, found 214.0 [M+H]$^+$.

To a solution of D3-6 (dr=50/50, 720 mg, 3.38 mmol, 1 eq.) in THF (20 mL) was added a solution of 1N BH$_3$ in THF (16.88 mL, 16.88 mmol, 5 eq.). The mixture was stirred in a sealed tube at 60° C. for 16 h. After cooling the solution to rt, methanol (15 mL) was added dropwise, and the mixture was stirred at reflux for 2 h. After cooling the solution to rt, the mixture was concentrated to dryness. The resulting residue was purified by flash chromatography on silica gel using dichloromethane methanol (100:0 to 95:5) as the eluent to afford D3-7 (dr=60/40, 331 mg, 1.66 mmol, 49%) as a brown oil. LCMS: m/z calcd C$_9$H$_{13}$NOS$_2$ 199.05, found 200.0 [M+H]$^+$.

To a solution of D3-7 (dr=50/50, 310 mg, 1.56 mmol, 1 eq.) in THF (13 mL) at 0° C., were added triethylamine (864.7 μL, 6.22 mmol, 4 eq.) and 3-chloro-4-fluorophenyl isocyanate (293.5 mg, 1.71 mmol, 1.1 eq.). The mixture was stirred at rt for 5 h. Water (100 mL) was added, and the aqueous layer was extracted with EA (3×50 mL). The organic layer was dried over sodium sulfate, filtered and concentrated to dryness to afford the crude product. The resulting residue was purified by flash chromatography on reverse phase using ACN:water (35:65 to 50:50) as the eluent to give D3-8 (98 mg, 0.26 mmol, 17%) and D3-9 (160 mg, 0.43 mmol, 28%) as a yellow oil. A fraction containing a mixture of both diastereomers was also recovered (200 mg, global yield=83%). D3-8: $^1$H NMR (400 MHz, DMSO-d$_6$, 25° C.): 1.33 (d, J=6.4 Hz, 3H), 2.52-2.55 (m, 1H), 3.08 (dd, J=14.0 Hz, 4.0 Hz, 1H), 3.59 (dd, J=14.8 Hz, 3.6 Hz, 1H), 4.37-4.39 (m, 1H), 4.55 (dd, J=14.4 Hz, 2.8 Hz, 1H), 4.60-4.66 (m, 1H), 6.92-6.95 (m, 1H), 7.03-7.04 (m, 1H), 7.27 (t, J=9.2 Hz, 1H), 7.33-7.36 (m, 1H), 7.37 (dd, J=5.2 Hz, 1.2 Hz, 1H), 7.67 (dd, J=7.2 Hz, 2.8 Hz, 1H), 8.65 (s, 1H). LCMS: m/z calcd C$_{16}$H$_{16}$ClFN$_2$OS$_2$ 370.04, found 370.9-372.9 [M+H]$^+$. D3-9: NMR (400 MHz, DMSO-d$_6$, 25° C.): 1.36 (d, J=6.8 Hz, 3H), 2.59 (dd, J=13.6 Hz, 2.8 Hz, 1H), 3.16 (dd, J=13.6 Hz, 3.6 Hz, 1H), 3.27-3.33 (m, 1H), 4.29-4.37 (m, 2H), 4.68-4.71 (m, 1H), 7.01-7.04 (m, 1H), 7.14 (d, J=3.2 Hz, 1H), 7.28 (t, J=9.2 Hz, 1H), 7.38-7.42 (m, 1H), 7.50 (dd, J=5.2 Hz, 1.2 Hz, 1H), 7.73 (dd, J=6.8 Hz, 2.8 Hz, 1H), 8.77 (s, 1H). LCMS: m/z calcd C$_{16}$H$_{16}$ClFN$_2$OS$_2$ 370.04, found 370.9-372.8 [M+H]$^+$.

Example 33

(2R,5R)-N-(3-chloro-4-fluoro-phenyl)-5-methyl-1,1-dioxo-2-(2-thienyl)-1,4-thiazinane-4-carboxamide (22)

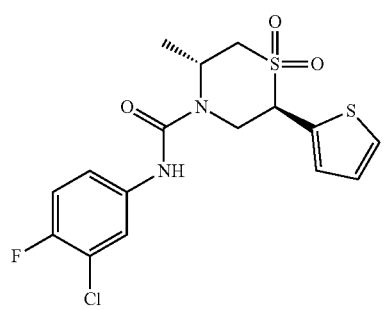 [SMILES: C[C@@H]1CS(=O)(=O)[C@@H](c2cccs2)CN1C(=O)Nc1ccc(F)c(Cl)c1]

To a solution of D3-8 (dr=0/100, 80.00 mg, 0.22 mmol, 1 eq.) in dichloromethane (2.5 mL) was added at 0° C., m-CPBA (77%, 97.00 mg, 0.43 mmol, 2 eq.). The mixture was stirred at 0° C. for 3 h. Water (5 mL) and a sat. aq. solution of sodium carbonate (8 mL) were added. The aqueous layer was extracted with dichloromethane (3×15 mL). The organic layer was dried over sodium sulfate, filtered and concentrated to dryness to afford the crude mixture as a beige solid. The resulting residue was purified by flash chromatography on silica gel using dichloromethane:methanol (100:0 to 95:5) as the eluent. After trituration in MTBE, compound 22 (dr=0/100, 18.00 mg, 0.045 mmol, 20%) was obtained as a white solid. $^1$H NMR (400 MHz, DMSO-d$_6$, 25° C.): 1.46 (d, J=7.0 Hz, 3H), 3.37-3.39 (m, 1H), 3.47 (dd, J=14.4 Hz, 4.4 Hz, 1H), 4.08 (dd, J=15.0 Hz, 2.2 Hz, 1H), 4.52 (dd, J=15.2 Hz, 4.8 Hz, 1H), 4.74-4.83 (m, 1H), 4.91-4.97 (m, 1H), 7.07 (dd, J=5.0 Hz, 4.2 Hz, 1H), 7.24 (d, J=2.9 Hz, 1H), 7.30 (t, J=9.4 Hz, 1H), 7.34-7.38 (m, 1H), 7.58 (d, J=4.8 Hz, 1H), 7.72 (dd, J=6.9 Hz, 2.7 Hz, 1H), 9.04 (s, 1H). LCMS: m/z calcd C$_{16}$H$_{16}$ClFN$_2$O$_3$S$_2$ 402.03, found 402.96-404.96 [M+H]$^+$.

Example 34

(2S,5R)-N-(3-chloro-4-fluorophenyl)-5-methyl-1,1-dioxo-2-(thiophen-2-yl)-1,4-thiomorpholine-4-carboxamide (23)

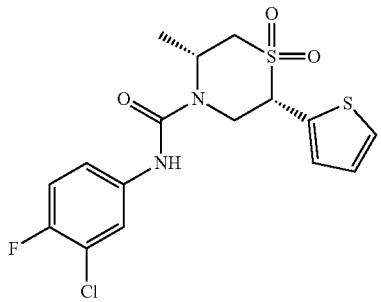 [SMILES: C[C@@H]1CS(=O)(=O)[C@H](c2cccs2)CN1C(=O)Nc1ccc(F)c(Cl)c1]

To a solution of D3-9 (dr=0/100, 160.00 mg, 0.43 mmol, 1 eq.) in dichloromethane (5 mL) was added at 0° C., m-CPBA (77%, 193.35 mg, 0.86 mmol, 2 eq.). The mixture was stirred at 0° C. for 3 h. Water (4 mL) and a sat. aq. solution of sodium carbonate (18 mL) were added. The aqueous layer was extracted with dichloromethane (3×15 mL). The organic layer was dried over sodium sulfate, filtered and concentrated to dryness to afford the crude mixture as a beige solid. The resulting residue was purified by flash chromatography on silica gel using dichloromethane:methanol (100:0 to 95:5) as the eluent. After trituration in diethyl ether, compound 23 (dr=0/100, 48.00 mg, 0.12 mmol, 28%) was obtained as a white solid. NMR (400 MHz, DMSO-d$_6$, 25° C.): 1.46 (d, J7=7.1 Hz, 3H), 3.39 (dd, J=14.2 Hz, 2.3 Hz, 1H), 3.53 (dd, J=14.3 Hz, 5.3 Hz, 1H), 3.78 (dd, J=15.1 Hz, 11.6 Hz, 1H), 4.50 (dt, 7=2.2 Hz, 14.9 Hz, 1H), 4.91 (dd, J=11.6 Hz, 3.1 Hz, 1H), 5.01 (quint, 7=6.8 Hz, 1H), 7.15 (dd, J=5.2 Hz, 3.5 Hz, 1H), 7.25 (d, J7=3.5 Hz, 1H), 7.30 (t, J=9.1 Hz, 1H), 7.35-7.39 (m, 1H), 7.67 (d, J7=5.3 Hz, 1H), 7.72 (dd, J=6.6 Hz, 2.5 Hz, 1H), 9.01 (s, 1H). LCMS: m/z calcd C$_{16}$H$_{16}$ClFN$_2$O$_3$S$_2$ 402.03, found 402.96-404.96 [M+H]$^+$.

Example 35

(4-bromo-3-chloro-phenyl)-[(2S,5S)-5-methyl-1,1-dioxo-2-(2-thienyl)-1,4-thiazinan-4-yl]methanone (24)

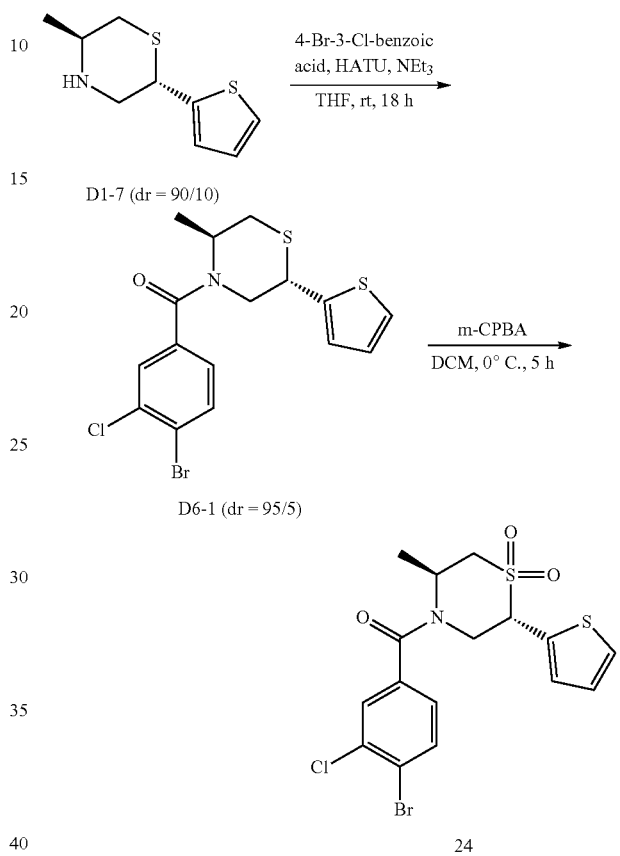

D1-7 was prepared as described herein. To a solution of compound D1-7 (100 mg, 0.502 mmol, 1 eq.) in THF (5 mL) were added 4-bromo-3-chlorobenzoic acid (130 mg, 0.55 mmol, 1.5 eq.), HATU (286.13 mg, 0.75 mmol, 1.5 eq.) and triethylamine (280 µL, 2.00 mmol, 4 eq.). The mixture was stirred at rt for 16 h. In order to complete the conversion, 4-bromo-3-chlorobenzoic acid (118.13 mg, 0.502 mmol, 1 eq.), HATU (190.76 mg, 0.502 mmol, 1 eq.) and triethylamine (70 µL, 0.502 mmol, 1 eq.) were added. Water (5 mL) was added, and the aqueous layer was extracted with EA (3×20 mL). The organic layers were dried over sodium sulfate, filtered and concentrated to dryness to afford the crude mixture. The resulting residue was purified by flash chromatography on silica gel using cyclohexane:EA (100:0 to 80:20) as the eluent to afford D6-1 (134 mg, 0.32 mmol, 64%) as a white solid. LCMS: m/z calcd C$_{16}$H$_{15}$BrClNOS$_2$ 415.95, found 415.9-417.9 [M+H]$^+$.

To a solution of D6-1 (134.00 mg, 0.32 mmol, 1 eq.) in dichloromethane (5.3 mL) was added at 0° C., m-CPBA (77%, 207.86 mg, 0.93 mmol, 2 eq.). The mixture was stirred at 0° C. for 3 h. Water (4 mL) and a sat. aq. solution of sodium carbonate (5 mL) were added. The aqueous layer was extracted with dichloromethane (3×15 mL). The combined organic layers were dried over sodium sulfate, filtered and concentrated to dryness to afford the crude mixture. The resulting residue was purified by flash chromatography on silica gel using cyclohexane:EA (100:0 to 70:30) as the eluent to afford compound 24 (21.30 mg, 0.047 mmol, 15%) as a white solid. NMR (400 MHz, DMSO-d$_6$, 80° C.): 1.51 (dd, J=7.1 Hz, 1.2 Hz, 3H), 3.26-3.33 (m, 1H), 3.61 (ddd, J=14.6 Hz, 5.9 Hz, 1.4 Hz, 1H), 4.14 (ddd, J=15.1 Hz, 3.7 Hz, 1.5 Hz, 1H), 4.47-4.51 (m, 1H), 4.80-4.81 (m, 1H), 4.9 (d, J=3.0 Hz, 1H), 7.09-7.11 (m, 1H), 7.22 (m, 1H), 7.27 (td, J=8.4 Hz, 1.7 Hz, 1H), 7.55 (t, J=1.7 Hz, 1H), 7.61 (td, J=5.1 Hz, 1.2 Hz, 1H), 7.82 (dd, J=8.1 Hz, 1.5 Hz, 1H). LCMS: m/z calcd C$_{16}$H$_{15}$BrClNO$_3$S$_2$ 446.96, found 447.88-449.88 [M+H]$^+$.

Example 36

(4-bromo-3-chloro-phenyl)-[(2R,5R)-5-methyl-1,1-dioxo-2-(2-thienyl)-1,4-thiazinan-4-yl]methanone (25) and (4-bromo-3-chloro-phenyl)-[(2S,5R)-5-methyl-1,1-dioxo-2-(2-thienyl)-1,4-thiazinan-4-yl] methanone (26)

To a solution of D7-1 (60.00 mg, 0.14 mmol, 1 eq.) in dichloromethane (1.5 mL) was added at rt, m-CPBA (77%, 64.52 mg, 0.29 mmol, 2 eq.). The mixture was stirred at rt for 2 h. Water (5 mL) and a sat. aq. solution of sodium carbonate (5 mL) were added. The aqueous layer was extracted with dichloromethane (3×10 mL). The organic layer was dried over sodium sulfate, filtered and concentrated to dryness to afford the crude mixture as a white solid. The resulting residue was purified by flash chromatography on silica gel using cyclohexane:EA (90:10 to 70:30) as the eluent to afford compound 25 (38.40 mg. 0.086 mmol, 59%) was obtained as a white solid. $^1$H NMR (400 MHz, DMSO-d$_6$, 80° C.): 1.50 (d, J=7.2 Hz, 3H), 3.27 (dt, J=15.2 Hz, 2.4 Hz, 1H), 3.60 (dd, J=14.8 Hz, 5.6 Hz, 1H), 4.13 (dd, J=14.8 Hz, 3.2 Hz, 1H), 4.48 (dd, J=14.8 Hz, 3.6 Hz, 1H), 4.75-4.84 (m, 1H), 4.87-4.90 (m, 1H), 7.09 (t, J=4.5 Hz, 1H), 7.21 (d, J=3.2 Hz, 1H), 7.26 (d, J=8.4 Hz, 1H), 7.54 (s, 1H), 7.59 (d, J=5.2 Hz, 1H), 7.80 (d, J=8.0 Hz, 1H). LCMS: m/z calcd C$_{16}$H$_{15}$BrClFNO$_3$S$_2$ 446.94, found 447.87-449.87 [M+H]$^+$.

To a solution of D7-2 (129 mg, 0.31 mmol, 1 eq.) in dichloromethane (3 mL) was added at rt, m-CPBA (77%,

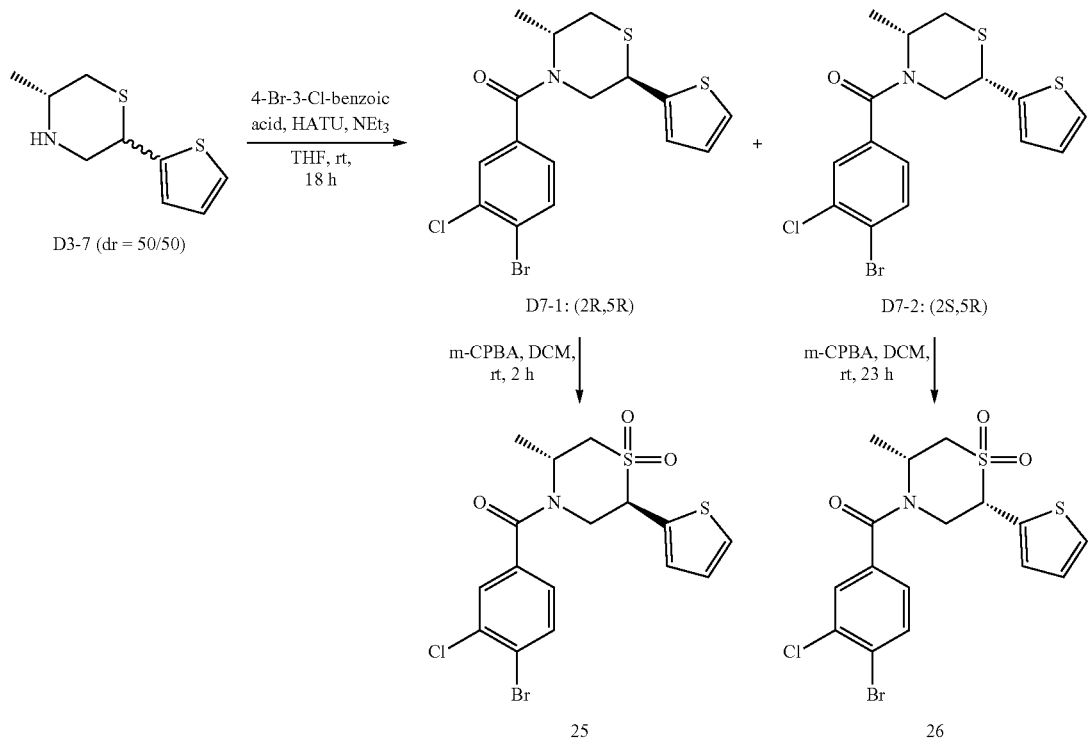

D3-7 was prepared as described herein. To a solution of D3-7 (215.00 mg, 1.079 mmol, 1 eq.) in THF (11 mL) were added 4-bromo-3-chlorobenzoic acid (381 mg, 1.62 mmol, 1.5 eq.), HATU (615.18 mg, 1.62 mmol, 1.5 eq.) and triethylamine (300 µL, 2.016 mmol, 2 eq.). The mixture was stirred at rt for 18 h. The mixture was evaporated to dryness to afford the crude product. The resulting residue was purified by flash chromatography on reverse phase using ACN:H$_2$O (0:100 to 45:55) as the eluent to afford D7-1 (60 mg, 0.143 mmol, 13%) and D7-2 (129 mg, 0.310 mmol, 29%) as white solids. D7-1: LCMS: m/z calcd C$_{16}$H$_{15}$BrClNOS$_2$ 414.95, found 415.9-417.9 [M+H]$^+$. D7-2: LCMS: m/z calcd C$_{16}$H$_{15}$BrClNOS$_2$ 414.95, found 415.9-417.9 [M+H]$^+$.

138.73 mg, 0.62 mmol, 2 eq.). The mixture was stirred at rt for 20 h. In order to complete the conversion, an additional amount of m-CPBA (77%, 34.68 mg, 0.15 mmol, 0.5 eq.) was added, and the mixture was stirred at rt for 3 h. Water (5 mL) and a sat. aq. solution of sodium carbonate (5 mL) were added. The aqueous layer was extracted with dichloromethane (3×10 mL). The combined organic layers were dried over sodium sulfate, filtered and concentrated to dryness to afford the crude mixture as a white solid. The resulting residue was purified by flash chromatography on silica gel using cyclohexane:EA (90:10 to 70:30) as the eluent to afford compound 26 (122 mg, 0.27 mmol, 88%) was obtained as a white solid. NMR (400 MHz, DMSO-d$_6$, 80° C.): 1.50 (d, J=6.8 Hz, 3H), 3.30 (d, J=14.8 Hz, 1H), 3.63 (dd, J=14.4 Hz, 5.6 Hz, 1H), 3.84 (t, J=12.8 Hz, 1H), 4.22-4.85 (m, 1H), 5.08 (d, J=10.8 Hz, 1H), 7.12 (t, J=4.4 Hz, 1H), 7.22 (s, 1H), 7.41 (dd, J=8.0 Hz, 1.4 Hz, 1H), 7.62 (d, J=4.8 Hz, 1H), 7.81 (s, 1H), 7.85 (d, J=8.4 Hz, 1H). LCMS: m/z calcd $C_{16}H_{15}BrClFNO_3S_2$ 446.94, found 447.87-449.87 $[M+H]^+$.

Example 37

(4-bromo-3-chloro-phenyl)-(1,1-dioxo-2-thiazol-2-yl-1,4-thiazinan-4-yl)methanone (27)

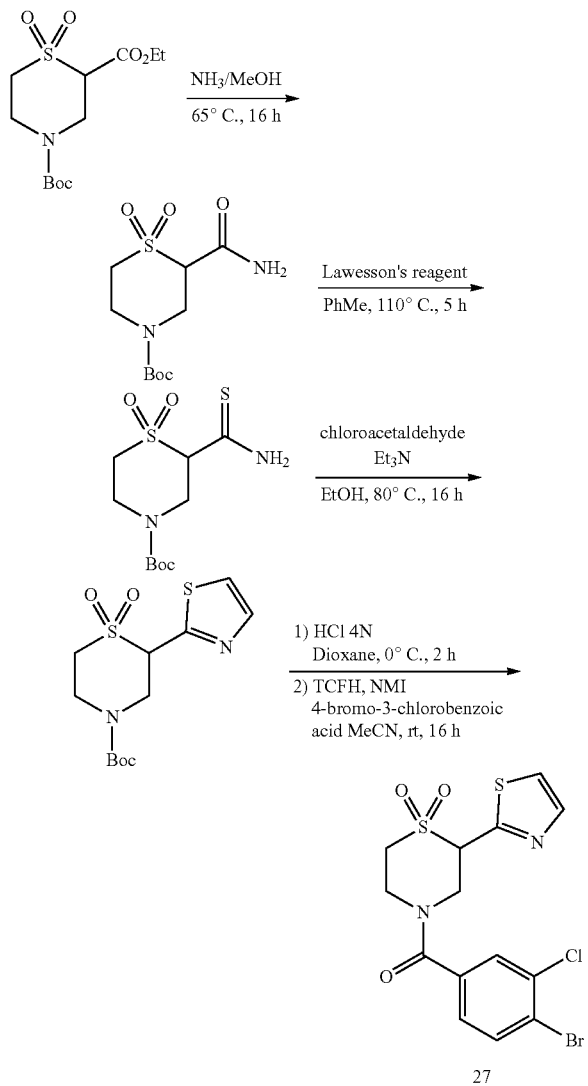

NH$_3$ (7N in MeOH, 30.0 eq., 41.8 mL) was added to 4-(tert-butyl) 2-ethyl thiomorpholine-2,4-dicarboxylate 1,1-dioxide (1.0 eq., 3.0 g, 9.76 mmol), and the mixture was stirred overnight at 65° C. Water (30 mL) was added, and the aqueous layer was extracted with CH$_2$Cl$_2$ (3×50 mL). The combined organic layers were dried over MgSO$_4$, filtered and evaporated to dryness to give tert-butyl 2-carbamoylthiomorpholine-4-carboxylate 1,1-dioxide (2.28 g, 84%) as a white solid. LCMS: $C_{10}H_{18}N_2O_5$ [M+H-tBu]$^+$: 223.

Lawesson's reagent (0.6 eq., 1.85 g) was added to a solution of tert-butyl 2-carbamoylthiomorpholine-4-carboxylate 1,1-dioxide (1.0 eq., 2.12 g, 7.62 mmol) in toluene (45 mL) under N$_2$. The mixture was stirred for 5 h at 110° C. The mixture was then evaporated to dryness to give a crude product, which was purified by flash chromatography on silica gel (20% to 50% AcOEt in Cyclohexane) to give tert-butyl 2-carbamothioylthiomorpholine-4-carboxylate 1,1-dioxide (1.70 g, 76%) as a white solid. LCMS: $C_{10}H_{18}N_2O_4S$ [M+H-tBu]$^+$: 239.

General procedure for the synthesis of the thiazoles: Et$_3$N (4.0 eq.) and the corresponding bromo- or chloro-aldehyde (2.0 eq.) were added to a solution of tert-butyl 2-carbamothioylthiomorpholine-4-carboxylate 1,1-dioxide (1.0 eq.) in EtOH (0.1 M) under N$_2$ at rt. The mixture was stirred overnight at 65° C. The mixture was then diluted with CH$_2$Cl$_2$ and washed with water. The aqueous layer was extracted with dichloromethane (2×) and ethyl acetate (2×). The combined organic layers were dried over MgSO$_4$, filtered and evaporated to dryness to give a crude product, which was purified by flash chromatography on silica gel (0% to 50% AcOEt in Cyclohexane) to give the corresponding thiazole.

Following the general procedure for the synthesis of the thiazoles, tert-butyl 2-(thiazol-2-yl)thiomorpholine-4-carboxylate 1,1-dioxide was obtained as a colorless oil (353 mg, 82%). LCMS: $C_{12}H_{18}N_2O_4S_2$ [M+H]$^+$: 319.

General procedure for the deprotection and the peptide coupling with 4-bromo-3-chlorobenzoic acid: A solution of HCl in dioxane (4N, 20 eq.) was added to the carbamate (1.0 eq.) at 0° C., and the mixture was stirred for 2 h. The volatiles were then removed under reduced pressure. The resulting hydrochloride salt was used without further purification in the next step. TCFH (1.3 eq.), N-methylimidazole (5.0 eq.) and the corresponding hydrochloride salt (1.0 eq.) were added to a suspension of 4-bromo-3-chlorobenzoic acid (1.2 eq.) in MeCN (0.2 M) under N$_2$ at rt. The mixture was stirred until complete conversion. Sat. Na$_2$CO$_3$ was added, and the aqueous layer was extracted with AcOEt (3×). The combined organic layers were washed with sat. Na$_2$CO$_3$, brine, dried over MgSO$_4$, filtered and evaporated to dryness to give a crude product which was purified by flash chromatography on silica gel (30% to 50% AcOEt in Cyclohexane) to give the corresponding amide. Recrystallization or trituration were performed when needed.

Following the general procedure for the deprotection and the peptide coupling with 4-bromo-3-chlorobenzoic acid, compound 27 was obtained as a white solid (240 mg, 48%) after recrystallization in EtOH. $^1$H-NMR (DMSO, 400 MHz, 80° C.): 3.47-3.55 (m, 2H); 3.79-3.87 (m, 1H); 4.01 (dd, J=14.4 Hz, 9.0 Hz, 1H); 4.07-4.66 (m, 2H); 5.29 (dd, J=9.0 Hz, 3.5 Hz, 1H); 7.36 (d, J=8.2 Hz, 1H); 7.70 (s, 1H); 7.80-7.85 (m, 2H); 7.93 (d, J=3.3 Hz, 1H) ppm. LCMS: $C_{14}H_{12}BrClN_2O_3S_2$ [M+H]$^+$: 434.9/436.9/438.9.

Example 38

(4-bromo-3-chloro-phenyl)-[2-(1,3,4-oxadiazol-2-yl)-1,1-dioxo-1,4-thiazinan-4-yl]methanone (28)

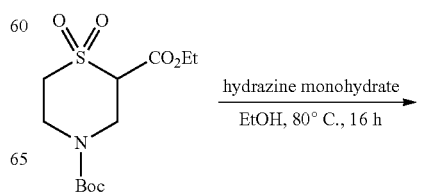

105

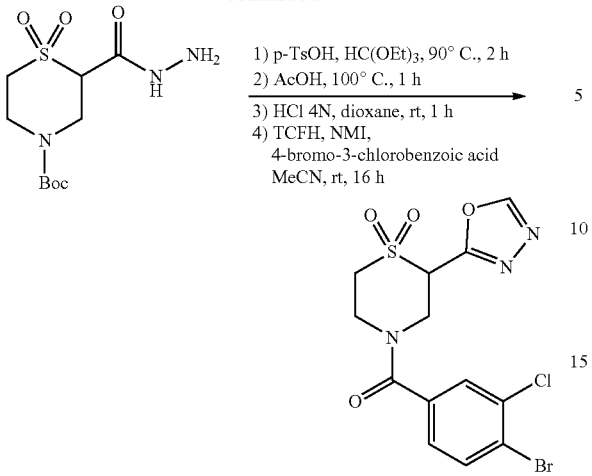

1) p-TsOH, HC(OEt)₃, 90° C., 2 h
2) AcOH, 100° C., 1 h
3) HCl 4N, dioxane, rt, 1 h
4) TCFH, NMI,
   4-bromo-3-chlorobenzoic acid
   MeCN, rt, 16 h Hydrazine monohydrate (10.0 eq., 1.42 mL) was added to a solution of 4-(tert-butyl) 2-ethyl thiomorpholine-2,4-dicarboxylate 1,1-dioxide (1.0 eq., 900 mg, 2.93 mmol) in EtOH (10 mL), and the mixture was stirred overnight at 80° C. The mixture was evaporated to dryness to give tert-butyl 2-(hydrazinecarbonyl)thiomorpholine-4-carboxylate 1,1-dioxide (859 mg, 100%) as a white solid. LCMS: $C_{10}H_{19}N_3O_5S$ [M+H-tBu]⁺: 238.

General procedure for the synthesis of the oxadiazoles and peptide coupling with 4-bromo-3-chlorobenzoic acid: p-TsOH (0.1 eq.) was added to a solution of tert-butyl 2-(hydrazinecarbonyl)thiomorpholine-4-carboxylate 1,1-dioxide (1.0 eq.) in triethyl orthoformate (0.45 M), and the mixture was stirred for 2 h at 90° C. The mixture was evaporated to dryness. The crude product was dissolved in acetic acid (0.07 M), and the reaction was heated to 100° C. for 1 h. The solvent was removed under reduced pressure. HCl in dioxane (4N, 40 eq.) was added, and the solution was stirred for 1 h at rt. The mixture was evaporated to dryness. The white solid was triturated with Et₂O to afford a white powder, which was collected by filtration to give the corresponding hydrochloride salt. This hydrochloride salt was used in the next step without further purification.

TCFH (1.3 eq.), N-methylimidazole (5.0 eq.) and the hydrochloride salt (1.0 eq.) were added to a suspension of 4-bromo-3-chlorobenzoic acid (1.2 eq.) in MeCN (0.2 M) under N₂ at rt. The mixture was stirred until complete conversion. Sat. Na₂CO₃ was added, and the aqueous layer was extracted with AcOEt (3x). The combined organic layers were washed with sat. Na₂CO₃, brine, dried over MgSO₄, filtered and evaporated to dryness to give a crude product. The crude product was purified by flash chromatography on silica gel (30% to 50% AcOEt in Cyclohexane) to give the corresponding amide. Further purifications were performed when necessary.

Compound 28 was obtained as a white solid (31 mg, 0.074 mmol, 5%) after recrystallization in EtOH, trituration in Et₂O and reverse phase chromatography (H₂O (0.1% of TFA):MeCN (98:2 to 0:100)). ¹H-NMR (DMSO, 400 MHz, 80° C.): 3.46-3.59 (m, 2H); 3.86-3.93 (m, 1H); 4.07-4.20 (m, 2H); 4.41-4.50 (m, 1H); 5.31 (dd, J=8.3 Hz, 2.4 Hz, 1H); 7.38 (dd, J=8.2 Hz, 1.2 Hz, 1H); 7.72 (d, J=1.2 Hz, 1H); 7.85 (d, J=8.2 Hz, 1H); 9.30 (s, 1H) ppm. LCMS: $C_{13}H_{11}BrClN_3O_4S$ [M+H]⁺: 419.9/421.9/423.9.

106

Example 39

(4-bromo-3-chloro-phenyl)-[2-(5-methylthiazol-2-yl)-1,1-dioxo-1,4-thiazinan-4-yl]methanone (29)

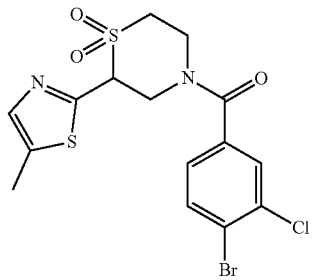 [SMILES: Cc1cnc(C2CN(C(=O)c3ccc(Br)c(Cl)c3)CCS2(=O)=O)s1]

Following the general procedure for the synthesis of the thiazoles, tert-butyl 2-(5-methylthiazol-2-yl)thiomorpholine-4-carboxylate 1,1-dioxide was obtained as a colorless oil (42 mg, 39%). LCMS: $C_{13}H_{20}N_2O_4S_2$ [M+H]⁺: 333.

Following the general procedure for the deprotection and the peptide coupling with 4-bromo-3-chlorobenzoic acid, compound 29 was obtained as a white solid (11 mg, 7%) after recrystallization in EtOH. ¹H-NMR (DMSO, 400 MHz, 80° C.): 2.48 (s, 3H); 3.45-3.52 (m, 2H); 3.80-3.86 (m, 1H); 3.97 (dd, J=14.3 Hz, 8.9 Hz, 1H); 4.06-4.28 (m, 1H); 4.29-4.65 (m, 1H); 5.15 (dd, J=9.0 Hz, 3.4 Hz, 1H); 7.37 (d, J=8.2 Hz, 1H); 7.59 (s, 1H); 7.68 (s, 1H); 7.83 (d, J=8.2 Hz, 1H) ppm. LCMS: $C_{15}H_{14}BrClN_2O_3S_2$ [M+H]⁺: 448.9/450.9/452.9.

Example 40

(2-(5-benzylthiazol-2-yl)-1,1-dioxidothiomorpholino)(4-bromo-3-chlorophenyl)methanone (30)

General Procedure for the Synthesis of the 2,5-Disubstituted Thiazoles

Et₃N (4 eq.) and the corresponding α-bromo- or α-chloro-aldehyde (2 eq.) were added to a solution of tert-butyl 2-carbamothioylthiomorpholine-4-carboxylate 1,1-dioxide (1 eq.) in EtOH (0.1 M) under N₂ at rt. The mixture was stirred overnight at 65° C. Then, the mixture was diluted with CH₂Cl₂ and washed with water. The aqueous layer was extracted with CH₂Cl₂ (2x) and AcOEt (2x). The combined organic layers were dried over MgSO₄, filtered and evaporated to dryness to give a crude product which was purified by flash chromatography on silica gel (from 0% to 50% of AcOEt in Cyclohexane) to give the desired thiazole.

tert-butyl 2-(5-benzylthiazol-2-yl)thiomorpholine-4-carboxylate 1,1-dioxide was obtained as a white solid (180 mg, 43%). LCMS: $C_{19}H_{24}N_2O_4S_2$ [M+H]⁺: 409.

General Procedure for the Deprotection and the Peptide Coupling with 4-Bromo-3-Chlorobenzoic Acid:

A solution of HCl in dioxane (4N, 20 eq.) was added to the tert-butylcarbamate (1 eq.) at 0° C., and the mixture was stirred for 2 h. Then, the volatiles were removed under reduced pressure. The resulting hydrochloride salt was used as such in the next step.

TCFH (1.3 eq.), N-methylimidazole (5 eq.) and the corresponding hydrochloride salt (1 eq.) were added to a suspension of 4-bromo-3-chlorobenzoic acid (1.2 eq.) in MeCN (0.2 M) under N₂ at rt. The mixture was stirred until complete conversion. Then, sat. Na₂CO₃ was added, and the aqueous layer was extracted with AcOEt (3×). The combined organic layers were washed with sat. Na$_2$CO$_3$, brine, dried over MgSO$_4$, filtered and evaporated to dryness to give a crude product which was purified by flash chromatography on silica gel (30% to 50% AcOEt in Cyclohexane) to give the corresponding compound. Afterwards, recrystallization or trituration were performed when necessary.

(2-(5-benzylthiazol-2-yl)-1,1-dioxidothiomorpholino)(4-bromo-3-chlorophenyl)methanone was obtained as a white solid (30) (8 mg, 10%) after recrystallization in EtOH. $^1$H-NMR (DMSO, 400 MHz, 80° C.): 3.38-3.57 (m, 2H); 3.75-3.87 (m, 1H); 3.94 (dd, J=14.4 Hz, 9.0 Hz, 1H); 4.12 (br. s. 1H); 4.21 (s. 2H), 4.40 (br. s. 1H), 5.14 (dd, J=9.0 Hz, 3.3 Hz, 1H), 7.22-7.43 (m, 6H), 7.68 (s, 2H), 7.79 (d, J=7.9 Hz, 1H) ppm. LCMS: C$_{21}$H$_{18}$BrClN$_2$O$_3$S$_2$ [M+H]$^+$: 525/527/529.

Example 41

(2-(4-benzylthiazol-2-yl)-1,1-dioxidothiomorpholino)(4-bromo-3-chlorophenyl)methanone (31)

General Procedure for the Synthesis of the 2,4-Disubstituted Thiazoles

Et$_3$N (4 eq.) and the corresponding α-bromo- or α-chlorocetone (2 eq.) were added to a solution of tert-butyl 2-carbamothioylthiomorpholine-4-carboxylate 1,1-dioxide (1 eq.) in EtOH (0.1 M) under N$_2$ at rt. The mixture was stirred overnight at 80° C. Then, the mixture was diluted with CH$_2$Cl$_2$ and washed with water. The aqueous layer was extracted with CH$_2$Cl$_2$ (2×) and AcOEt (2×). The combined organic layers were dried over MgSO$_4$, filtered and evaporated to dryness to give a crude product which was purified by flash chromatography on silica gel (from 10% to 50% of AcOEt in Cyclohexane) to give the desired thiazole.

tert-butyl 2-(4-benzylthiazol-2-yl)thiomorpholine-4-carboxylate 1,1-dioxide was obtained as a colorless oil (148 mg, 36%). LCMS: C$_{19}$H$_{24}$N$_2$O$_4$S$_2$ [M+H]$^+$: 409.

(2-(4-benzylthiazol-2-yl)-1,1-dioxidothiomorpholino)(4-bromo-3-chlorophenyl)methanone (31) was obtained as a white solid (14 mg, 14%) after recrystallization in EtOH. $^1$H-NMR (DMSO, 400 MHz, 80° C.): 3.42-3.55 (m, 2H); 3.78-3.90 (m, 1H); 4.01 (dd, J=14.5 Hz, 9.1 Hz, 1H); 4.12 (s, 2H); 4.25-4.71 (br. s., 2H); 5.24 (dd, J=9.0 Hz, 3.3 Hz, 1H); 7.19-7.23 (m, 1H); 7.25-7.35 (m, 5H); 7.37 (s, 1H); 7.67 (s, 1H); 7.81 (d, J=8.7 Hz, 1H) ppm. LCMS: C$_{21}$H$_{18}$BrClN$_2$O$_3$S$_2$ [M+H]$^+$: 525/527/529.

Example 42

(4-bromo-3-chloro-phenyl)-[rac-(2S)-2-(5-benzylthiazol-2-yl)-2-methyl-1,1-dioxo-1,4-thiazinan-4-yl]methanone (36a) and (4-bromo-3-chloro-phenyl)-[rac-(2R)-2-(5-benzylthiazol-2-yl)-2-methyl-1,1-dioxo-1,4-thiazinan-4-yl]methanone (36b)

tert-butyl 2-(5-benzylthiazol-2-yl)-2-methylthiomorpholine-4-carboxylate 1,1-dioxide: NaH 60% (1 eq., 24.48 mg, 0.61 mmol) was added to a solution of tert-butyl 2-(5-benzylthiazol-2-yl)thiomorpholine-4-carboxylate 1,1-dioxide (1 eq., 250 mg, 0.61 mmol) in anhydrous THF (25 mL) at 0° C. under N$_2$. The mixture was stirred for 30 min at 0° C., and MeI (1 eq., 0.038 mL, 0.61 mmol) was added. The mixture was stirred at this temperature for 30 min. The mixture was allowed to warm to rt and stirred for 4 h. Additional NaH 60% (0.25 eq., 6.12 mg, 0.15 mmol) and MeI (0.25 eq., 0.01 mL, 0.15 mmol) were added. The mixture was stirred overnight at rt. Then, sat. NH$_4$Cl (20 mL) was added to the mixture which was extracted with AcOEt (3×50 mL). The organic layers were combined, washed with sat. NH$_4$Cl (20 mL), dried over MgSO$_4$ and evaporated to dryness to give a crude product which was purified by flash chromatography (from 10 to 40% of AcOEt in Cyclohexane) to afford the desired compound (183 mg, 0.43 mmol, 71%) as a white solid. $^1$H-NMR (DMSO, 600 MHz, 80° C.): 1.32 (s, 9H); 1.71 (s, 3H); 3.33-3.40 (m, 1H); 3.42-3.48 (m, 1H); 3.57-3.64 (m, 1H); 3.83-3.93 (m, 3H); 4.21 (s, 2H); 7.21-7.27 (m, 1H); 7.28-7.35 (m, 4H); 7.64 (s, 1H) ppm. LCMS: C$_{20}$H$_{26}$FN$_2$O$_4$S$_2$ [M+H]$^+$: 427.

(2-(5-benzylthiazol-2-yl)-2-methyl-1,1-dioxidothiomorpholino)(4-bromo-3-chlorophenyl)methanone was obtained as a white solid (28 mg, 14%) after trituration in Et$_2$O.

Procedure for the Chiral Separation:

(2-(5-benzylthiazol-2-yl)-2-methyl-1,1-dioxidothiomorpholino)(4-bromo-3-chlorophenyl)methanone (26.6 mg) was dissolved to 1.67 mg/mL in MeCN and was then purified by HPLC. Combined fractions of each of the first enantiomer and the second enantiomer were then evaporated to near dryness using a rotary evaporator, transferred into final vessels with DCM, which was removed on a Biotage V10 at 35° C. before being stored in a vacuum oven at 35° C. and 5 mbar until constant weight to afford the first enantiomer (6.8 mg) (36a) and the second enantiomer (7.7 mg) (36b) as white solids. $^1$H-NMR (DMSO, 400 MHz, 80° C.): 1.72 (s, 3H); 3.46-3.55 (m, 1H); 3.59-3.69 (m, 1H); 3.85-3.93 (m, 1H); 3.93-4.19 (m, 2H); 4.19-4.29 (m, 3H); 7.12-7.45 (m, 6H); 7.55 (br. s, 1H); 7.70 (s, 1H); 7.72-7.89 (br. s, 1H) ppm. LCMS: C$_{22}$H$_{20}$BrClFN$_2$O$_3$S$_2$ [M+H]$^+$: 539/541/543.

Example 43

(4-bromo-3-chloro-phenyl)-[(2S)-2-(5-benzylthiazol-2-yl)-2-fluoro-1,1-dioxo-1,4-thiazinan-4-yl]methanone (37a) and (4-bromo-3-chloro-phenyl)-[(2R)-2-(5-benzylthiazol-2-yl)-2-fluoro-1,1-dioxo-1,4-thiazinan-4-yl]methanone (37b)

tert-butyl 2-(5-benzylthiazol-2-yl)-2-fluorothiomorpholine-4-carboxylate 1,1-dioxide: NaH 60% (1.5 eq., 51.4 mg, 1.29 mmol) was added to a solution of tert-butyl 2-(5-benzylthiazol-2-yl)thiomorpholine-4-carboxylate 1,1-dioxide (1 eq., 350 mg, 0.86 mmol) in anhydrous THF (30 mL) at 0° C. under N$_2$. The mixture was stirred for 30 min at 0° C. and NFSI (1.5 eq., 405.23 mg, 1.29 mmol) was added. The mixture was stirred at this temperature for 30 min. The mixture was allowed to warm to rt and stirred for 2 h. Additional NaH 60% (0.5 eq., 17.13 mg, 0.43 mmol) and NFSI (0.5 eq., 135.01 mg, 0.43 mmol) were added. The mixture was stirred overnight at rt. Further additional NaH 60% in oil (1.5 eq., 51.4 mg, 1.29 mmol) and NFSI (1.5 eq., 405.23 mg, 1.29 mmol) were added, and the mixture was stirred for 3 h at rt. Then, sat. NH$_4$Cl (30 mL) was added to the mixture which was extracted with AcOEt (3×50 mL). The organic layers were combined, washed with sat. Na$_2$CO$_3$, dried over MgSO$_4$, filtered and evaporated to dryness to give a crude product which was purified by flash chromatography (from 10 to 40% of AcOEt in Cyclohexane) to the desired compound (179 mg, 0.42 mmol, 49%) as a yellow solid. $^1$H-NMR (DMSO, 600 MHz, 80° C.): 1.44 (s, 9H); 3.39-3.48 (m, 1H); 3.50-3.64 (m, 2H); 4.22 (dd, J=30.0 Hz, 15.8 Hz, 1H); 4.29 (s, 2H); 4.38-4.44 (m, 1H); 4.75-4.83 (m, 1H); 7.24-7.29 (m, 1H); 7.30-7.39 (m, 4H); 7.81 (s, 1H) ppm. LCMS: C$_{19}$H$_{23}$FN$_2$O$_4$S$_2$ [M+H]$^+$: 427.

(2-(5-benzylthiazol-2-yl)-2-fluoro-1,1-dioxidothiomorpholino)(4-bromo-3-chlorophenyl)methanone was obtained as a white solid (99 mg, 52%) after trituration in EtOH.

Procedure for the Chiral Separation:

(2-(5-benzylthiazol-2-yl)-2-fluoro-1,1-dioxidothiomorpholino)(4-bromo-3-chlorophenyl)methanone (88 mg) was dissolved to 3 mg/mL in MeCN and was then purified by HPLC. Combined fractions of each of the first enantiomer and the second enantiomer were then evaporated to near dryness using a rotary evaporator, transferred into final vessels with DCM, which was removed on a Biotage V10 at 35° C. before being stored in a vacuum oven at 35° C. and 5 mbar until constant weight to afford the first enantiomer (36.9 mg) (37a) and the second enantiomer (35.7 mg) (37b) as white solids. $^1$H-NMR (DMSO, 400 MHz, 80° C.): 3.62-3.75 (m, 3H); 4.25 (s, 2H); 4.35-4.57 (m, 2H); 4.72-5.01 (m, 1H); 7.24-7.29 (m, 1H); 7.29-7.40 (m, 5H); 7.70 (s, 1H); 7.80-7.88 (m, 2H) ppm. LCMS: $C_{21}H_{17}BrClFN_2O_3S_2$ [M+H]$^+$: 542.9/544.9/546.9.

Example 44

4-(4-bromo-3-chlorobenzoyl)-2-fluoro-2-[5-[1-(2-fluorophenyl)ethyl]-1,3-thiazol-2-yl]-1λ$^6$-thiomorpholine-1,1-dione (42) and separation into four diastereoisomers (42a), (42b), (42c) and (42d)

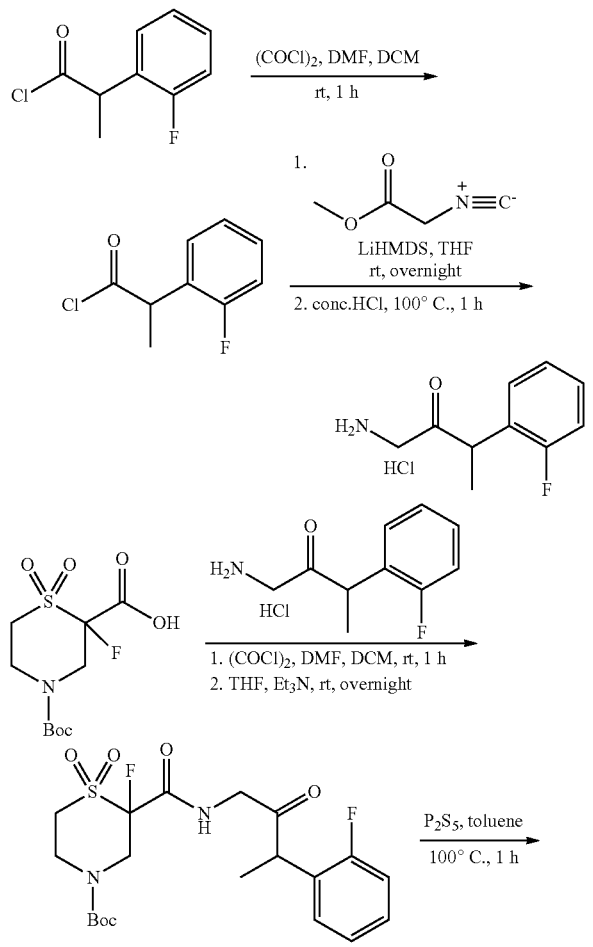

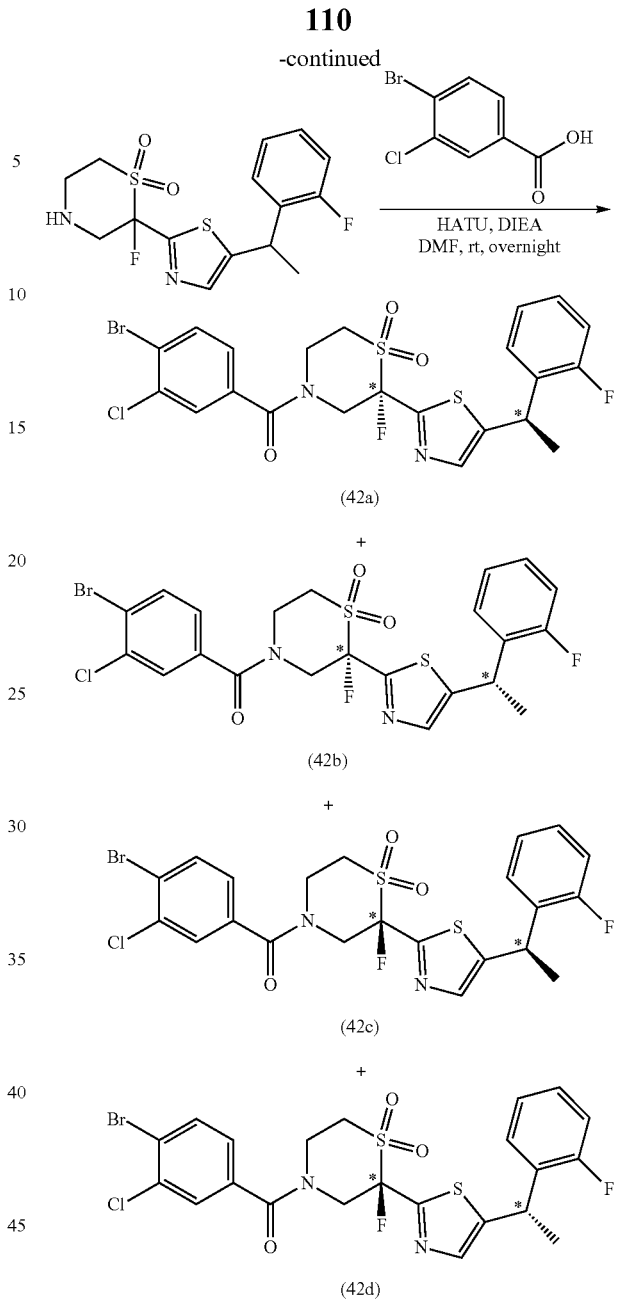

2-(2-fluorophenyl)propanoyl chloride: A mixture of 2-(2-fluorophenyl)propanoic acid (2.00 g, 11.9 mmol, 1.00 eq.), dichloromethane (30 mL), oxalyl chloride (3.02 g, 23.8 mmol, 2.00 eq,) and N,N-dimethylformamide (86.9 mg, 1.19 mmol, 0.10 eq.) was stirred for 1 h at rt. The mixture was concentrated under reduced pressure to afford 2-(2-fluorophenyl)propanoyl chloride (2.20 g, crude) as a brown oil, which was used for next step directly without further purification.

1-amino-3-(2-fluorophenyl)butan-2-one hydrochloride: A 250 mL round-bottom flask was charged with THF (30 mL) and lithium bis(trimethylsilyl)amide (19.6 mL, 19.6 mmol, 1.66 eq., 1 M in THF) under N$_2$. Methyl 2-isocyanoacetate (1.75 g, 17.7 mmol, 1.50 eq.) in THF (3 mL) was added at −78° C. The mixture was stirred for 30 mins at −78° C. under N$_2$ atmosphere. Then 2-(2-fluorophenyl)propanoyl chloride (2.20 g, 11.8 mmol, 1.00 eq.) in THF (5 mL) was added at −78° C. The mixture was stirred for overnight at rt under N$_2$ atmosphere, and the reaction was quenched with water (100 mL). The mixture was extracted with ethyl acetate (3×100 mL). The organic layers were combined, washed with water (3×100 mL), dried over anhydrous sodium sulfate, filtered and concentrated under reduced pressure. The residue was diluted with concentrated hydrochloric acid (50 mL) and stirred for 1 h at 100° C. The mixture was concentrated under reduced pressure and triturated with ethyl acetate (100 mL) to afford 1-amino-3-(2-fluorophenyl)butan-2-one hydrochloride (2.33 g, 91% yield) as a grey solid. LCMS (ESI, m/z): 182 [M−HCl+H]$^+$.

Tert-butyl 2-fluoro-2-[[3-(2-fluorophenyl)-2-oxobutyl]carbamoyl]-1,1-dioxo-1$\lambda^6$-thiomorpholine-4-carboxylate: A 50 mL round-bottom flask was charged with 4-(tert-butoxycarbonyl)-2-fluoro-1,1-dioxo-1$\lambda^6$-thiomorpholine-2-carboxylic acid (1.20 g, 4.04 mmol, 1.00 eq.) and dichloromethane (10 mL) under N$_2$. Oxalyl chloride (0.870 g, 6.86 mmol, 1.70 eq.) in dichloromethane (1 mL) was added at 0° C. Then N,N-dimethylformamide (0.0295 g, 0.404 mmol, 0.10 eq.) in dichloromethane (0.5 mL) was added. The mixture was stirred for 1 h at rt and concentrated under reduced pressure. The residue was diluted with THF (5 mL) and added into a solution of 1-amino-3-(2-fluorophenyl)butan-2-one hydrochloride (0.878 g, 4.04 mmol, 1.00 eq.), THF (15 mL) and triethylamine (2.04 g, 20.2 mmol, 5.00 eq.). The mixture was stirred for overnight at rt and concentrated under reduced pressure. The residue was purified by silica gel column chromatography, eluted with petroleum ether:ethyl acetate (1:1) to afford tert-butyl 2-fluoro-2-[[3-(2-fluorophenyl)-2-oxobutyl]carbamoyl]-1,1-dioxo-1$\lambda^6$-thiomorpholine-4-carboxylate (670 mg, 36% yield) as a white solid. LCMS (ESI, m/z): 461 [M+H]$^+$.

2-fluoro-2-[5-[1-(2-fluorophenyl)ethyl]-1,3-thiazol-2-yl]-1$\lambda^6$-thiomorpholine-1,1-dione: A 40 mL vial was charged with tert-butyl 2-fluoro-2-[[3-(2-fluorophenyl)-2-oxobutyl]carbamoyl]-1,1-dioxo-1$\lambda^6$-thiomorpholine-4-carboxylate (650 mg, 1.27 mmol, 1.00 eq.), phosphorus pentasulfide (157 mg, 0.706 mmol, 0.50 eq.) and toluene (20 mL). The mixture was stirred for 1 h at 100° C. and concentrated under reduced pressure. The residue was diluted with dichloromethane (20 mL). Triethylamine was added until the solids were disappeared. The mixture was concentrated under reduced pressure. The residue was purified by silica gel column chromatography, eluted with dichloromethane:methanol (10:1) to afford 2-fluoro-2-[5-[1-(2-fluorophenyl)ethyl]-1,3-thiazol-2-yl]-1$\lambda^6$-thiomorpholine-1,1-dione (350 mg, 69% yield) as a white solid. LCMS (ESI, m/f): 359 [M+H]$^+$.

Compound (42a), (42b), (42c) and (42d): A 100 mL round-bottom flask was charged with 2-fluoro-2-[5-[1-(2-fluorophenyl)ethyl]-1,3-thiazol-2-yl]-1$\lambda^6$-thiomorpholine-1,1-dione (350 mg, 0.977 mmol, 1.00 eq.), N,N-dimethylformamide (5 mL), 4-bromo-3-chlorobenzoic acid (299 mg, 1.27 mmol, 1.30 eq.), O-(7-Azabenzotriazol-1-yl)-N,N,N',N'-tetramethyluronium hexafluorophosphate (483 mg, 1.27 mmol, 1.30 eq.) and N,N-diisopropylethylamine (252 mg, 1.95 mmol, 2.00 eq.). The mixture was stirred for overnight at rt and diluted with ethyl acetate (200 mL). The mixture was washed with water (3×20 mL) and brine (1×20 mL), dried over anhydrous sodium sulfate, filtered and concentrated under reduced pressure. The residue was purified by silica gel column chromatography, eluted with petroleum ether:ethyl acetate (1:1) to afford the mixture of products. The products were separated by Prep-Chiral-HPLC with the following conditions: Column: CHIRALPAK IF-2, 2×25 cm, 5 μm; Mobile Phase A: Hex:DCM=3:1 (0.5% 2 M NH$_3$-MeOH)-HPLC, Mobile Phase B: EtOH-HPLC; Flow rate: 20 mL/min; Gradient: 15% B to 15% B in 11.8 min to afford (rac-2R)-4-(4-bromo-3-chlorobenzoyl)-2-fluoro-2-[5-[1-(2-fluorophenyl)ethyl]-1,3-thiazol-2-yl]-1$\lambda^6$-thiomorpholine-1,1-dione (the first peak) and (rac-2S)-4-(4-bromo-3-chlorobenzoyl)-2-fluoro-2-[5-[1-(2-fluorophenyl)ethyl]-1,3-thiazol-2-yl]-1$\lambda^6$-thiomorpholine-1,1-dione (the second peak).

The product (rac-2R)-4-(4-bromo-3-chlorobenzoyl)-2-fluoro-2-[5-[1-(2-fluorophenyl)ethyl]-1,3-thiazol-2-yl]-1$\lambda^6$-thiomorpholine-1,1-dione was separated by Prep-Chiral-HPLC with the following conditions: Column: Reg-AD, 30×250 mm, 5 μm; Mobile Phase A: Hex (0.5% 2M NH$_3$-MeOH)-HPLC, Mobile Phase B: EtOH-HPLC; Flow rate: 45 mL/min; Gradient: 30% B to 30% B in 30 min to afford the product (rac-2R)-4-(4-bromo-3-chlorobenzoyl)-2-fluoro-2-[5-[(rac-1R)-1-(2-fluorophenyl)ethyl]-1,3-thiazol-2-yl]-1$\lambda^6$-thiomorpholine-1,1-dione (42a) (48.4 mg, 9% yield, the first peak, as a white solid. LCMS (ESI, m/z): 575 [M+H]$^+$. NMR (400 MHz, Chloroform-d) δ7.73-7.60 (m, 2H), 7.54 (d, J=2.0 Hz, 1H), 7.26-7.00 (m, 5H), 5.10-4.90 (m, 1H), 4.80-4.47 (m, 3H), 3.78-3.50 (m, 2H), 3.32 (d, J=12.8 Hz, 1H), 1.73 (d, J=7.2 Hz, 3H) and (rac-2R)-4-(4-bromo-3-chlorobenzoyl)-2-fluoro-2-[5-[(rac-1S)-1-(2-fluorophenyl)ethyl]-1,3-thiazol-2-yl]-1$\lambda^6$-thiomorpholine-1,1-dione (42b) (47.8 mg, 9% yield, the second peak) as a white solid. LCMS (ESI, m/z): 575 [M+H]$^+$. $^1$H NMR (400 MHz, Chloroform-d) δ7.75-7.60 (m, 2H), 7.55 (d, J=2.0 Hz, 1H), 7.26-7.18 (m, 3H), 7.18-6.99 (m, 2H), 5.13-4.82 (m, 1H), 4.79-4.45 (m, 3H), 3.85-3.48 (m, 2H), 3.31 (d, J=12.8 Hz, 1H), 1.73 (d, J=7.2 Hz, 3H).

The product (rac-2S)-4-(4-bromo-3-chlorobenzoyl)-2-fluoro-2-[5-[1-(2-fluorophenyl)ethyl]-1,3-thiazol-2-yl]-1$\lambda^6$-thiomorpholine-1,1-dione was separated by Prep-SFC with the following conditions: Column: CHIRAL ART Amylose-C NEO, 3×25 cm, 5 μm; Mobile Phase A: CO$_2$, Mobile Phase B: MEOH (0.1% 2M NH$_3$-MEOH); Flow rate: 100 mL/min; Gradient: 50% B to afford (rac-2S)-4-(4-bromo-3-chlorobenzoyl)-2-fluoro-2-[5-[(rac-1R)-1-(2-fluorophenyl)ethyl]-1,3-thiazol-2-yl]-1$\lambda^6$-thiomorpholine-1,1-dione (42c) (56.0 mg, 11% yield, the first peak) as a white solid. LCMS (ESI, m/z): 575 [M+H]$^+$. $^1$H NMR (400 MHz, Chloroform-d) δ7.79-7.60 (m, 2H), 7.55 (d, J=2.0 Hz, 1H), 7.25-7.15 (m, 3H), 7.15-7.01 (m, 2H), 5.15-4.81 (m, 1H), 4.80-4.48 (m, 3H), 3.75-3.45 (m, 2H), 3.31 (d, J=12.0 Hz, 1H), 1.73 (d, J=7.2 Hz, 3H) and (rac-2S)-4-(4-bromo-3-chlorobenzoyl)-2-fluoro-2-[5-[(rac-1S)-1-(2-fluorophenyl)ethyl]-1,3-thiazol-2-yl]-1$\lambda^6$-thiomorpholine-1,1-dione (42d) (58.7 mg, 11% yield, the second peak) as a white solid. LCMS (ESI, m/z): 575 [M+H]$^+$. $^1$H NMR (400 MHz, Chloroform-d) δ7.80-7.60 (m, 2H), 7.55 (d, J=2.0 Hz, 1H), 7.25-7.18 (m, 3H), 7.18-7.10 (m, 1H), 7.10-6.99 (m, 1H), 5.19-4.85 (m, 1H), 4.81-4.32 (m, 3H), 3.80-3.50 (m, 2H), 3.32 (d, J=12.8 Hz, 1H), 1.73 (d, J7=7.2 Hz, 3H).

Example 45

(rac-2R)-4-(4-bromo-3-chlorobenzoyl)-2-fluoro-2-(5-[[2-(pyrimidin-2-yl)phenyl]methyl]-1,3-thiazol-2-yl)-1λ⁶-thiomorpholine-1,1-dione (44a) and (rac-2S)-4-(4-bromo-3-chlorobenzoyl)-2-fluoro-2-(5-[[2-(pyrimidin-2-yl)phenyl]methyl]-1,3-thiazol-2-yl)-1λ⁶-thiomorpholine-1,1-dione (44b)

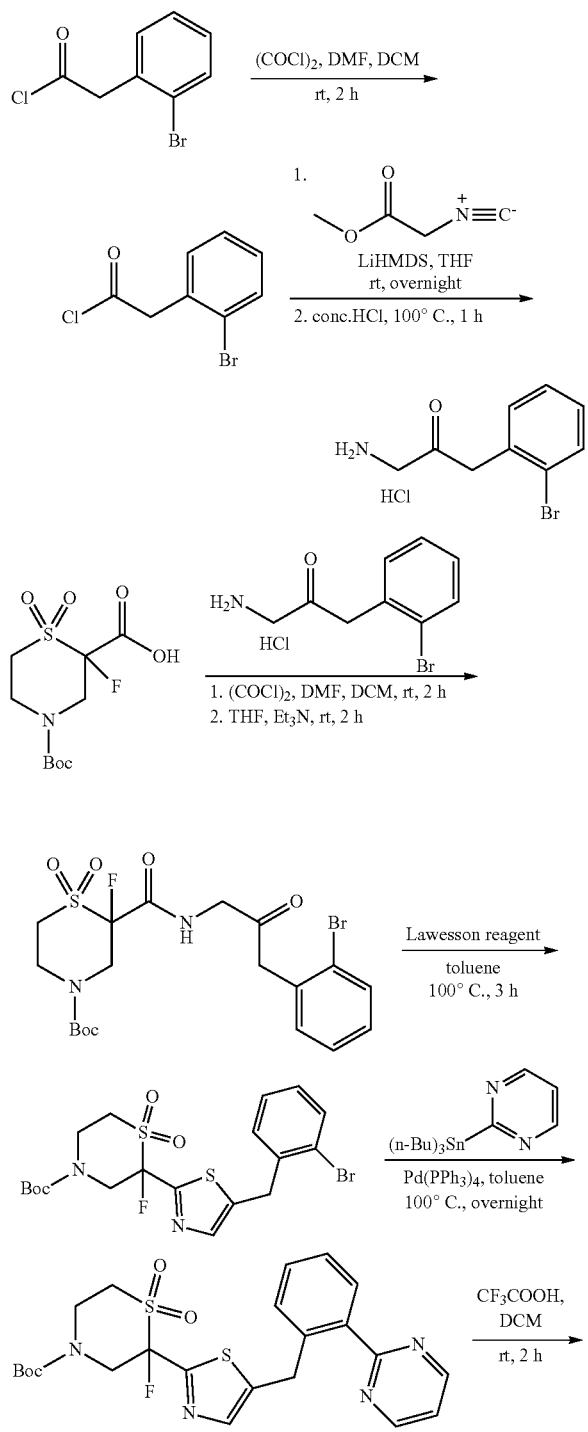

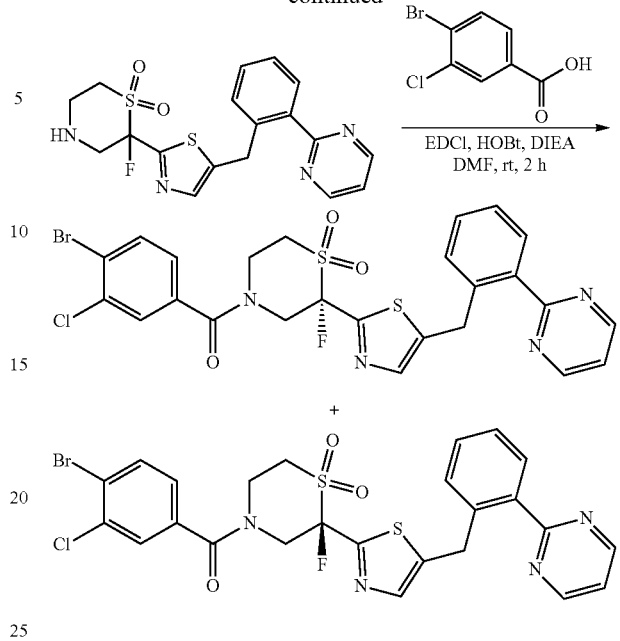

(2-bromophenyl)acetyl chloride: A 100 mL round-bottom flask was charged with (2-bromophenyl)acetic acid (5.00 g, 23.2 mmol, 1.00 eq.), dichloromethane (80 mL), oxalyl chloride (5.02 g, 39.5 mmol, 1.70 eq.) and N,N-dimethylformamide (0.170 mg, 2.32 mmol, 0.10 eq.). The mixture was stirred for 2 h at rt and concentrated under reduced pressure to afford (2-bromophenyl)acetyl chloride (5.42 g, crude) as a light yellow oil, which was used for next directly without further purification 1-amino-3-(2-bromophenyl)propan-2-one hydrochloride: A 250 mL round-bottom flask was charged with THF (50 mL) and lithium bis(trimethylsilyl)amide (38.5 mL, 38.5 mmol, 1.66 eq., 1 M in THF) under N₂. Methyl 2-isocyanoacetate (3.45 g, 34.8 mmol, 1.50 eq.) in THF (5 mL) was added at −78° C. The mixture was stirred for 30 mins at −78° C. under N₂ atmosphere. Then (2-bromophenyl)acetyl chloride (5.42 g, 23.2 mmol, 1.00 eq.) in THF (10 mL) was added at −78° C. The mixture was allowed to warm to rt and stirred for overnight at rt. The reaction was quenched with water (200 mL), extracted with ethyl acetate (3×300 mL). The combined organic layers were dried over anhydrous sodium sulfate, filtered and concentrated under reduced pressure. The residue was diluted with concentrated hydrochloric acid (100 mL) and stirred for 1 h at 100° C. The mixture was concentrated under reduced pressure to afford 1-amino-3-(2-bromophenyl)propan-2-one hydrochloride (5.17 g, 84% yield) as a brown solid. LCMS (ESI, m/z): 228 [M-HCl+H]⁺.

tert-butyl 2-[[3-(2-bromophenyl)-2-oxopropyl]carbamoyl]-2-fluoro-1,1-dioxo-1 λ6-thiomorpholine-4-carboxylate: A 250 mL round-bottom flask was charged with 4-(tert-butoxycarbonyl)-2-fluoro-1,1-dioxo-1λ⁶-thiomorpholine-2-carboxylic acid (2.00 g, 6.73 mmol, 1.00 eq.), dichloromethane (30 mL), oxalyl chloride (1.45 g, 11.4 mmol, 1.70 eq.) and N,N-dimethylformamide (0.0492 g, 0.673 mmol, 0.10 eq.). The mixture was stirred for 2 h at rt and concentrated under reduced pressure to afford tert-butyl 2-(chlorocarbonyl)-2-fluorothiomorpholine-4-carboxylate 1,1-dioxide. Another 250 mL round-bottom flask was charged with 1-amino-3-(2-bromophenyl)propan-2-one hydrochloride (1.78 g, 6.73 mmol, 1.0 eq.), THF (30 mL) and triethylamine (3.40 g, 33.6 mmol, 4.99 eq.). Then the tert-butyl 2-(chlorocarbonyl)-2-fluorothiomorpholine-4-carboxylate 1,1-dioxide was added into this mixture. The mixture was stirred for 2 h at rt and concentrated under reduced pressure. The residue was purified by silica gel column chromatography, eluted with petroleum ether:ethyl acetate (1:1) to afford tert-butyl 2-[[3-(2-bromophenyl)-2-oxopropyl]carbamoyl]-2-fluoro-1,1-dioxo-1$\lambda^6$-thiomorpholine-4-carboxylate (1.53 g, 44% yield) as a light brown solid. LCMS (ESI, m/z): 507 [M+H]$^+$.

tert-butyl 2-[5-[(2-bromophenyl)methyl]-1,3-thiazol-2-yl]-2-fluoro-1,1-dioxo-1 $\lambda$6-thiomorpholine-4-carboxylate: A 40 mL vial was charged with tert-butyl 2-[[3-(2-bromophenyl)-2-oxopropyl]carbamoyl]-2-fluoro-1,1-dioxo-1$\lambda^6$-thiomorpholine-4-carboxylate (200 mg, 0.394 mmol, 1.00 eq.), Lawesson reagent (128 mg, 0.315 mmol, 0.80 eq.) and toluene (5 mL). The mixture was stirred for 3 h at 100° C. and concentrated under reduced pressure. The residue was purified by Prep-TLC (petroleum ether:ethyl acetate, 3:1) to afford tert-butyl 2-[5-[(2-bromophenyl)methy l]-1,3-thiazol-2-yl]-2-fluoro-1,1-dioxo-1$\lambda^6$-thiomorpholine-4-carboxylate (90.0 mg, 45% yield) as a white solid. LCMS (ESI, m/z): 505 [M+H]$^+$.

Tert-butyl 2-fluoro-1,1-dioxo-2-(5-[[2-(pyrimidin-2-yl)phenyl]methyl]-1,3-thiazol-2-yl)-1$\lambda^6$-thiomorpholine-4-carboxylate: A 100 mL round-bottom flask was charged with tert-butyl 2-[5-[(2-bromophenyl)methyl]-1,3-thiazol-2-yl]-2-fluoro-1,1-dioxo-1$\lambda^6$-thiomorpholine-4-carboxylate (170 mg, 0.336 mmol, 1.00 eq.), toluene (20 mL), tetrakis(triphenylphosphine)palladium (38.9 mg, 0.0340 mmol, 0.10 eq.) and 2-(tributylstannyl)pyrimidine (186 mg, 0.505 mmol, 1.50 eq.) under N$_2$. The mixture was stirred for overnight at 100° C. under N$_2$ atmosphere and concentrated under reduced pressure. The residue was purified by Prep-TLC (petroleum ether:ethyl acetate, 1:1) to afford tert-butyl 2-fluoro-1,1-dioxo-2-(5-[[2-(pyrimidin-2-yl)phenyl]methyl]-1,3-thiazol-2-yl)-1$\lambda$6-thiomorpholine-4-carboxylate (80.0 mg, 47% yield) as a light yellow solid. LCMS (ESI, m/z): 505 [M+H]$^+$.

2-fluoro-2-(5-[[2-(pyrimidin-2-yl)phenyl]methyl]-1,3-thiazol-2-yl)-1$\lambda^6$-thiomorpholine-1,1-dione: A 100 mL round-bottom flask was charged with dichloromethane (10 mL), trifluoroacetic acid (2 mL) and tert-butyl 2-fluoro-1,1-dioxo-2-(5-[[2-(pyrimidin-2-yl)phenyl]methyl]-1,3-thiazol-2-yl)-1$\lambda$6-thiomorpholine-4-carboxylate (140 mg, 0.277 mmol, 1.00 eq.). The mixture was stirred for 2 h at rt and concentrated under reduced pressure to afford 2-fluoro-2-(5-[[2-(pyrimidin-2-yl)phenyl]methyl]-1,3-thiazol-2-yl)-1$\lambda$6-thiomorpholine-1,1-dione (112 mg, crude) as light yellow oil. LCMS (ESI, m/z): 405 [M+H]$^+$.

Compounds (44a) and (44b): A 40 mL vial was charged with 4-bromo-3-chlorobenzoic acid (42.4 mg, 0.180 mmol, 1.30 eq.), N-(3-dimethylaminopropyl)-N'-ethylcarbodiimide hydrochloride (34.5 mg, 0.180 mmol, 1.30 eq.), 1-hydroxybenzotrizole (24.3 mg, 0.180 mmol, 1.30 eq.), 2-fluoro-2-(5-[[2-(pyrimidin-2-yl)phenyl]methyl]-1,3-thiazol-2-yl)-1$\lambda^6$-thiomorpholine-1,1-dione (56.0 mg, 0.138 mmol, 1.00 eq.), N,N-dimethylformamide (5 mL) and N,N-diisopropylethylamine (71.6 mg, 0.554 mmol, 4.00 eq.). The mixture was stirred for 2 h at rt and concentrated under reduced pressure. The residue was diluted with dichloromethane (3 mL) and purified by Prep-TLC (petroleum ether:ethyl acetate, 1:1) to afford the mixture of products. The mixture was separated by Prep-Chiral-HPLC with the following conditions (Column: CHIRALPAK IF, 2×25 cm, 5 µm; Mobile Phase A: MTBE(0.5% 2M NH$_3$-MeOH)-HPLC, Mobile Phase B: EtOH-HPLC; Flow rate: 12 mL/min; Gradient: 50% B to 50% B in 15 min to afford (rac-2R)-4-(4-bromo-3-chlorobenzoyl)-2-fluoro-2-(5-[[2-(pyrimidin-2-yl)phenyl]methyl]-1,3-thiazol-2-yl)-1$\lambda$6-thiomorpholine-1,1-dione (44a) (17.3 mg, 20% yield, the first peak) as a white solid. LCMS (ESI, m/z): 621 [M+H]$^+$. NMR (400 MHz, Chloroform-d) δ 8.95-8.75 (m, 2H), 8.11-7.92 (m, 1H), 7.75-7.31 (m, 6H), 7.26-7.20 (m, 1H), 7.20-7.11 (m, 1H), 5.12-4.87 (m, 1H), 4.75-4.38 (m, 4H), 3.80-3.45 (m, 2H), 3.35-3.10 (m, 1H) and (rac-2S)-4-(4-bromo-3-chlorobenzoyl)-2-fluoro-2-(5-[[2-(pyrimidin-2-yl)phenyl]methyl]-1,3-thiazol-2-yl)-1$\lambda$6-thiomorpholine-1,1-dione (44b) (16.0 mg, 18% yield, the second peak) as a white solid. LCMS (ESI, m/z): 621 [M+H]$^+$. NMR (400 MHz, Chloroform-d) δ 8.90-8.68 (m, 2H), 8.10-7.90 (m, 1H), 7.80-7.32 (m, 6H), 7.26-7.21 (m, 1H), 7.20-7.11 (m, 1H), 5.19-4.80 (m, 1H), 4.70-4.18 (m, 4H), 3.73-3.40 (m, 2H), 3.38-3.18 (m, 1H).

Example 46

(R)-(2-(5-benzyloxazol-2-yl)-2-fluoro-1,1-dioxidothiomorpholino)(4-bromo-3-chlorophenyl)methanone (46a) and (S)-(2-(5-benzyloxazol-2-yl)-2-fluoro-1,1-dioxidothiomorpholino)(4-bromo-3-chlorophenyl) methanone (46b)

(R)-4-(4-bromo-3-chlorobenzoyl)-2-fluoro-N-(2-oxo-3-phenylpropyl)thiomorpholine-2-carboxamide 1,1-dioxide: SOCl$_2$ (1.2 eq., 0.10 mL, 1.45 mmol) and DMAP (0.1 eq., 14.73 mg, 0.12 mmol) were added to a solution of (R)-4-(4-bromo-3-chlorobenzoyl)-2-fluorothiomorpholine-2-carboxylic acid 1,1-dioxide (1 eq., 500 mg, 1.206 mmol) in anhydrous CH$_2$Cl$_2$ (70 mL) under N$_2$. The mixture was stirred at rt for 1 d. Then, SOCl$_2$ (1.2 eq., 0.105 mL, 1.45 mmol) and DMAP (0.1 eq., 14.73 mg, 0.12 mmol) were added. The mixture was stirred at rt for 3 h. Then, l-amino-3-phenylpropan-2-one hydrochloride (1.3 eq., 291.03 mg, 1.57 mmol) and K$_2$CO$_3$ (3 eq., 499.98 mg, 3.62 mmol) were added. The mixture was stirred at 40° C. for 2 h. Then, sat. Na$_2$CO$_3$ (30 mL) was added to the mixture which was extracted with AcOEt (3×30 mL). The organic layers were combined, washed with sat. Na$_2$CO$_3$ (20 mL), water (30 mL), brine (30 mL), dried over MgSO$_4$ and evaporated to dryness to give a crude product which was purified by flash chromatography (from 30 to 50% of AcOEt in Cyclohexane) to afford a brown solid. The resulting solid was triturated in Et$_2$O to afford the desired compound (328 mg, 0.601 mmol, 50%). LCMS: C$_{21}$H$_{19}$BrClFN$_2$O$_5$S [M+H]$^+$: 545/547/549.

Compound (46a): POCl$_3$ (3.3 eq., 185.4 mg, 0.114 mL, 1.20 mmol) was added to a solution of (R)-4-(4-bromo-3-chlorobenzoyl)-2-fluoro-N-(2-oxo-3-phenylpropyl)thiomorpholine-2-carboxamide 1,1-dioxide (1 eq., 200 mg, 0.37 mmol) in anhydrous toluene (8.3 mL) under N$_2$. The mixture was stirred at 110° C. until full conversion of the starting material. Then, sat. Na$_2$CO$_3$ (30 mL) was added to the mixture which was extracted with AcOEt (3×30 mL). The organic layers were combined, washed with sat. Na$_2$CO$_3$ (20 mL), water (30 mL), brine (30 mL), dried over MgSO$_4$ and evaporated to dryness to afford a crude product which was purified by flash chromatography (from 20 to 40% of AcOEt in Cyclohexane) to afford a yellow solid. The resulting solid was triturated in Et$_2$O to afford the desired compound (40 mg, 0.15 mmol, 77%) as a white solid. $^1$H-NMR (DMSO, 600 MHz, 80° C.): 3.58-3.74 (m, 4H); 4.14 (s, 2H); 4.29-4.46 (m, 2H); 7.13 (s, 1H); 7.25-7.29 (m, 3H); 7.32-7.35 (m, 2H); 7.37 (dd, J=8.1, 1.5 Hz, 1H); 7.71 (br s, 1H); 7.86 (d, J=8.2 Hz, 1H) ppm. LCMS: C$_{21}$H$_{17}$BrClFN$_2$O$_4$S$_2$ [M+H]$^+$: 527/529/531.

Compound (46b): (S)-(2-(5-benzyloxazol-2-yl)-2-fluoro-1,1-dioxidothiomorpholino)(4-bromo-3-chlorophenyl)methanone (46b) was synthetized following the protocol described for the synthesis of (R)-(2-(5-benzyloxazol-2-yl)-2-fluoro-1,1-dioxidothiomorpholino)(4-bromo-3-chlorophenyl)methanone (46a), using (S)-4-(4-bromo-3-chlorobenzoyl)-2-fluorothiomorpholine-2-carboxylic acid 1,1-dioxide instead of (R)-4-(4-bromo-3-chlorobenzoyl)-2-fluorothiomorpholine-2-carboxylic acid 1,1-dioxide. $^1$H-NMR (DMSO, 600 MHz, 80° C.): 3.58-3.74 (m, 4H); 4.14 (s, 2H); 4.29-4.46 (m, 2H); 7.13 (s, 1H); 7.25-7.29 (m, 3H); 7.32-7.35 (m, 2H); 7.37 (dd, J=8.1, 1.5 Hz, 1H); 7.71 (br s, 1H); 7.86 (d, J=8.2 Hz, 1H) ppm. LCMS: $C_{21}H_{17}BrClFN_2O_4S_2$ [M+H]$^+$: 527/529/531.

Example 47

(4-bromo-3-chloro-phenyl)-[(rac-2S,5R)-2-(5-benzylthiazol-2-yl)-2-fluoro-5-methyl-1,1-dioxo-1,4-thiazinan-4-yl]methanone (47a) and (4-bromo-3-chloro-phenyl)-[(rac-2R,5R)-2-(5-benzylthiazol-2-yl)-2-fluoro-5-methyl-1,1-dioxo-1,4-thiazinan-4-yl]methanone (47b)

(R)-2(tert-Butoxycarbonylamino)-1-propanol: Boc$_2$O (1.0 eq., 43.6 g, 199.7 mmol) was added to (R)-(−)-2-amino-1-propanol (1.0 eq., 15.0 g, 199.7 mmol) in THF (750 mL). The mixture was stirred for 4 h at rt. The mixture was evaporated to dryness. Water (200 mL) and AcOEt (200 mL) were added, and the aqueous layer was extracted with AcOEt (2×100 mL). The combined organic layers were dried over Na$_2$SO$_4$, filtered and evaporated to dryness to (R)-2(tert-Butoxycarbonylamino)-1-propanol (30.36 g, 175.2 mmol, 87%) as a white gum. $^1$H-NMR (DMSO, 400 MHz, 25° C.): 0.98 (d, J=6.6 Hz, 3H); 1.38 (s, 9H), 3.16 (qd, J=10.5, 6.3 Hz, 1H), 3.28-3.38 (m, 2H); 3.39-3.49 (m, 1H); 4.58 (t, J=5.8 Hz, 1H); 6.59 (d, J=7.1 Hz, 1H) ppm. LCMS: $C_8H_{17}NO_3$ [M+Na]$^+$: 198.

tert-butyl N-[(2R)-1-(methanesulfonyloxy)propan-2-yl]carbamate: MsCl (1.3 eq., 25.8 g, 225.2 mmol) and Et$_3$N (1.6 eq., 38.53 mL, 277.2 mmol) were added to a solution of (R)-2-(tert-Butoxycarbonylamino)-1-propanol (1.0 eq., 30.36 g, 173.2 mmol) in CH$_2$Cl$_2$ (520 mL) under N$_2$. The mixture was stirred for 2.5 h at 0° C., and then diluted with water (400 mL). The aqueous layer was extracted with dichlorometane (2×150 mL). The combined organic layers were dried over Na$_2$SO$_4$, filtered and evaporated to dryness to provide tert-butyl N-[(2R)-1-(methanesulfonyloxy)propan-2-yl]carbamate (41.7 g, 95%) as a pale beige solid. $^1$H-NMR (DMSO, 400 MHz, 25° C.): 1.05 (d, J=6.9 Hz, 3H); 1.38 (s, 9H), 3.16 (s, 3H); 3.69-3.79 (m, 1H); 4.03 (d, J=5.8 Hz, 2H); 6.94 (d, J=7.8 Hz, 1H) ppm. LCMS: $C_9H_{19}NO_5S$ [M+Na]$^+$: 276.

tert-butyl N-[(2R)-1-(acetylsulfanyl)propan-2-yl]carbamate: Potassium thioacetate (1.3 eq., 24.6 g, 215.6 mmol) was added to a solution tert-butyl N-[(2R)-1-(methanesulfonyloxy)propan-2-yl]carbamate (1.0 eq., 41.7 g, 164.6 mmol) in DMF (505 mL) under N$_2$, and the mixture was stirred for 18 h at rt. Then, the mixture was diluted with water (200 mL) and Et$_2$O (250 mL). The aqueous layer was extracted with Et$_2$O (2×200 mL). The combined organic layers were washed with brine (2×400 mL), dried over Na$_2$SO$_4$, filtered and evaporated to dryness tert-butyl N-[(2R)-1-(acetylsulfanyl)propan-2-yl]carbamate (37.7 g, 90%) as a beige solid. $^1$H-NMR (DMSO, 400 MHz, 25° C.): 1.04 (d, J=6.8 Hz, 3H); 1.37 (s, 9H); 2.32 (s, 3H); 2.83 (dd, J=13.3, 7.3 Hz, 1H); 2.96 (dd, J=12.6, 6.3 Hz, 1H); 3.50-3.60 (m, 1H); 6.82 (d, J=7.9 Hz, 1H) ppm. LCMS: $C_{10}H_{19}NO_3S$ [M+Na]$^+$: 256.

methyl 2-{[(2R)-2-{[(tert-butoxy)carbonyl]amino}propyl]sulfanyl}acetate: Methyl bromoacetate (1.5 eq., 34 g, 222.4 mmol) and K$_2$CO$_3$ (1.5 eq., 30.74 g, 222.4 mmol) were added to a solution tert-butyl 1N-[(2R)-1-(acetylsulfanyl)propan-2-yl]carbamate (1.0 eq., 34.6 g, 148.3 mmol) in MeOH (1090 mL) under N$_2$, and the mixture was stirred for 22 h at rt. Then, the mixture was concentrated then diluted with AcOEt (300 mL) and water (300 mL). The organic layer was washed with brine (400 mL), dried over Na$_2$SO$_4$, filtered and evaporated to dryness to give a crude product which was purified by flash chromatography on silica gel (5% to 50% AcOEt in Cyclohexane) to give methyl 2-{[(2R)-2-{[(tert-butoxy)carbonyl]amino}propyl]sulfanyl}acetate (35.46 g, 89%) as a colorless oil. $^1$H-NMR (DMSO, 400 MHz, 25° C.): 1.06 (d, J=6.6 Hz, 3H); 1.38 (s, 9H); 2.52-2.64 (m, 2H); 3.34 (d, J=2.8 Hz, 2H); 3.55-3.61 (m, 1H); 3.63 (s, 3H); 6.78 (d, J=8.3 Hz, 1H) ppm. LCMS: $C_{11}H_{21}NO_4S$ [M+Na]$^+$: 286.

(5R)-5-methylthiomorpholin-3-one: TFA (3.4 eq., 34.5 mL, 465.7 mmol) was added to a solution 2-{[(2R)-2-{[(tert-butoxy)carbonyl]amino}propyl]sulfanyl}acetate (1.0 eq., 35.46 g, 134.6 mmol) in CH$_2$Cl$_2$ (385 mL) under N$_2$, and the mixture was stirred for 24 h at rt. Then, the mixture was evaporated to dryness to give the Boc-deprotection product. A sat. solution of NaHCO$_3$ (450 mL) was added to the Boc-deprotection product in CH$_2$Cl$_2$ (800 mL), and the mixture was stirred for 96 h at rt. The aqueous layer was extracted with CH$_2$Cl$_2$ (4×250 mL). The combined organic layers were dried over Na$_2$SO$_4$, filtered and evaporated to dryness to give a crude product which was purified by flash chromatography on silica gel (0% to 7% MeOH in CH$_2$Cl$_2$) to give (5R)-5-methylthiomorpholin-3-one (13.1 g, 74%) as a white solid. LCMS: $C_5H_9NOS$ [M+H]$^+$: 132.

tert-butyl (3R)-3-methylthiomorpholine-4-carboxylate: BH$_3$•THF (1 M, 3.0 eq., 93.53 mL, 93.53 mmol) was added to a solution of (5R)-5-methylthiomorpholin-3-one (1 eq., 4.09 g, 31.18 mmol) in THF (180 mL) under N$_2$. The mixture was stirred for 2 h at 60° C., and then cooled at 0° C. The reaction was quenched by dropwise addition of MeOH (126 mL). The mixture was evaporated in vacuo at 30° C. The residue was dissolved in MeOH (195 mL). The mixture was stirred for 19 h at 60° C., and then concentrated at 30° C. to give the N-deprotected intermediate. NaOH 10% (2 eq., 250 mL, 62.35 mmol) was added to a solution of the intermediate in CH$_2$Cl$_2$ (122 mL). After 15 mins of stirring, Boc$_2$O (1.5 eq., 10.20 g, 46.76 mmol) in CH$_2$Cl$_2$ (122 mL) was added. The mixture was stirred for 1.5 h at rt. The organic layer was separated. The aqueous layer was extracted with CH$_2$Cl$_2$ (2×100 mL). The combined organic layers were washed with brine (300 mL), dried over Na$_2$SO$_4$, filtered and evaporated to dryness to give a crude product which was purified by flash chromatography on silica gel (0% to 25% AcOEt in cyclohexane) to give tert-butyl (3R)-3-methylthiomorpholine-4-carboxylate (5.0 g, 72%) as a white solid. $^1$H-NMR (DMSO, 400 MHz, 25° C.): 1.23 (d, J=6.6 Hz, 3H); 1.40 (s, 9H); 2.38-2.47 (m, 2H); 2.50-2.56 (m, 1H); 2.85 (dd, J=13.5, 3.9, 1H); 3.00-3.06 (m, 1H); 4.02 (dt, J=14.0, 3.1 Hz, 1H); 4.42-4.49 (m, 1H) ppm. LCMS: $C_{10}H_{19}NO_2S$ [M-Boc+H]$^+$: 118.

(R)-tert-butyl 2-methylthiomorpholine-4-carboxylate-1,1-dioxide: mCPBA (2.1 eq., 18.12 g, 80.8 mmol) was added by portions to a solution of tert-butyl (3R)-3-methylthio-morpholine-4-carboxylate (1 eq., 8.37 g, 38.5 mmol) in CH$_2$Cl$_2$ (220 mL) under N$_2$, and the mixture was stirred for 1 h at 0° C. Then, sat. Na$_2$CO$_3$ (150 mL) and water (150 mL)

were added. The aqueous layer was extracted with $CH_2Cl_2$ (3×150 mL). The combined organic layers were washed with brine (150 mL), dried over $Na_2SO_4$, filtered and evaporated to dryness to give a crude product which was purified by flash chromatography on silica gel (10% to 50% AcOEt in cyclohexane) to give (R)-tert-butyl 2-methylthiomorpholine-4-carboxylate-1,1-dioxide (8.5 g, 89%) as a white solid. $^1$H-NMR (DMSO, 400 MHz, 25° C.): 1.30 (d, J=7.1 Hz, 3H); 1.41 (s, 9H); 3.07-3.14 (m, 3H); 3.27-3.32 (m, 1H); 3.36-3.44 (m, 1H); 4.25-4.29 (m, 1H); 4.68-4.75 (m, 1H) ppm. LCMS: $C_{10}H_{19}NO_4S$ [M+Na]$^+$: 272.

4-tert-butyl 2-ethyl (5R)-5-methyl-1,1-dioxo-1λ$^6$-thiomorpholine-2,4-dicarboxylate: LiHMDS (1 M in THF, 1.0 eq., 18.65 mL, 18.65 mmol) was added to a solution of (R)-tert-butyl 2-methylthiomorpholine-4-carboxylate-1,1-dioxide (1 eq., 4.65 g, 18.65 mmol) in THF (140 mL) under $N_2$, and the mixture was stirred for 0.5 h at −78° C. Then, Ethyl chloroformate (1.0 eq., 1.78 mL, 18.65 mmol) was added at −78° C., and the mixture was stirred for 0.5 h. Then, LiHMDS (1 M in THF, 1.0 eq., 18.65 mL, 18.65 mmol) was added. The mixture was stirred for 1.5 h at −78° C. Water and sat. $NH_4Cl$ were added to the mixture until an ice block forms. Then, the mixture was diluted with AcOEt (150 mL) and water, and sat. $NH_4Cl$ were added. The aqueous layer was extracted with AcOEt (2×250 mL). The combined organic layers were washed with water (100 mL) and brine (200 mL), dried over $Na_2SO_4$, filtered and evaporated to dryness to give a crude product which was purified by flash chromatography on silica gel (0% to 40% AcOEt in cyclohexane) to give 4-tert-butyl 2-ethyl (5R)-5-methyl-1,1-dioxo-1λ$^6$-thiomorpholine-2,4-dicarboxylate (4.32 g, 68%) as a pale yellow oil. LCMS: $C_{13}H_{23}NO_6S$ [M+Na]$^+$: 344.

4-tert-butyl 2-ethyl (5R)-2-fluoro-5-methyl-1,1-dioxo-1λ$^6$-thiomorpholine-2,4-dicarboxylate: NaH 60% (1.2 eq., 1.52 g, 37.94 mmol) was added at 0° C. to a solution of 4-tert-butyl 2-ethyl (5R)-5-methyl-1,1-dioxo-1λ$^6$-thiomorpholine-2,4-dicarboxylate (1 eq., 10.16 g, 31.61 mmol) in THF (100 mL) under $N_2$. After 0.5 h of stirring, NFSI (1.2 eq., 11.96 g, 37.94 mmol) was added at 0° C., and the mixture was stirred at rt for 3 h. The reaction was quenched with water (100 mL) and concentrated. The residue was diluted with AcOEt (150 mL) and water (150 mL), and the aqueous layer was extracted with AcOEt (2×150 mL). The combined organic layers were washed with brine (200 mL), dried over $Na_2SO_4$, filtered and evaporated to dryness to give a crude product which was purified by flash chromatography on silica gel (5% to 50% AcOEt in cyclohexane) to give 4-tert-butyl 2-ethyl (5R)-2-fluoro-5-methyl-1,1-dioxo-1λ$^6$-thiomorpholine-2,4-dicarboxylate (9.4 g, 78%) as a colorless oil. LCMS: $C_{13}H_{22}FNO_6S$ [M+Na]$^+$: 362.

(5R)-4-[(tert-butoxy)carbonyl]-2-fluoro-5-methyl-1,1-dioxo-1λ$^6$-thiomorpholine-2-carboxylic acid: LiOH•$H_2O$ (3.0 eq., 3.10 g, 74 mmol) was added to a solution of 2-ethyl (5R)-2-fluoro-5-methyl-1,1-dioxo-1λ$^6$-thiomorpholine-2,4-dicarboxylate (1 eq., 8.37 g, 24.6 mmol) in a mixture of THF (250 mL) and water (50 mL). The mixture was stirred at rt for 1.5 h. THF was evaporated, then HCl 1 M was added until pH=2, and the aqueous layer was extracted with AcOEt (4×200 mL). The combined organic layers were washed with brine (500 mL), dried over $Na_2SO_4$, filtered and evaporated to dryness to give (5R)-4-[(tert-butoxy)carbonyl]-2-fluoro-5-methyl-1,1-dioxo-1λ$^6$-thiomorpholine-2-carboxylic acid (6.0 g, 72%) as a beige solid. $^1$H-NMR (DMSO, 400 MHz, 25° C.): 1.32-1.52 (m, 12H), 3.29-3.43 (m, 1H), 3.48-3.82 (m, 3H), 4.23-4.82 (m, 2H) ppm. LCMS: $C_{11}H_{18}FNO_6S$ [M-Boc+H]$^+$: 212.

tert-butyl (5R)-2-fluoro-5-methyl-1,1-dioxo-2-[(2-oxo-3-phenylpropyl)carbamoyl]-1λ$^6$-thiomorpholine-4-carboxylate: TCFH (2.0 eq., 1.96 g, 7.0 mmol) was added to a solution of (5R)-4-[(tert-butoxy)carbonyl]-2-fluoro-5-methyl-1,1-dioxo-1λ$^6$-thiomorpholine-2-carboxylic acid (1 eq., 1.09 g, 3.50 mmol) in MeCN (45 mL) under $N_2$. After 5 min of stirring, l-amino-3-phenylpropan-2-one hydrochloride (1.1 eq., 720 mg, 3.85 mmol) and N-methyl imidazole (5 eq., 1.44 mL, 17.5 mmol) were added. The mixture was stirred at rt for 20 h. The mixture was diluted with AcOEt and sat. $Na_2CO_3$ (50 mL), and the aqueous layer was extracted with AcOEt (3×75 mL). The combined organic layers were washed with brine (100 mL), dried over $Na_2SO_4$, filtered and evaporated to dryness to give a crude product which was purified by flash chromatography on silica gel (0% to 50% AcOEt in Cyclohexane) to give tert-butyl (5R)-2-fluoro-5-methyl-1,1-dioxo-2-[(2-oxo-3-phenylpropyl)carbamoyl]-1λ$^6$-thiomorpholine-4-carboxylate (930 mg, 57%) as an orange sticky solid. LCMS: $C_{20}H_{27}FN_2O_6S$ [M+Na]$^+$: 465.

(5R)-2-fluoro-2-{5-[(4-fluorophenyl)methyl]-1,3-thiazol-2-yl}-5-methyl-1λ$^6$-thiomorpholine-1,1-dione: $P_2S_5$ (2.0 eq., 1.82 g, 4.09 mmol) was added to a solution of (5R)-2-fluoro-5-methyl-1,1-dioxo-2-[(2-oxo-3-phenylpropyl)carbamoyl]-1λ$^6$-thiomorpholine-4-carboxylate (1 eq., 906 mg, 2.047 mmol) in toluene (22 mL) under $N_2$. The mixture was stirred at 100° C. for 6 h. The mixture was evaporated to dryness to give a crude product which was purified by flash chromatography on silica gel (0% to 10% MeOH+2% $NH_4OH$ in $CH_2Cl_2$) to (5R)-2-fluoro-2-{5-[(4-fluorophenyl)methyl]-1,3-thiazol-2-yl}-5-methyl-1λ$^6$-thiomorpholine-1,1-dione (140 mg, 20%) as a yellow oil. LCMS: $C_{15}H_{17}FN_2O_6S_2$ [M+H]$^+$: 341.

Compounds (47a) and (47b): TCFH (3.0 eq., 247 mg, 0.88 mmol), N-methylimidazole (7.5 eq., 0.18 mL, 2.20 mmol) and (5R)-2-fluoro-2-{5-[(4-fluorophenyl)methyl]-1,3-thiazol-2-yl}-5-methyl-1λ$^6$-thiomorpholine-1,1-dione (1.0 eq., 100 mg, 0.29 mmol) were added to a suspension of 4-bromo-3-chlorobenzoic acid (1.7 eq., 117.6 mg, 0.50 mmol) in MeCN (3.5 mL) under $N_2$ at rt, and the mixture was stirred 36 h at rt. Then, sat. $Na_2CO_3$ (30 mL) was added, and the aqueous layer was extracted with AcOEt (3×50 mL). The combined organic layers were washed with water (2×30 mL) and brine (2×30 mL), dried over $Na_2SO_4$, filtered and evaporated to dryness to give a crude product which was purified by flash chromatography on silica gel (0% to 60% AcOEt in Cyclohexane) to give a mixture of diastereoisomers (41 mg, 25%). The mixture of diastereoisomers was purified by preparative HPLC (XBridge prep C18 5 μm, 30×150 mm, 40 mL/min, $H_2O$+0.1% AcOH/MeCN: 57% to 68% MeCN, 25 min) to give (47a) (12.2 mg, 7%) and (47b) (3.4 mg, 2%).

Compound (47a): $^1$H-NMR (DMSO, 400 MHz, 80° C.): 1.51 (d, J7=7.1 Hz, 3H), 3.62-3.65 (m, 1H), 3.78-3.84 (m, 1H), 4.28 (s, 2H), 4.45-4.58 (m, 1H) 4.92 (br s, 2H), 7.24-7.36 (m, 6H), 7.70 (s, 1H), 7.83-7.87 (m, 2H) ppm. LCMS: $C_{22}H_{19}BrClFN_2O_3S_2$ [M+H]$^+$: 556.9/558.9/560.9.

Compound (47b): $^1$H-NMR (DMSO, 400 MHz, 80° C.): 1.56 (d, J=7.0 Hz, 3H), 3.72 (dt, J=14.6, 5.4 Hz, 1H), 3.96 (dd, J=14.7, 4.6 Hz, 1H), 4.20-4.25 (m, 1H), 4.26 (s, 2H), 4.65-4.77 (m, 2H) 7.20 (dd, J=8.1, 1.8 Hz, 1H), 7.24-7.36 (m, 5H), 7.52 (d, J=1.9 Hz, 1H), 7.75 (d, J=8.2 Hz, 1H), 7.81 (d, J=2.7 Hz, 1H) ppm. LCMS: $C_{22}H_{19}BrClFN_2O_3S_2$ [M+H]$^+$: 556.9/558.9/560.9.

Example 48

(4-bromo-3-chloro-phenyl)-[(rac-2S,5S)-2-(5-benzylthiazol-2-yl)-2-fluoro-5-methyl-1,1-dioxo-1,4-thiazinan-4-yl]methanone (48a) and (4-bromo-3-chloro-phenyl)-[(rac-2R,5S)-2-(5-benzylthiazol-2-yl)-2-fluoro-5-methyl-1,1-dioxo-1,4-thiazinan-4-yl]methanone (48b)

(S)-2(tert-Butoxycarbonylamino)-1-propanol: $Boc_2O$ (1.0 eq., 41.1 g, 188.2 mmol) was added to (S)-(−)-2-amino-1-propanol (1.0 eq., 14 g, 188.2 mmol) in THF (755 mL), and the mixture was stirred for 4 h at rt. The mixture was evaporated to dryness. Water (300 mL) and AcOEt (300 mL) were added, and the aqueous layer was extracted with AcOEt (2×300 mL). The combined organic layers were dried over $Na_2SO_4$, filtered and evaporated to dryness to give (S)-2(tert-Butoxycarbonylamino)-1-propanol (30.4 g, 175.2 mmol, 92%) as a white gum. $^1$H-NMR (DMSO, 400 MHz, 25° C.): 0.98 (d, J=6.8 Hz, 3H); 1.37 (s, 9H), 3.15 (dt, J=10.6, 6.3 Hz, 1H), 3.28-3.33 (m, 1H); 3.38-3.47 (m, 1H); 4.55 (t, J=5.6 Hz, 1H); 6.48 (d, J=7.3 Hz, 1H) ppm. LCMS: $C_8H_{17}NO_3$ [M+Na]$^+$: 198.

tert-butyl N-[(2S)-1-(methanesulfonyloxy)propan-2-yl]carbamate: MsCl (1.3 eq., 26.7 g, 230.5 mmol) and $Et_3N$ (1.6 eq., 39.44 mL, 283.7 mmol) were added to a solution of (S)-2(tert-Butoxycarbonylamino)-1-propanol (1.0 eq., 30.4 g, 173.5 mmol) in $CH_2Cl_2$ (532 mL) under $N_2$. The mixture was stirred for 4 h at 0° C. The mixture was diluted with water (200 mL). The aqueous layer was extracted with dichloromethane (200 mL). The combined organic layers were dried over $Na_2SO_4$, filtered and evaporated to dryness to tert-butyl N-[(2S)-1-(methanesulfonyloxy)propan-2-yl]carbamate (46.0 g, quant.) as a pale beige solid. $^1$H-NMR (DMSO, 400 MHz, 25° C.): 1.05 (d, J=6.9 Hz, 3H); 1.38 (s, 9H), 3.03-3.10 (m, 1H); 3.16 (s, 3H); 3.69-3.79 (m, 1H); 4.03 (d, J=5.9 Hz, 2H) ppm. LCMS: $C_9H_{19}NO_5S$ [M+Na]$^+$: 276.

tert-butyl N-[(2S)-1-(acetylsulfanyl)propan-2-yl]carbamate: Potassium thioacetate (1.5 eq., 29.75 g, 260.5 mmol) was added to a solution of tert-butyl N-[(2S)-1-(methanesulfonyloxy)propan-2-yl]carbamate (1.0 eq., 44 g, 173.7 mmol) in DMF (545 mL) under $N_2$, and the mixture was stirred for 24 h at rt. The mixture was diluted with water (500 mL) and $Et_2O$ (500 mL). The aqueous layer was extracted with $Et_2O$ (200 mL). The combined organic layers were washed with brine (5×400 mL), dried over $Na_2SO_4$, filtered and evaporated to dryness to tert-butyl N-[(2S)-1-(acetylsulfanyl)propan-2-yl]carbamate (38.3 g, 94%) as a yellow oil. $^1$H-NMR (DMSO, 400 MHz, 25° C.): 1.05 (d, J=6.6 Hz, 3H); 1.37 (s, 9H), 2.32 (s, 3H); 2.83 (dd, J=13.3, 7.3 Hz, 1H); 2.96 (dd, J=13.2, 5.8 Hz, 1H); 3.50-3.61 (m, 1H); 6.83 (d, J=8.2 Hz, 1H) ppm. LCMS: $C_{10}H_{19}NO_3S$ [M+Na]$^+$: 256.

methyl 2-{[(2S)-2-{[(tert-butoxy)carbonyl]amino}propyl]sulfanyl}acetate: Methyl bromoacetate (1.5 eq., 37.47 g, 245 mmol) and $K_2CO_3$ (1.5 eq., 33.85 g, 245 mmol) were added to a solution tert-butyl N-[(2S)-1-(acetylsulfanyl)propan-2-yl]carbamate (1.0 eq., 34.6 g, 148.3 mmol) in MeOH (1090 mL) under $N_2$, and the mixture was stirred for 18 h at rt. The mixture was concentrated then diluted with AcOEt (300 mL) and water (300 mL). The organic layer was washed with brine (400 mL), dried over $Na_2SO_4$, filtered and evaporated to dryness to give a crude product which was purified by flash chromatography on silica gel (0% to 50% AcOEt in Cyclohexane) to give methyl 2-{[(2S)-2-{[(tert-butoxy)carbonyl]amino}propyl]sulfanyl}acetate (36.06 g, 84%) as a yellow oil. $^1$H-NMR (DMSO, 400 MHz, 25° C.): 1.06 (d, J=6.8 Hz, 3H); 1.37 (s, 9H); 2.49-2.64 (m, 2H); 3.34 (d, J=2.8 Hz, 2H); 3.54-3.61 (m, 1H); 3.63 (s, 3H); 6.78 (d, J=8.1 Hz, 1H) ppm. LCMS: $C_{11}H_{21}NO_4S$ [M+Na]$^+$: 286.

(5S)-5-methylthiomorpholin-3-one: TFA (3.4 eq., 34.6 mL, 465.7 mmol) was added to a solution 2-{[(2S)-2-{[(tert-butoxy)carbonyl]amino}propyl]sulfanyl}acetate (1.0 eq., 36 g, 136.9 mmol) in $CH_2Cl_2$ (385 mL) under $N_2$, and the mixture was stirred for 2 h at rt. The mixture was evaporated to dryness to give the Boc-deprotection product. A sat. solution of $NaHCO_3$ (450 mL) was added to the Boc-deprotection product in $CH_2Cl_2$ (800 mL). The mixture was stirred for 89 h at rt. The aqueous layer was extracted with $CH_2Cl_2$ (4×250 mL). The combined organic layers were dried over $Na_2SO_4$, filtered and evaporated to dryness to give (5S)-5-methylthiomorpholin-3-one (14 g, 71%) as a beige solid. LCMS: $C_5H_9NOS$ [M+H]$^+$: 132.

tert-butyl (3S)-3-methylthiomorpholine-4-carboxylate: $BH_3$•THF (1 M, 3.0 eq., 100 mL, 100 mmol) was added to a solution of (5S)-5-methylthiomorpholin-3-one (1 eq., 5.12 g, 39.0 mmol) in THF (225 mL) under $N_2$. The mixture was stirred for 20 h at 60° C. The mixture was cooled at 0° C. The reaction was quenched by dropwise addition of MeOH (195 mL). The mixture was evaporated in vacuo at 30° C. The residue was dissolved in MeOH (240 mL), and the mixture was stirred for 24 h at 60° C. The mixture was concentrated at 30° C. to give the N-deprotected intermediate. NaOH 10% (2 eq., 312 mL, 78.13 mmol) was added to a solution of the intermediate in $CH_2Cl_2$ (155 mL). After 15 min of stirring, $Boc_2O$ (1.5 eq., 12.8 g, 58.6 mmol) in $CH_2Cl_2$ (155 mL) was added. The mixture was stirred for 3 h at rt. The organic layer was separated, and the aqueous layer was extracted with $CH_2Cl_2$ (2×100 mL). The combined organic layers were washed with brine (300 mL), dried over $Na_2SO_4$, filtered and evaporated to dryness to give a crude product which was purified by flash chromatography on silica gel (0% to 40% AcOEt in cyclohexane) to give tert-butyl (3S)-3-methylthiomorpholine-4-carboxylate (5.84 g, 52%) as a white solid. $^1$H-NMR (DMSO, 400 MHz, 25° C.): 1.23 (d, J=6.8 Hz, 3H); 1.40 (s, 9H); 2.38-2.47 (m, 2H); 2.51-2.55 (m, 1H); 2.85 (dd, J=13.5, 3.9, 1H); 3.00-3.06 (m, 1H); 4.00-4.04 (m, 1H); 4.45-4.47 (m, 1H) ppm. LCMS: $C_{10}H_{19}NO_2S$ [M-Boc+H]$^+$: 118.

(S)-tert-butyl 2-methylthiomorpholine-4-carboxylate-1,1-dioxide: mCpBA (2.1 eq., 11.26 g, 50.25 mmol) was added by portions to a solution of tert-butyl (3S)-3-methylthiomorpholine-4-carboxylate (1 eq., 5.2 g, 23.93 mmol) in $CH_2Cl_2$ (135 mL) under $N_2$, and the mixture was stirred for 1 h at 0° C. Then, sat. $Na_2CO_3$ (100 mL) and water (100 mL) were added, and the aqueous layer was extracted with $CH_2Cl_2$ (3×100 mL). The combined organic layers were washed with brine (150 mL), dried over $Na_2SO_4$, filtered and evaporated to dryness to give a crude product which was purified by flash chromatography on silica gel (10% to 60% AcOEt in cyclohexane) to give (S)-tert-butyl 2-methylthiomorpholine-4-carboxylate-1,1-dioxide (5.58 g, 94%) as a white solid. $^1$H-NMR (DMSO, 400 MHz, 25° C.): 1.31 (d, J=7.3 Hz, 3H); 1.41 (s, 9H); 3.07-3.17 (m, 3H); 3.27-3.32 (m, 1H); 3.36-3.44 (m, 1H); 4.24-4.30 (m, 1H); 4.68-4.76 (m, 1H) ppm. LCMS: $C_{10}H_{19}NO_4S$ [M+Na]$^+$: 272.

4-tert-butyl 2-ethyl (5S)-5-methyl-1,1-dioxo-1λ$^6$-thiomorpholine-2,4-dicarboxylate: LiHMDS (1 M in THF, 1.0 eq., 18.1 mL, 18.1 mmol) was added to a solution of (S)-tert-butyl 2-methylthiomorpholine-4-carboxylate-1,1-dioxide (1 eq., 4.51 g, 18.1 mmol) in THF (135 mL) under $N_2$, and the mixture was stirred for 0.5 h at −78° C. Then, Ethyl chloroformate (1.0 eq., 1.73 mL, 18.1 mmol) was added at −78° C., and the mixture was stirred for 0.5 h. LiHMDS (1 M in THF, 1.0 eq., 18.1 mL, 18.1 mmol) was added, and the mixture was stirred for 1.5 h at −78° C. Water and sat. NH$_4$Cl were added to the mixture until an ice block forms. The mixture was diluted with AcOEt (150 mL) and water and sat. NH$_4$Cl were added. The aqueous layer was extracted with AcOEt (2×250 mL). The combined organic layers were washed with water (100 mL) and brine (200 mL), dried over Na$_2$SO$_4$, filtered and evaporated to dryness to give a crude product which was purified by flash chromatography on silica gel (0% to 40% AcOEt in cyclohexane) to give 4-tert-butyl 2-ethyl (5S)-5-methyl-1,1-dioxo-1$\lambda^6$-thiomorpholine-2,4-dicarboxylate (5.19 g, 80%) as a pale yellow oil. LCMS: C$_{13}$H$_{23}$NO$_6$S [M+Na]$^+$: 344.

4-tert-butyl 2-ethyl (5S)-2-fluoro-5-methyl-1,1-dioxo-1$\lambda^6$-thiomorpholine-2,4-dicarboxylate: NaH 60% (1.2 eq., 750 mg, 18.67 mmol) was added at 0° C. to a solution of 4-tert-butyl 2-ethyl (5S)-5-methyl-1,1-dioxo-1$\lambda^6$-thiomorpholine-2,4-dicarboxylate (1.0 eq., 5 g, 15.56 mmol) in THF (50 mL) under N$_2$. After 0.5 h of stirring, NFSI (1.2 eq., 5.89 g, 18.67 mmol) was added at 0° C., and the mixture was stirred at rt for 2 h. The reaction was quenched with water (100 mL) and concentrated. The residue was diluted with AcOEt (150 mL) and water (150 mL), and the aqueous layer was extracted with AcOEt (2×150 mL). The combined organic layers were washed with brine (200 mL), dried over Na$_2$SO$_4$, filtered and evaporated to dryness to give a crude product which was purified by flash chromatography on silica gel (0% to 60% AcOEt in cyclohexane) to give 4-tert-butyl 2-ethyl (5S)-2-fluoro-5-methyl-1,1-dioxo-1$\lambda^6$-thiomorpholine-2,4-dicarboxylate (5.7 g, 76%) as a pale yellow oil. $^1$H-NMR (DMSO, 400 MHz, 25° C.): 1.25-1.28 (m, 3H), 1.36-1.44 (m, 12H), 3.33-3.82 (m, 3H), 4.00-4.38 (m, 2H), 4.52-5.05 (m, 2H) ppm. LCMS: C$_{13}$H$_{22}$FNO$_6$S [M+Na]$^+$: 362.

(5S)-4-[(tert-butoxy)carbonyl]-2-fluoro-5-methyl-1,1-dioxo-1$\lambda^6$-thiomorpholine-2-carboxylic acid: LiOH•H$_2$O (3.0 eq., 2.41 g, 57.5 mmol) was added to a solution of 2-ethyl (5S)-2-fluoro-5-methyl-1,1-dioxo-1$\lambda^6$-thiomorpholine-2,4-dicarboxylate (1 eq., 6.5 g, 19.15 mmol) in a mixture of THF (195 mL) and water (40 mL), and the mixture was stirred at rt for 1 h. THF was evaporated, then HCl 1 M was added until pH=2, and the aqueous layer was extracted with AcOEt (4×100 mL). The combined organic layers were washed with brine (300 mL), dried over Na$_2$SO$_4$, and evaporated to dryness to give (5S)-4-[(tert-butoxy)carbonyl]-2-fluoro-5-methyl-1,1-dioxo-1$\lambda^6$-Thiomorpholine-2-carboxylic acid (6.61 g, 96%) as a beige solid. $^1$H-NMR (DMSO, 400 MHz, 25° C.): 1.32-1.42 (m, 12H), 3.26-3.36 (m, 1H), 3.45-3.59 (m, 2H), 3.66-3.80 (m, 1H), 4.20-4.65 (m, 1H), 4.76-5.01 (m, 1H), ppm. LCMS: C$_{11}$H$_{18}$FNO$_6$S [M-Boc+H]$^+$: 212.

tert-butyl (5S)-2-fluoro-5-methyl-1,1-dioxo-2-[(2-oxo-3-phenylpropyl)carbamoyl]-1$\lambda^6$-thiomorpholine-4-carboxylate: TCFH (2.0 eq., 3.79 g, 13.5 mmol) was added to a solution of (5S)-4-[(tert-butoxy)carbonyl]-2-fluoro-5-methyl-1,1-dioxo-1$\lambda^6$-thiomorpholine-2-carboxylic acid (1 eq., 2.1 g, 6.75 mmol) in MeCN (85 mL) under N$_2$. After 5 min of stirring, 1-amino-3-phenylpropan-2-one hydrochloride (1.1 eq., 1.38 g, 7.42 mmol) and N-methylimidazole (5 eq., 2.70 mL, 33.73 mmol) were added, and the mixture was stirred at rt for 20 h. The mixture was diluted with AcOEt and sat. Na$_2$CO$_3$ (100 mL), and the aqueous layer was extracted with AcOEt (3×100 mL). The combined organic layers were washed with brine (100 mL), dried over Na$_2$SO$_4$, filtered and evaporated to dryness to give a crude product which was purified by flash chromatography on silica gel (0% to 50% AcOEt in Cyclohexane) to give tert-butyl (5S)-2-fluoro-5-methyl-1,1-dioxo-2-[(2-oxo-3-phenylpropyl)carbamoyl]-1$\lambda^6$-thiomorpholine-4-carboxylate (1.75 g, 59%) as an orange sticky solid. LCMS: C$_{20}$H$_{27}$FN$_2$O$_6$S [M+Na]$^+$: 465.

(5 S)-2-fluoro-2-{5-[(4-fluorophenyl)methyl]-1,3-thiazol-2-yl}-5-methyl-1$\lambda^6$-thiomorpholine-1,1-dione: P$_2$S$_5$ (2.0 eq., 1.76 g, 7.91 mmol) was added to a solution of (5 S)-2-fluoro-5-methyl-1,1-dioxo-2-[(2-oxo-3-phenylpropyl)carbamoyl]-1$\lambda^6$-thiomorpholine-4-carboxylate (1 eq., 1.75 g, 3.95 mmol) in toluene (43 mL) under N$_2$, and the mixture was stirred at 100° C. for 20 h. The mixture was evaporated to dryness to give a crude product which was purified by flash chromatography on silica gel (0% to 10% MeOH +5% NH$_4$OH in CH$_2$Cl$_2$) to (5S)-2-fluoro-2-{5-[(4-fluorophenyl)methyl]-1,3-thiazol-2-yl}-5-methyl-1$\lambda^6$-thiomorpholine-1,1-dione (835 mg, 62%) as a brown sticky solid. LCMS: C$_{15}$H$_{17}$FN$_2$O$_6$S$_2$ [M+H]$^+$: 341.

Compounds (48a) and (48b): TCFH (3.5 eq., 928 mg, 3.31 mmol), N-methylimidazole (7.5 eq., 0.57 mL, 7.09 mmol) and (5S)-2-fluoro-2-{5-[(4-fluorophenyl)methyl]-1,3-thiazol-2-yl}-5-methyl-1$\lambda^6$-thiomorpholine-1,1-dione (1.0 eq., 370 mg, 0.95 mmol) were added to a suspension of 4-bromo-3-chlorobenzoic acid (1.1 eq., 245 mg, 1.04 mmol) in MeCN (12 mL) under N$_2$ at rt, and the mixture was stirred 20 h at rt. Then, sat. Na$_2$CO$_3$ (70 mL) was added, and the aqueous layer was extracted with AcOEt (3×70 mL). The combined organic layers were washed with water (2×100 mL) and brine (2×100 mL), dried over Na$_2$SO$_4$, filtered and evaporated to dryness to give a crude product which was purified by flash chromatography on silica gel (0% to 40% AcOEt in Cyclohexane) to give a mixture of diastereoisomers (170 mg, 32%). The mixture of diastereoisomers was purified by preparative HPLC (XBridge prep C18 5 µm, 30×150 mm, 40 mL/min, H$_2$O+0.1% AcOH/MeCN: 57% to 68% MeCN, 25 min) to give (48a) (76.6 mg, 15%) and (48b) (23.4 mg, 4%).

Compound (48a): $^1$H-NMR (DMSO, 400 MHz, 80° C.): 1.51 (d, J7=7.1 Hz, 3H), 3.62-3.65 (m, 1H), 3.78-3.84 (m, 1H), 4.28 (s, 2H), 4.45-4.58 (m, 1H) 4.92 (br s, 2H), 7.24-7.36 (m, 6H), 7.70 (s, 1H), 7.83-7.87 (m, 2H) ppm. LCMS: C$_{22}$H$_{19}$BrClFN$_2$O$_3$S$_2$ [M+H]$^+$: 556.9/558.9/560.9.

Compound (48b): $^1$H-NMR (DMSO, 400 MHz, 80° C.): 1.56 (d, J7=7.0 Hz, 3H), 3.72 (dt, 7=14.6, 5.4 Hz, 1H), 3.96 (dd, J=14.7, 4.6 Hz, 1H), 4.20-4.25 (m, 1H), 4.26 (s, 2H), 4.65-4.77 (m, 2H) 7.20 (dd, J=8.1, 1.8 Hz, 1H), 7.24-7.36 (m, 5H), 7.52 (d, J7=1.9 Hz, 1H), 7.75 (d, J7=8.2 Hz, 1H), 7.81 (d, J7=2.7 Hz, 1H) ppm. LCMS: C$_{22}$H$_{19}$BrClFN$_2$O$_3$S$_2$ [M+H]$^+$: 556.9/558.9/560.9.

Example 49

(rac-2R)-2-bromo-4-(4-bromo-3-chlorobenzoyl)-2-(1,3-thiazol-2-yl)-1$\lambda^6$-thiomorpholine-1,1-dione (50a) and (rac-2S)-2-bromo-4-(4-bromo-3-chlorobenzoyl)-2-(1,3-thiazol-2-yl)-1$\lambda^6$-thiomorpholine-1,1-dione (50b)

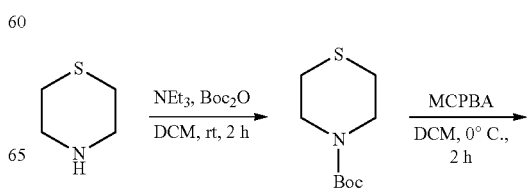

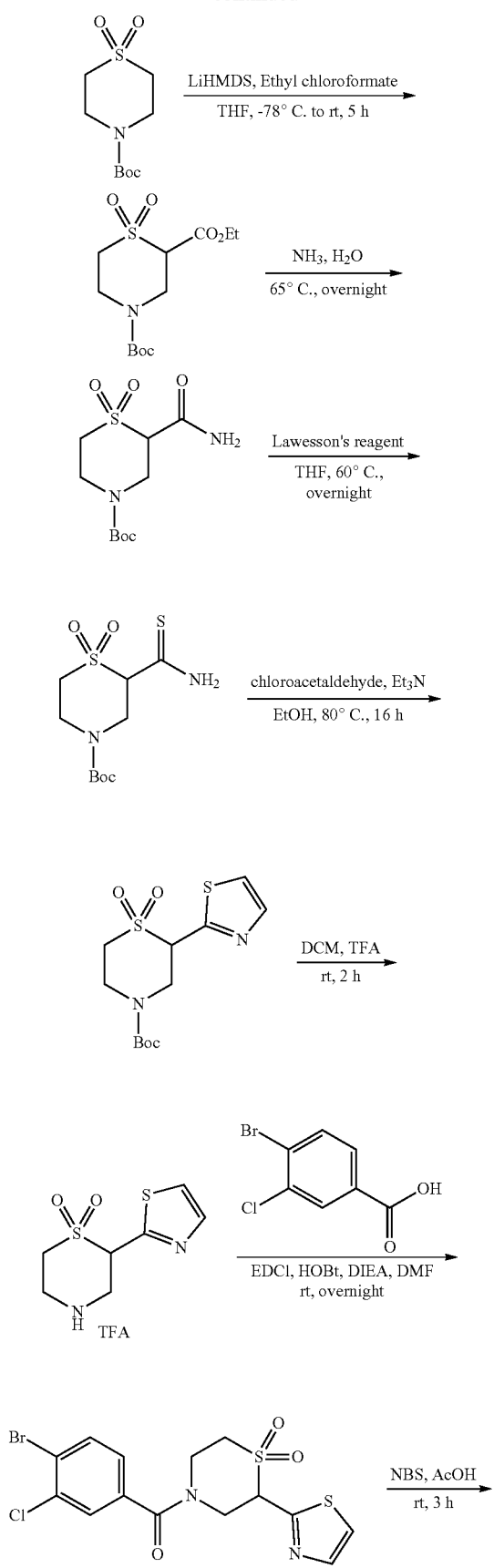

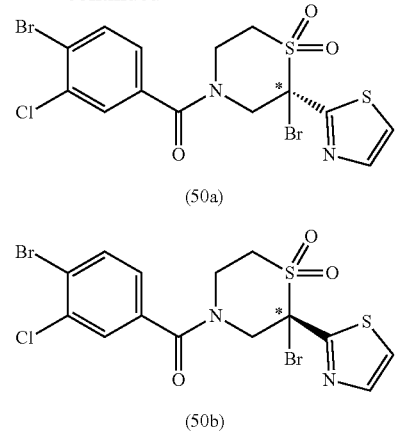 [SMILES: O=C(c1ccc(Br)c(Cl)c1)N1CCS(=O)(=O)[C@](Br)(c2nccs2)C1 ; O=C(c1ccc(Br)c(Cl)c1)N1CCS(=O)(=O)[C@@](Br)(c2nccs2)C1]

(50a)

(50b)

Synthesis of tert-butyl thiomorpholine-4-carboxylate: To a stirred solution of thiomorpholine (20.0 g, 0.194 mol, 1.00 eq.) and triethylamine (23.5 g, 0.233 mol, 1.20 eq.) in dichloromethane (200 mL) was added tert-butyldicarbonate (42.3 g, 0.194 mol, 1.00 eq.) in dichloromethane (100 mL) at rt. The mixture was stirred for 2 h at rt and concentrated under reduced pressure. The mixture was diluted with water (500 mL). The mixture was extracted with ethyl acetate (3×500 mL). The combined organic layers were washed with hydrochloric acid (1 M, 1×500 mL) and water (3×500 mL), dried over anhydrous sodium sulfate, filtered and concentrated under reduced pressure to afford tert-butyl thiomorpholine-4-carboxylate (35.0 g, crude) as a white solid. LCMS (ESI, m/z): 204 [M+H]$^+$.

tert-butyl 1,1-dioxo-1$\lambda^6$-thiomorpholine-4-carboxylate: To a stirred solution of tert-butyl thiomorpholine-4-carboxylate (35.0 g, 0.172 mol, 1.00 eq.) in dichloromethane (500 mL) was added 3-chloroperoxybenzoic acid (73.5 g, 0.362 mol, 2.10 eq., 85% purity) in portions at 0° C. The mixture was stirred for 2 h at 0° C. The reaction was quenched with sat. sodium carbonate (200 mL) and water (200 mL) at 0° C. The mixture was extracted with dichloromethane (3×500 mL). The organic layers were combined, washed with water (3×300 mL), dried over anhydrous sodium sulfate, filtered and concentrated under reduced pressure. The resulting solid was dissolved in ethyl acetate (500 mL). The resulting solution was washed with sat. sodium carbonate (3×200 mL) and water (3×200 mL), dried over anhydrous sodium sulfate, filtered and concentrated under reduced pressure to afford tert-butyl 1,1-dioxo-1$\lambda^6$-thiomorpholine-4-carboxylate (35.0 g, 86% yield) as a white solid. LCMS (ESI, m/z): 236 [M+H]$^+$.

4-tert-butyl 2-ethyl 1,1-dioxo-1$\lambda^6$-thiomorpholine-2,4-dicarboxylate: To a solution of tert-butyl 1,1-dioxo-1$\lambda^6$-thiomorpholine-4-carboxylate (10.0 g, 42.6 mmol, 1.00 eq.) and anhydrous THF (150 mL) was added lithium hexamethyldisilazide (42.5 mL, 42.5 mmol, 1.00 eq., 1 M in THF) at −78° C. under N$_2$. The resulting solution was stirred for 1.5 h at −78° C. Then ethyl chloroformate (4.61 g, 42.5 mmol, 1.00 eq.) was added dropwise at −78° C., and the mixture was stirred for 1 h at −78° C. The mixture was warmed to rt and stirred for 5 h at rt. The reaction was quenched with sat. ammonium chloride solution (200 mL) and extracted with ethyl acetate (3×100 mL). The organic layers were combined, washed with water (3×50 mL), dried over anhydrous sodium sulfate, filtered and concentrated under reduced pressure to afford 4-tert-butyl 2-ethyl 1,1-dioxo- 1λ⁶-thiomorpholine-2,4-dicarboxylate (11.0 g, 84% yield) as a white solid. LCMS (ESI, m/f): 308 [M+H]⁺.

tert-butyl 2-carbamoyl-1,1-dioxo-1λ⁶-thiomorpholine-4-carboxylate: The solution of 4-tert-butyl 2-ethyl 1,1-dioxo-1λ⁶-thiomorpholine-2,4-dicarboxylate (4.00 g, 13.0 mmol, 1.00 eq.) and ammonia (40 mL, 28% in water) was stirred for overnight at 65° C. The mixture was concentrated under reduced pressure to afford tert-butyl 2-carbamoyl-1,1-dioxo-1λ⁶-thiomorpholine-4-carboxylate (3.30 g, 91% yield) as a light yellow solid. LCMS (ESI, m/z): 279 [M+H]⁺.

tert-butyl 2-carbamothioyl-1,1-dioxo-1λ⁶-thiomorpholine-4-carboxylate: A 250 mL round-bottom flask was charged with tert-butyl 2-carbamoyl-1,1-dioxo-1λ⁶-thiomorpholine-4-carboxylate (3.00 g, 10.8 mmol, 1.00 eq.), Lawesson reagent (2.18 g, 5.39 mmol, 0.50 eq.) and THF (100 mL). The resulting solution was stirred for overnight at 60° C. and concentrated under reduced pressure. The residue was dissolved with ethyl acetate (200 mL), washed with water (3×100 mL), dried over anhydrous sodium sulfate, filtered and concentrated under reduced pressure. The residue was purified by silica gel column chromatography with ethyl acetate:petroleum (1:4) to afford tert-butyl 2-carbamothioyl-1,1-dioxo-1λ⁶-thiomorpholine-4-carboxylate (1.55 g, 49% yield) as a light yellow solid. LCMS (ESI, m/z): 295 [M+H]⁺.

tert-butyl 1,1-dioxo-2-(1,3-thiazol-2-yl)-1λ⁶-thiomorpholine-4-carboxylate: A solution of tert-butyl 2-carbamothioyl-1,1-dioxo-1λ⁶-thiomorpholine-4-carboxylate (1.00 g, 3.40 mmol, 1.00 eq.), chloroacetaldehyde (1.20 g, 6.15 mmol, 1.80 eq., 40% in water), triethylamine (0.687 g, 6.80 mmol, 2.00 eq.) and ethanol (20 mL) was stirred for 16 h at 80° C., and the mixture was concentrated under reduced pressure. The residue was purified by silica gel column chromatography, eluted with ethyl acetate:petroleum (1:5) to afford tert-butyl 1,1-dioxo-2-(1,3-thiazol-2-yl)-1λ⁶-thiomorpholine-4-carboxylate (700 mg, 65% yield) as a light yellow solid. LCMS (ESI, m/z): 319 [M+H]⁺.

2-(1,3-thiazol-2-yl)-1λ⁶-thiomorpholine-1,1-dione trifluoroacetic acid salt: A 50 mL round bottom flask was charged with tert-butyl 1,1-dioxo-2-(1,3-thiazol-2-yl)-1λ⁶-thiomorpholine-4-carboxylate (100 mg, 0.314 mmol, 1.00 eq.), dichloromethane (10 mL) and trifluoroacetic acid (3 mL). The resulting solution was stirred for 2 h at rt, and then concentrated under reduced pressure to provide 2-(1,3-thiazol-2-yl)-1λ⁶-thiomorpholine-1,1-dione trifluoroacetic acid salt (90.0 mg, crude) as a light yellow solid. LCMS (ESI, m/z): 219 [M+H-TFA]⁺.

4-(4-bromo-3-chlorobenzoyl)-2-(1,3-thiazol-2-yl)-1λ⁶-thiomorpholine-1,1-dione: A 40 mL vial was charged with 2-(1,3-thiazol-2-yl)-1λ⁶-thiomorpholine-1,1-dione trifluoroacetic acid salt (90.0 mg, 0.271 mmol, 1.00 eq.), 4-bromo-3-chlorobenzoic acid (80.4 mg, 0.342 mmol, 1.26 eq.), N-ethyl-N'-(3-dimethylaminopropyl)carbodiimide hydrochloride (81.8 mg, 0.427 mmol, 1.57 eq.), hydroxybenzotriazole (57.7 mg, 0.427 mmol, 1.57 eq.), N,N-diisopropylethylamine (147 mg, 1.14 mmol, 4.20 eq.) and N,N-dimethylformamide (10 mL). The resulting solution was stirred overnight at rt. The mixture was diluted with ethyl acetate (100 mL). The mixture was washed with water (3×50 mL), dried over anhydrous sodium sulfate, filtered and concentrated under reduced pressure. The residue was purified by silica gel column chromatography, eluted with ethyl acetate:petroleum ether (1:1) to afford 4-(4-bromo-3-chlorobenzoyl)-2-(1,3-thiazol-2-yl)-1λ⁶-thiomorpholine-1,1-dione (90.0 mg, 76% yield) as a white solid. LCMS (ESI, m/z): 435 [M+H]⁺.

Compounds (50a) and (50b): A 20 mL vial was charged with 4-(4-bromo-3-chlorobenzoyl)-2-(1,3-thiazol-2-yl)-1λ⁶-thiomorpholine-1,1-dione (80.0 mg, 0.184 mmol, 1.00 eq.) and acetic acid (5.0 mL). N-bromosuccinimide (65.4 mg, 0.367 mmol, 2.00 eq.) was added at rt. The resulting solution was stirred for 3 h at rt and then diluted with ethyl acetate (100 mL). The mixture was washed with sat. sodium bicarbonate solution (2×50 mL) and water (50 mL). The organic layer was dried over anhydrous sodium sulfate, filtered and concentrated under reduced pressure. The residue was purified by silica gel column chromatography with ethyl acetate: petroleum ether (1:1) to afford a crude product. The crude product was purified by SEC with the following conditions: Column: (S,S)-Whelk-01, 4.6×50 mm, 3.5 μm; Mobile Phase A: CO₂, Mobile Phase B: MeOH (0.1% DEA); Flow rate: 2 mL/min; Gradient: 10% B to afford (rac-2R)-2-bromo-4-(4-bromo-3-chlorobenzoyl)-2-(1,3-thiazol-2-yl)-1λ⁶-thiomorpholine-1,1-dione (50a) (26.5 mg, 28% yield, the first peak) as a white solid. NMR (300 MHz, Chloroform-d) δ 7.93 (s, 1H), 7.81-7.49 (m, 3H), 7.24 (dd, J=8.2, 2.0 Hz, 1H), 4.89 (d, J=14.7 Hz, 1H), 4.82-4.45 (m, 2H), 4.18-3.68 (m, 2H), 3.52 (s, 1H). LCMS (ESI, m/z): 513 [M+H]⁺, and (rac-2S)-2-bromo-4-(4-bromo-3-chlorobenzoyl)-2-(1,3-thiazol-2-yl)-1λ⁶-thiomorpholine-1,1-dione (50b) (25.7 mg, 27% yield, the second peak) as a white solid. ¹H NMR (300 MHz, Chloroform-d) δ 7.93 (s, 1H), 7.77-7.54 (m, 3H), 7.24 (dd, J=8.2, 2.0 Hz, 1H), 4.89 (d, J=14.8 Hz, 1H), 4.82-4.45 (m, 2H), 4.16-3.76 (m, 2H), 3.52 (s, 1H). LCMS (ESI, m/z): 513 [M+H]⁺.

Example 50

Compounds 32, 33a, 33b, 34, 35a, 35b, 38a, 38b, 39, 40a, 40b, 41a, 41b, 41c, 41d, 43a, 43b, 43c, 43d, 45a, 45b, 46b and 49a Compounds 32, 33a, 33b, 34, 35a, 35b, 38a, 38b, 39, 40a, 40b, 41a, 41b, 41c, 41d, 43a, 43b, 43c, 43d, 45a, 45b, 46b and 49a provided in Table A were synthesized using the intermediates and/or protocols of Examples 1-49, using methods and conditions known to those skilled in the art.

TABLE A

| Structure | Cmpd No. | ¹H NMR | LCMS |
|---|---|---|---|
| [chemical structure] | 32 | (DMSO, 600 MHz, 80° C.): 3.46-3.56 (m, 2H); 3.78-3.90 (m, 1H); 4.01 (dd, J = 14.3 Hz, 9.4 Hz, 1H); 4.07-4.27 (br. s., 1H); 4.30-4.61 (br. s., 1H); 5.29 (dd, J = 9.0 Hz, 3.4 Hz, 1H); 7.46 (d, J = 7.8 Hz, 1H); 7.67-7.74 (m, 2H); 7.84 (d, J = 3.1 Hz, 1H); 7.93 (d, J = 3.1 Hz, 1H) ppm. | 390.9 |

TABLE A-continued

| Structure | Cmpd No. | ¹H NMR | LCMS |
|---|---|---|---|
| (structure) | 33a | (DMSO, 600 MHz, 80° C.): 1.56 (s, 3H); 3.34-3.45 (m, 1H); 3.52-3.63 (m, 1H); 3.67-3.87 (m, 2H); 3.91-4.22 (m, 3H); 4.44 (dd, J = 15.4 Hz, 6.3 Hz, 1H); 7.20-7.36 (m, 6H); 7.65 (s, 1H); 7.82 (d, J = 8.2 Hz, 1H); 8.23 (s, 1H) ppm. | 501 |
| (structure) | 33b | (DMSO, 600 MHz, 80° C.): 1.56 (s, 3H); 3.34-3.45 (m, 1H); 3.52-3.63 (m, 1H); 3.67-3.87 (m, 2H); 3.91-4.32 (m, 3H); 4.44 (dd, J = 15.4 Hz, 6.3 Hz, 1H); 7.20-7.36 (m, 6H); 7.65 (s, 1H); 7.82 (d, J = 8.2 Hz, 1H); 8.23 (s, 1H) ppm. | 501 |
| (structure) | 34 | (DMSO, 600 MHz, 80° C.): 1.79 (s, 3H); 3.48-3.58 (m, 1H); 3.59-3.69 (m, 1H); 3.77-3.97 (m, 1H); 3.98-4.20 (m, 2H); 4.22-4.38 (m, 1H); 7.22-7.38 (br. s., 1H); 7.47-7.68 (br. s., 1H); 7.79 (d, J = 6.8 Hz, 1H); 7.84 (d, J = 3.2 Hz, 1H); 7.92 (d, J = 3.2 Hz, 1H) ppm. | 450.9 |
| (structure) | 35a | (DMSO, 600 MHz, 80° C.): 3.55-3.69 (m, 2H); 3.76-3.88 (m, 1H); 4.09-4.51 (m, 5H); 7.17-7.40 (m, 6H); 7.67 (s, 1H); 7.85 (d, J = 8.8 Hz, 1H); 9.07 (s, 1H) ppm. | 504.9 |
| (structure) | 35b | (DMSO, 600 MHz, 80° C.): 3.55-3.69 (m, 2H); 3.76-3.88 (m, 1H); 4.10-4.48 (m, 5H); 7.15-7.38 (m, 6H); 7.67 (s, 1H); 7.85 (d, J = 8.8 Hz, 1H); 9.07 (s, 1H) ppm. | 504.9 |
| (structure) | 39 | (DMSO-d6, 600 MHz, 80° C.): 3.67-3.78 (m, 3H); 4.52 (br. s, 2H); 4.90 (br. s, 1H); 7.39 (dd, J = 8.0 Hz, 1.4 Hz, 1H); 7.42-7.46 (m, 1H); 7.46-7.52 (m, 2H); 7.68-7.77 (m; 3H); 7.86 (d, J = 8.0 Hz, 1H); 8.37 (s, 1H) ppm. | 530.9 |
| (structure) | 38a | (DMSO-d6, 600 MHz, 80° C.): 2.72-2.82 (m, 2H); 3.32-3.46 (m, 2H); 3.50-3.58 (m, 1H); 3.58-3.65 (m, 1H); 3.74-3.84 (m, 1H); 4.11-4.41 (m, 3H); 7.06-7.20 (m, 3H); 7.20-7.27 (m, 2H); 7.34 (dd, J = 8.1 Hz, J = 1.6 Hz, 1H); 7.66 (d, J = 1.6 Hz, 1H); 7.84-7.89 (m, 1H); 8.43 (br. s, 1H) ppm. | 518.9 |
| (structure) | 38b | (DMSO-d6, 600 MHz, 80° C.): 2.72-2.82 (m, 2H); 3.32-3.46 (m, 2H); 3.50-3.58 (m, 1H); 3.58-3.65 (m, 1H); 3.74-3.84 (m, 1H); 4.11-4.41 (m, 3H); 7.06-7.20 (m, 3H); 7.20-7.27 (m, 2H); 7.34 (dd, J = 8.1 Hz, J = 1.6 Hz, 1H); 7.66 (d, J = 1.6 Hz, 1H); 7.84-7.89 (m, 1H); 8.43 (br. s, 1H) ppm. | 518.9 |

TABLE A-continued

| Structure | Cmpd No. | ¹H NMR | LCMS |
|---|---|---|---|
| (structure) | 40a | (400 MHz, Chloroform-d) δ 7.79-7.71 (m, 2H), 7.62 (s, 1H), 7.52 (dd, J = 8.3, 2.1 Hz, 1H), 7.37-7.22 (m, 3H), 7.25-7.81 (m, 2H), 5.01 (br s, 1H), 4.68 (m, 1H), 4.44 (m, 1H), 4.17 (d, J = 4.0 Hz, 2H), 3.65 (m, 2H), 3.32 (d, J = 13.2 Hz, 1H). | 536 |
| (structure) | 40b | (400 MHz, Chloroform-d) δ 7.79-7.72 (m, 2H), 7.62 (s, 1H), 7.52 (dd, J = 8.3, 2.1 Hz, 1H), 7.36-7.26 (m, 3H), 7.24-7.19 (m, 2H), 5.01 (br s, 1H), 4.68 (m, 1H), 4.45 (m, 1H), 4.17 (d, J = 4.0 Hz, 2H), 3.64 (m, 2H), 3.32 (d, J = 13.3 Hz, 1H). | 536 |
| (structure) | 41a | (400 MHz, Chloroform-d) δ 7.75-7.50 (m, 3H), 7.39-7.28 (m, 3H), 7.25-7.15 (m, 3H), 5.12-4.88 (m, 1H), 4.78-4.42 (m, 2H), 4.42-4.25 (m, 1H), 3.80-3.45 (m, 2H), 3.30 (d, J = 12.4 Hz, 1H), 1.72 (d, J = 7.2 Hz, 3H). | 558.9 |
| (structure) | 41b | (400 MHz, Chloroform-d) δ 7.66 (d, J = 8.0 Hz, 1H), 7.60-7.50 (m, 2H), 7.40-7.27 (m, 3H), 7.25-7.13 (m, 3H), 5.20-4.87 (m, 1H), 4.75-4.43 (m, 2H), 4.43-4.20 (m, 1H), 3.80-3.48 (m, 2H), 3.31 (d, J = 13.6 Hz, 1H), 1.72 (d, J = 7.2 Hz, 3H). | 558.9 |
| (structure) | 41c | (400 MHz, Chloroform-d) δ 7.77-7.62 (m, 1H), 7.62-7.51 (m, 2H), 7.38-7.30 (m, 2H), 7.21-7.25 (m, 3H), 7.20-7.15 (m, 1H), 5.15-4.83 (m, 1H), 4.75-4.42 (m, 2H), 4.42-4.17 (m, 1H), 3.78-3.48 (m, 2H), 3.31 (d, J = 13.2 Hz, 1H), 1.72 (d, J = 7.2 Hz, 3H). | 558.9 |
| (structure) | 41d | (400 MHz, Chloroform-d) δ 7.80-7.60 (m, 2H), 7.55 (d, J = 2.0 Hz, 1H), 7.39-7.27 (m, 3H), 7.25-7.15 (m, 3H), 5.11-4.88 (m, 1H), 4.75-4.45 (m, 2H), 4.45-4.18 (m, 1H), 3.80-3.49 (m, 2H), 3.31 (d, J = 12.8 Hz, 1H), 1.72 (d, J = 7.2 Hz, 3H). | 558.9 |
| (structure) | 43a | (400 MHz, Chloroform-d) δ 7.82-7.70 (m, 2H), 7.62 (s, 1H), 7.59-7.45 (m, 1H), 7.25-7.20 (m, 2H), 7.19-7.10 (m, 1H), 7.10-6.96 (m, 1H), 5.03 (d, J = 10.8 Hz, 1H), 4.80-4.60 (m, 2H), 4.55-4.32 (m, 1H), 3.81-3.51 (m, 2H), 3.34 (d, J = 13.2 Hz, 1H), 1.73 (d, J = 7.2 Hz, 3H). | 567.95 |

TABLE A-continued

| Structure | Cmpd No. | ¹H NMR | LCMS |
|---|---|---|---|
| 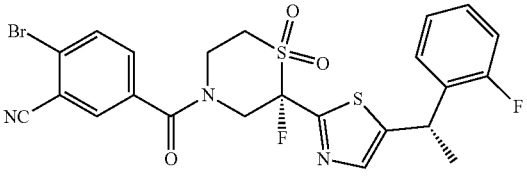 [SMILES: C[C@H](c1cnc([C@@]2(F)CN(C(=O)c3ccc(Br)c(C#N)c3)CCS2(=O)=O)s1)c1ccccc1F] | 43b | (400 MHz, Chloroform-d) δ 7.85-7.69 (m, 2H), 7.62 (s, 1H), 7.59-7.42 (m, 1H), 7.26-7.19 (m, 2H), 7.16-7.10 (m, 1H), 7.10-7.00 (m, 1H), 5.02 (d, J = 10.0 Hz, 1H), 4.80-4.62 (m, 2H), 4.55-4.28 (m, 1H), 3.85-3.45 (m, 2H), 3.33 (d, J = 13.6 Hz, 1H), 1.73 (d, J = 7.2 Hz, 3H). | 567.95 |
| 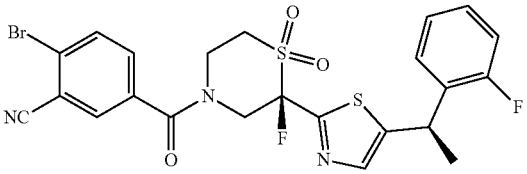 [SMILES: C[C@@H](c1cnc([C@]2(F)CN(C(=O)c3ccc(Br)c(C#N)c3)CCS2(=O)=O)s1)c1ccccc1F] | 43c | (400 MHz, Chloroform-d) δ 7.82-7.70 (m, 2H), 7.62 (s, 1H), 7.59-7.45 (m, 1H), 7.26-7.19 (m, 2H), 7.15-6.99 (m, 2H), 5.02 (d, J = 12.8 Hz, 1H), 4.80-4.58 (m, 2H), 4.52-4.36 (m, 1H), 3.81-3.53 (m, 2H), 3.33 (d, J = 12.4 Hz, 1H), 1.73 (d, J = 7.2 Hz, 3H). | 567.95 |
| 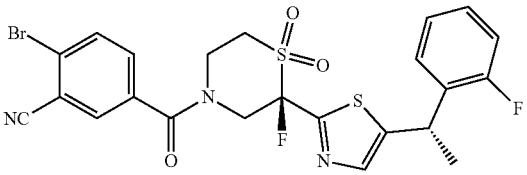 [SMILES: C[C@H](c1cnc([C@]2(F)CN(C(=O)c3ccc(Br)c(C#N)c3)CCS2(=O)=O)s1)c1ccccc1F] | 43d | (400 MHz, Chloroform-d) δ 7.81-7.69 (m, 2H), 7.62 (s, 1H), 7.55-7.45 (m, 1H), 7.26-7.20 (m, 1H), 7.19-7.10 (m, 1H), 7.10-6.91 (m, 1H), 5.02 (d, J = 12.0 Hz, 1H), 4.78-4.60 (m, 2H), 4.50-4.29 (m, 1H), 3.75-3.50 (m, 2H), 3.33 (d, J = 13.2 Hz, 1H), 1.73 (d, J = 7.2 Hz, 3H). | 567.95 |
| 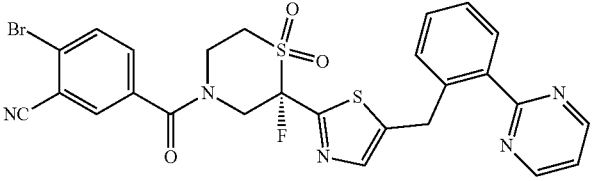 [SMILES: N#Cc1cc(C(=O)N2CCS(=O)(=O)[C@@](F)(c3ncc(Cc4ccccc4-c4ncccn4)s3)C2)ccc1Br] | 45a | (400 MHz, Chloroform-d) δ 8.98-8.71 (m, 2H), 8.01-7.94 (m, 1H), 7.79-7.65 (m, 2H), 7.60 (s, 1H), 7.52-7.48 (m, 1H), 7.48-7.31 (m, 3H), 7.26-7.21 (m, 1H), 5.15-4.90 (m, 1H), 4.78-4.48 (m, 3H), 4.45-4.30 (m, 1H), 3.81-3.52 (m, 2H), 3.40-3.23 (m, 1H). | 614 |
| 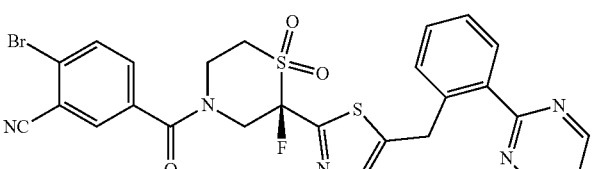 | 45b | (400 MHz, Chloroform-d) δ 8.99-8.78 (m, 2H), 8.14-7.90 (m, 1H), 7.80-7.65 (m, 2H), 7.60 (s, 1H), 7.56-7.31 (m, 4H), 7.26-7.21 (m, 1H), 5.12-4.88 (m, 1H), 4.80-4.49 (m, 3H), 4.49-4.18 (m, 1H), 3.75-3.41 (m, 2H), 3.38-3.08 (m, 1H). | 614 |
| 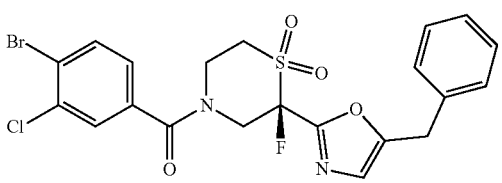 | 46b | (DMSO, 600 MHz, 80° C.): 3.55-3.86 (m, 4H); 4.13 (s, 2H); 4.31-4.38 (m, 2H); 7.12 (s, 1H); 7.23-7.29 (m, 3H); 7.30-7.35 (m, 2H); 7.37 (dd, J = 8.2, 1.4 Hz, 1H); 7.70 (d, J = 1.5 Hz, 1H); 7.85 (d, J = 8.3 Hz, 1H) ppm. | 529 (Br, Cl pattern) |

TABLE A-continued

| Structure | Cmpd No. | ¹H NMR | LCMS |
|---|---|---|---|
| [Structure of compound 49a: 4-bromo-3-chlorophenyl with thiomorpholine dioxide, fluoro, thiazole linked to 2,4-dimethoxybenzyl] | 49a | (DMSO, 600 MHz, 80° C.): 3.60-3.72 (m, 3H); 3.77 (s, 3H); 3.82 (s, 3H); 4.11 (s, 2H); 4.31-4.55 (m, 2H); 4.67-4.98 (m, 1H); 6.50 (dd, J = 8.2 Hz, 2.5 Hz, 1H); 6.59 (d, J = 2.5 Hz, 1H); 7.15 (d, J = 8.2 Hz, 1H); 7.36 (d, J = 7.9 Hz, 1H); 7.70 (s, 1H); 7.76 (s, 1H); 7.84 (d, J = 8.2 Hz, 1H) ppm. | 604.9 |

Example 51

Compounds 51-59

Compounds 51-59 provided in Table B can be obtained using the intermediates and/or protocols of Examples 1-49, using methods and conditions known to those skilled in the art. Compounds 51-59 can be further separated to their enantiomers using methods known in the art.

TABLE B

| Structure | Compound No. | Name |
|---|---|---|
| [Structure 51] | 51 | (4-bromo-3-chlorophenyl)(2-fluoro-1,1-dioxido-2-(5-(quinoxalin-5-ylmethyl)thiazol-2-yl)thiomorpholino)methanone |
| [Structure 52] | 52 | (2-(5-benzylthiazol-2-yl)-2-fluoro-1,1-dioxidothiomorpholino)(4-bromo-3-ethynylphenyl)methanone |
| [Structure 53] | 53 | (4-bromo-3-chlorophenyl)(2-fluoro-1,1-dioxido-2-(5-(2-(pyridazin-3-yl)benzyl)thiazol-2-yl)morpholino)methanone |
| [Structure 54] | 54 | (4-bromo-3-chlorophenyl)(2-fluoro-1,1-dioxido-2-(5-(2-(pyrimidin-4-yl)benzyl)thiazol-2-yl)thiomorpholino)methanone |
| [Structure 55] | 55 | (4-bromo-3-chlorophenyl)(2-fluoro-2-(5-(2-(4-fluoro-1H-pyrazol-1-yl)benzyl)thiazol-2-yl)-1,1-dioxidomorpholino)methanone |

TABLE B-continued

| Structure | Compound No. | Name |
|---|---|---|
| 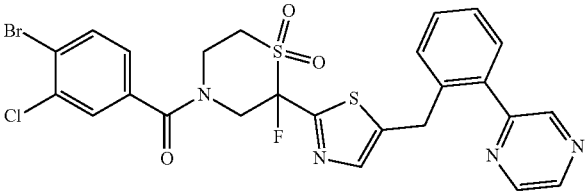 [SMILES: O=C(c1ccc(Br)c(Cl)c1)N1CCS(=O)(=O)C(F)(c2ncc(Cc3ccccc3-c3cnccn3)s2)C1] | 56 | (4-bromo-3-chlorophenyl)(2-fluoro-1,1-dioxido-2-(5-(2-(pyrazin-2-yl)benzyl)thiazol-2-yl)morpholino)methanone |
| 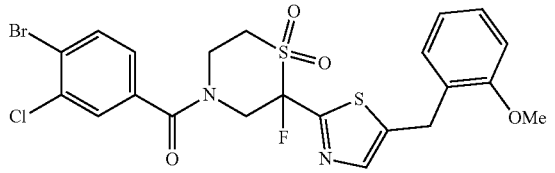 [SMILES: COc1ccccc1Cc1cnc(C2(F)CN(C(=O)c3ccc(Br)c(Cl)c3)CCS2(=O)=O)s1] | 57 | (4-bromo-3-chlorophenyl)(2-fluoro-2-(5-(2-methoxybenzyl)thiazol-2-yl)-1,1-dioxidothiomorpholino)methanone |
| 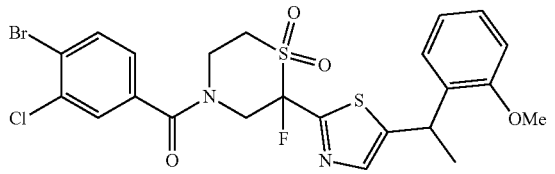 [SMILES: COc1ccccc1C(C)c1cnc(C2(F)CN(C(=O)c3ccc(Br)c(Cl)c3)CCS2(=O)=O)s1] | 58 | (4-bromo-3-chlorophenyl)(2-fluoro-2-(5-(1-(2-methoxyphenyl)ethyl)thiazol-2-yl)-1,1-dioxidothiomorpholino)methanone |
| 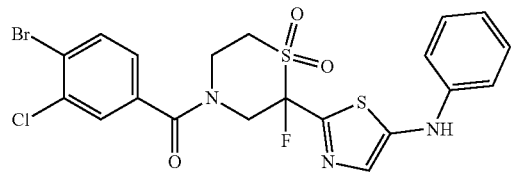 [SMILES: O=C(c1ccc(Br)c(Cl)c1)N1CCS(=O)(=O)C(F)(c2ncc(Nc3ccccc3)s2)C1] | 59 | (4-bromo-3-chlorophenyl)(2-fluoro-1,1-dioxido-2-(5-(phenylamino)thiazol-2-yl)thiomorpholino)methanone |

For all of the compounds shown herein, except for the 5-position of the thiomorpholine dioxide cyclyl, the stereochemistry shown for each of compounds is relative and not absolute.

Example A

HBV-DNA Antiviral Assay Using HepG2.2.15 Cells

The following assay procedure describes the HBV antiviral assay. This assay uses HepG2.2.15 cells, which have been transfected with HBV genome, and extracellular HBV DNA quantification as endpoint. Cell viability is assessed in parallel by measuring the intracellular ATP content using the CellTiter-Glo® reagent from Promega.

On day 0, HepG2.2.15 cells were seeded in 96-well plates at a density of $6.0 \times 10^4$ cells/well (0.1 mL/well). The cells were incubated at 37° C. and 5% $CO_2$.

On day 1, the test articles were diluted and added to cell culture wells (8 concentrations, 4-fold dilution, in duplicate). GLS4, Tenofovir and Sorafenib were used as reference compounds. 100 μL of culture medium containing the compounds was added to the plate, and the final total volume per well was 200 μL. The final concentration of DMSO in the culture medium was 0.5%. The plate map of compound treatment is shown below. The cells were cultured at 37° C. and 5% $CO_2$ for 3 days. The plate map of compound treatment is shown in FIG. 1.

On day 4, the plates were refreshed with culture media with compounds.

On day 7, cell viability was assessed using the CellTiter-Glo®, and the cell culture supernatants were collected for determination of HBV DNA by qPCR.

HBV DNA Quantification by qPCR

Extracellular DNA was isolated with QIAamp 96 DNA Blood Kit per the manufacturer's manual. HBV DNA was then quantified by qPCR with HBV specific primers and probes as specified in Table 1 using the FastStart Universal MasterMix from Roche on an ABI-7900HT. The PCR cycle program consisted of 95° C. for 10 min, followed by 40 cycles at 95° C. for 15 sec and 60° C. for 1 min.

TABLE 1

HBV DNA Primers and Probe

| Items | Name | Sequence (5'→3') |
|---|---|---|
| HBV Primer | HBV-forward | GTGTCTGCGGCGTTTTATCA (SEQ. ID. NO. 1) |
| | HBV-reverse | GACAAACGGGCAACATACCTT (SEQ. ID. NO. 2) |
| HBV Probe | HBV probe | FAM-CCTCTKCATCCTGCTGC TATGCCTCATC-TAMRA (SEQ. ID. NO. 3) |

A DNA standard was prepared by dilution of the pAAV2 HBV1.3 plasmid with concentrations ranging from 10 to $1 \times 10^7$ copies/uL and used to generate a standard curve by plotting Ct value vs. the concentration of the HBV plasmid DNA standard. The quantity of HBV DNA in each sample was determined by interpolating from the standard curve.

Cell Viability

After harvest of the supernatants, the cell viability was detected by CellTiter-Glo® according to the manufacturer's manual. In brief, 50 µL of fresh cell culture medium was added to the culture plates, followed by addition of 50 µL CellTiter-Glo into each well. The plates were incubated at rt for 10 mins. The luminescence signal was collected on a BioTek Synergy 2 plate reader.

Data Analysis

Cell viability was calculated as follows: % Cell viability= (luminescence value of test sample−average luminescence value of blank)/(average luminescence value of 0.5% DMSO control−average luminescence of blank)×100%. HBV DNA inhibition was calculated as follows: 100-(HBV DNA copy number of test sample−HBV DNA copy number of ETV)/HBV DNA copy number of 0.5% DMSO control−HBV DNA copy number of ETV)×100%. The $CC_{50}$, $EC_{50}$ and $EC_{90}$ values were determined by dose-response curves fitted by GraphPad Prism using "log (agonist) vs. response-Variable slope".

Compounds of Formula (I) are active against HBV as shown in Table 3, where 'A' indicates an $EC_{50} \leq 100$ nM, 'B' indicates an $EC_{50} > 100$ nM and $\leq 500$ nM, 'C' indicates an $EC_{50} > 500$ nM and $\leq 5000$ nM, and 'D' indicates an $EC_{50} > 5000$ nM. Cell viability assessments indicated a large window between effective antiviral concentrations and cytotoxic compound concentrations.

Example B

HBV-DNA Antiviral Assay Using HepG2.117 Cells

The following assay procedure describes the HBV antiviral assay, using HepG2.117 cells, which carry a stably integrated genotype D HBV genome under the control of a Tet-off promoter, and intracellular HBV DNA quantification as endpoint. Cell viability is assessed in parallel by measuring the intracellular ATP content using ATPlite (Perkin Elmer).

On day 0, HepG2.117 cells (which are maintained in routine cell culture with doxycycline present in the medium at a final concentration of 1 µg/mL) were seeded in 96-well plates (white with clear bottom) at a density of $2.0 \times 10^4$ cells/well (0.1 mL/well) in medium without doxycycline to induce pgRNA transcription and subsequent formation of HBV particles. The cells were incubated at 37° C. and 5% $CO_2$.

On day 1, medium was removed from each well, the test articles were diluted in culture medium without doxycycline and 100 µL was added to cell culture wells (9 concentrations, 4-fold dilution). For each plate, 6 untreated (merely DMSO) wells were included. The final concentration of DMSO in the culture medium was 2%. Each plate was prepared in duplicate (one for HBV DNA extraction, one for ATPlite measurement). The cells were incubated at 37° C. and 5% $CO_2$ for 3 days.

On day 4, cell viability was assessed using ATPlite and cell lysates were prepared for HBV DNA extraction and subsequent quantification by qPCR.

HBV DNA Quantification by qPCR

Medium was removed from each well and 100 µL of 0.33% NP-40 in $H_2O$ was added to each well. Plates were sealed, incubated at 4° C. for 5 mins, vortexed extensively and centrifuged briefly. Next, 35 µL of lysate was added to 65 µL QuickExtract DNA Extraction Solution (Epicentre) in a PCR plate for each well. PCR plate was incubated at 65° C. for 6 mins, 98° C. for 2 mins and finally cooled to 4° C.

HBV DNA was then quantified by qPCR with HBV-specific primers and probes as specified in Table 2 using the Bio-Rad SSOAdvanced Universal Probes Supermix on a CFX96 machine (Bio-Rad). The PCR cycle program consisted of 95° C. for 3 mins, followed by 40 cycles at 95° C. for 10 sec and 60° C. for 30 sec.

TABLE 2

HBV DNA Primers and Probe for HepG2.117 assay

| Items | Name | Sequence (5'→3') |
|---|---|---|
| HBV Primer | HBV-forward | GTGTCTGCGGCGTTTTATCA (SEQ. ID. NO. 1) |
| | HBV-reverse | GACAAACGGGCAACATACCTT (SEQ. ID. NO. 2) |
| HBV Probe | HBV probe | FAM/CCTCTKCAT/ZEN/CCTGCTGCTAT GCCTCATC/3IABkFQ/ (SEQ. ID. NO. 4) |

A DNA standard was prepared by dilution of an IDT gBlock corresponding to the amplicon with concentrations ranging from 10^2 to 10^8 copies/input (i.e. per 4 µL) and used to generate a standard curve by plotting Cq values vs. HBV DNA standard concentration. The quantity of HBV DNA in each sample was determined by interpolating from the standard curve.

Cell Viability

Using the other plates, the cell viability was quantified by ATPlite according to the manufacturer's manual. In brief, 50 µL of cell lysis solution was added to the culture plates and shaken for 5', followed by addition of 50 µL substrate into each well and further shaking. The plates were incubated at rt for 10 mins and luminescence signal was subsequently measured on a VarioSkan Lux (ThermoFisher) plate reader.

Data Analysis

Cell viability was calculated as follows: % Cell viability= (luminescence value of test sample)/(average luminescence value of 2% DMSO control)×100%. HBV DNA inhibition was calculated as follows: 100−(HBV DNA copy number of test sample)/(average HBV DNA copy number of 2% DMSO control)×100%. No normalization to entecavir was required due to the excellent dynamic window of this assay. The $CC_{50}$, $EC_{50}$ and $EC_{90}$ values were determined by dose-response curves fitted by GraphPad Prism using "log (agonist) vs. response—Variable slope".

Compounds of Formula (I) are active against HBV as shown in Table 3, where 'A' indicates an $EC_{50} \leq 100$ nM, 'B' indicates an $EC_{50} > 100$ nM and $\leq 500$ nM, 'C' indicates an $EC_{50} > 500$ nM and $\leq 5000$ nM, and 'D' indicates an $EC_{50} > 5000$ nM. Cell viability assessments indicated a large window between effective antiviral concentrations and cytotoxic compound concentrations.

TABLE 3

| Cmpd No. | $EC_{50}$ HepG2.2.15 | $EC_{50}$ HepG2.117 |
|---|---|---|
| 1 | | C |
| 2 | | C |
| 3 | | B |
| 4 | | C |
| 5a | B | |
| 5b | C | |
| 6a | A | |
| 6b | B | |
| 7a | | B |
| 7b | | C |
| 8a | C | |

TABLE 3-continued

| Cmpd No. | EC$_{50}$ HepG2.2.15 | EC$_{50}$ HepG2.117 |
|---|---|---|
| 8b | B | |
| 9a | C | |
| 9b | B | |
| 10a | D | |
| 10b | | C |
| 11a | C | |
| 11b | C | |
| 12a | | D |
| 12b | | C |
| 13a | | C |
| 13b | | C |
| 14a | D | |
| 14b | D | |
| 15a | | C |
| 15b | | C |
| 16a | B | |
| 16b | C | |
| 17 | | C |
| 18a | | C |
| 18b | | D |
| 19a | | B |
| 20 | | C |
| 19b | | C |
| 21 | | B |
| 22 | D | |
| 23 | | C |
| 24 | B | |
| 25 | | C |
| 26 | | C |
| 27 | | B |
| 28 | | C |
| 29 | | A |
| 30 | | B |
| 31 | | B |
| 32 | | C |
| 33a | | B |
| 33b | | C |
| 34 | | C |
| 35a | | A |
| 35b | | C |
| 36a | | C |
| 36b | | B |
| 37a | | A |
| 37b | | C |
| 38a | | D |
| 38b | | C |
| 39 | | C |
| 40a | | C |
| 40b | | A |
| 41a | | A |
| 41b | | A |
| 41c | | C |
| 41d | | C |
| 42a | | A |
| 42b | | A |
| 42c | | D |
| 42d | | C |
| 43a | | A |
| 43b | | A |
| 43c | | C |
| 43d | | C |
| 44a | | A |
| 44b | | C |
| 45a | | A |
| 45b | | C |
| 46a | | A |
| 46b | | |
| 47a | | D |
| 47b | | A |
| 48a | | B |
| 48b | | B |
| 49a | | C |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

---

What is claimed is:

1. A compound of Formula (I), or a pharmaceutically acceptable salt thereof, having the structure:

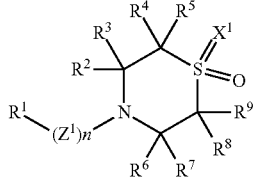

(I)

wherein:

n is 0 or 1;

$Z^1$ is —C(=O)—, —NH—C(=O)— or —O—C(=O)—;

$R^1$ is selected from the group consisting of

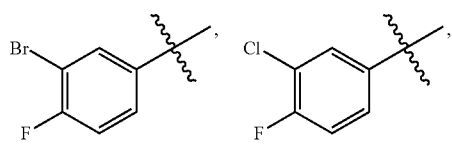

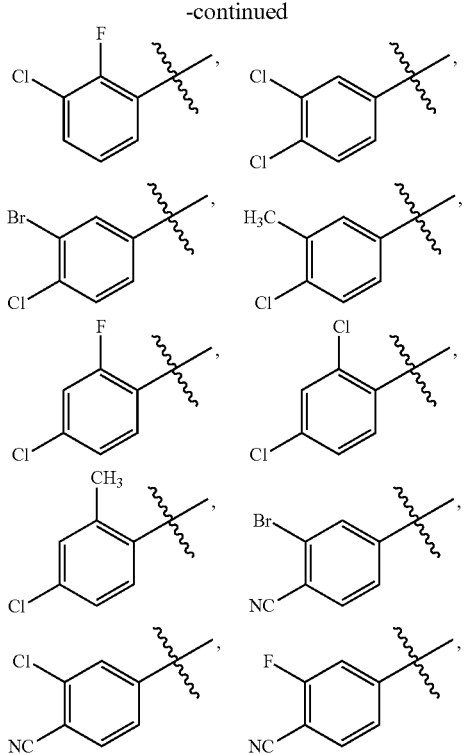

145
-continued

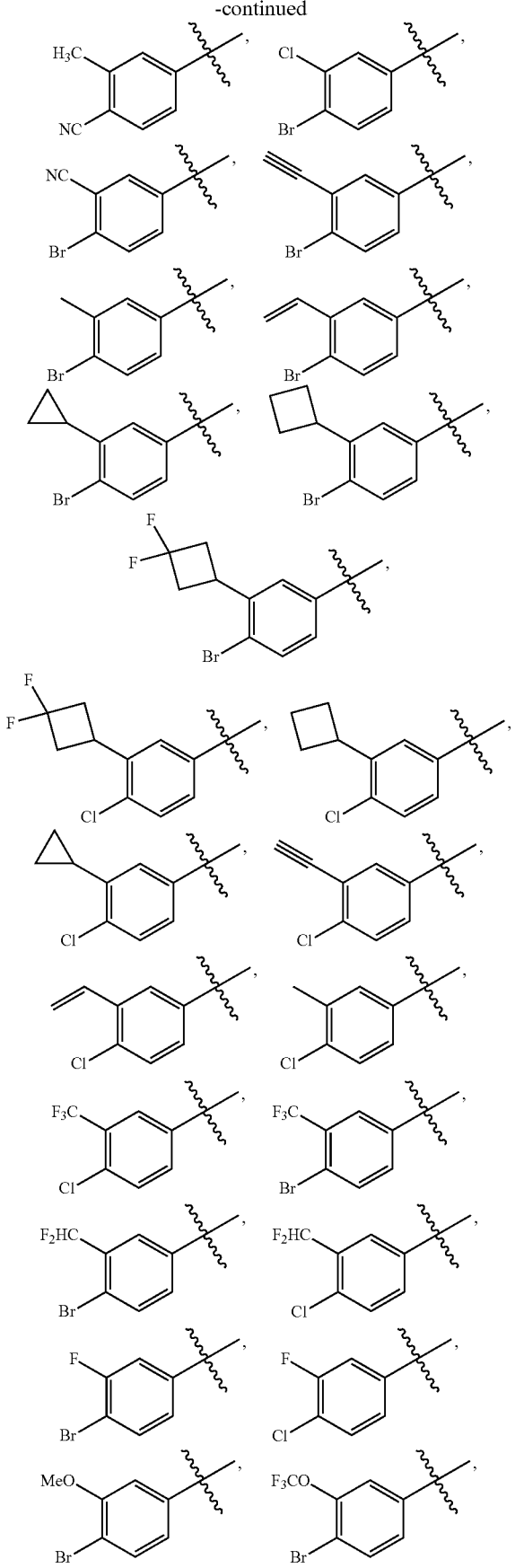

146
-continued

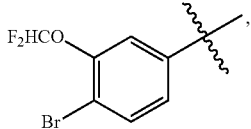

a substituted heteroaryl and a substituted heterocyclyl, wherein the heteroaryl and the heterocyclyl of $R^1$ is substituted with substituents independently selected from deuterium, halogen, cyano, an unsubstituted $C_{1-6}$ alkyl, an unsubstituted $C_{1-6}$ haloalkyl, an unsubstituted $C_{1-6}$ alkoxy, an unsubstituted acyl, an unsubstituted C-amido, an unsubstituted sulfonyl, an unsubstituted amino, a mono-alkyl substituted amine and a di-alkyl substituted amine;

$R^2$ and $R^3$ are independently selected from the group consisting of hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl);

$R^4$ and $R^5$ are independently selected from the group consisting of hydrogen, an unsubstituted $C_{1-4}$ alkyl, an unsubstituted $C_{1-4}$ haloalkyl, an optionally substituted aryl, an optionally substituted heteroaryl, an optionally substituted heterocyclyl, an optionally substituted aryl($C_{1-4}$ alkyl), an optionally substituted heteroaryl($C_{1-4}$ alkyl) and an optionally substituted heterocyclyl($C_{1-4}$ alkyl);

$R^6$ and $R^7$ are independently selected from the group consisting of hydrogen and an unsubstituted $C_{1-4}$ haloalkyl;

$R^8$ is hydrogen or halogen;

$R^9$ is selected from the group consisting of a substituted $C_{1-4}$ alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl), an optionally substituted heterocyclyl($C_{1-4}$ alkyl), —$NR^{10}R^{11}$ and —$C(=O)NR^{12}R^{13}$, wherein the substituted $C_{1-4}$ alkyl is substituted with one or more substituents selected from the group consisting of halogen, cyano, hydroxy, an unsubstituted $C_{1-4}$ alkoxy, amino, C-amido and N-amido;

$R^{10}$ and $R^{12}$ are independently hydrogen or an unsubstituted $C_{1-4}$ alkyl;

$R^{11}$ and $R^{13}$ are independently selected from the group consisting of hydrogen, an optionally substituted $C_{1-4}$ alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-4}$ alkyl), an optionally substituted cycloalkenyl($C_{1-4}$ alkyl), an optionally substituted aryl($C_{1-4}$ alkyl), an optionally substituted heteroaryl($C_{1-4}$ alkyl) and an optionally substituted heterocyclyl($C_{1-4}$ alkyl), wherein when the $C_{1-4}$ alkyl is substituted, the substituted $C_{1-4}$ alkyl is substituted with one or more substituents selected from the group consisting of halogen, cyano, hydroxy, an unsubstituted $C_{1-4}$ alkoxy, amino, C-amido and N-amido; or R[10] and R[11] are taken together along with the nitrogen to which R[10] and R[11] are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl;

R[12] and R[13] are taken together along with the nitrogen to which R[12] and R[13] are attached to form an optionally substituted 4- to 8-membered monocyclic heterocyclyl, an optionally substituted 8- to 13-membered fused-bicyclic heterocyclyl or an optionally substituted 7- to 13-membered spiro-bicyclic heterocyclyl;

R[2] and R[3] are taken together along with the carbon to which R[2] and R[3] are attached to form an optionally substituted monocyclic $C_{3-6}$ cycloalkyl or an optionally substituted 3 to 6 member monocyclic heterocyclyl; or R[4] and R[5] are taken together along with the carbon to which R[4] and R[5] are attached to form an optionally substituted monocyclic $C_{3-6}$ cycloalkyl or an optionally substituted 3 to 6 member monocyclic heterocyclyl; or R[2] and R[4] are taken together along with the carbons to which R[2] and R[4] are each attached to form an optionally monocyclic $C_{5-7}$ cycloalkyl or an optionally substituted 5 to 7 member monocyclic heterocyclyl; or R[3] and R[5] are taken together along with the carbons to which R[3] and R[5] are each attached to form an optionally monocyclic $C_{5-7}$ cycloalkyl or an optionally substituted 5 to 7 member monocyclic heterocyclyl; or R[6] and R[7] are taken together along with the carbon to which R[6] and R[7] are attached to form an optionally substituted monocyclic $C_{3-4}$ cycloalkyl, an optionally substituted oxetane or an optionally substituted thietane; and X[1] is O or NR[14], wherein R[14] is hydrogen, an unsubstituted $C_{1-4}$ alkyl, an unsubstituted $C_{1-4}$ haloalkyl, an optionally substituted aryl or an optionally substituted aryl($C_{1-4}$ alkyl).

2. The compound of claim 1, wherein n is 1; and Z[1] is —C(=O)—.

3. The compound of claim 1, wherein n is 1; and Z[1] is —NH—C(=O)—.

4. The compound of claim 1, wherein R[1] is selected from the group consisting of

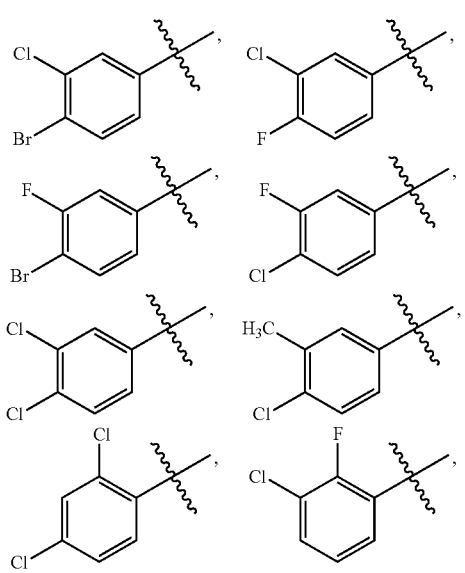

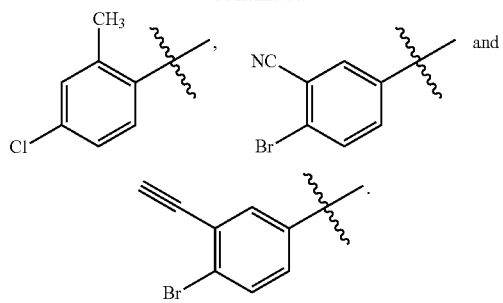

5. The compound of claim 4, wherein R[1] is

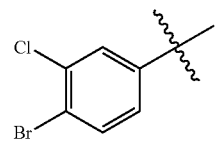 [SMILES: *c1ccc(Br)c(Cl)c1]

6. The compound of claim 1, wherein R[2], R[3], R[4], R[5], R[6], R[7] and R[8] are each hydrogen.

7. The compound of claim 1, wherein R[2], R[3], R[4], R[5], R[6] and R[7] are each hydrogen; and R[8] is halogen.

8. The compound of claim 1, wherein R[9] is an optionally substituted aryl or an optionally substituted heteroaryl.

9. The compound of claim 1, wherein R[9] is —C(=O) NR[12]R[13].

10. The compound of claim 9, wherein R[12] is hydrogen.

11. The compound of claim 10, wherein R[13] is selected from the group consisting of an unsubstituted $C_{1-4}$ alkyl, an optionally substituted aryl and an optionally substituted aryl($C_{1-4}$ alkyl).

12. The compound of claim 1, wherein X[1] is O.

13. A compound is selected from the group consisting of:

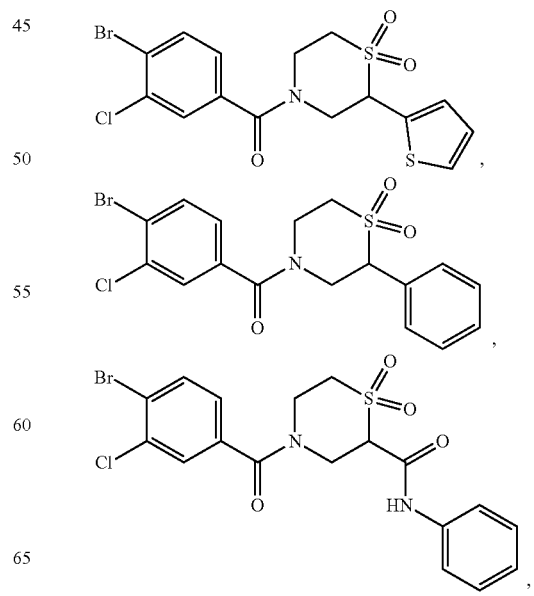

149
-continued
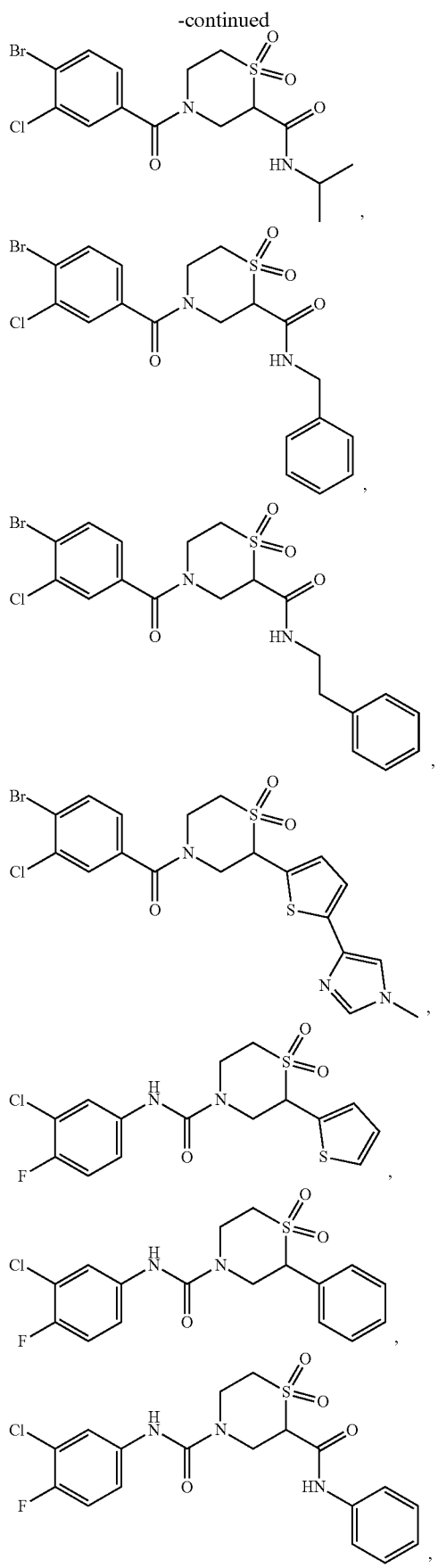
150
-continued
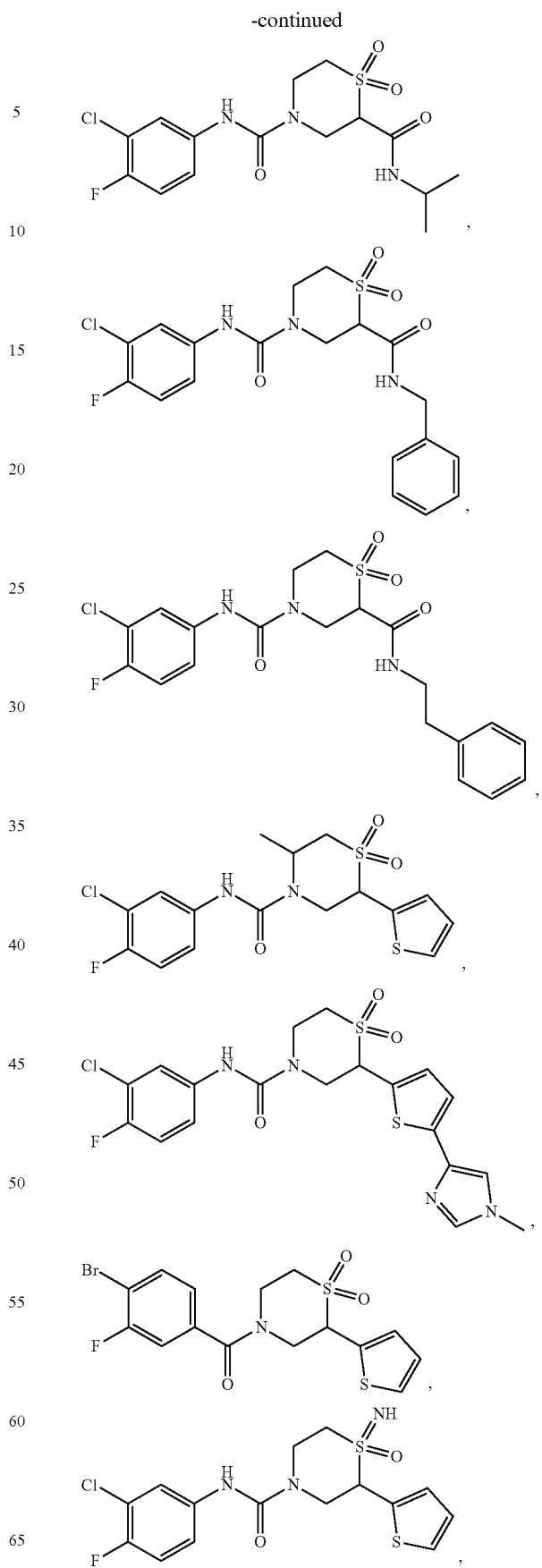

151
-continued
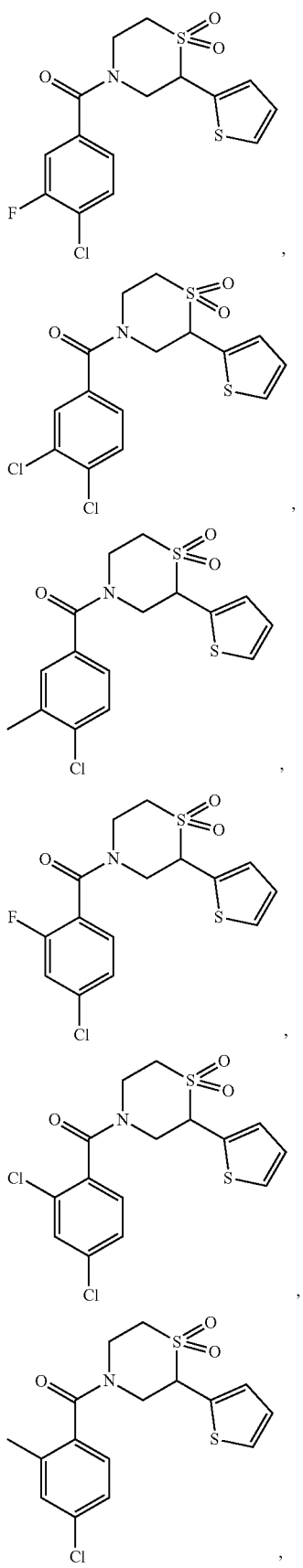
152
-continued
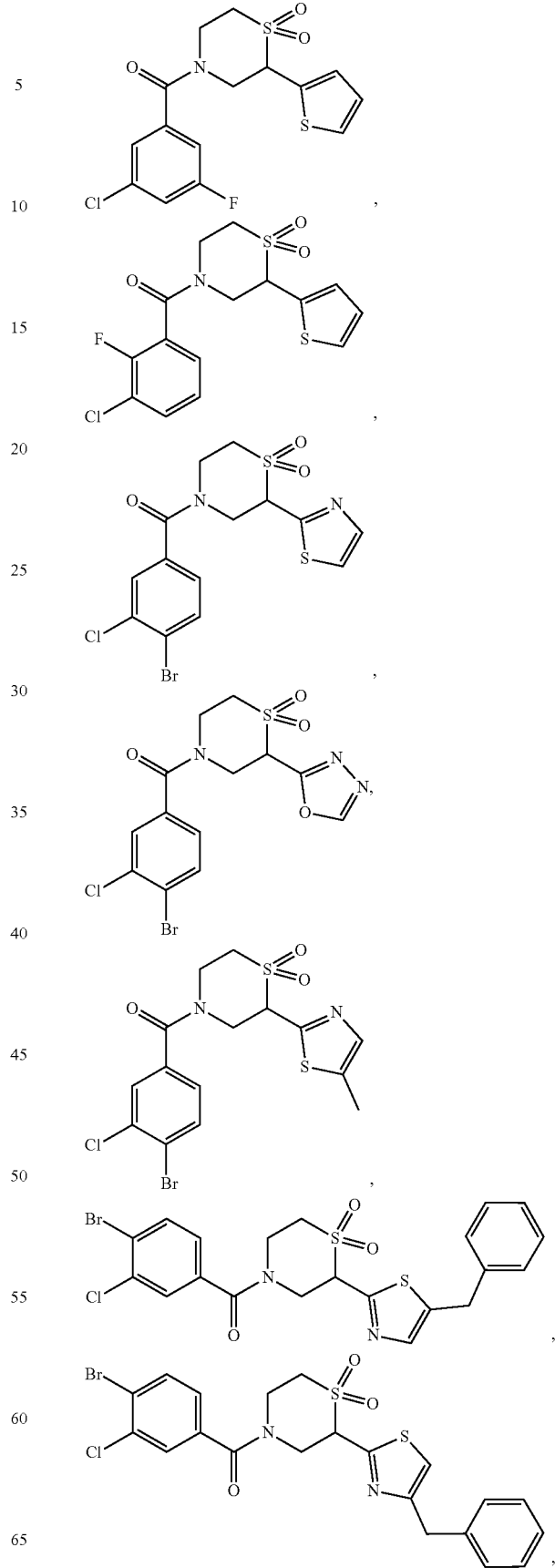

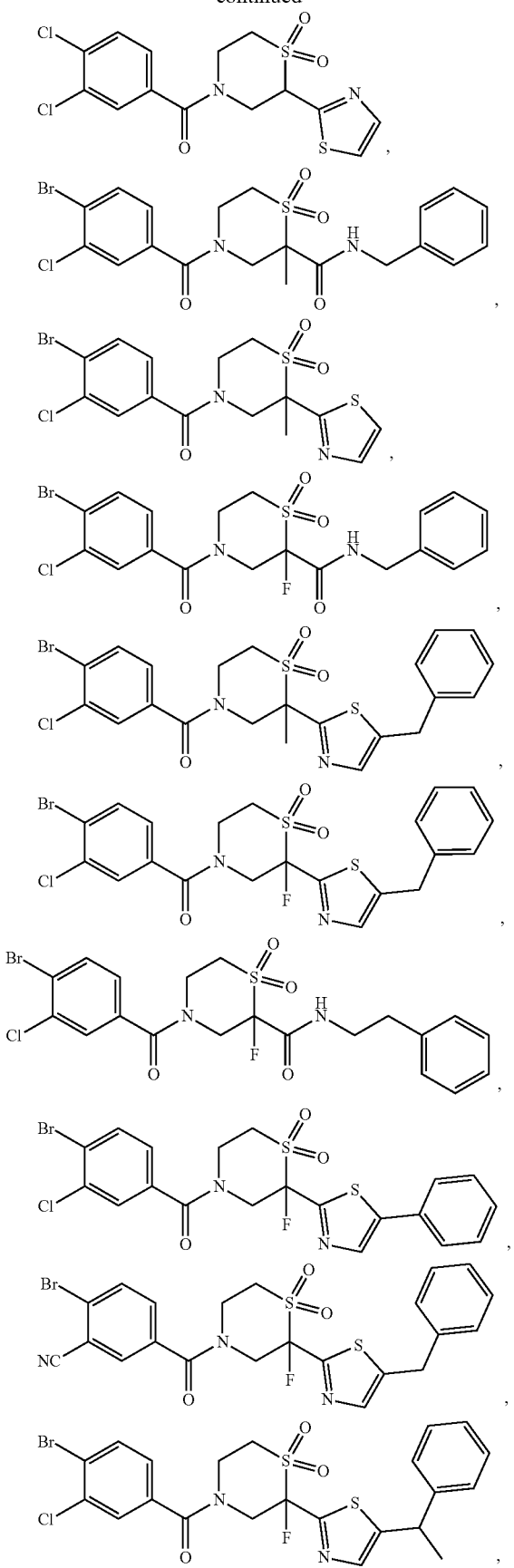
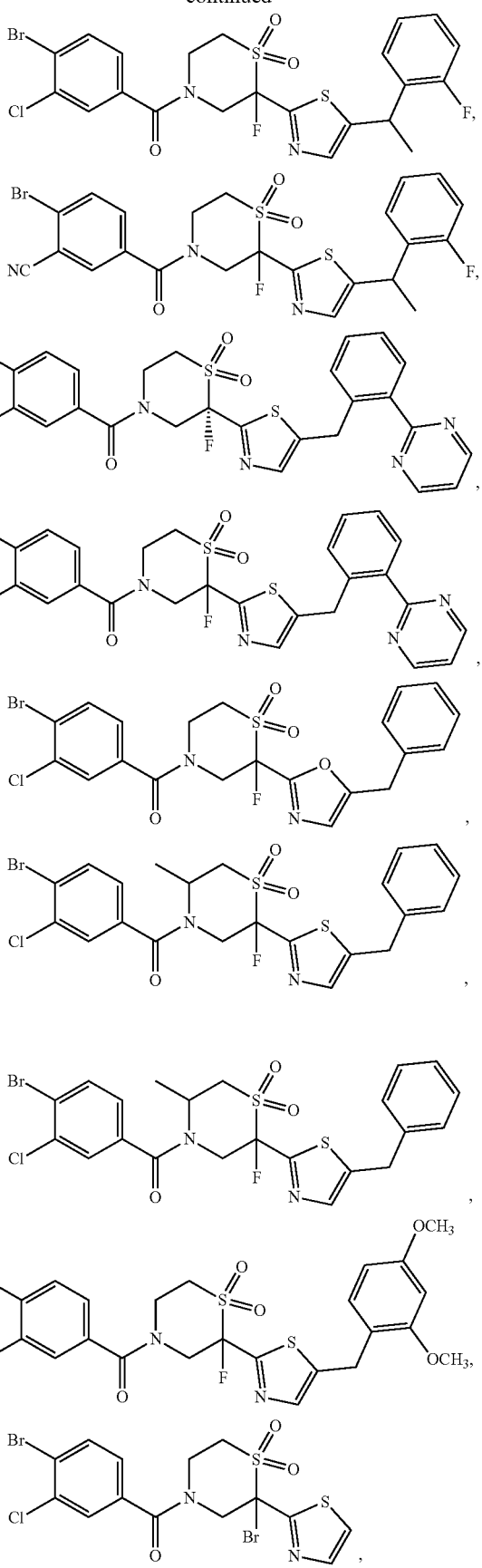

-continued
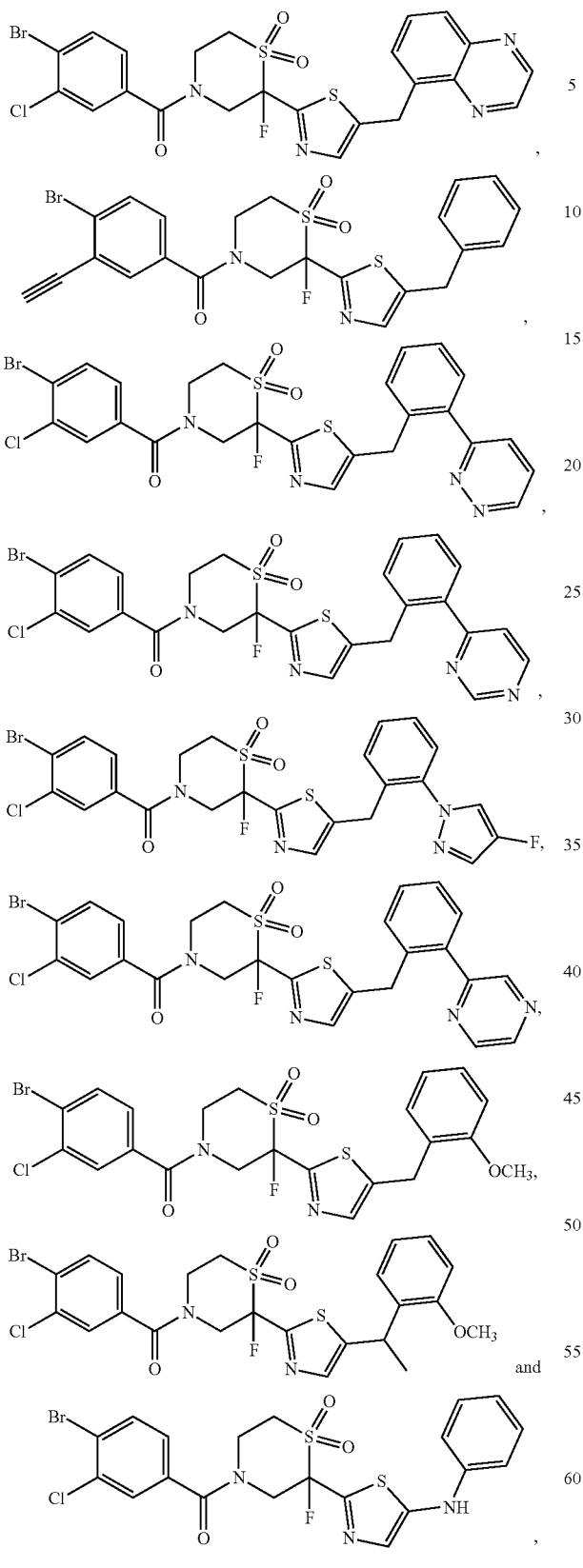
or a pharmaceutically acceptable salt of any of the foregoing.
14. A compound is selected from the group consisting of:
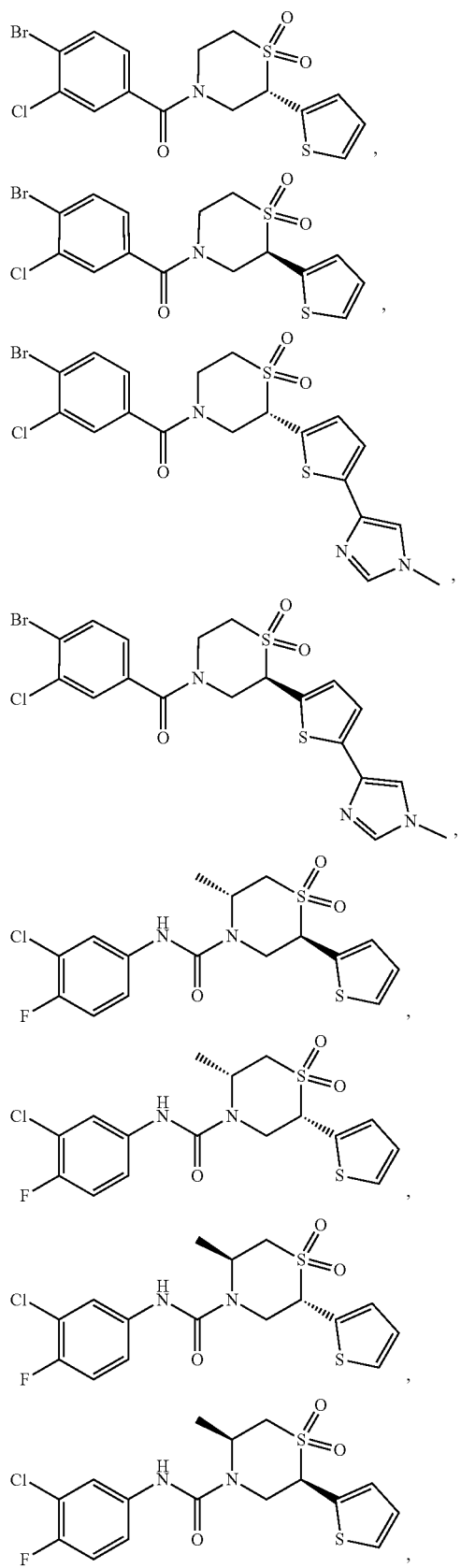

157
-continued
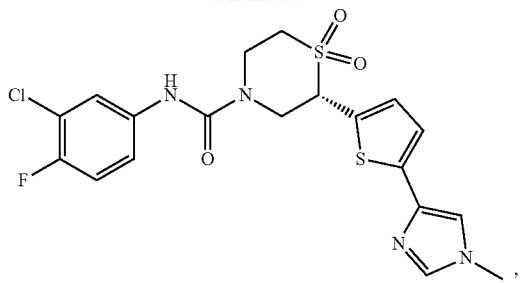
,
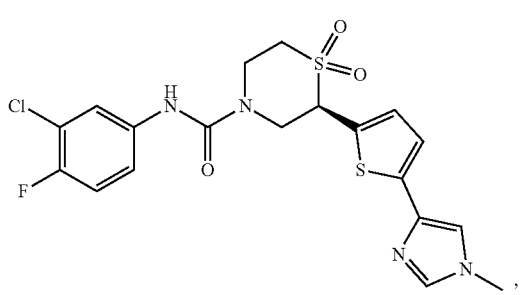
,
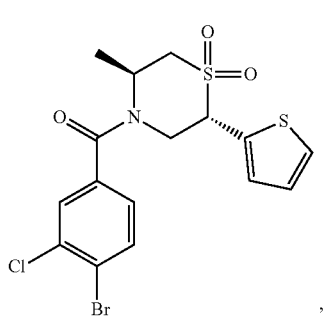
,
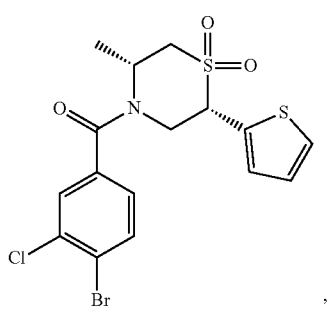
,
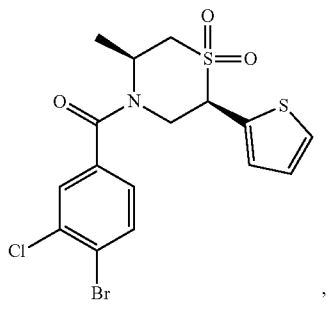
,
158
-continued
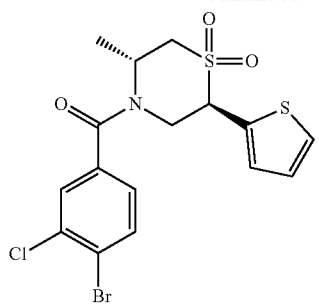
,
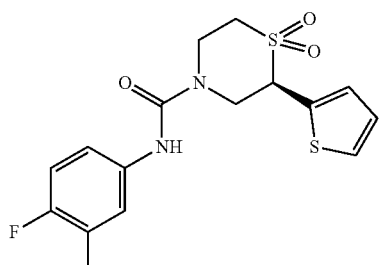
,
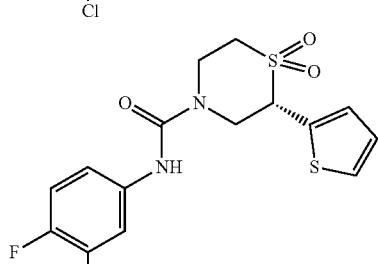
,
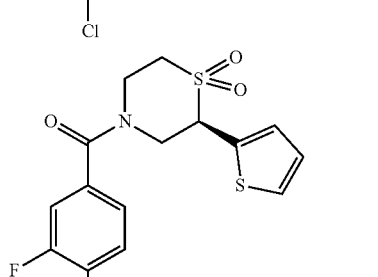
,
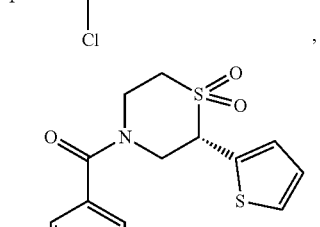
,
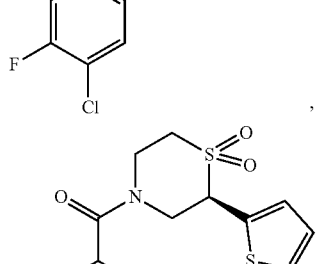
,
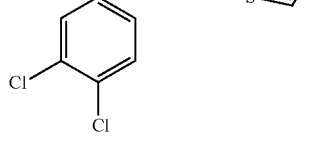
, 159
-continued
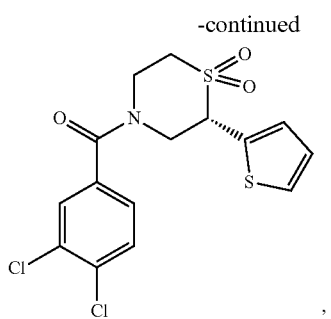
,
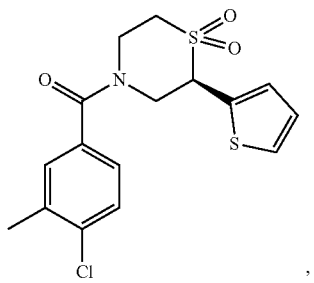
,
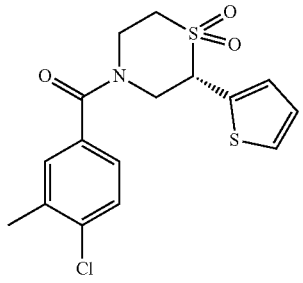
,
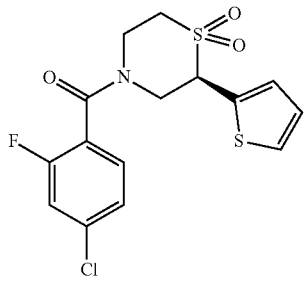
,
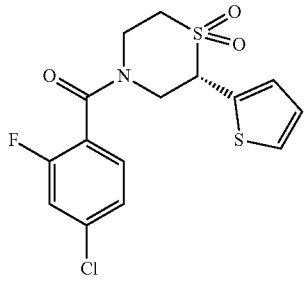
,
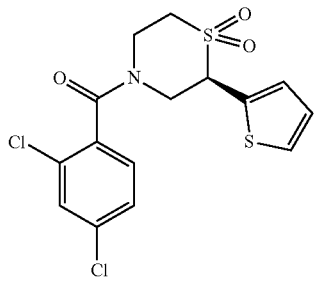
,
160
-continued
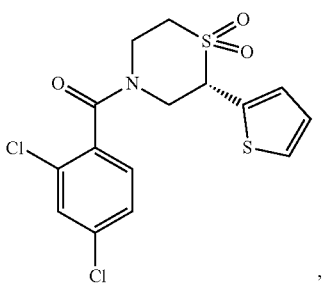
,
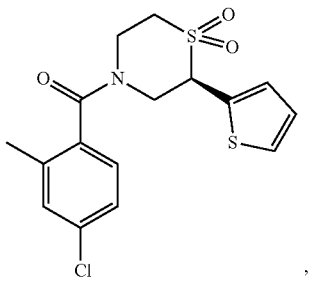
,
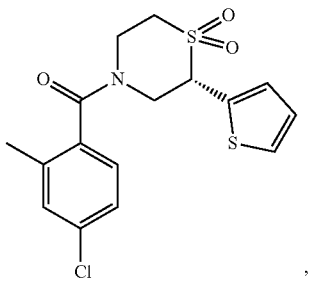
,
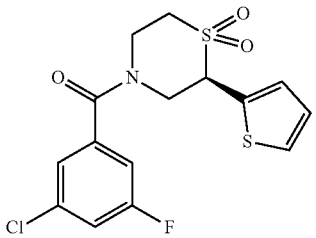
,
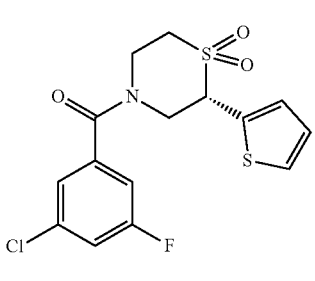
,
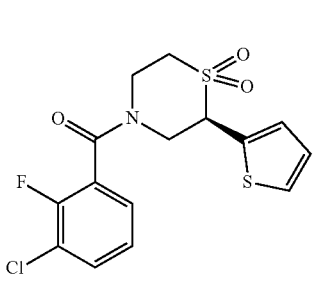
, 161
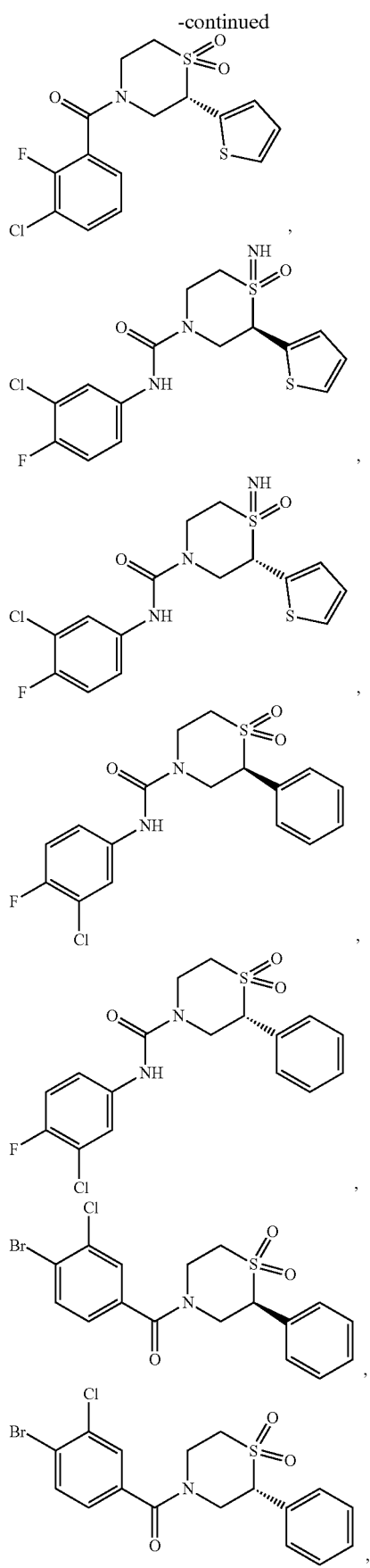
162
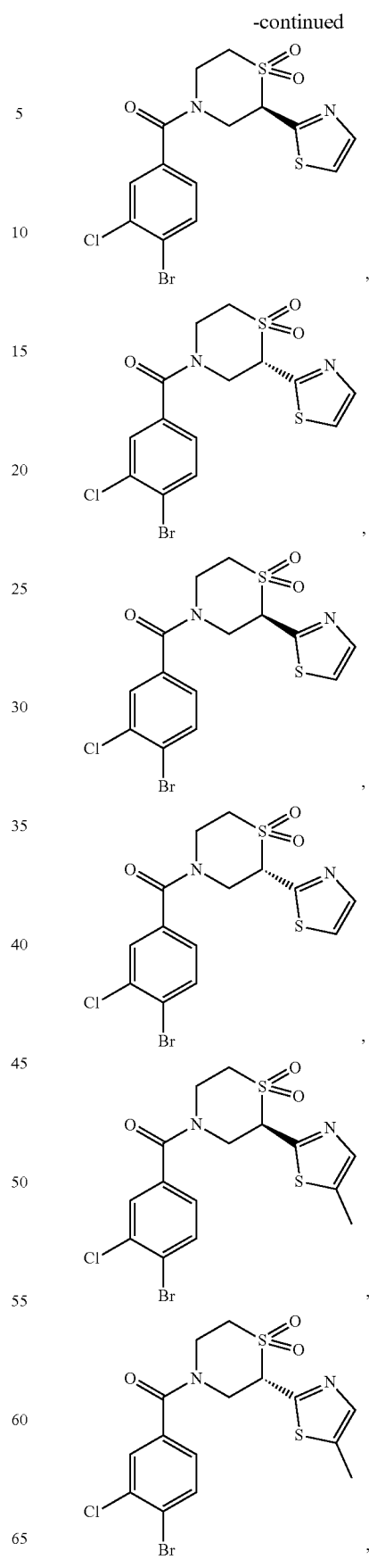

163
-continued
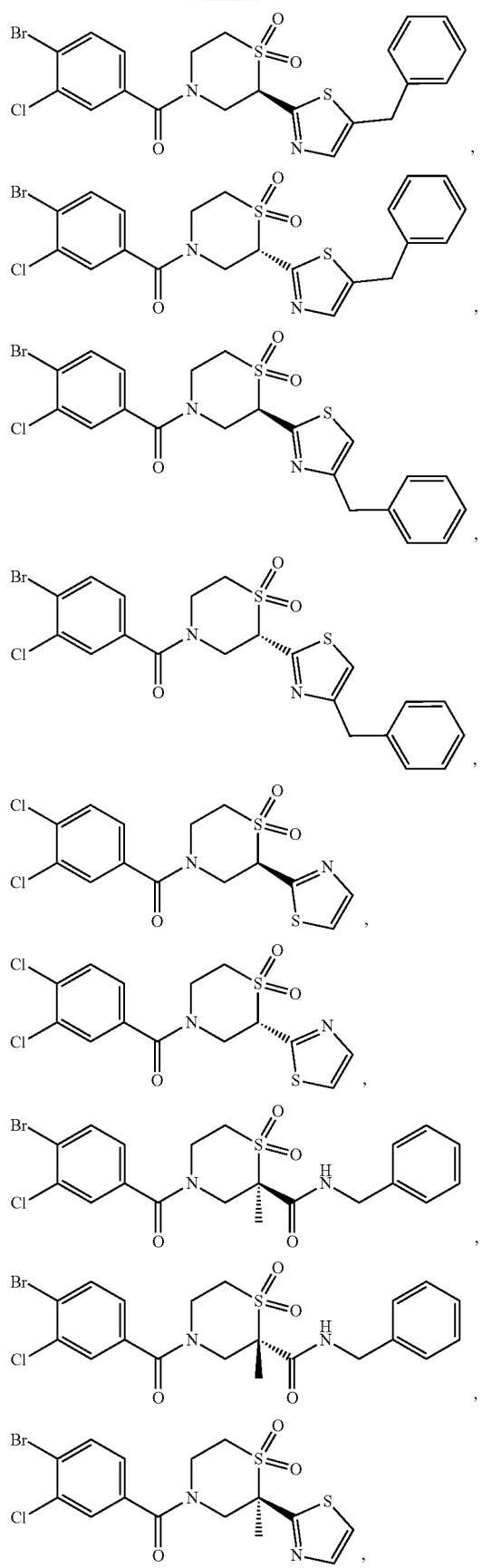
164
-continued
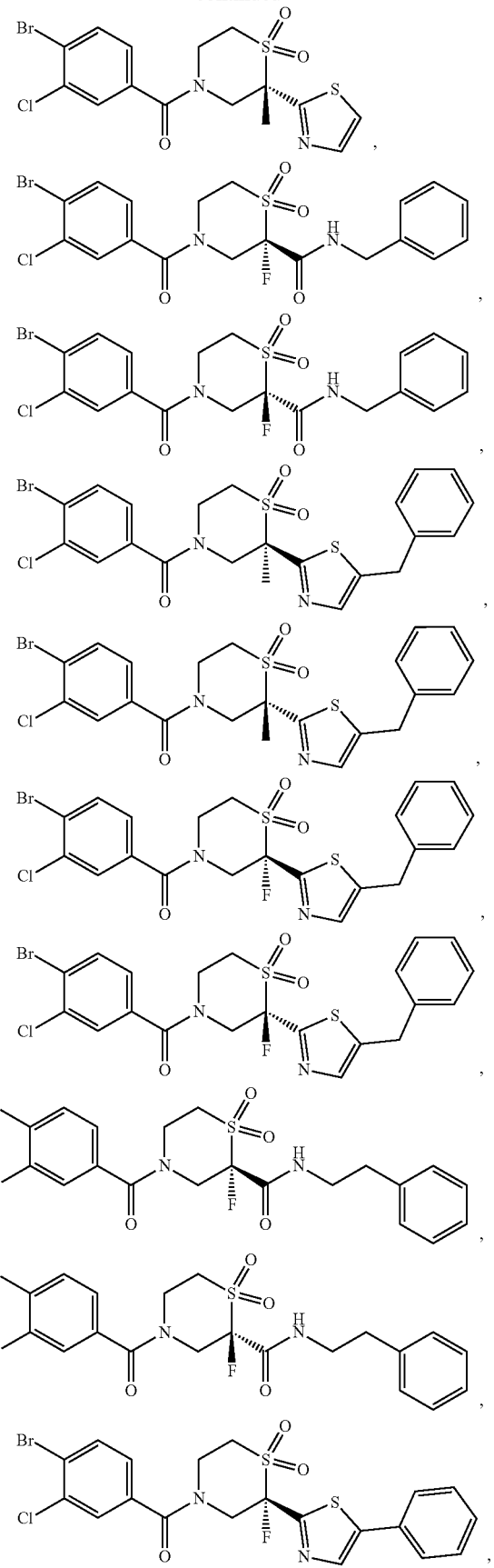

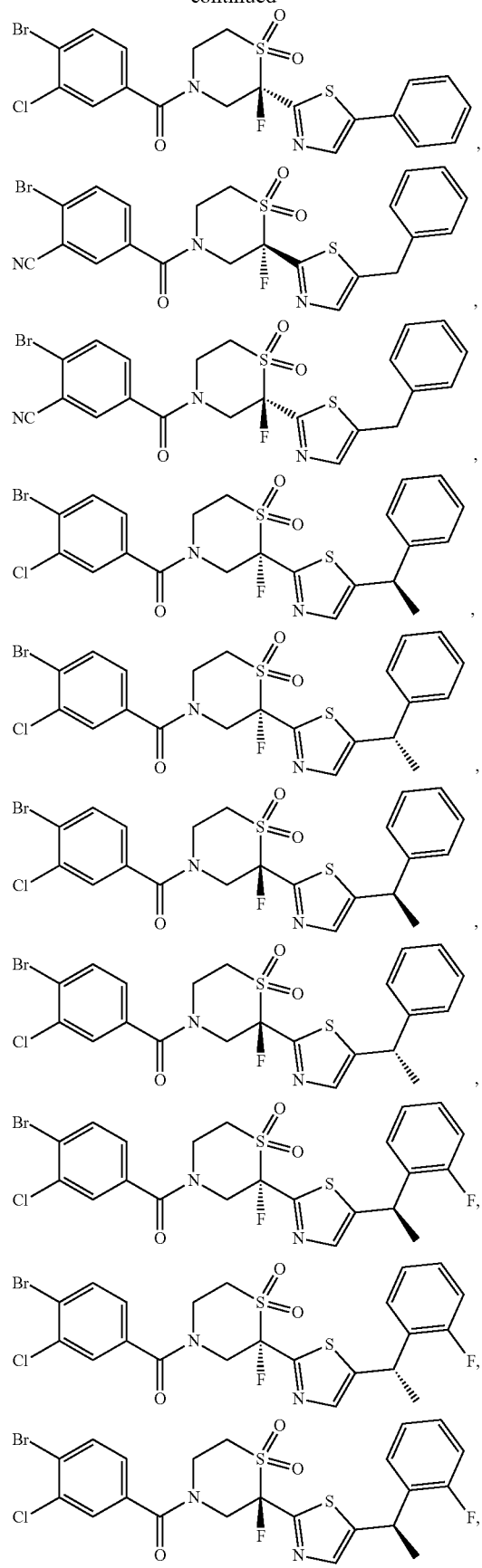
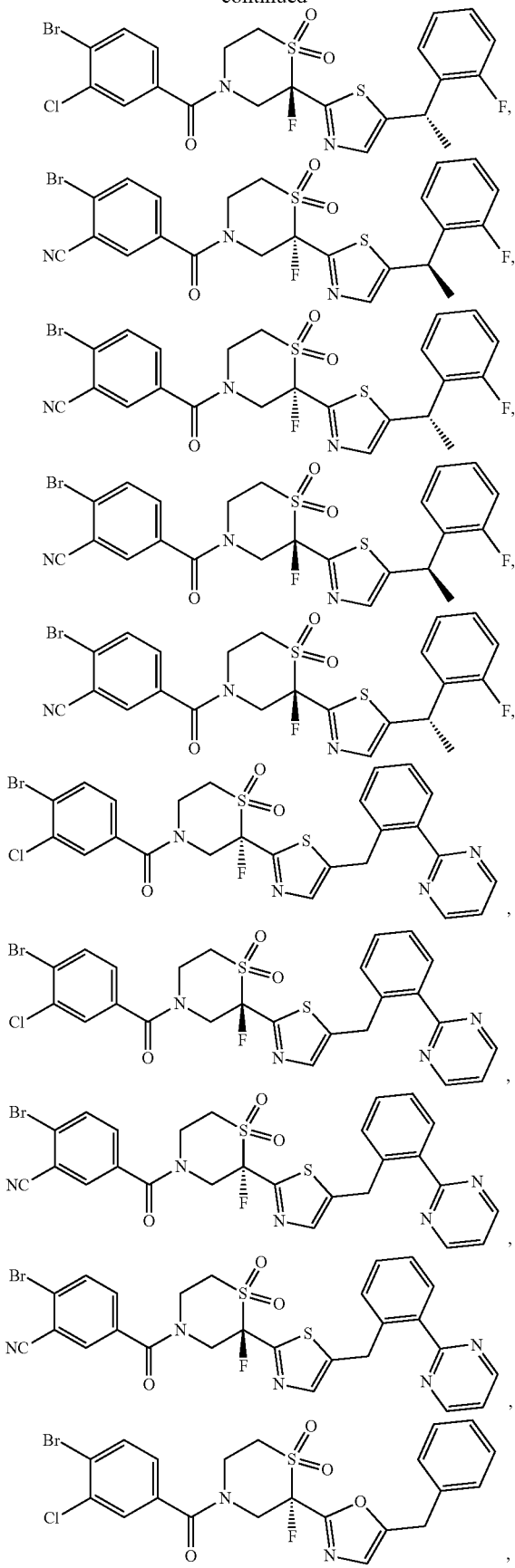

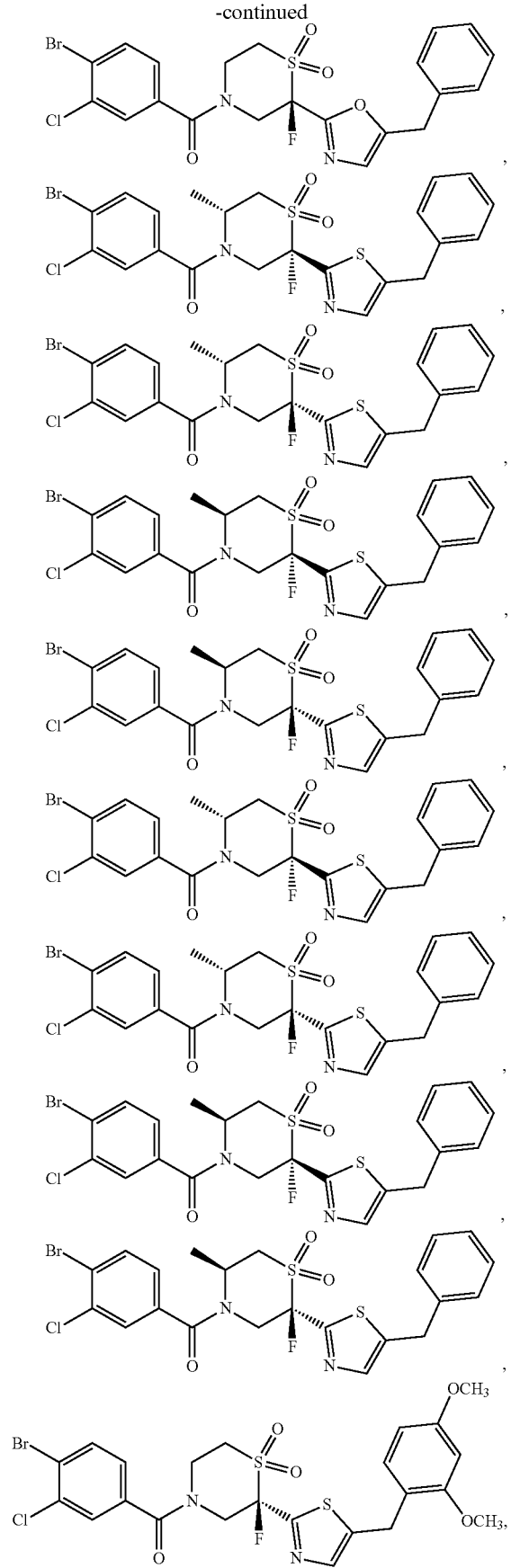
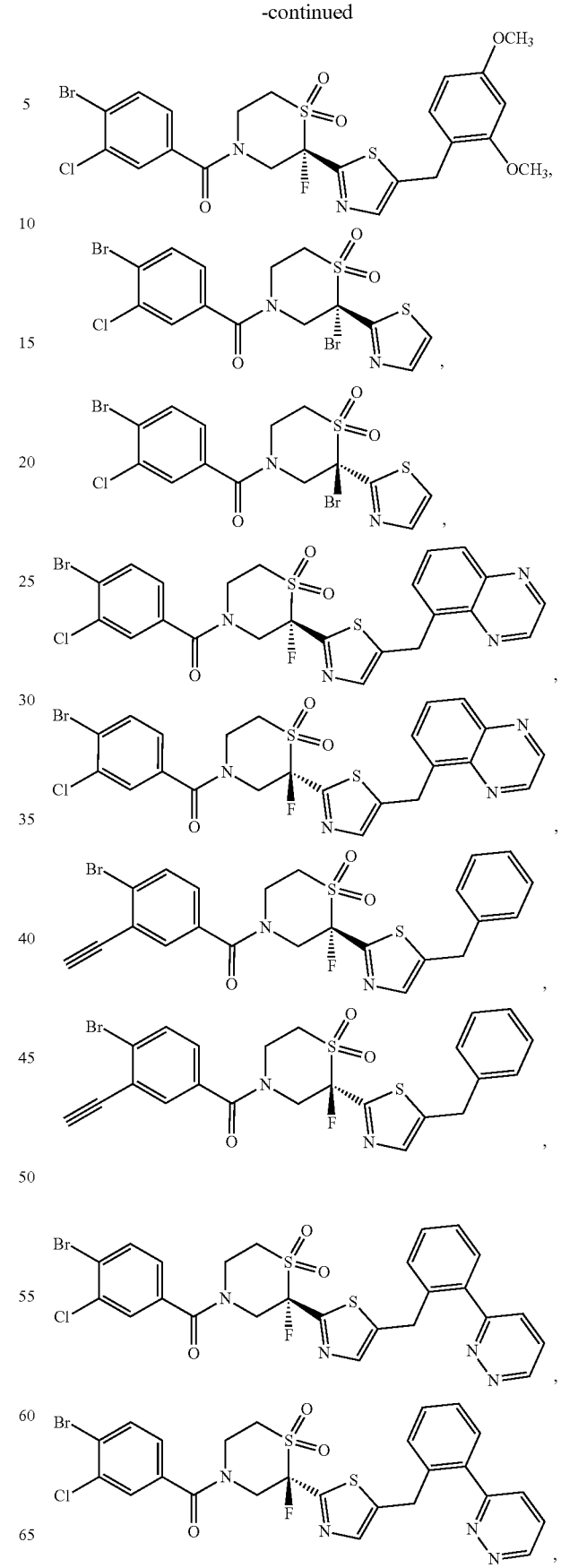

-continued

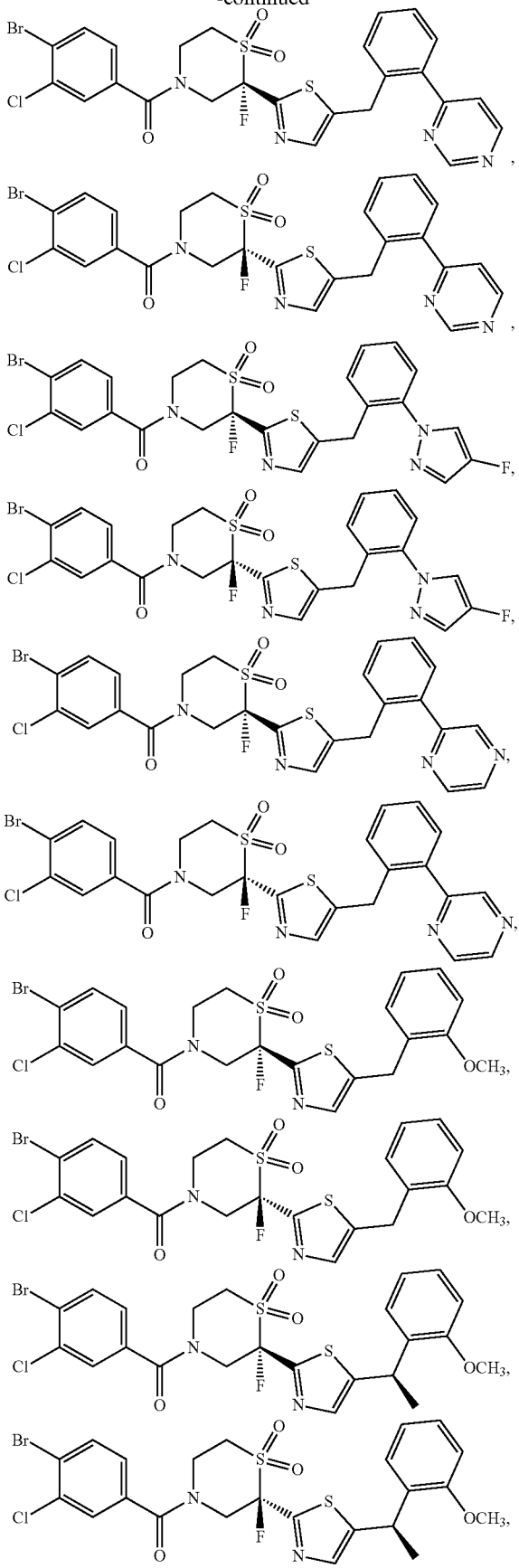

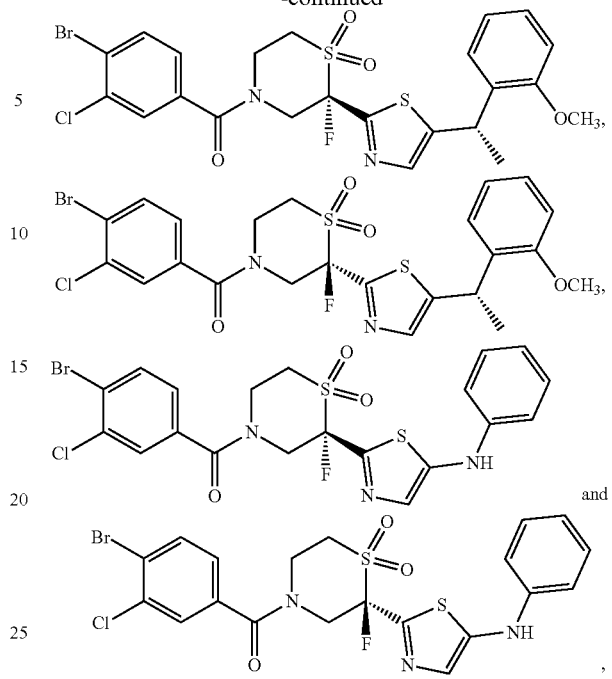

or a pharmaceutically acceptable salt of any of the foregoing.

15. A pharmaceutical composition comprising an effective amount of a compound of claim 1, or a pharmaceutically acceptable salt thereof, and excipient.

16. The compound of claim 8, wherein $R^9$ is an unsubstituted aryl or an unsubstituted heteroaryl.

17. The compound of claim 8, wherein $R^9$ is a substituted heteroaryl substituted by $R^{c1}$, wherein $R^{c1}$ is selected from an unsubstituted $C_{1-4}$ alkyl, an unsubstituted or a substituted aryl, an unsubstituted or a substituted heteroaryl, an unsubstituted or a substituted aryl($C_{1-4}$ alkyl), an unsubstituted or a substituted heteroaryl($C_{1-4}$ alkyl), an amino, a mono-substituted amine and a di-substituted amine.

18. A method for treating hepatitis B in a subject comprising administering to the subject in need thereof an effective amount of a compound of claim 1, or a pharmaceutically acceptable salt thereof, suffering from hepatitis B.

19. A method for treating hepatitis D in a subject comprising administering to the subject in need thereof an effective amount of a compound of claim 1, or a pharmaceutically acceptable salt thereof, suffering from hepatitis D.

20. The method of claim 18, further comprising administering an additional agent selected from the group consisting of an interferon, a nucleoside analog, a nucleotide analog, a sequence specific oligonucleotide, a nucleic acid polymer, an entry inhibitor and a small molecule immunomodulator.

21. The compound of claim 1, wherein:
n is 1;
$Z^1$ is —C(=O)—;
$R^1$ is selected from the group consisting of

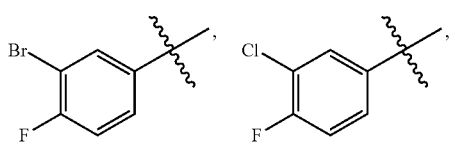

-continued

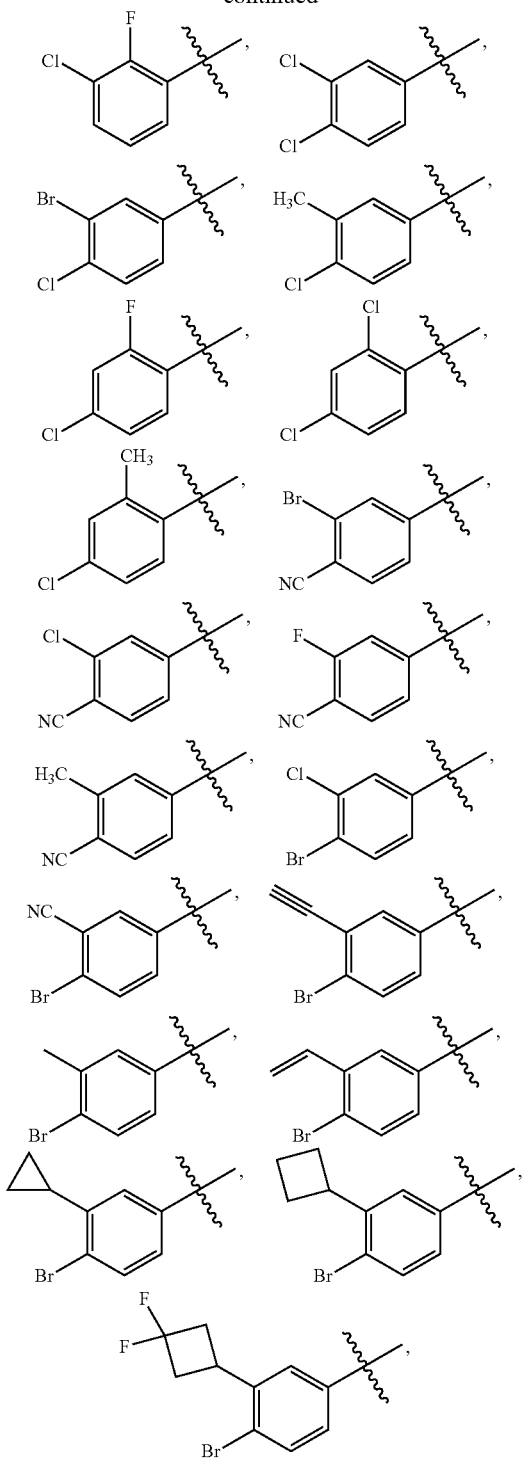

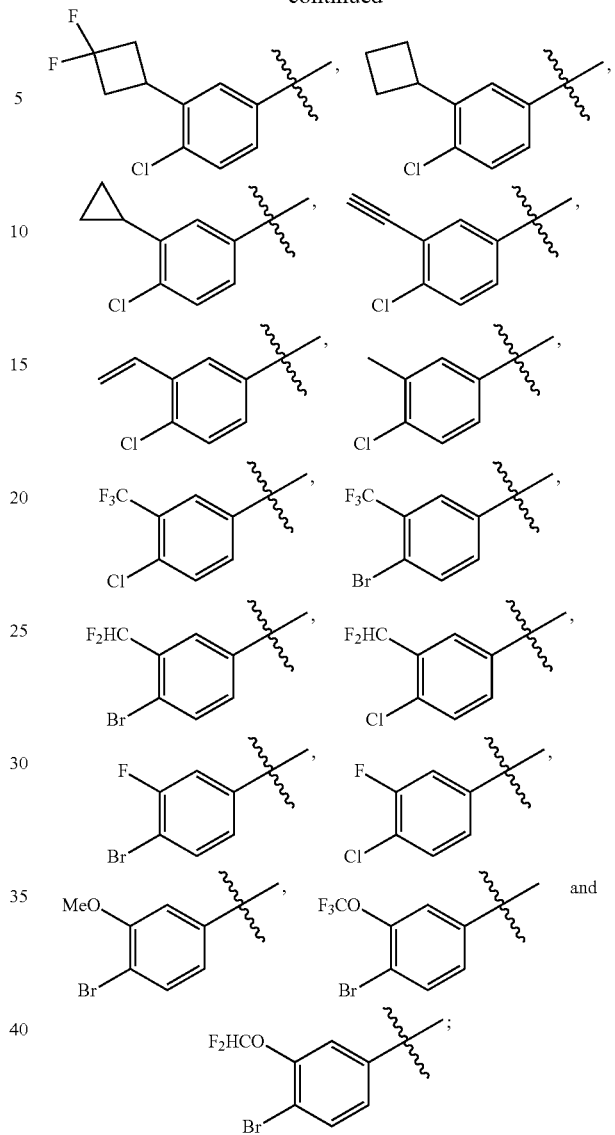

$R^2$ hydrogen or an unsubstituted $C_{1-4}$ alkyl;
$R^3$, $R^4$, $R^5$, $R^6$ and $R^7$ are each hydrogen;
$R^8$ is hydrogen or halogen;
$R^9$ is selected from the group consisting of an optionally substituted phenyl, an optionally substituted monocyclic heteroaryl, and —C(=O)NR$^{12}$R$^{13}$;
$R^{12}$ is hydrogen;
$R^{13}$ is selected from the group consisting of an unsubstituted $C_{1-4}$ alkyl and an optionally substituted aryl($C_{1-4}$ alkyl); and
$X^1$ is O or NH.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic HBV-forward primer

<400> SEQUENCE: 1
gtgtctgcgg cgttttatca                                      20

<210> SEQ ID NO 2
<211> LENGTH: 21
<212> TYPE: DNA
<213> ORGANISM: Artificial Sequence
<220> FEATURE:
<223> OTHER INFORMATION: Synthetic HBV-reverse primer

<400> SEQUENCE: 2
gacaaacggg caacatacct t                                    21

<210> SEQ ID NO 3

```
<211> LENGTH: 28
<212> TYPE: DNA
<213> ORGANISM: Artificial Sequence
<220> FEATURE:
<221> NAME/KEY: modified_base
<222> LOCATION: 1
<223> OTHER INFORMATION: N = FAM-C
<220> FEATURE:
<221> NAME/KEY: modified_base
<222> LOCATION: 28
<223> OTHER INFORMATION: N = C-TAMRA
<220> FEATURE:
<223> OTHER INFORMATION: Synthetic HBV-probe

<400> SEQUENCE: 3
nctctkcatc ctgctgctat gcctcatn                                      28

<210> SEQ ID NO 4
<211> LENGTH: 28
<212> TYPE: DNA
<213> ORGANISM: Artificial Sequence
<220> FEATURE:
<221> NAME/KEY: modified_base
<222> LOCATION: 1
<223> OTHER INFORMATION: N=FAM-C
<220> FEATURE:
<221> NAME/KEY: modified_base
<222> LOCATION: 9
<223> OTHER INFORMATION: N=T-ZEN
<220> FEATURE:
<221> NAME/KEY: modified_base
<222> LOCATION: 28
<223> OTHER INFORMATION: N = C-3AIBkFq
<220> FEATURE:
<223> OTHER INFORMATION: Synthetic HBV-probe

<400> SEQUENCE: 4
nctctkcanc ctgctgctat gcctcatn                                      28
```